US008778676B2

(12) United States Patent
Croce et al.

(10) Patent No.: US 8,778,676 B2
(45) Date of Patent: Jul. 15, 2014

(54) DIAGNOSIS AND TREATMENT OF CANCERS WITH MICRORNA LOCATED IN OR NEAR CANCER-ASSOCIATED CHROMOSOMAL FEATURES

(71) Applicant: Thomas Jefferson University, Philadelphia, PA (US)

(72) Inventors: Carlo M. Croce, Columbus, OH (US); Chang-Gong Liu, Pearland, TX (US); George A. Calin, Pearland, TX (US); Cinzia Sevignani, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 13/972,759

(22) Filed: Aug. 21, 2013

(65) Prior Publication Data
US 2013/0330403 A1 Dec. 12, 2013

Related U.S. Application Data

(60) Division of application No. 12/767,279, filed on Apr. 26, 2010, now abandoned, which is a continuation of application No. 11/194,055, filed on Jul. 29, 2005, now Pat. No. 7,723,030, which is a continuation-in-part of application No. PCT/US2005/004865, filed on Feb. 9, 2005.

(60) Provisional application No. 60/543,119, filed on Feb. 9, 2004, provisional application No. 60/542,929, filed on Feb. 9, 2004, provisional application No. 60/542,963, filed on Feb. 9, 2004, provisional application No. 60/542,940, filed on Feb. 9, 2004, provisional application No. 60/580,959, filed on Jun. 18, 2004, provisional application No. 60/580,797, filed on Jun. 18, 2004.

(51) Int. Cl.
*C12N 15/85* (2006.01)
*C07H 21/02* (2006.01)
*C07H 21/04* (2006.01)

(52) U.S. Cl.
USPC .... 435/325; 536/23.1; 536/24.31; 536/24.33; 536/24.3; 536/24.5

(58) Field of Classification Search
None
See application file for complete search history.

(56) References Cited

U.S. PATENT DOCUMENTS

| 7,723,030 B2 | 5/2010 | Croce et al. |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2010/0203544 A1 | 8/2010 | Croce et al. |
| 2011/0052502 A1 | 3/2011 | Croce et al. |

FOREIGN PATENT DOCUMENTS

| WO | WO 03/029459 A2 | 4/2003 |
| WO | WO 2004/043387 A2 | 5/2004 |
| WO | WO 2005/013901 A2 * | 2/2005 ..................... 514/44 |

OTHER PUBLICATIONS

Bartel, D. P., "MicroRNAs: Genomics, Biogenesis, Mechanism, and Function," *Cell*,116:281-297 (Jan. 2004).
Calin, G. A., et al., "Frequent Deletions and Down-Regulation of Micro-RNA Genes miR15 and miR16 at 13q14 in Chronic Lymphocytic Leukemia," *Proc. Natl. Acad. Sci. USA*, 99 (24):15524-15529 (Oct. 2002).
Calin, G. A., et al., "Human MicroRNA Genes are Frequently Located at Fragile Sites and Genomic Regions Involved in Cancers," *Proc. Natl. Acad. Sci. USA*, 101 (9):2999-3004 (Mar. 2004).
Calin, G. A., et al., "MicroRNA Profiling Reveals Distinct Signatures in B Cell Chronic Lymphocytic Leukemias," *Proc. Natl. Acad. Sci. USA*, 101 (32):11755-11760 (Jun. 2004).
Calin, G. A., et al., "A MicroRNA Signature Associated with Prognosis and Progression in Chronic Lymphocytic Leukemia," *N. Engl. J. Med.*, 353 (17):1793-1801 (Oct. 2005).
Fabbri, M. and R. Garzon, "Implications of MicroRNAs in Normal Hematopoiesis and Human Leukemia," *Clinical Leukemia*, 2:96-101 (May 2008).
McManus, M.T., "MicroRNAs and Cancer," *Sem. Cancer Biol.*,13:253-258 (Mar. 2003).
Metzler, M. et al., "High Expression of Precursor MicroRNA—155/BIC RNA in Children with Burkitt Lymphoma," *Genes, Chromosomes & Cancer*, 39:167-169 (2004) (month not available).
Michael, M.Z., et al., "Reduced Accumulation of Specific MicroRNAs in Colorectal Neoplasia," *Molecular Cancer Research*, 1:882-891 (Aug. 2003).
Wang, M., et al., "miRNA Analysis in B-Cell Chronic Lymphocytic Leukemia: Proliferation Centres Characterized by Low miR-150 and High BIC/miR-155 Expression," *Journal of Pathology*, 215:13-20 (Feb. 2008).

(Continued)

*Primary Examiner* — Amy Bowman
(74) *Attorney, Agent, or Firm* — Hamilton, Brook, Smith & Reynolds, P.C.

(57) ABSTRACT

MicroRNA genes are highly associated with chromosomal features involved in the etiology of different cancers. The perturbations in the genomic structure or chromosomal architecture of a cell caused by these cancer-associated chromosomal features can affect the expression of the miR gene(s) located in close proximity to that chromosomal feature. Evaluation of miR gene expression can therefore be used to indicate the presence of a cancer-causing chromosomal lesion in a subject. As the change in miR gene expression level caused by a cancer-associated chromosomal feature may also contribute to cancerigenesis, a given cancer can be treated by restoring the level of miR gene expression to normal. microRNA expression profiling can be used to diagnose cancer and predict whether a particular cancer is associated with an adverse prognosis. The identification of specific mutations associated with genomic regions that harbor miR genes in CLL patients provides a means for diagnosing CLL and possibly other cancers.

5 Claims, 9 Drawing Sheets
(6 of 9 Drawing Sheet(s) Filed in Color)

(56) References Cited

OTHER PUBLICATIONS

Restriction Requirement dated Sep. 20, 2007 U.S. Appl. No. 11/194,055, "Diagnosis and Treatment of Cancers With MicroRNA Located in or Near Cancer-Associated Chromosomal Features."
Reply to Restriction Requirement dated Mar. 5, 2008, U.S. Appl. No. 11/194,055, "Diagnosis and Treatment of Cancers With MicroRNA Located in or Near Cancer-Associated Chromosomal Features."
Restriction Requirement dated May 23, 2008, U.S. Appl. No. 11/194,055, "Diagnosis and Treatment of Cancers With MicroRNA Located in or Near Cancer-Associated Chromosomal Features."
Reply to Restriction Requirement dated Jul. 7, 2008, U.S. Appl. No. 11/194,055, "Diagnosis and Treatment of Cancers With MicroRNA Located in or Near Cancer-Associated Chromosomal Features."
Reply to Restriction Requirement dated Dec. 16, 2008, U.S. Appl. No. 11/194,055, "Diagnosis and Treatment of Cancers With MicroRNA Located in or Near Cancer-Associated Chromosomal Features."
Office Action dated Mar. 18, 2009, U.S. Appl. No. 11/194,055, "Diagnosis and Treatment of Cancers With MicroRNA Located in or Near Cancer-Associated Chromosomal Features."
Reply dated Jul. 16, 2009, U.S. Appl. No. 11/194,055, "Diagnosis and Treatment of Cancers With MicroRNA Located in or Near Cancer-Associated Chromosomal Features."
Notice of Non-Compliant Amendment (37 CFR 1.121) dated Oct. 7, 2009, U.S. Appl. No. 11/194,055, "Diagnosis and Treatment of Cancers With MicroRNA Located in or Near Cancer-Associated Chromosomal Features."
Supplemental Amendment dated Oct. 15, 2009, U.S. Appl. No. 11/194,055, "Diagnosis and Treatment of Cancers With MicroRNA Located in or Near Cancer-Associated Chromosomal Features."
Amendment After Allowance dated Feb. 2, 2010, U.S. Appl. No. 11/194,055, "Diagnosis and Treatment of Cancers With MicroRNA Located in or Near Cancer-Associated Chromosomal Features."
International Search Report dated Jan. 2, 2006, Application No. PCT/US2005/004865, "Diagnosis and Treatment of Cancers With MicroRna Located in or Near Cancer-Associated Chromosomal Features."
International Preliminary Report on Patentability dated Aug. 14, 2006, Application No. PCT/US2005/004865, "Diagnosis and Treatment of Cancers With MicroRna Located in or Near Cancer-Associated Chromosomal Features."
Communication Pursuant to Article 94(3) EPC dated Dec. 13, 2007, Application No. EP 05 723130.0, "Diagnosis and Treatment of Cancers With MicroRna Located in or Near Cancer-Associated Chromosomal Features."
Response to official communication dated Jun. 20, 2008, Application No. EP 05 723130.0, "Diagnosis and Treatment of Cancers With MicroRna Located in or Near Cancer-Associated Chromosomal Features."
Restriction Requirement dated Feb. 13, 2012, U.S. Appl. No. 12/751,463, "Diagnosis and Treatment of Cancers With MicroRNA Located in or Near Cancer Associated Chromosomal Features."
Office Action dated Jun. 13, 2012, U.S. Appl. No. 12/751,463, "Diagnosis and Treatment of Cancers With MicroRNA Located in or Near Cancer Associated Chromosomal Features."
Pekarsky, Y., and Croce, C.M., "Is miR-29 an oncogene or tumor suppressor in CLL?," *Oncotarget, Advance Publications 2010*:1-4 (Jul. 2010).
Moussay, E., et al., "MicroRNA as biomarkers and regulators in B-cell chronic lymphocytic leukemia," *PNAS*, 108(16): 6573-6578 (Apr. 2011).
European Search Report and Written Opinion dated Apr. 12, 2012, Application No. EP 10 17 9994, "Diagnosis and Treatment of Cancers With MicroRna Located in or Near Cancer-Associated Chromosomal Features."
Volinia, S., et al., "A microRNA expression signature of human solid tumors defines cancer gene targets," *PNAS*, 103(7): 2257-2261 (Feb. 2006).

Yanaihara, N., et al., "Unique microRNA molecular profiles in lung cancer diagnosis and prognosis," *Cancer Cell*, 9(3): 189-198 (Mar. 2006).
Examination Report dated Apr. 12, 2013, Application No. EP 10 17 9994, "Diagnosis and Treatment of Cancers With MicroRna Located in or Near Cancer-Associated Chromosomal Features."
Cheung, et al., "Natural variation in human gene expression assessed in lymphoblastoid cells," *Nature Genetics*, 2003, vol. 33, p. 422.
Cobb, et al., "Sepsis gene expression profiling: Murine splenic compared with hepatic responses determined by using complementary DNA microarrays," *Crit Care Med*, 2002, vol. 30, p. 2711.
Heegaard, et al., "Circulating micro-RNA expression profiles in early stage nonsmall cell lung cancer," *Int J. Cancer*, 2011, vol. 130, p. 1378.
Newton, et al., "On Differential Variability of Expression Ratios: Improving Statistical Inference about Gene Expression Changes from Microarray Data," *Journal of Computational Biology*, 2001, vol. 8, p. 37.
Roa, et al., "Identification of a new microRNA expression profile as a potential cancer screening tool," *Clin Investigates Med*, 2010, vol. 33, E124.
Rokah, et al., "Downregulation of Mir-31, Mir-155, and Mir-564 in Chronic Myeloid Leukemia Cells," *PLOSONE*, Apr. 2012, vol. 7, p. e35501.
Wu, "Analysing gene expression data from DNA microarrays to identify candidate genes," *Journal of Pathology*, 2001, vol. 195, p. 53.
Xie, et al., "Altered miRNA expression in sputum for diagnosis of non-small cell lung cancer," *Lung Cancer*, 2010, vol. 67, p. 170.
Fei, J., et al., "Inhibitory effects of anti-miRNA oligonucleotides (AMOs) on A549 cell growth," *J. Drug Target* 16(9): 688-693 (2008).
Li, T., et al., "miR-21 as an Independent Biochemical Recurrence Predictor and Potential Therapeutic Target for Prostate Cancer," *J. Urology* 187:1466-1472 (2012).
Sicard, F., et al., "Targeting miR-21 for the Therapy of Pancreatic Cancer," *Molecular Therapy*, 21(5):986-994 (May 2013).
Asangani, IA, et al., "MicroRNA-21 (miR-21) post-transcriptionally downregulates tumor suppressor Pdcd4 and stimulates invasion, intravasation and metastasis in colorectal cancer," *Oncogene*, 27:2128-2136 (2008).
Banno, K., et al., "MicroRNA in Cervical Cancer: OncomiRs and Tumor Suppressor miRs in Diagnosis and Treatment," *The Scientific World Journal*, vol. 2014, Article ID 178075, 8 pages, (2014). doi:10.1155/2014/178075.
Chen et al., "Micro-RNA-21 regulates the sensitivity to cisplatin in human neuroblastoma cells," *J. Pediatr. Surg.* 47(10):1797-1805 (2012).
Fabbri et al., "MicroRNAs bind to Toll-like receptors to induce prometastatic inflammatory response," *PNAS* 109(31): E2110-E2116 (2012).
Fei, J., et al., "Inhibitory effects of anti-miRNA oligonucleotides (AMOs) on A549 cell growth," *Journal of Drug Targeting*, 16(9):688-693 (2008).
Ferracin, M., et al., "MicroRNAs involvement in fludarabine refractory chronic lymphocytic leukemia," *Molecular Cancer*, 9:123, 14 pages (2010). doi:10.1186/1476-4598-9-123.
Si, M-L, et al., "miR-21-mediated tumor growth," *Oncogene*, 26:2799-2803 (2007).
Yao, Q., et al., "MicroRNA-21 promotes cell proliferation and downregulates the expression of programmed cell death 4 (PDCD4) in HeLa cervical carcinoma cells," *Biochemical and Biophysical Research Communications*, 388:539-542 (2009).
Zhang, J.-G., et al., "MicroRNA-21 (miR-21) represses tumor suppressor PTEN and promotes growth and invasion in non-small cell lung cancer (NSCLC)," *Clinica Chimica Acta*, 411:846-852 (2010).
Zhong, Z., et al., "miR-21 induces cell cycle at S phase and modulates cell proliferation by down-regulating hMSH2 in lung cancer," *J. Cancer Res. Clin. Oncol.*, 138:1781-1788 (2012).

(56) References Cited

OTHER PUBLICATIONS

Zhu, S., et al., "MicroRNA-21 targets tumor suppressor genes in invasion and metastasis," *Cell Research*, 18:350-359 (2008).

Anderson, C.L., et al., "High-Throughput Copy Number Analysis of 17q23 in 3520 Tissue Specimens by Fluorescence in Situ Hybridization to Tissue Microarrays," *American Journal of Pathology*, 161(1):73-79 (Jul. 2002).

Birren, B., et al., *Homo sapiens* chromosome 17, clone hRPC.1073_F_15, complete sequence, GenBank Accession No. AC004686.1 [online], Oct. 1998 [retrieved on Apr. 23, 2014]. Retrieved from the Internet URL: www.ncbi.nlm.nih.gov/nuccore/AC004686.1.

Esquela-Kerscher, A., et al. "Oncomirs—microRNAs with a role in cancer," *Nat Rev Cancer*, 6(4):259-269 (Apr. 2006).

Monni, O., et al., "Comprehensive copy number and gene expression profiling of the 17q23 amplicon in human breast cancer," *PNAS*, 98(10):5711-5716 (May 2001).

Santarius, T., et al. "A census of amplified and overexpressed human cancer genes," *Nat Rev Cancer*, 10(1):59-64 (Jan. 2010).

* cited by examiner

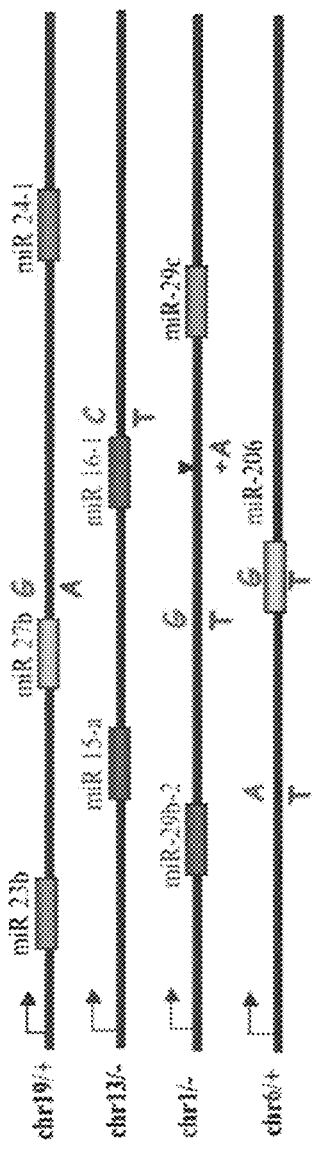
FIG. 7A
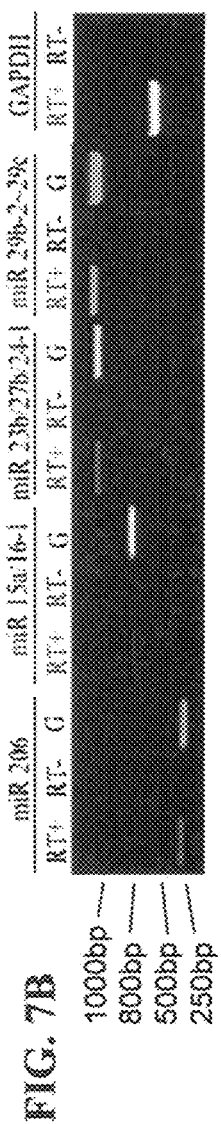
FIG. 7B
FIGS. 7A-7B

SEQUENCE LISTING

```
<160> NUMBER OF SEQ ID NOS: 664

<210> SEQ ID NO 1
<211> LENGTH: 90
<212> TYPE: DNA
<213> ORGANISM: Homo sapiens

<400> SEQUENCE: 1
cactgtggga tgaggtagta ggttgtatag ttttagggtc acacccacca ctgggagata    60
actatacaat ctactgtctt tcctaacgtg                                     90

<210> SEQ ID NO 2
<211> LENGTH: 72
<212> TYPE: DNA
<213> ORGANISM: Homo sapiens

<400> SEQUENCE: 2
aggttgaggt agtaggttgt atagtttaga attacatcaa gggagataac tgtacagcct    60
cctagctttc ct                                                        72

<210> SEQ ID NO 3
<211> LENGTH: 74
<212> TYPE: DNA
<213> ORGANISM: Homo sapiens

<400> SEQUENCE: 3
gggtgaggta gtaggttgta tagtttgggg ctctgccctg ctatgggata actatacaat    60
ctactgtctt tcct                                                      74

<210> SEQ ID NO 4
<211> LENGTH: 107
<212> TYPE: DNA
<213> ORGANISM: Homo sapiens

<400> SEQUENCE: 4
gtgactgcat gctcccaggt tgaggtagta ggttgtatag tttagaatta cacaagggag    60
ataactgtac agcctcctag ctttccttgg gtcttgcact aaacaac                  107

<210> SEQ ID NO 5
<211> LENGTH: 85
<212> TYPE: DNA
<213> ORGANISM: Homo sapiens

<400> SEQUENCE: 5
ggcggggtga ggtagtaggt tgtgtggttt cagggcagtg atgttgcccc tcggaagata    60
actatacaac ctactgcctt ccctg                                          85
```

```
<210> SEQ ID NO 6
<211> LENGTH: 84
<212> TYPE: DNA
<213> ORGANISM: Homo sapiens

<400> SEQUENCE: 6
gcatccgggt tgaggtagta ggttgtatgg tttagagtta caccctggga gttaactgta      60
caaccttcta gctttccttg gagc                                            84

<210> SEQ ID NO 7
<211> LENGTH: 87
<212> TYPE: DNA
<213> ORGANISM: Homo sapiens

<400> SEQUENCE: 7
cctaggaaga ggtagtaggt tgcatagttt tagggcaggg attttgccca caaggaggta     60
actatacgac ctgctgcctt tcttagg                                         87

<210> SEQ ID NO 8
<211> LENGTH: 85
<212> TYPE: DNA
<213> ORGANISM: Homo sapiens

<400> SEQUENCE: 8
ctaggaagag gtagtagttt gcatagtttt agggcaaaga ttttgcccac aagtagttag     60
ctatacgacc tgcagccttt tgtag                                           85

<210> SEQ ID NO 9
<211> LENGTH: 85
<212> TYPE: DNA
<213> ORGANISM: Homo sapiens

<400> SEQUENCE: 9
ctggctgagg tagtagtttg tgctgttggt cgggttgtga cattgcccgc tgtggagata     60
actgcgcaag ctactgcctt gctag                                           85

<210> SEQ ID NO 10
<211> LENGTH: 79
<212> TYPE: DNA
<213> ORGANISM: Homo sapiens

<400> SEQUENCE: 10
cccgggctga ggtaggaggt tgtatagttg aggaggacac ccaaggagat cactatacgg     60
cctcctagct ttccccagg                                                  79

<210> SEQ ID NO 11
<211> LENGTH: 87
<212> TYPE: DNA
<213> ORGANISM: Homo sapiens

<400> SEQUENCE: 11
tcagagtgag gtagtagatt gtatagttgt ggggtagtga ttttaccctg ttcaggagat     60
aactatacaa tctattgcct tccctga                                         87

<210> SEQ ID NO 12
<211> LENGTH: 89
<212> TYPE: DNA
<213> ORGANISM: Homo sapiens

<400> SEQUENCE: 12
```

```
ctgtgggatg aggtagtaga ttgtatagtt gtggggtagt gattttaccc tgttcaggag    60
ataactatac aatctattgc cttccctga                                       89

<210> SEQ ID NO 13
<211> LENGTH: 85
<212> TYPE: DNA
<213> ORGANISM: Homo sapiens

<400> SEQUENCE: 13
ctgtgggatg aggtagtaga ttgtatagtt ttagggtcat accccatctt ggagataact    60
atacagtcta ctgtctttcc cacgg                                           85

<210> SEQ ID NO 14
<211> LENGTH: 108
<212> TYPE: DNA
<213> ORGANISM: Homo sapiens

<400> SEQUENCE: 14
ttgcctgatt ccaggctgag gtagtagttt gtacagtttg agggtctatg ataccacccg    60
gtacaggaga taactgtaca ggccactgcc ttgccaggaa cagcgcgc                 108

<210> SEQ ID NO 15
<211> LENGTH: 85
<212> TYPE: DNA
<213> ORGANISM: Homo sapiens

<400> SEQUENCE: 15
ctggctgagg tagtagtttg tgctgttggt cgggttgtga cattgcccgc tgtggagata    60
actgcgcaag ctactgcctt gctag                                           85

<210> SEQ ID NO 16
<211> LENGTH: 85
<212> TYPE: DNA
<213> ORGANISM: Homo sapiens

<400> SEQUENCE: 16
acctactcag agtacatact tctttatgta cccatatgaa catacaatgc tatggaatgt    60
aaagaagtat gtattttgg taggc                                            85

<210> SEQ ID NO 17
<211> LENGTH: 108
<212> TYPE: DNA
<213> ORGANISM: Homo sapiens

<400> SEQUENCE: 17
cagctaacaa cttagtaata cctactcaga gtacatactt ctttatgtac ccatatgaac    60
atacaatgct atggaatgta aagaagtatg tattttggt aggcaata                  108

<210> SEQ ID NO 18
<211> LENGTH: 85
<212> TYPE: DNA
<213> ORGANISM: Homo sapiens

<400> SEQUENCE: 18
gcctgcttgg gaaacatact tctttatatg cccatatgga cctgctaagc tatggaatgt    60
aaagaagtat gtatctcagg ccggg                                           85

<210> SEQ ID NO 19
<211> LENGTH: 71
<212> TYPE: DNA
```

-continued

<213> ORGANISM: Homo sapiens

<400> SEQUENCE: 19
tgggaaacat acttctttat atgcccatat ggacctgcta agctatggaa tgtaaagaag    60
tatgtatctc a                                                         71

<210> SEQ ID NO 20
<211> LENGTH: 85
<212> TYPE: DNA
<213> ORGANISM: Homo sapiens

<400> SEQUENCE: 20
acctactcag agtacatact tctttatgta cccatatgaa catacaatgc tatggaatgt    60
aaagaagtat gtattttttgg taggc                                         85

<210> SEQ ID NO 21
<211> LENGTH: 108
<212> TYPE: DNA
<213> ORGANISM: Homo sapiens

<400> SEQUENCE: 21
tggatgttgg cctagttctg tgtggaagac tagtgatttt gttgttttta gataactaaa    60
tcgacaacaa atcacagtct gccatatggc acaggccatg cctctaca               108

<210> SEQ ID NO 22
<211> LENGTH: 110
<212> TYPE: DNA
<213> ORGANISM: Homo sapiens

<400> SEQUENCE: 22
ttggatgttg gcctagttct gtgtggaaga ctagtgattt tgttgttttt agataactaa    60
atcgacaaca aatcacagtc tgccatatgg cacaggccat gcctctacag              110

<210> SEQ ID NO 23
<211> LENGTH: 110
<212> TYPE: DNA
<213> ORGANISM: Homo sapiens

<400> SEQUENCE: 23
ctggatacag agtggaccgg ctggccccat ctggaagact agtgattttg ttgttgtctt    60
actgcgctca acaacaaatc ccagtctacc taatggtgcc agccatcgca              110

<210> SEQ ID NO 24
<211> LENGTH: 110
<212> TYPE: DNA
<213> ORGANISM: Homo sapiens

<400> SEQUENCE: 24
ctggatacag agtggaccgg ctggccccat ctggaagact agtgattttg ttgttgtctt    60
actgcgctca acaacaaatc ccagtctacc taatggtgcc agccatcgca              110

<210> SEQ ID NO 25
<211> LENGTH: 110
<212> TYPE: DNA
<213> ORGANISM: Homo sapiens

<400> SEQUENCE: 25
agattagagt ggctgtggtc tagtgctgtg tggaagacta gtgattttgt tgttctgatg    60
tactacgaca acaagtcaca gccggcctca tagcgcagac tcccttcgac              110

<210> SEQ ID NO 26
<211> LENGTH: 110
<212> TYPE: DNA
<213> ORGANISM: Homo sapiens

<400> SEQUENCE: 26
agattagagt ggctgtggtc tagtgctgtg tggaagacta gtgattttgt tgttctgatg     60
tactacgaca acaagtcaca gccggcctca tagcgcagac tcccttcgac               110

<210> SEQ ID NO 27
<211> LENGTH: 89
<212> TYPE: DNA
<213> ORGANISM: Homo sapiens

<400> SEQUENCE: 27
cggggttggt tgttatcttt ggttatctag ctgtatgagt ggtgtggagt cttcataaag     60
ctagataacc gaaagtaaaa ataacccca                                      89

<210> SEQ ID NO 28
<211> LENGTH: 87
<212> TYPE: DNA
<213> ORGANISM: Homo sapiens

<400> SEQUENCE: 28
ggaagcgagt tgttatcttt ggttatctag ctgtatgagt gtattggtct tcataaagct     60
agataaccga agtaaaaac tccttca                                         87

<210> SEQ ID NO 29
<211> LENGTH: 90
<212> TYPE: DNA
<213> ORGANISM: Homo sapiens

<400> SEQUENCE: 29
ggaggcccgt ttctctcttt ggttatctag ctgtatgagt gccacagagc cgtcataaag     60
ctagataacc gaaagtagaa atgattctca                                     90

<210> SEQ ID NO 30
<211> LENGTH: 110
<212> TYPE: DNA
<213> ORGANISM: Homo sapiens

<400> SEQUENCE: 30
gatctgtctg tcttctgtat ataccctgta gatccgaatt tgtgtaagga attttgtggt     60
cacaaattcg tatctagggg aatatgtagt tgacataaac actccgctct               110

<210> SEQ ID NO 31
<211> LENGTH: 110
<212> TYPE: DNA
<213> ORGANISM: Homo sapiens

<400> SEQUENCE: 31
ccagaggttg taacgttgtc tatatatacc ctgtagaacc gaatttgtgt ggtatccgta     60
tagtcacaga ttcgattcta ggggaatata tggtcgatgc aaaaacttca               110

<210> SEQ ID NO 32
<211> LENGTH: 108
<212> TYPE: DNA
<213> ORGANISM: Homo sapiens

<400> SEQUENCE: 32

```
gcgcgaatgt gtgtttaaaa aaaataaaac cttggagtaa agtagcagca cataatggtt    60
tgtggatttt gaaaaggtgc aggccatatt gtgctgcctc aaaaatac                108
```

<210> SEQ ID NO 33
<211> LENGTH: 83
<212> TYPE: DNA
<213> ORGANISM: Homo sapiens

<400> SEQUENCE: 33

```
ccttggagta agtagcagc acataatggt ttgtggattt tgaaaaggtg caggccatat    60
tgtgctgcct caaaaataca agg                                           83
```

<210> SEQ ID NO 34
<211> LENGTH: 64
<212> TYPE: DNA
<213> ORGANISM: Homo sapiens

<400> SEQUENCE: 34

```
ctgtagcagc acatcatggt ttacatgcta cagtcaagat gcgaatcatt atttgctgct    60
ctag                                                                 64
```

<210> SEQ ID NO 35
<211> LENGTH: 98
<212> TYPE: DNA
<213> ORGANISM: Homo sapiens

<400> SEQUENCE: 35

```
ttgaggcctt aaagtactgt agcagcacat catggtttac atgctacagt caagatgcga    60
atcattattt gctgctctag aaatttaagg aaattcat                            98
```

<210> SEQ ID NO 36
<211> LENGTH: 89
<212> TYPE: DNA
<213> ORGANISM: Homo sapiens

<400> SEQUENCE: 36

```
gtcagcagtg ccttagcagc acgtaaatat tggcgttaag attctaaaat tatctccagt    60
attaactgtg ctgctgaagt aaggttgac                                      89
```

<210> SEQ ID NO 37
<211> LENGTH: 81
<212> TYPE: DNA
<213> ORGANISM: Homo sapiens

<400> SEQUENCE: 37

```
gttccactct agcagcacgt aaatattggc gtagtgaaat atatattaaa caccaatatt    60
actgtgctgc tttagtgtga c                                              81
```

<210> SEQ ID NO 38
<211> LENGTH: 81
<212> TYPE: DNA
<213> ORGANISM: Homo sapiens

<400> SEQUENCE: 38

```
gcagtgcctt agcagcacgt aaatattggc gttaagattc taaaattatc tccagtatta    60
actgtgctgc tgaagtaagg t                                              81
```

<210> SEQ ID NO 39
<211> LENGTH: 84
<212> TYPE: DNA

-continued

<213> ORGANISM: Homo sapiens

<400> SEQUENCE: 39
gtcagaataa tgtcaaagtg cttacagtgc aggtagtgat atgtgcatct actgcagtga     60
aggcacttgt agcattatgg tgac                                            84

<210> SEQ ID NO 40
<211> LENGTH: 71
<212> TYPE: DNA
<213> ORGANISM: Homo sapiens

<400> SEQUENCE: 40
tgttctaagg tgcatctagt gcagatagtg aagtagatta gcatctactg ccctaagtgc     60
tccttctggc a                                                          71

<210> SEQ ID NO 41
<211> LENGTH: 81
<212> TYPE: DNA
<213> ORGANISM: Homo sapiens

<400> SEQUENCE: 41
tttttgttct aaggtgcatc tagtgcagat agtgaagtag attagcatct actgccctaa     60
gtgctccttc tggcataaga a                                               81

<210> SEQ ID NO 42
<211> LENGTH: 82
<212> TYPE: DNA
<213> ORGANISM: Homo sapiens

<400> SEQUENCE: 42
gcagtcctct gttagttttg catagttgca ctacaagaag aatgtagttg tgcaaatcta     60
tgcaaaactg atggtggcct gc                                              82

<210> SEQ ID NO 43
<211> LENGTH: 80
<212> TYPE: DNA
<213> ORGANISM: Homo sapiens

<400> SEQUENCE: 43
cagtcctctg ttagttttgc atagttgcac tacaagaaga atgtagttgt gcaaatctat     60
gcaaaactga tggtggcctg                                                 80

<210> SEQ ID NO 44
<211> LENGTH: 87
<212> TYPE: DNA
<213> ORGANISM: Homo sapiens

<400> SEQUENCE: 44
cactgttcta tggttagttt tgcaggtttg catccagctg tgtgatattc tgctgtgcaa     60
atccatgcaa aactgactgt ggtagtg                                         87

<210> SEQ ID NO 45
<211> LENGTH: 96
<212> TYPE: DNA
<213> ORGANISM: Homo sapiens

<400> SEQUENCE: 45
acattgctac ttacaattag ttttgcaggt ttgcatttca gcgtatatat gtatatgtgg     60
ctgtgcaaat ccatgcaaaa ctgattgtga taatgt                               96

```
<210> SEQ ID NO 46
<211> LENGTH: 80
<212> TYPE: DNA
<213> ORGANISM: Homo sapiens

<400> SEQUENCE: 46
ttctatggtt agttttgcag gtttgcatcc agctgtgtga tattctgctg tgcaaatcca      60
tgcaaaactg actgtggtag                                                 80

<210> SEQ ID NO 47
<211> LENGTH: 81
<212> TYPE: DNA
<213> ORGANISM: Homo sapiens

<400> SEQUENCE: 47
ttacaattag ttttgcaggt ttgcatttca gcgtatatat gtatatgtgg ctgtgcaaat      60
ccatgcaaaa ctgattgtga t                                               81

<210> SEQ ID NO 48
<211> LENGTH: 71
<212> TYPE: DNA
<213> ORGANISM: Homo sapiens

<400> SEQUENCE: 48
gtagcactaa agtgcttata gtgcaggtag tgtttagtta tctactgcat tatgagcact      60
taaagtactg c                                                          71

<210> SEQ ID NO 49
<211> LENGTH: 72
<212> TYPE: DNA
<213> ORGANISM: Homo sapiens

<400> SEQUENCE: 49
tgtcgggtag cttatcagac tgatgttgac tgttgaatct catggcaaca ccagtcgatg      60
ggctgtctga ca                                                         72

<210> SEQ ID NO 50
<211> LENGTH: 81
<212> TYPE: DNA
<213> ORGANISM: Homo sapiens

<400> SEQUENCE: 50
accttgtcgg gtagcttatc agactgatgt tgactgttga atctcatggc aacaccagtc      60
gatgggctgt ctgacatttt g                                               81

<210> SEQ ID NO 51
<211> LENGTH: 85
<212> TYPE: DNA
<213> ORGANISM: Homo sapiens

<400> SEQUENCE: 51
ggctgagccg cagtagttct tcagtggcaa gctttatgtc ctgacccagc taaagctgcc      60
agttgaagaa ctgttgccct ctgcc                                           85

<210> SEQ ID NO 52
<211> LENGTH: 73
<212> TYPE: DNA
<213> ORGANISM: Homo sapiens

<400> SEQUENCE: 52
```

```
ggccggctgg ggttcctggg gatgggattt gcttcctgtc acaaatcaca ttgccaggga    60
tttccaaccg acc                                                      73

<210> SEQ ID NO 53
<211> LENGTH: 97
<212> TYPE: DNA
<213> ORGANISM: Homo sapiens

<400> SEQUENCE: 53
ctcaggtgct ctggctgctt gggttcctgg catgctgatt tgtgacttaa gattaaaatc    60
acattgccag ggattaccac gcaaccacga ccttggc                             97

<210> SEQ ID NO 54
<211> LENGTH: 81
<212> TYPE: DNA
<213> ORGANISM: Homo sapiens

<400> SEQUENCE: 54
ccacggccgg ctggggttcc tggggatggg atttgcttcc tgtcacaaat cacattgcca    60
gggatttcca accgaccctg a                                              81

<210> SEQ ID NO 55
<211> LENGTH: 68
<212> TYPE: DNA
<213> ORGANISM: Homo sapiens

<400> SEQUENCE: 55
ctccggtgcc tactgagctg atatcagttc tcattttaca cactggctca gttcagcagg    60
aacaggag                                                             68

<210> SEQ ID NO 56
<211> LENGTH: 73
<212> TYPE: DNA
<213> ORGANISM: Homo sapiens

<400> SEQUENCE: 56
ctctgcctcc cgtgcctact gagctgaaac acagttggtt tgtgtacact ggctcagttc    60
agcaggaaca ggg                                                       73

<210> SEQ ID NO 57
<211> LENGTH: 81
<212> TYPE: DNA
<213> ORGANISM: Homo sapiens

<400> SEQUENCE: 57
ccctgggctc tgcctcccgt gcctactgag ctgaaacaca gttggtttgt gtacactggc    60
tcagttcagc aggaacaggg g                                              81

<210> SEQ ID NO 58
<211> LENGTH: 71
<212> TYPE: DNA
<213> ORGANISM: Homo sapiens

<400> SEQUENCE: 58
ccctccggtg cctactgagc tgatatcagt tctcatttta cactggct cagttcagca     60 ggaacagcat c                                                         71

<210> SEQ ID NO 59
<211> LENGTH: 84
<212> TYPE: DNA
```

<213> ORGANISM: Homo sapiens

<400> SEQUENCE: 59
ggccagtgtt gagaggcgga gacttgggca attgctggac gctgccctgg gcattgcact    60
tgtctcggtc tgacagtgcc ggcc    84

<210> SEQ ID NO 60
<211> LENGTH: 86
<212> TYPE: DNA
<213> ORGANISM: Homo sapiens

<400> SEQUENCE: 60
aggccgtggc ctcgttcaag taatccagga taggctgtgc aggtcccaat ggcctatctt    60
ggttacttgc acggggacgc gggcct    86

<210> SEQ ID NO 61
<211> LENGTH: 77
<212> TYPE: DNA
<213> ORGANISM: Homo sapiens

<400> SEQUENCE: 61
ccgggaccca gttcaagtaa ttcaggatag gttgtgtgct gtccagcctg ttctccatta    60
cttggctcgg ggaccgg    77

<210> SEQ ID NO 62
<211> LENGTH: 78
<212> TYPE: DNA
<213> ORGANISM: Homo sapiens

<400> SEQUENCE: 62
ctgaggagca gggcttagct gcttgtgagc agggtccaca ccaagtcgtg ttcacagtgg    60
ctaagttccg cccccccag    78

<210> SEQ ID NO 63
<211> LENGTH: 73
<212> TYPE: DNA
<213> ORGANISM: Homo sapiens

<400> SEQUENCE: 63
aggtgcagag cttagctgat tggtgaacag tgattggttt ccgctttgtt cacagtggct    60
aagttctgca cct    73

<210> SEQ ID NO 64
<211> LENGTH: 97
<212> TYPE: DNA
<213> ORGANISM: Homo sapiens

<400> SEQUENCE: 64
acctctctaa caaggtgcag agcttagctg attggtgaac agtgattggt ttccgctttg    60
ttcacagtgg ctaagttctg cacctgaaga gaaggtg    97

<210> SEQ ID NO 65
<211> LENGTH: 80
<212> TYPE: DNA
<213> ORGANISM: Homo sapiens

<400> SEQUENCE: 65
cctgaggagc agggcttagc tgcttgtgag cagggtccac accaagtcgt gttcacagtg    60
gctaagttcc gccccccagg    80

```
<210> SEQ ID NO 66
<211> LENGTH: 86
<212> TYPE: DNA
<213> ORGANISM: Homo sapiens

<400> SEQUENCE: 66
ggtccttgcc ctcaaggagc tcacagtcta ttgagttacc tttctgactt tcccactaga    60
ttgtgagctc ctggagggca ggcact                                          86

<210> SEQ ID NO 67
<211> LENGTH: 108
<212> TYPE: DNA
<213> ORGANISM: Homo sapiens

<400> SEQUENCE: 67
ccttctgtga ccccttagag gatgactgat ttcttttggt gttcagagtc aatataattt    60
tctagcacca tctgaaatcg gttataatga ttggggaaga gcaccatg                 108

<210> SEQ ID NO 68
<211> LENGTH: 64
<212> TYPE: DNA
<213> ORGANISM: Homo sapiens

<400> SEQUENCE: 68
atgactgatt tcttttggtg ttcagagtca atataatttt ctagcaccat ctgaaatcgg    60
ttat                                                                  64

<210> SEQ ID NO 69
<211> LENGTH: 110
<212> TYPE: DNA
<213> ORGANISM: Homo sapiens

<400> SEQUENCE: 69
accactggcc catctcttac acaggctgac cgatttctcc tggtgttcag agtctgtttt    60
tgtctagcac catttgaaat cggttatgat gtaggggaa aagcagcagc                110

<210> SEQ ID NO 70
<211> LENGTH: 71
<212> TYPE: DNA
<213> ORGANISM: Homo sapiens

<400> SEQUENCE: 70
gcgactgtaa acatcctcga ctggaagctg tgaagccaca gatgggcttt cagtcggatg    60
tttgcagctg c                                                          71

<210> SEQ ID NO 71
<211> LENGTH: 60
<212> TYPE: DNA
<213> ORGANISM: Homo sapiens

<400> SEQUENCE: 71
atgtaaacat cctacactca gctgtaatac atggattggc tgggaggtgg atgtttacgt    60

<210> SEQ ID NO 72
<211> LENGTH: 88
<212> TYPE: DNA
<213> ORGANISM: Homo sapiens

<400> SEQUENCE: 72
accaagtttc agttcatgta aacatcctac actcagctgt aatacatgga ttggctggga    60
```

```
ggtggatgtt tacttcagct gacttgga                                              88

<210> SEQ ID NO 73
<211> LENGTH: 72
<212> TYPE: DNA
<213> ORGANISM: Homo sapiens

<400> SEQUENCE: 73
agatactgta aacatcctac actctcagct gtggaaagta agaaagctgg gagaaggctg          60
tttactcttt ct                                                               72

<210> SEQ ID NO 74
<211> LENGTH: 70
<212> TYPE: DNA
<213> ORGANISM: Homo sapiens

<400> SEQUENCE: 74
gttgttgtaa acatccccga ctggaagctg taagacacag ctaagctttc agtcagatgt          60
ttgctgctac                                                                  70

<210> SEQ ID NO 75
<211> LENGTH: 71
<212> TYPE: DNA
<213> ORGANISM: Homo sapiens

<400> SEQUENCE: 75
ggagaggagg caagatgctg gcatagctgt tgaactggga acctgctatg ccaacatatt          60
gccatctttc c                                                                71

<210> SEQ ID NO 76
<211> LENGTH: 70
<212> TYPE: DNA
<213> ORGANISM: Homo sapiens

<400> SEQUENCE: 76
ggagatattg cacattacta agttgcatgt tgtcacggcc tcaatgcaat ttagtgtgtg          60
tgatattttc                                                                  70

<210> SEQ ID NO 77
<211> LENGTH: 110
<212> TYPE: DNA
<213> ORGANISM: Homo sapiens

<400> SEQUENCE: 77
gggggccgag agaggcgggc ggccccgcgg tgcattgctg ttgcattgca cgtgtgtgag          60
gcgggtgcag tgcctcggca gtgcagcccg gagccggccc ctggcaccac                    110

<210> SEQ ID NO 78
<211> LENGTH: 69
<212> TYPE: DNA
<213> ORGANISM: Homo sapiens

<400> SEQUENCE: 78
ctgtggtgca ttgtagttgc attgcatgtt ctggtggtac ccatgcaatg tttccacagt          60
gcatcacag                                                                   69

<210> SEQ ID NO 79
<211> LENGTH: 110
<212> TYPE: DNA
<213> ORGANISM: Homo sapiens
```

-continued

<400> SEQUENCE: 79
ggccagctgt gagtgtttct ttggcagtgt cttagctggt tgttgtgagc aatagtaagg      60
aagcaatcag caagtatact gccctagaag tgctgcacgt tgtggggccc                110

<210> SEQ ID NO 80
<211> LENGTH: 82
<212> TYPE: DNA
<213> ORGANISM: Homo sapiens

<400> SEQUENCE: 80
tcagaataat gtcaaagtgc ttacagtgca ggtagtgata tgtgcatcta ctgcagtgaa      60
ggcacttgta gcattatggt ga                                               82

<210> SEQ ID NO 81
<211> LENGTH: 78
<212> TYPE: DNA
<213> ORGANISM: Homo sapiens

<400> SEQUENCE: 81
ctttctacac aggttgggat cggttgcaat gctgtgtttc tgtatggtat tgcacttgtc      60
ccggcctgtt gagtttgg                                                    78

<210> SEQ ID NO 82
<211> LENGTH: 75
<212> TYPE: DNA
<213> ORGANISM: Homo sapiens

<400> SEQUENCE: 82
tcatccctgg gtggggattt gttgcattac ttgtgttcta tataaagtat tgcacttgtc      60
ccggcctgtg gaaga                                                       75

<210> SEQ ID NO 83
<211> LENGTH: 80
<212> TYPE: DNA
<213> ORGANISM: Homo sapiens

<400> SEQUENCE: 83
ctgggggctc caaagtgctg ttcgtgcagg tagtgtgatt acccaaccta ctgctgagct      60
agcacttccc gagcccccgg                                                  80

<210> SEQ ID NO 84
<211> LENGTH: 80
<212> TYPE: DNA
<213> ORGANISM: Homo sapiens

<400> SEQUENCE: 84 ctggggctc caaagtgctg ttcgtgcagg tagtgtgatt acccaaccta ctgctgagct       60
agcacttccc gagcccccgg                                                  80

<210> SEQ ID NO 85
<211> LENGTH: 81
<212> TYPE: DNA
<213> ORGANISM: Homo sapiens

<400> SEQUENCE: 85
aacacagtgg gcactcaata aatgtctgtt gaattgaaat gcgttacatt caacgggtat      60
ttattgagca cccactctgt g                                                81

<210> SEQ ID NO 86

```
<211> LENGTH: 78
<212> TYPE: DNA
<213> ORGANISM: Homo sapiens

<400> SEQUENCE: 86
tggccgattt tggcactagc acattttgc ttgtgtctct ccgctctgag caatcatgtg      60
cagtgccaat atgggaaa                                                   78

<210> SEQ ID NO 87
<211> LENGTH: 80
<212> TYPE: DNA
<213> ORGANISM: Homo sapiens

<400> SEQUENCE: 87
gtgaggtagt aagttgtatt gttgtggggt agggatatta ggccccaatt agaagataac      60
tatacaactt actactttcc                                                 80

<210> SEQ ID NO 88
<211> LENGTH: 70
<212> TYPE: DNA
<213> ORGANISM: Homo sapiens

<400> SEQUENCE: 88
ggcacccacc cgtagaaccg accttgcggg gccttcgccg cacacaagct cgtgtctgtg      60
ggtccgtgtc                                                            70

<210> SEQ ID NO 89
<211> LENGTH: 81
<212> TYPE: DNA
<213> ORGANISM: Homo sapiens

<400> SEQUENCE: 89
cccattggca taaacccgta gatccgatct tgtggtgaag tggaccgcac aagctcgctt      60
ctatgggtct gtgtcagtgt g                                               81

<210> SEQ ID NO 90
<211> LENGTH: 108
<212> TYPE: DNA
<213> ORGANISM: Homo sapiens

<400> SEQUENCE: 90
aagagagaag atattgaggc ctgttgccac aaacccgtag atccgaactt gtggtattag      60
tccgcacaag cttgtatcta taggtatgtg tctgttaggc aatctcac                 108

<210> SEQ ID NO 91
<211> LENGTH: 80
<212> TYPE: DNA
<213> ORGANISM: Homo sapiens

<400> SEQUENCE: 91
cctgttgcca caaacccgta gatccgaact tgtggtatta gtccgcacaa gcttgtatct      60
ataggtatgt gtctgttagg                                                 80

<210> SEQ ID NO 92
<211> LENGTH: 110
<212> TYPE: DNA
<213> ORGANISM: Homo sapiens

<400> SEQUENCE: 92
aggctgccct ggctcagtta tcacagtgct gatgctgtct attctaaagg tacagtactg      60
```

-continued

```
tgataactga aggatggcag ccatcttacc ttccatcaga ggagcctcac           110
```

<210> SEQ ID NO 93
<211> LENGTH: 57
<212> TYPE: DNA
<213> ORGANISM: Homo sapiens

<400> SEQUENCE: 93

```
tcagttatca cagtgctgat gctgtccatt ctaaaggtac agtactgtga taactga    57
```

<210> SEQ ID NO 94
<211> LENGTH: 75
<212> TYPE: DNA
<213> ORGANISM: Homo sapiens

<400> SEQUENCE: 94

```
tgccctggct cagttatcac agtgctgatg ctgtctattc taaaggtaca gtactgtgat 60
aactgaagga tggca                                                  75
```

<210> SEQ ID NO 95
<211> LENGTH: 75
<212> TYPE: DNA
<213> ORGANISM: Homo sapiens

<400> SEQUENCE: 95

```
tgtcctttt cggttatcat ggtaccgatg ctgtatatct gaaaggtaca gtactgtgat  60
aactgaagaa tggtg                                                  75
```

<210> SEQ ID NO 96
<211> LENGTH: 81
<212> TYPE: DNA
<213> ORGANISM: Homo sapiens

<400> SEQUENCE: 96

```
cttctggaag ctggtttcac atggtggctt agattttcc atctttgtat ctagcaccat  60
ttgaaatcag tgttttagga g                                           81
```

<210> SEQ ID NO 97
<211> LENGTH: 81
<212> TYPE: DNA
<213> ORGANISM: Homo sapiens

<400> SEQUENCE: 97

```
cttcaggaag ctggtttcat atggtggttt agatttaaat agtgattgtc tagcaccatt 60
tgaaatcagt gttcttgggg g                                           81
```

<210> SEQ ID NO 98
<211> LENGTH: 81
<212> TYPE: DNA
<213> ORGANISM: Homo sapiens

<400> SEQUENCE: 98

```
cttcaggaag ctggtttcat atggtggttt agatttaaat agtgattgtc tagcaccatt 60
tgaaatcagt gttcttgggg g                                           81
```

<210> SEQ ID NO 99
<211> LENGTH: 78
<212> TYPE: DNA
<213> ORGANISM: Homo sapiens

<400> SEQUENCE: 99

```
ttgtgctttc agcttctttta cagtgctgcc ttgtagcatt caggtcaagc aacattgtac    60
agggctatga aagaacca                                                   78

<210> SEQ ID NO 100
<211> LENGTH: 78
<212> TYPE: DNA
<213> ORGANISM: Homo sapiens

<400> SEQUENCE: 100
ttgtgctttc agcttctttta cagtgctgcc ttgtagcatt caggtcaagc aacattgtac    60
agggctatga aagaacca                                                   78

<210> SEQ ID NO 101
<211> LENGTH: 78
<212> TYPE: DNA
<213> ORGANISM: Homo sapiens

<400> SEQUENCE: 101
tactgccctc ggcttctttta cagtgctgcc ttgttgcata tggatcaagc agcattgtac    60
agggctatga aggcattg                                                   78

<210> SEQ ID NO 102
<211> LENGTH: 78
<212> TYPE: DNA
<213> ORGANISM: Homo sapiens

<400> SEQUENCE: 102
aaatgtcaga cagcccatcg actggtgttg ccatgagatt caacagtcaa catcagtctg    60
ataagctacc cgacaagg                                                   78

<210> SEQ ID NO 103
<211> LENGTH: 81
<212> TYPE: DNA
<213> ORGANISM: Homo sapiens

<400> SEQUENCE: 103
tgtgcatcgt ggtcaaatgc tcagactcct gtggtggctg ctcatgcacc acggatgttt    60
gagcatgtgc tacggtgtct a                                               81

<210> SEQ ID NO 104
<211> LENGTH: 81
<212> TYPE: DNA
<213> ORGANISM: Homo sapiens

<400> SEQUENCE: 104
tgtgcatcgt ggtcaaatgc tcagactcct gtggtggctg ctcatgcacc acggatgttt    60
gagcatgtgc tacggtgtct a                                               81

<210> SEQ ID NO 105
<211> LENGTH: 81
<212> TYPE: DNA
<213> ORGANISM: Homo sapiens

<400> SEQUENCE: 105
ccttggccat gtaaaagtgc ttacagtgca ggtagctttt tgagatctac tgcaatgtaa    60
gcacttctta cattaccatg g                                               81

<210> SEQ ID NO 106
<211> LENGTH: 81
<212> TYPE: DNA
```

```
<213> ORGANISM: Homo sapiens

<400> SEQUENCE: 106
ctctctgctt tcagcttctt tacagtgttg ccttgtggca tggagttcaa gcagcattgt      60
acagggctat caaagcacag a                                                81

<210> SEQ ID NO 107
<211> LENGTH: 85
<212> TYPE: DNA
<213> ORGANISM: Homo sapiens

<400> SEQUENCE: 107
ccttagcaga gctgtggagt gtgacaatgg tgtttgtgtc taaactatca aacgccatta      60
tcacactaaa tagctactgc taggc                                            85

<210> SEQ ID NO 108
<211> LENGTH: 66
<212> TYPE: DNA
<213> ORGANISM: Homo sapiens

<400> SEQUENCE: 108
agctgtggag tgtgacaatg gtgtttgtgt ccaaactatc aaacgccatt atcacactaa      60
atagct                                                                 66

<210> SEQ ID NO 109
<211> LENGTH: 61
<212> TYPE: DNA
<213> ORGANISM: Homo sapiens

<400> SEQUENCE: 109
acattattac ttttggtacg cgctgtgaca cttcaaactc gtaccgtgag taataatgcg      60
c                                                                      61

<210> SEQ ID NO 110
<211> LENGTH: 100
<212> TYPE: DNA
<213> ORGANISM: Homo sapiens

<400> SEQUENCE: 110
tccttcctca ggagaaaggc ctctctctcc gtgttcacag cggaccttga tttaaatgtc      60
catacaatta aggcacgcgg tgaatgccaa gaatggggct                           100

<210> SEQ ID NO 111
<211> LENGTH: 85
<212> TYPE: DNA
<213> ORGANISM: Homo sapiens

<400> SEQUENCE: 111
aggcctctct ctccgtgttc acagcggacc ttgatttaaa tgtccataca attaaggcac      60
gcggtgaatg ccaagaatgg ggctg                                            85

<210> SEQ ID NO 112
<211> LENGTH: 110
<212> TYPE: DNA
<213> ORGANISM: Homo sapiens

<400> SEQUENCE: 112
atcaagatta gaggctctgc tctccgtgtt cacagcggac cttgatttaa tgtcatacaa      60
ttaaggcacg cggtgaatgc caagagcgga gcctacggct gcacttgaag              110
```

<210> SEQ ID NO 113
<211> LENGTH: 110
<212> TYPE: DNA
<213> ORGANISM: Homo sapiens

<400> SEQUENCE: 113
cccgccccag ccctgagggc ccctctgcgt gttcacagcg gaccttgatt taatgtctat    60
acaattaagg cacgcggtga atgccaagag aggcgcctcc gccgctcctt              110

<210> SEQ ID NO 114
<211> LENGTH: 87
<212> TYPE: DNA
<213> ORGANISM: Homo sapiens

<400> SEQUENCE: 114
tgagggcccc tctgcgtgtt cacagcggac cttgatttaa tgtctataca attaaggcac    60
gcggtgaatg ccaagagagg cgcctcc                                        87

<210> SEQ ID NO 115
<211> LENGTH: 68
<212> TYPE: DNA
<213> ORGANISM: Homo sapiens

<400> SEQUENCE: 115
ctctgcgtgt tcacagcgga ccttgattta atgtctatac aattaaggca cgcggtgaat    60
gccaagag                                                             68

<210> SEQ ID NO 116
<211> LENGTH: 67
<212> TYPE: DNA
<213> ORGANISM: Homo sapiens

<400> SEQUENCE: 116
ctctccgtgt tcacagcgga ccttgattta atgtcataca attaaggcac gcggtgaatg    60
ccaagag                                                              67

<210> SEQ ID NO 117
<211> LENGTH: 86
<212> TYPE: DNA
<213> ORGANISM: Homo sapiens

<400> SEQUENCE: 117
tgccagtctc taggtccctg agacccttta acctgtgagg catccaggg tcacaggtga    60 ggttcttggg agcctggcgt ctggcc                                         86

<210> SEQ ID NO 118
<211> LENGTH: 65
<212> TYPE: DNA
<213> ORGANISM: Homo sapiens

<400> SEQUENCE: 118
ggtccctgag acccttta ac ctgtgaggac atccagggtc acaggtgagg ttcttgggag    60
cctgg                                                                65

<210> SEQ ID NO 119
<211> LENGTH: 108
<212> TYPE: DNA
<213> ORGANISM: Homo sapiens

<400> SEQUENCE: 119

```
acattgttgc gctcctctca gtccctgaga ccctaacttg tgatgtttac cgtttaaatc    60
cacgggttag gctcttggga gctgcgagtc gtgcttttgc atcctgga                108
```

<210> SEQ ID NO 120
<211> LENGTH: 88
<212> TYPE: DNA
<213> ORGANISM: Homo sapiens

<400> SEQUENCE: 120

```
tgcgctcctc tcagtccctg agaccctaac ttgtgatgtt taccgtttaa atccacgggt    60
taggctcttg ggagctgcga gtcgtgct                                       88
```

<210> SEQ ID NO 121
<211> LENGTH: 89
<212> TYPE: DNA
<213> ORGANISM: Homo sapiens

<400> SEQUENCE: 121

```
accagacttt tcctagtccc tgagaccctt acttgtgagg tattttagta acatcacaag    60
tcaggctctt gggacctagg cggaggggga                                     89
```

<210> SEQ ID NO 122
<211> LENGTH: 70
<212> TYPE: DNA
<213> ORGANISM: Homo sapiens

<400> SEQUENCE: 122

```
cctagtccct gagaccctaa cttgtgaggt attttagtaa catcacaagt caggctcttg    60
ggacctaggc                                                           70
```

<210> SEQ ID NO 123
<211> LENGTH: 85
<212> TYPE: DNA
<213> ORGANISM: Homo sapiens

<400> SEQUENCE: 123

```
cgctggcgac gggacattat tactttggt acgcgctgtg acacttcaaa ctcgtaccgt     60
gagtaataat gcgccgtcca cggca                                          85
```

<210> SEQ ID NO 124
<211> LENGTH: 61
<212> TYPE: DNA
<213> ORGANISM: Homo sapiens

<400> SEQUENCE: 124

```
acattattac ttttggtacg cgctgtgaca cttcaaactc gtaccgtgag taataatgcg    60
c                                                                    61
```

<210> SEQ ID NO 125
<211> LENGTH: 97
<212> TYPE: DNA
<213> ORGANISM: Homo sapiens

<400> SEQUENCE: 125

```
tgtgatcact gtctccagcc tgctgaagct cagagggctc tgattcagaa agatcatcgg    60
atccgtctga gcttggctgg tcggaagtct catcatc                             97
```

<210> SEQ ID NO 126
<211> LENGTH: 70
<212> TYPE: DNA

-continued

<213> ORGANISM: Homo sapiens

<400> SEQUENCE: 126
ccagcctgct gaagctcaga gggctctgat tcagaaagat catcggatcc gtctgagctt    60
ggctggtcgg    70

<210> SEQ ID NO 127
<211> LENGTH: 82
<212> TYPE: DNA
<213> ORGANISM: Homo sapiens

<400> SEQUENCE: 127
tgagctgttg gattcggggc cgtagcactg tctgagaggt ttacatttct cacagtgaac    60
cggtctcttt ttcagctgct tc    82

<210> SEQ ID NO 128
<211> LENGTH: 110
<212> TYPE: DNA
<213> ORGANISM: Homo sapiens

<400> SEQUENCE: 128
gcccggcagc cactgtgcag tgggaagggg ggccgataca ctgtacgaga gtgagtagca    60
ggtctcacag tgaaccggtc tctttcccta ctgtgtcaca ctcctaatgg    110

<210> SEQ ID NO 129
<211> LENGTH: 70
<212> TYPE: DNA
<213> ORGANISM: Homo sapiens

<400> SEQUENCE: 129
gttggattcg gggccgtagc actgtctgag aggtttacat ttctcacagt gaaccggtct    60
ctttttcagc    70

<210> SEQ ID NO 130
<211> LENGTH: 74
<212> TYPE: DNA
<213> ORGANISM: Homo sapiens

<400> SEQUENCE: 130
tggatctttt tgcggtctgg gcttgctgtt cctctcaaca gtagtcagga agcccttacc    60
ccaaaaagta tcta    74

<210> SEQ ID NO 131
<211> LENGTH: 89
<212> TYPE: DNA
<213> ORGANISM: Homo sapiens

<400> SEQUENCE: 131
tgctgctggc cagagctctt ttcacattgt gctactgtct gcacctgtca ctagcagtgc    60
aatgttaaaa gggcattggc cgtgtagtg    89

<210> SEQ ID NO 132
<211> LENGTH: 110
<212> TYPE: DNA
<213> ORGANISM: Homo sapiens

<400> SEQUENCE: 132
gccaggaggc ggggttggtt gttatctttg gttatctagc tgtatgagtg gtgtggagtc    60
ttcataaagc tagataaccg aaagtaaaaa taaccccata cactgcgcag    110

<210> SEQ ID NO 133
<211> LENGTH: 110
<212> TYPE: DNA
<213> ORGANISM: Homo sapiens

<400> SEQUENCE: 133
cacggcgcgg cagcggcact ggctaaggga ggcccgtttc tctctttggt tatctagctg        60
tatgagtgcc acagagccgt cataaagcta gataaccgaa agtagaaatg                  110

<210> SEQ ID NO 134
<211> LENGTH: 72
<212> TYPE: DNA
<213> ORGANISM: Homo sapiens

<400> SEQUENCE: 134
gttgttatct ttggttatct agctgtatga gtgtattggt cttcataaag ctagataacc        60
gaaagtaaaa ac                                                            72

<210> SEQ ID NO 135
<211> LENGTH: 101
<212> TYPE: DNA
<213> ORGANISM: Homo sapiens

<400> SEQUENCE: 135
ccgcccccgc gtctccaggg caaccgtggc tttcgattgt tactgtggga actggaggta        60
acagtctaca gccatggtcg ccccgcagca cgcccacgcg c                           101

<210> SEQ ID NO 136
<211> LENGTH: 66
<212> TYPE: DNA
<213> ORGANISM: Homo sapiens

<400> SEQUENCE: 136
gggcaaccgt ggctttcgat tgttactgtg ggaactggag gtaacagtct acagccatgg        60
tcgccc                                                                   66

<210> SEQ ID NO 137
<211> LENGTH: 88
<212> TYPE: DNA
<213> ORGANISM: Homo sapiens

<400> SEQUENCE: 137
acaatgcttt gctagagctg gtaaaatgga accaaatcgc ctcttcaatg gatttggtcc        60
ccttcaacca gctgtagcta tgcattga                                           88

<210> SEQ ID NO 138
<211> LENGTH: 102
<212> TYPE: DNA
<213> ORGANISM: Homo sapiens

<400> SEQUENCE: 138
gggagccaaa tgctttgcta gagctggtaa aatggaacca atcgactgt ccaatggatt         60 tggtcccctt caaccagctg tagctgtgca ttgatggcgc cg                          102

<210> SEQ ID NO 139
<211> LENGTH: 68
<212> TYPE: DNA
<213> ORGANISM: Homo sapiens

<400> SEQUENCE: 139

```
gctagagctg gtaaaatgga accaaatcgc ctcttcaatg gatttggtcc ccttcaacca    60
gctgtagc                                                            68

<210> SEQ ID NO 140
<211> LENGTH: 73
<212> TYPE: DNA
<213> ORGANISM: Homo sapiens

<400> SEQUENCE: 140
cagggtgtgt gactggttga ccagaggggc atgcactgtg ttcaccctgt gggccaccta    60
gtcaccaacc ctc                                                      73

<210> SEQ ID NO 141
<211> LENGTH: 71
<212> TYPE: DNA
<213> ORGANISM: Homo sapiens

<400> SEQUENCE: 141
agggtgtgtg actggttgac cagaggggca tgcactgtgt tcaccctgtg gccacctag    60 tcaccaaccc t                                                        71

<210> SEQ ID NO 142
<211> LENGTH: 90
<212> TYPE: DNA
<213> ORGANISM: Homo sapiens

<400> SEQUENCE: 142
aggcctcgct gttctctatg gcttttatt cctatgtgat tctactgctc actcatatag    60
ggattggagc cgtggcgcac ggcggggaca                                    90

<210> SEQ ID NO 143
<211> LENGTH: 100
<212> TYPE: DNA
<213> ORGANISM: Homo sapiens

<400> SEQUENCE: 143
agataaattc actctagtgc tttatggctt tttattccta tgtgatagta ataaagtctc    60
atgtagggat ggaagccatg aaatacattg tgaaaaatca                        100

<210> SEQ ID NO 144
<211> LENGTH: 60
<212> TYPE: DNA
<213> ORGANISM: Homo sapiens

<400> SEQUENCE: 144
ctatggcttt ttattcctat gtgattctac tgctcactca tatagggatt ggagccgtgg    60

<210> SEQ ID NO 145
<211> LENGTH: 82
<212> TYPE: DNA
<213> ORGANISM: Homo sapiens

<400> SEQUENCE: 145
tgagccctcg gaggactcca tttgttttga tgatggattc ttatgctcca tcatcgtctc    60
aaatgagtct tcagagggtt ct                                            82

<210> SEQ ID NO 146
<211> LENGTH: 62
<212> TYPE: DNA
<213> ORGANISM: Homo sapiens
```

<400> SEQUENCE: 146
gaggactcca tttgttttga tgatggattc ttatgctcca tcatcgtctc aaatgagtct    60
tc    62

<210> SEQ ID NO 147
<211> LENGTH: 73
<212> TYPE: DNA
<213> ORGANISM: Homo sapiens

<400> SEQUENCE: 147
cttcggtgac gggtattctt gggtggataa tacggattac gttgttattg cttaagaata    60
cgcgtagtcg agg    73

<210> SEQ ID NO 148
<211> LENGTH: 99
<212> TYPE: DNA
<213> ORGANISM: Homo sapiens

<400> SEQUENCE: 148
ccctggcatg gtgtggtggg gcagctggtg ttgtgaatca ggccgttgcc aatcagagaa    60
cggctacttc acaacaccag ggccacacca cactacagg    99

<210> SEQ ID NO 149
<211> LENGTH: 84
<212> TYPE: DNA
<213> ORGANISM: Homo sapiens

<400> SEQUENCE: 149
cgttgctgca gctggtgttg tgaatcaggc cgacgagcag cgcatcctct tacccggcta    60
tttcacgaca ccagggttgc atca    84

<210> SEQ ID NO 150
<211> LENGTH: 71
<212> TYPE: DNA
<213> ORGANISM: Homo sapiens

<400> SEQUENCE: 150
cagctggtgt tgtgaatcag gccgacgagc agcgcatcct cttacccggc tatttcacga    60
caccagggtt g    71

<210> SEQ ID NO 151
<211> LENGTH: 68
<212> TYPE: DNA
<213> ORGANISM: Homo sapiens

<400> SEQUENCE: 151
gtgtattcta cagtgcacgt gtctccagtg tggctcggag gctggagacg cggccctgtt    60
ggagtaac    68

<210> SEQ ID NO 152
<211> LENGTH: 100
<212> TYPE: DNA
<213> ORGANISM: Homo sapiens

<400> SEQUENCE: 152
tgtgtctctc tctgtgtcct gccagtggtt ttaccctatg gtaggttacg tcatgctgtt    60
ctaccacagg gtagaaccac ggacaggata ccggggcacc    100

<210> SEQ ID NO 153

```
<211> LENGTH: 72
<212> TYPE: DNA
<213> ORGANISM: Homo sapiens

<400> SEQUENCE: 153
tcctgccagt ggttttaccc tatggtaggt tacgtcatgc tgttctacca cagggtagaa    60
ccacggacag ga                                                        72

<210> SEQ ID NO 154
<211> LENGTH: 70
<212> TYPE: DNA
<213> ORGANISM: Homo sapiens

<400> SEQUENCE: 154
cctgccagtg gttttaccct atggtaggtt acgtcatgct gttctaccac agggtagaac    60
cacggacagg                                                           70

<210> SEQ ID NO 155
<211> LENGTH: 95
<212> TYPE: DNA
<213> ORGANISM: Homo sapiens

<400> SEQUENCE: 155
cggccggccc tgggtccatc ttccagtaca gtgttggatg gtctaattgt gaagctccta    60
acactgtctg gtaaagatgg ctcccgggtg ggttc                               95

<210> SEQ ID NO 156
<211> LENGTH: 72
<212> TYPE: DNA
<213> ORGANISM: Homo sapiens

<400> SEQUENCE: 156
gggtccatct tccagtacag tgttggatgg tctaattgtg aagctcctaa cactgtctgg    60
taaagatggc cc                                                        72

<210> SEQ ID NO 157
<211> LENGTH: 64
<212> TYPE: DNA
<213> ORGANISM: Homo sapiens

<400> SEQUENCE: 157
acccataaag tagaaagcac tactaacagc actggagggt gtagtgtttc ctactttatg    60
gatg                                                                 64

<210> SEQ ID NO 158
<211> LENGTH: 87
<212> TYPE: DNA
<213> ORGANISM: Homo sapiens

<400> SEQUENCE: 158
gacagtgcag tcacccataa agtagaaagc actactaaca gcactggagg gtgtagtgtt    60
tcctacttta tggatgagtg tactgtg                                        87

<210> SEQ ID NO 159
<211> LENGTH: 64
<212> TYPE: DNA
<213> ORGANISM: Homo sapiens

<400> SEQUENCE: 159
acccataaag tagaaagcac tactaacagc actggagggt gtagtgtttc ctactttatg    60
```

```
<210> SEQ ID NO 160
<211> LENGTH: 106
<212> TYPE: DNA
<213> ORGANISM: Homo sapiens

<400> SEQUENCE: 160
gcgcagcgcc ctgtctccca gcctgaggtg cagtgctgca tctctggtca gttgggagtc      60
tgagatgaag cactgtagct caggaagaga gaagttgttc tgcagc                    106

<210> SEQ ID NO 161
<211> LENGTH: 63
<212> TYPE: DNA
<213> ORGANISM: Homo sapiens

<400> SEQUENCE: 161
cctgaggtgc agtgctgcat ctctggtcag ttgggagtct gagatgaagc actgtagctc      60
agg                                                                    63

<210> SEQ ID NO 162
<211> LENGTH: 86
<212> TYPE: DNA
<213> ORGANISM: Homo sapiens

<400> SEQUENCE: 162
tggggccctg gctgggatat catcatatac tgtaagtttg cgatgagaca ctacagtata      60
gatgatgtac tagtccgggc accccc                                           86

<210> SEQ ID NO 163
<211> LENGTH: 66
<212> TYPE: DNA
<213> ORGANISM: Homo sapiens

<400> SEQUENCE: 163
ggctgggata tcatcatata ctgtaagttt gcgatgagac actacagtat agatgatgta      60
ctagtc                                                                 66

<210> SEQ ID NO 164
<211> LENGTH: 88
<212> TYPE: DNA
<213> ORGANISM: Homo sapiens

<400> SEQUENCE: 164
caccttgtcc tcacggtcca gttttcccag gaatcccttaga tgctaaga tggggattcc      60 tggaaatact gttcttgagg tcatggtt                                         88

<210> SEQ ID NO 165
<211> LENGTH: 70
<212> TYPE: DNA
<213> ORGANISM: Homo sapiens

<400> SEQUENCE: 165
ctcacggtcc agttttccca ggaatccctt agatgctaag atggggattc ctggaaatac      60
tgttcttgag                                                             70

<210> SEQ ID NO 166
<211> LENGTH: 99
<212> TYPE: DNA
<213> ORGANISM: Homo sapiens
```

-continued

```
<400> SEQUENCE: 166
ccgatgtgta tcctcagctt tgagaactga attccatggg ttgtgtcagt gtcagacctc    60
tgaaattcag ttcttcagct gggatatctc tgtcatcgt                           99

<210> SEQ ID NO 167
<211> LENGTH: 65
<212> TYPE: DNA
<213> ORGANISM: Homo sapiens

<400> SEQUENCE: 167
agctttgaga actgaattcc atgggttgtg tcagtgtcag acctgtgaaa ttcagttctt    60
cagct                                                               65

<210> SEQ ID NO 168
<211> LENGTH: 72
<212> TYPE: DNA
<213> ORGANISM: Homo sapiens

<400> SEQUENCE: 168
aatctaaaga caacatttct gcacacacac cagactatgg aagccagtgt gtggaaatgc    60
ttctgctaga tt                                                       72

<210> SEQ ID NO 169
<211> LENGTH: 68
<212> TYPE: DNA
<213> ORGANISM: Homo sapiens

<400> SEQUENCE: 169
gaggcaaagt tctgagacac tccgactctg agtatgatag aagtcagtgc actacagaac    60
tttgtctc                                                            68

<210> SEQ ID NO 170
<211> LENGTH: 89
<212> TYPE: DNA
<213> ORGANISM: Homo sapiens

<400> SEQUENCE: 170
gccggcgccc gagctctggc tccgtgtctt cactcccgtg cttgtccgag gagggaggga    60
gggacggggg ctgtgctggg gcagctgga                                     89

<210> SEQ ID NO 171
<211> LENGTH: 53
<212> TYPE: DNA
<213> ORGANISM: Homo sapiens

<400> SEQUENCE: 171
gctctggctc cgtgtcttca ctcccgtgct tgtccgagga gggagggagg gac          53

<210> SEQ ID NO 172
<211> LENGTH: 84
<212> TYPE: DNA
<213> ORGANISM: Homo sapiens

<400> SEQUENCE: 172
ctccccatgg ccctgtctcc caaccccttgt accagtgctg ggctcagacc ctggtacagg   60
cctgggggac agggacctgg ggac                                          84

<210> SEQ ID NO 173
<211> LENGTH: 64
<212> TYPE: DNA
```

```
<213> ORGANISM: Homo sapiens

<400> SEQUENCE: 173
ccctgtctcc aacccttgt accagtgctg ggctcagacc ctggtacagg cctgggggac      60
aggg                                                                  64

<210> SEQ ID NO 174
<211> LENGTH: 69
<212> TYPE: DNA
<213> ORGANISM: Homo sapiens

<400> SEQUENCE: 174
cctgccctcg aggagctcac agtctagtat gtctcatccc ctactagact gaagctcctt      60
gaggacagg                                                             69

<210> SEQ ID NO 175
<211> LENGTH: 87
<212> TYPE: DNA
<213> ORGANISM: Homo sapiens

<400> SEQUENCE: 175
tgtccccccc ggcccaggtt ctgtgataca ctccgactcg ggctctggag cagtcagtgc      60
atgacagaac ttgggcccgg aaggacc                                         87

<210> SEQ ID NO 176
<211> LENGTH: 71
<212> TYPE: DNA
<213> ORGANISM: Homo sapiens

<400> SEQUENCE: 176
ggcccaggtt ctgtgataca ctccgactcg ggctctggag cagtcagtgc atgacagaac      60
ttgggccccg g                                                          71

<210> SEQ ID NO 177
<211> LENGTH: 90
<212> TYPE: DNA
<213> ORGANISM: Homo sapiens

<400> SEQUENCE: 177
ctcacagctg ccagtgtcat ttttgtgatc tgcagctagt attctcactc cagttgcata      60
gtcacaaaag tgatcattgg caggtgtggc                                      90

<210> SEQ ID NO 178
<211> LENGTH: 71
<212> TYPE: DNA
<213> ORGANISM: Homo sapiens

<400> SEQUENCE: 178
tctctctctc cctcacagct gccagtgtca ttgtcacaaa agtgatcatt ggcaggtgtg      60
gctgctgcat g                                                          71

<210> SEQ ID NO 179
<211> LENGTH: 87
<212> TYPE: DNA
<213> ORGANISM: Homo sapiens

<400> SEQUENCE: 179
agcggtggcc agtgtcattt ttgtgatgtt gcagctagta atatgagccc agttgcatag      60
tcacaaaagt gatcattgga aactgtg                                         87
```

```
<210> SEQ ID NO 180
<211> LENGTH: 69
<212> TYPE: DNA
<213> ORGANISM: Homo sapiens

<400> SEQUENCE: 180
cagtgtcatt tttgtgatgt tgcagctagt aatatgagcc cagttgcata gtcacaaaag    60
tgatcattg                                                            69

<210> SEQ ID NO 181
<211> LENGTH: 84
<212> TYPE: DNA
<213> ORGANISM: Homo sapiens

<400> SEQUENCE: 181
gtggtacttg aagataggtt atccgtgttg ccttcgcttt atttgtgacg aatcatacac    60
ggttgaccta tttttcagta ccaa                                           84

<210> SEQ ID NO 182
<211> LENGTH: 66
<212> TYPE: DNA
<213> ORGANISM: Homo sapiens

<400> SEQUENCE: 182
gaagataggt tatccgtgtt gccttcgctt tatttgtgac gaatcataca cggttgacct    60
attttt                                                               66

<210> SEQ ID NO 183
<211> LENGTH: 65
<212> TYPE: DNA
<213> ORGANISM: Homo sapiens

<400> SEQUENCE: 183
ctgttaatgc taatcgtgat aggggttttt gcctccaact gactcctaca tattagcatt    60
aacag                                                                65

<210> SEQ ID NO 184
<211> LENGTH: 108
<212> TYPE: DNA
<213> ORGANISM: Homo sapiens

<400> SEQUENCE: 184
caatgtcagc agtgccttag cagcacgtaa atattggcgt taagattcta aaattatctc    60
cagtattaac tgtgctgctg aagtaaggtt gaccatactc tacagttg                108

<210> SEQ ID NO 185
<211> LENGTH: 110
<212> TYPE: DNA
<213> ORGANISM: Homo sapiens

<400> SEQUENCE: 185
agaagggcta tcaggccagc cttcagagga ctccaaggaa cattcaacgc tgtcggtgag    60
tttgggattt gaaaaaacca ctgaccgttg actgtacctt ggggtcctta              110

<210> SEQ ID NO 186
<211> LENGTH: 110
<212> TYPE: DNA
<213> ORGANISM: Homo sapiens

<400> SEQUENCE: 186
```

```
tgagttttga ggttgcttca gtgaacattc aacgctgtcg gtgagtttgg aattaaaatc    60
aaaaccatcg accgttgatt gtaccctatg gctaaccatc atctactcca              110

<210> SEQ ID NO 187
<211> LENGTH: 110
<212> TYPE: DNA
<213> ORGANISM: Homo sapiens

<400> SEQUENCE: 187
cggaaaattt gccaagggtt tgggggaaca ttcaacctgt cggtgagttt gggcagctca    60
ggcaaaccat cgaccgttga gtggaccctg aggcctggaa ttgccatcct              110

<210> SEQ ID NO 188
<211> LENGTH: 110
<212> TYPE: DNA
<213> ORGANISM: Homo sapiens

<400> SEQUENCE: 188
gagctgcttg cctcccccg tttttggcaa tggtagaact cacactggtg aggtaacagg     60
atccggtggt tctagacttg ccaactatgg ggcgaggact cagccggcac              110

<210> SEQ ID NO 189
<211> LENGTH: 70
<212> TYPE: DNA
<213> ORGANISM: Homo sapiens

<400> SEQUENCE: 189 ttttggcaa tggtagaact cacactggtg aggtaacagg atccggtggt tctagacttg     60
ccaactatgg                                                           70

<210> SEQ ID NO 190
<211> LENGTH: 110
<212> TYPE: DNA
<213> ORGANISM: Homo sapiens

<400> SEQUENCE: 190
ccgcagagtg tgactcctgt tctgtgtatg gcactggtag aattcactgt gaacagtctc    60
agtcagtgaa ttaccgaagg gccataaaca gagcagagac agatccacga              110

<210> SEQ ID NO 191
<211> LENGTH: 84
<212> TYPE: DNA
<213> ORGANISM: Homo sapiens

<400> SEQUENCE: 191
ccagtcacgt cccttatca cttttccagc ccagctttgt gactgtaagt gttggacgga     60
gaactgataa gggtaggtga ttga                                           84

<210> SEQ ID NO 192
<211> LENGTH: 65
<212> TYPE: DNA
<213> ORGANISM: Homo sapiens

<400> SEQUENCE: 192
ccttatcact tttccagccc agctttgtga ctgtaagtgt tggacggaga actgataagg    60
gtagg                                                                65

<210> SEQ ID NO 193
<211> LENGTH: 82
<212> TYPE: DNA
```

<213> ORGANISM: Homo sapiens

<400> SEQUENCE: 193 aggggggcgag ggattggaga gaaaggcagt tcctgatggt cccctcccca ggggctggct    60
ttcctctggt ccttccctcc ca    82

<210> SEQ ID NO 194
<211> LENGTH: 66
<212> TYPE: DNA
<213> ORGANISM: Homo sapiens

<400> SEQUENCE: 194
agggattgga gagaaaggca gttcctgatg gtccctccc caggggctgg ctttcctctg    60
gtcctt    66

<210> SEQ ID NO 195
<211> LENGTH: 86
<212> TYPE: DNA
<213> ORGANISM: Homo sapiens

<400> SEQUENCE: 195
tgcttgtaac tttccaaaga attctccttt tgggctttct ggttttattt taagcccaaa    60
ggtgaatttt ttgggaagtt tgagct    86

<210> SEQ ID NO 196
<211> LENGTH: 71
<212> TYPE: DNA
<213> ORGANISM: Homo sapiens

<400> SEQUENCE: 196
actttccaaa gaattctcct tttgggcttt ctggttttat tttaagccca aaggtgaatt    60
ttttgggaag t    71

<210> SEQ ID NO 197
<211> LENGTH: 109
<212> TYPE: DNA
<213> ORGANISM: Homo sapiens

<400> SEQUENCE: 197
ggtcgggctc accatgacac agtgtgagac tcgggctaca acacaggacc cggggcgctg    60
ctctgacccc tcgtgtcttg tgttgcagcc ggagggacgc aggtccgca    109

<210> SEQ ID NO 198
<211> LENGTH: 86
<212> TYPE: DNA
<213> ORGANISM: Homo sapiens

<400> SEQUENCE: 198
tgctccctct ctcacatccc ttgcatggtg gagggtgagc tttctgaaaa cccctcccac    60
atgcagggtt tgcaggatgg cgagcc    86

<210> SEQ ID NO 199
<211> LENGTH: 68
<212> TYPE: DNA
<213> ORGANISM: Homo sapiens

<400> SEQUENCE: 199
tctcacatcc cttgcatggt ggagggtgag ctttctgaaa accctcccca catgcagggt    60
ttgcagga    68

<210> SEQ ID NO 200
<211> LENGTH: 102
<212> TYPE: DNA
<213> ORGANISM: Homo sapiens

<400> SEQUENCE: 200
ctgtcgattg gacccgccct ccggtgccta ctgagctgat atcagttctc attttacaca      60
ctggctcagt tcagcaggaa caggagtcga gcccttgagc aa                         102

<210> SEQ ID NO 201
<211> LENGTH: 68
<212> TYPE: DNA
<213> ORGANISM: Homo sapiens

<400> SEQUENCE: 201
ctccggtgcc tactgagctg atatcagttc tcattttaca cactggctca gttcagcagg      60
aacaggag                                                               68

<210> SEQ ID NO 202
<211> LENGTH: 85
<212> TYPE: DNA
<213> ORGANISM: Homo sapiens

<400> SEQUENCE: 202
tgcaggcctc tgtgtgatat gtttgatata ttaggttgtt atttaatcca actatatatc      60
aaacatattc ctacagtgtc ttgcc                                            85

<210> SEQ ID NO 203
<211> LENGTH: 67
<212> TYPE: DNA
<213> ORGANISM: Homo sapiens

<400> SEQUENCE: 203
ctgtgtgata tgtttgatat attaggttgt tatttaatcc aactatatat caaacatatt      60
cctacag                                                                67

<210> SEQ ID NO 204
<211> LENGTH: 92
<212> TYPE: DNA
<213> ORGANISM: Homo sapiens

<400> SEQUENCE: 204
cggctggaca gcgggcaacg gaatcccaaa agcagctgtt gtctccagag cattccagct      60
gcgcttggat ttcgtcccct gctctcctgc ct                                    92

<210> SEQ ID NO 205
<211> LENGTH: 74
<212> TYPE: DNA
<213> ORGANISM: Homo sapiens

<400> SEQUENCE: 205
agcgggcaac ggaatcccaa aagcagctgt tgtctccaga gcattccagc tgcgcttgga      60
tttcgtcccc tgct                                                        74

<210> SEQ ID NO 206
<211> LENGTH: 108
<212> TYPE: DNA
<213> ORGANISM: Homo sapiens

<400> SEQUENCE: 206

```
ccgagaccga gtgcacaggg ctctgaccta tgaattgaca gccagtgctc tcgtctcccc    60
tctggctgcc aattccatag gtcacaggta tgttcgcctc aatgccag                108
```

<210> SEQ ID NO 207
<211> LENGTH: 110
<212> TYPE: DNA
<213> ORGANISM: Homo sapiens

<400> SEQUENCE: 207

```
gccgagaccg agtgcacagg gctctgacct atgaattgac agccagtgct ctcgtctccc    60
ctctggctgc caattccata ggtcacaggt atgttcgcct caatgccagc              110
```

<210> SEQ ID NO 208
<211> LENGTH: 88
<212> TYPE: DNA
<213> ORGANISM: Homo sapiens

<400> SEQUENCE: 208

```
cgaggatggg agctgagggc tgggtctttg cgggcgagat gagggtgtcg atcaactgg     60 cctacaaagt cccagttctc ggccccg                                        88
```

<210> SEQ ID NO 209
<211> LENGTH: 58
<212> TYPE: DNA
<213> ORGANISM: Homo sapiens

<400> SEQUENCE: 209

```
gctgggtctt tgcgggcgag atgagggtgt cggatcaact ggcctacaaa gtcccagt      58
```

<210> SEQ ID NO 210
<211> LENGTH: 85
<212> TYPE: DNA
<213> ORGANISM: Homo sapiens

<400> SEQUENCE: 210

```
atggtgttat caagtgtaac agcaactcca tgtggactgt gtaccaattt ccagtggaga    60
tgctgttact tttgatggtt accaa                                          85
```

<210> SEQ ID NO 211
<211> LENGTH: 63
<212> TYPE: DNA
<213> ORGANISM: Homo sapiens

<400> SEQUENCE: 211

```
gtgtaacagc aactccatgt ggactgtgta ccaatttcca gtggagatgc tgttactttt    60
gat                                                                  63
```

<210> SEQ ID NO 212
<211> LENGTH: 87
<212> TYPE: DNA
<213> ORGANISM: Homo sapiens

<400> SEQUENCE: 212

```
agcttccctg gctctagcag cacagaaata ttggcacagg gaagcgagtc tgccaatatt    60
ggctgtgctg ctccaggcag ggtggtg                                        87
```

<210> SEQ ID NO 213
<211> LENGTH: 58
<212> TYPE: DNA
<213> ORGANISM: Homo sapiens

```
<400> SEQUENCE: 213
tagcagcaca gaaatattgg cacagggaag cgagtctgcc aatattggct gtgctgct         58

<210> SEQ ID NO 214
<211> LENGTH: 110
<212> TYPE: DNA
<213> ORGANISM: Homo sapiens

<400> SEQUENCE: 214
ctagagcttg aattggaact gctgagtgaa ttaggtagtt tcatgttgtt gggcctgggt       60
ttctgaacac aacaacatta aaccacccga ttcacggcag ttactgctcc                 110

<210> SEQ ID NO 215
<211> LENGTH: 70
<212> TYPE: DNA
<213> ORGANISM: Homo sapiens

<400> SEQUENCE: 215
gtgaattagg tagtttcatg ttgttgggcc tgggtttctg aacacaacaa cattaaacca      60
cccgattcac                                                             70

<210> SEQ ID NO 216
<211> LENGTH: 110
<212> TYPE: DNA
<213> ORGANISM: Homo sapiens

<400> SEQUENCE: 216
tgctcgctca gctgatctgt ggcttaggta gtttcatgtt gttgggattg agttttgaac      60
tcggcaacaa gaaactgcct gagttacatc agtcggtttt cgtcgagggc                 110

<210> SEQ ID NO 217
<211> LENGTH: 70
<212> TYPE: DNA
<213> ORGANISM: Homo sapiens

<400> SEQUENCE: 217
gtgaattagg tagtttcatg ttgttgggcc tgggtttctg aacacaacaa cattaaacca      60
cccgattcac                                                             70

<210> SEQ ID NO 218
<211> LENGTH: 75
<212> TYPE: DNA
<213> ORGANISM: Homo sapiens

<400> SEQUENCE: 218
ggctgtgccg ggtagagagg gcagtgggag gtaagagctc ttcacccttc accaccttct      60
ccacccagca tggcc                                                       75

<210> SEQ ID NO 219
<211> LENGTH: 62
<212> TYPE: DNA
<213> ORGANISM: Homo sapiens

<400> SEQUENCE: 219
tcattggtcc agaggggaga taggttcctg tgattttttcc ttcttctcta tagaataaat     60
ga                                                                     62

<210> SEQ ID NO 220
<211> LENGTH: 71
<212> TYPE: DNA
```

```
<213> ORGANISM: Homo sapiens

<400> SEQUENCE: 220
gccaacccag tgttcagact acctgttcag gaggctctca atgtgtacag tagtctgcac      60
attggttagg c                                                          71

<210> SEQ ID NO 221
<211> LENGTH: 110
<212> TYPE: DNA
<213> ORGANISM: Homo sapiens

<400> SEQUENCE: 221
aggaagcttc tggagatcct gctccgtcgc cccagtgttc agactacctg ttcaggacaa      60
tgccgttgta cagtagtctg cacattggtt agactgggca agggagagca               110

<210> SEQ ID NO 222
<211> LENGTH: 110
<212> TYPE: DNA
<213> ORGANISM: Homo sapiens

<400> SEQUENCE: 222
ccagaggaca cctccactcc gtctacccag tgtttagact atctgttcag gactcccaaa      60
ttgtacagta gtctgcacat tggttaggct gggctgggtt agaccctcgg               110

<210> SEQ ID NO 223
<211> LENGTH: 71
<212> TYPE: DNA
<213> ORGANISM: Homo sapiens

<400> SEQUENCE: 223
gccaacccag tgttcagact acctgttcag gaggctctca atgtgtacag tagtctgcac      60
attggttagg c                                                          71

<210> SEQ ID NO 224
<211> LENGTH: 70
<212> TYPE: DNA
<213> ORGANISM: Homo sapiens

<400> SEQUENCE: 224
gccgtggcca tcttactggg cagcattgga tggagtcagg tctctaatac tgcctggtaa      60
tgatgacggc                                                            70

<210> SEQ ID NO 225
<211> LENGTH: 95
<212> TYPE: DNA
<213> ORGANISM: Homo sapiens

<400> SEQUENCE: 225
ccagctcggg cagccgtggc catcttactg ggcagcattg gatggagtca ggtctctaat      60
actgcctggt aatgatgacg gcggagccct gcacg                                95

<210> SEQ ID NO 226
<211> LENGTH: 72
<212> TYPE: DNA
<213> ORGANISM: Homo sapiens

<400> SEQUENCE: 226 gttcctttt cctatgcata tacttctttg aggatctggc ctaaagaggt atagggcatg       60
ggaagatgga gc                                                         72
```

<210> SEQ ID NO 227
<211> LENGTH: 110
<212> TYPE: DNA
<213> ORGANISM: Homo sapiens

<400> SEQUENCE: 227
gtgttgggga ctcgcgcgct gggtccagtg gttcttaaca gttcaacagt tctgtagcgc        60
aattgtgaaa tgtttaggac cactagaccc ggcgggcgcg gcgacagcga                  110

<210> SEQ ID NO 228
<211> LENGTH: 110
<212> TYPE: DNA
<213> ORGANISM: Homo sapiens

<400> SEQUENCE: 228
ggctacagtc tttcttcatg tgactcgtgg acttcccttt gtcatcctat gcctgagaat        60
atatgaagga ggctgggaag gcaaagggac gttcaattgt catcactggc                  110

<210> SEQ ID NO 229
<211> LENGTH: 110
<212> TYPE: DNA
<213> ORGANISM: Homo sapiens

<400> SEQUENCE: 229
aaagatcctc agacaatcca tgtgcttctc ttgtccttca ttccaccgga gtctgtctca        60
tacccaacca gatttcagtg gagtgaagtt caggaggcat ggagctgaca                  110

<210> SEQ ID NO 230
<211> LENGTH: 86
<212> TYPE: DNA
<213> ORGANISM: Homo sapiens

<400> SEQUENCE: 230
tgcttcccga ggccacatgc ttctttatat ccccatatgg attactttgc tatggaatgt        60
aaggaagtgt gtggtttcgg caagtg                                             86

<210> SEQ ID NO 231
<211> LENGTH: 69
<212> TYPE: DNA
<213> ORGANISM: Homo sapiens

<400> SEQUENCE: 231
aggccacatg cttctttata tccccatatg gattactttg ctatggaatg taaggaagtg        60
tgtggtttt                                                                69

<210> SEQ ID NO 232
<211> LENGTH: 71
<212> TYPE: DNA
<213> ORGANISM: Homo sapiens

<400> SEQUENCE: 232
tgacgggcga gcttttggcc cgggttatac ctgatgctca cgtataagac gagcaaaaag        60
cttgttggtc a                                                             71

<210> SEQ ID NO 233
<211> LENGTH: 110
<212> TYPE: DNA
<213> ORGANISM: Homo sapiens

<400> SEQUENCE: 233

```
acccggcagt gcctccaggc gcagggcagc ccctgcccac cgcacactgc gctgcccag      60 acccactgtg cgtgtgacag cggctgatct gtgcctgggc agcgcgaccc               110

<210> SEQ ID NO 234
<211> LENGTH: 110
<212> TYPE: DNA
<213> ORGANISM: Homo sapiens

<400> SEQUENCE: 234
tcacctggcc atgtgacttg tgggcttccc tttgtcatcc ttcgcctagg gctctgagca    60
gggcagggac agcaaagggg tgctcagttg tcacttccca cagcacggag              110

<210> SEQ ID NO 235
<211> LENGTH: 110
<212> TYPE: DNA
<213> ORGANISM: Homo sapiens

<400> SEQUENCE: 235
cggggcaccc cgcccggaca gcgcgccggc accttggctc tagactgctt actgcccggg    60
ccgccctcag taacagtctc cagtcacggc caccgacgcc tggccccgcc              110

<210> SEQ ID NO 236
<211> LENGTH: 110
<212> TYPE: DNA
<213> ORGANISM: Homo sapiens

<400> SEQUENCE: 236
cctgtgcaga gattattttt taaaaggtca caatcaacat tcattgctgt cggtgggttg    60
aactgtgtgg acaagctcac tgaacaatga atgcaactgt ggccccgctt              110

<210> SEQ ID NO 237
<211> LENGTH: 108
<212> TYPE: DNA
<213> ORGANISM: Homo sapiens

<400> SEQUENCE: 237
gagttttgag gttgcttcag tgaacattca acgctgtcgg tgagtttgga attaaaatca    60
aaaccatcga ccgttgattg tacccctatgg ctaaccatca tctactcc               108

<210> SEQ ID NO 238
<211> LENGTH: 110
<212> TYPE: DNA
<213> ORGANISM: Homo sapiens

<400> SEQUENCE: 238
ggcctggctg gacagagttg tcatgtgtct gcctgtctac acttgctgtg cagaacatcc    60
gctcacctgt acagcaggca cagacaggca gtcacatgac aacccagcct              110

<210> SEQ ID NO 239
<211> LENGTH: 110
<212> TYPE: DNA
<213> ORGANISM: Homo sapiens

<400> SEQUENCE: 239
atcattcaga aatggtatac aggaaaatga cctatgaatt gacagacaat atagctgagt    60
ttgtctgtca tttctttagg ccaatattct gtatgactgt gctacttcaa              110

<210> SEQ ID NO 240
<211> LENGTH: 110
<212> TYPE: DNA
```

<213> ORGANISM: Homo sapiens

<400> SEQUENCE: 240
gatggctgtg agttggctta atctcagctg gcaactgtga gatgttcata caatccctca    60
cagtggtctc tgggattatg ctaaacagag caatttccta gccctcacga              110

<210> SEQ ID NO 241
<211> LENGTH: 110
<212> TYPE: DNA
<213> ORGANISM: Homo sapiens

<400> SEQUENCE: 241
agtataatta ttacatagtt tttgatgtcg cagatactgc atcaggaact gattggataa    60
gaatcagtca ccatcagttc ctaatgcatt gccttcagca tctaaacaag              110

<210> SEQ ID NO 242
<211> LENGTH: 110
<212> TYPE: DNA
<213> ORGANISM: Homo sapiens

<400> SEQUENCE: 242
gtgataatgt agcgagattt tctgttgtgc ttgatctaac catgtggttg cgaggtatga    60
gtaaaacatg gttccgtcaa gcaccatgga acgtcacgca gctttctaca              110

<210> SEQ ID NO 243
<211> LENGTH: 110
<212> TYPE: DNA
<213> ORGANISM: Homo sapiens

<400> SEQUENCE: 243
gaccagtcgc tgcggggctt tcctttgtgc ttgatctaac catgtggtgg aacgatggaa    60
acggaacatg gttctgtcaa gcaccgcgga aagcaccgtg ctctcctgca              110

<210> SEQ ID NO 244
<211> LENGTH: 110
<212> TYPE: DNA
<213> ORGANISM: Homo sapiens

<400> SEQUENCE: 244
ccgccccggg ccgcggctcc tgattgtcca aacgcaattc tcgagtctat ggctccggcc    60
gagagttgag tctggacgtc ccgagccgcc gcccccaaac ctcgagcggg              110

<210> SEQ ID NO 245
<211> LENGTH: 110
<212> TYPE: DNA
<213> ORGANISM: Homo sapiens

<400> SEQUENCE: 245
gacagtgtgg cattgtaggg ctccacaccg tatctgacac tttgggcgag ggcaccatgc    60
tgaaggtgtt catgatgcgg tctgggaact cctcacggat cttactgatg              110

<210> SEQ ID NO 246
<211> LENGTH: 110
<212> TYPE: DNA
<213> ORGANISM: Homo sapiens

<400> SEQUENCE: 246
tgaacatcca ggtctggggc atgaacctgg catacaatgt agatttctgt gttcgttagg    60
caacagctac attgtctgct gggtttcagg ctacctggaa acatgttctc              110

```
<210> SEQ ID NO 247
<211> LENGTH: 110
<212> TYPE: DNA
<213> ORGANISM: Homo sapiens

<400> SEQUENCE: 247
gctgctggaa ggtgtaggta ccctcaatgg ctcagtagcc agtgtagatc ctgtctttcg      60
taatcagcag ctacatctgg ctactgggtc tctgatggca tcttctagct               110

<210> SEQ ID NO 248
<211> LENGTH: 110
<212> TYPE: DNA
<213> ORGANISM: Homo sapiens

<400> SEQUENCE: 248
cctggcctcc tgcagtgcca cgctccgtgt atttgacaag ctgagttgga cactccatgt      60
ggtagagtgt cagtttgtca aatacccaa gtgcggcaca tgcttaccag                110

<210> SEQ ID NO 249
<211> LENGTH: 81
<212> TYPE: DNA
<213> ORGANISM: Homo sapiens

<400> SEQUENCE: 249
gggctttcaa gtcactagtg gttccgttta gtagatgatt gtgcattgtt tcaaaatggt      60
gccctagtga ctacaaagcc c                                              81

<210> SEQ ID NO 250
<211> LENGTH: 81
<212> TYPE: DNA
<213> ORGANISM: Homo sapiens

<400> SEQUENCE: 250
cttctggaag ctggtttcac atggtggctt agattttcc atctttgtat ctagcaccat       60
ttgaaatcag tgttttagga g                                              81

<210> SEQ ID NO 251
<211> LENGTH: 81
<212> TYPE: DNA
<213> ORGANISM: Homo sapiens

<400> SEQUENCE: 251
cttcaggaag ctggtttcat atggtggttt agatttaaat agtgattgtc tagcaccatt      60
tgaaatcagt gttcttgggg g                                              81

<210> SEQ ID NO 252
<211> LENGTH: 81
<212> TYPE: DNA
<213> ORGANISM: Homo sapiens

<400> SEQUENCE: 252
cttcaggaag ctggtttcat atggtggttt agatttaaat agtgattgtc tagcaccatt      60
tgaaatcagt gttcttgggg g                                              81

<210> SEQ ID NO 253
<211> LENGTH: 80
<212> TYPE: DNA
<213> ORGANISM: Homo sapiens

<400> SEQUENCE: 253
```

```
gtgagcgact gtaaacatcc tcgactggaa gctgtgaagc cacagatggg ctttcagtcg      60
gatgtttgca gctgcctact                                                  80

<210> SEQ ID NO 254
<211> LENGTH: 88
<212> TYPE: DNA
<213> ORGANISM: Homo sapiens

<400> SEQUENCE: 254
accaagtttc agttcatgta aacatcctac actcagctgt aatacatgga ttggctggga      60
ggtggatgtt tacttcagct gacttgga                                         88

<210> SEQ ID NO 255
<211> LENGTH: 75
<212> TYPE: DNA
<213> ORGANISM: Homo sapiens

<400> SEQUENCE: 255
tgccctggct cagttatcac agtgctgatg ctgtctattc taaaggtaca gtactgtgat      60
aactgaagga tggca                                                       75

<210> SEQ ID NO 256
<211> LENGTH: 90
<212> TYPE: DNA
<213> ORGANISM: Homo sapiens

<400> SEQUENCE: 256
acactgcaag aacaataagg attttaaggg gcattatgac tgagtcagaa aacacagctg      60
cccctgaaag tccctcattt ttcttgctgt                                       90

<210> SEQ ID NO 257
<211> LENGTH: 80
<212> TYPE: DNA
<213> ORGANISM: Homo sapiens

<400> SEQUENCE: 257
actgcaagag caataaggat ttttaggggc attatgatag tggaatggaa acacatctgc      60
ccccaaaagt ccctcatttt                                                  80

<210> SEQ ID NO 258
<211> LENGTH: 85
<212> TYPE: DNA
<213> ORGANISM: Homo sapiens

<400> SEQUENCE: 258
cgctggcgac gggacattat tactttggt acgcgctgtg acacttcaaa ctcgtaccgt       60
gagtaataat gcgccgtcca cggca                                            85

<210> SEQ ID NO 259
<211> LENGTH: 61
<212> TYPE: DNA
<213> ORGANISM: Homo sapiens

<400> SEQUENCE: 259
acattattac ttttggtacg cgctgtgaca cttcaaactc gtaccgtgag taataatgcg      60
c                                                                      61

<210> SEQ ID NO 260
<211> LENGTH: 74
<212> TYPE: DNA
```

```
<213> ORGANISM: Homo sapiens

<400> SEQUENCE: 260
tggatctttt tgcggtctgg gcttgctgtt cctctcaaca gtagtcagga agcccttacc      60
ccaaaaagta tcta                                                       74

<210> SEQ ID NO 261
<211> LENGTH: 90
<212> TYPE: DNA
<213> ORGANISM: Homo sapiens

<400> SEQUENCE: 261
tgcccttcgc gaatcttttt gcggtctggg cttgctgtac ataactcaat agccggaagc      60
ccttacccca aaaagcattt gcggagggcg                                      90

<210> SEQ ID NO 262
<211> LENGTH: 80
<212> TYPE: DNA
<213> ORGANISM: Homo sapiens

<400> SEQUENCE: 262 gcccctgct ctggctggtc aaacggaacc aagtccgtct tcctgagagg tttggtcccc       60
ttcaaccagc tacagcaggg                                                 80

<210> SEQ ID NO 263
<211> LENGTH: 100
<212> TYPE: DNA
<213> ORGANISM: Homo sapiens

<400> SEQUENCE: 263
agataaattc actctagtgc tttatggctt tttattccta tgtgatagta ataaagtctc      60
atgtagggat ggaagccatg aaatacattg tgaaaaatca                           100

<210> SEQ ID NO 264
<211> LENGTH: 70
<212> TYPE: DNA
<213> ORGANISM: Homo sapiens

<400> SEQUENCE: 264
aagcacgatt agcatttgag gtgaagttct gttatacact caggctgtgg ctctctgaaa      60
gtcagtgcat                                                            70

<210> SEQ ID NO 265
<211> LENGTH: 69
<212> TYPE: DNA
<213> ORGANISM: Homo sapiens

<400> SEQUENCE: 265
cctgtcctca aggagcttca gtctagtagg ggatgagaca tactagactg tgagctcctc      60
gagggcagg                                                             69

<210> SEQ ID NO 266
<211> LENGTH: 65
<212> TYPE: DNA
<213> ORGANISM: Homo sapiens

<400> SEQUENCE: 266
ctgttaatgc taatcgtgat aggggttttt gcctccaact gactcctaca tattagcatt      60
aacag                                                                 65
```

<210> SEQ ID NO 267
<211> LENGTH: 82
<212> TYPE: DNA
<213> ORGANISM: Homo sapiens

<400> SEQUENCE: 267
cctaacactg tctggtaaag atggctcccg ggtgggttct ctcggcagta accttcaggg    60
agccctgaag accatggagg ac                                            82

<210> SEQ ID NO 268
<211> LENGTH: 110
<212> TYPE: DNA
<213> ORGANISM: Homo sapiens

<400> SEQUENCE: 268
gccgagaccg agtgcacagg gctctgacct atgaattgac agccagtgct ctcgtctccc    60
ctctggctgc caattccata ggtcacaggt atgttcgcct caatgccagc              110

<210> SEQ ID NO 269
<211> LENGTH: 80
<212> TYPE: DNA
<213> ORGANISM: Homo sapiens

<400> SEQUENCE: 269
tcccgccccc tgtaacagca actccatgtg gaagtgccca ctggttccag tggggctgct    60
gttatctggg gcgagggcca                                               80

<210> SEQ ID NO 270
<211> LENGTH: 70
<212> TYPE: DNA
<213> ORGANISM: Homo sapiens

<400> SEQUENCE: 270
aaagctgggt tgagagggcg aaaaaggatg aggtgactgg tctgggctac gctatgctgc    60
ggcgctcggg                                                          70

<210> SEQ ID NO 271
<211> LENGTH: 64
<212> TYPE: DNA
<213> ORGANISM: Homo sapiens

<400> SEQUENCE: 271
cattggcctc ctaagccagg gattgtgggt tcgagtccca cccggggtaa agaaaggccg    60
aatt                                                                64

<210> SEQ ID NO 272
<211> LENGTH: 70
<212> TYPE: DNA
<213> ORGANISM: Homo sapiens

<400> SEQUENCE: 272
cctaagccag ggattgtggg ttcgagtccc acctggggta gaggtgaaag ttccttttac    60 ggaattttttt                                                         70

<210> SEQ ID NO 273
<211> LENGTH: 81
<212> TYPE: DNA
<213> ORGANISM: Homo sapiens

<400> SEQUENCE: 273

```
gggctttcaa gtcactagtg gttccgttta gtagatgatt gtgcattgtt tcaaaatggt      60
gccctagtga ctacaaagcc c                                                81

<210> SEQ ID NO 274
<211> LENGTH: 70
<212> TYPE: DNA
<213> ORGANISM: Homo sapiens

<400> SEQUENCE: 274
acgcaagtgt cctaaggtga gctcaggag cacagaaacc tccagtggaa cagaagggca       60
aaagctcatt                                                            70

<210> SEQ ID NO 275
<211> LENGTH: 70
<212> TYPE: DNA
<213> ORGANISM: Homo sapiens

<400> SEQUENCE: 275
catgtgtcac tttcaggtgg agtttcaaga gtcccttcct ggttcaccgt ctcctttgct      60
cttccacaac                                                            70

<210> SEQ ID NO 276
<211> LENGTH: 109
<212> TYPE: DNA
<213> ORGANISM: Homo sapiens

<400> SEQUENCE: 276
ggtcgggctc accatgacac agtgtgagac tcgggctaca acacaggacc cggggcgctg      60
ctctgacccc tcgtgtcttg tgttgcagcc ggagggacgc aggtccgca                 109

<210> SEQ ID NO 277
<211> LENGTH: 86
<212> TYPE: DNA
<213> ORGANISM: Homo sapiens

<400> SEQUENCE: 277
tgctccctct ctcacatccc ttgcatggtg gagggtgagc tttctgaaaa cccctcccac      60
atgcagggtt tgcaggatgg cgagcc                                          86

<210> SEQ ID NO 278
<211> LENGTH: 85
<212> TYPE: DNA
<213> ORGANISM: Homo sapiens

<400> SEQUENCE: 278
tgcaggcctc tgtgtgatat gtttgatata ttaggttgtt atttaatcca actatatatc      60
aaacatattc ctacagtgtc ttgcc                                           85

<210> SEQ ID NO 279
<211> LENGTH: 60
<212> TYPE: DNA
<213> ORGANISM: Homo sapiens

<400> SEQUENCE: 279
gtgcatgtgt atgtatgtgt gcatgtgcat gtgtatgtgt atgagtgcat gcgtgtgtgc      60

<210> SEQ ID NO 280
<211> LENGTH: 75
<212> TYPE: DNA
<213> ORGANISM: Homo sapiens
```

```
<400> SEQUENCE: 280
ggctgtgccg ggtagagagg gcagtgggag gtaagagctc ttcacccttc accaccttct    60
ccacccagca tggcc                                                    75

<210> SEQ ID NO 281
<211> LENGTH: 72
<212> TYPE: DNA
<213> ORGANISM: Homo sapiens

<400> SEQUENCE: 281 gttcctttt cctatgcata tacttctttg aggatctggc ctaaagaggt atagggcatg     60
ggaagatgga gc                                                       72

<210> SEQ ID NO 282
<211> LENGTH: 60
<212> TYPE: DNA
<213> ORGANISM: Homo sapiens

<400> SEQUENCE: 282
caatcttcct ttatcatggt attgattttt cagtgcttcc cttttgtgtg agagaagata    60

<210> SEQ ID NO 283
<211> LENGTH: 102
<212> TYPE: DNA
<213> ORGANISM: Homo sapiens

<400> SEQUENCE: 283
atggagctgc tcaccctgtg ggcctcaaat gtggaggaac tattctgatg tccaagtgga    60
aagtgctgcg acatttgagc gtcaccggtg acgcccatat ca                      102

<210> SEQ ID NO 284
<211> LENGTH: 101
<212> TYPE: DNA
<213> ORGANISM: Homo sapiens

<400> SEQUENCE: 284
gcatcccctc agcctgtggc actcaaactg tgggggcact ttctgctctc tggtgaaagt    60
gccgccatct tttgagtgtt accgcttgag aagactcaac c                       101

<210> SEQ ID NO 285
<211> LENGTH: 102
<212> TYPE: DNA
<213> ORGANISM: Homo sapiens

<400> SEQUENCE: 285
cgaggagctc atactgggat actcaaaatg ggggcgcttt cctttttgtc tgttactggg    60
aagtgcttcg attttggggt gtccctgttt gagtagggca tc                      102

<210> SEQ ID NO 286
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 286
tgacagaaga gagtgagcac acaaaggcaa tttgcatatc                         40

<210> SEQ ID NO 287
<211> LENGTH: 40
<212> TYPE: DNA
```

<210> SEQ ID NO 288
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 287
cattgcactt gcttctcttg cgtgctcact gctctttctg          40

<210> SEQ ID NO 288
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 288
gtgttgacag aagatagaga gcacagatga tgagatacaa          40

<210> SEQ ID NO 289
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 289
catcttactc ctttgtgctc tctagccttc tgtcatcacc          40

<210> SEQ ID NO 290
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 290
gatggacggt ggtgattcac tctccacaaa gttctctatg          40

<210> SEQ ID NO 291
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 291
tgagaatctt gatgatgctg catcggcaat caacgactat          40

<210> SEQ ID NO 292
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 292
tgaggtagta ggttgtatag ttttagggtc acacccacca          40

<210> SEQ ID NO 293
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 293
tacagcctcc tagcttttcct tgggtcttgc actaaacaac          40

<210> SEQ ID NO 294
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 294
actgcatgct cccaggttga ggtagtaggt tgtatagttt                              40

<210> SEQ ID NO 295
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 295
gggtgaggta gtaggttgta tagtttgggg ctctgccctg                              40

<210> SEQ ID NO 296
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 296
tgaggtagta ggttgtgtgg tttcagggca gtgatgttgc                              40

<210> SEQ ID NO 297
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 297
gcatccgggt tgaggtagta ggttgtatgg tttagagtta                              40

<210> SEQ ID NO 298
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 298
cctaggaaga ggtagtaggt tgcatagttt tagggcaggg                              40

<210> SEQ ID NO 299
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 299
ctaggaagag gtagtagttt gcatagtttt agggcaaaga                              40

<210> SEQ ID NO 300
<211> LENGTH: 40
<212> TYPE: DNA
<213> ORGANISM: Artificial Sequence
<220> FEATURE:
<223> OTHER INFORMATION: oligonucleotide probe

```
<400> SEQUENCE: 300
ttggtcgggt tgtgacattg cccgctgtgg agataactgc                          40

<210> SEQ ID NO 301
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 301
gctgaggtag tagtttgtgc tgttggtcgg gttgtgacat                          40

<210> SEQ ID NO 302
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 302
ggctgaggta ggaggttgta tagttgagga ggacacccaa                          40

<210> SEQ ID NO 303
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 303
ggtagtgatt ttaccctgtt caggagataa ctatacaatc                          40

<210> SEQ ID NO 304
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 304
gggatgaggt agtagattgt atagttgtgg ggtagtgatt                          40

<210> SEQ ID NO 305
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 305
tgaggtagta gattgtatag ttttagggtc atacccccatc                         40

<210> SEQ ID NO 306
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 306
ctgattccag gctgaggtag tagtttgtac agtttgaggg                          40

<210> SEQ ID NO 307
<211> LENGTH: 40
<212> TYPE: DNA
```

```
<213> ORGANISM: Artificial Sequence
<220> FEATURE:
<223> OTHER INFORMATION: oligonucleotide probe

<400> SEQUENCE: 307
ttgagggtct atgataccac ccggtacagg agataactgt                    40

<210> SEQ ID NO 308
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 308
aatgctatgg aatgtaaaga agtatgtatt tttggtaggc                    40

<210> SEQ ID NO 309
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 309
taagctatgg aatgtaaaga agtatgtatc tcaggccggg                    40

<210> SEQ ID NO 310
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 310
tgttggccta gttctgtgtg aagactagt gattttgttg                     40

<210> SEQ ID NO 311
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 311
tactgcgctc aacaacaaat cccagtctac ctaatggtgc                    40

<210> SEQ ID NO 312
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 312
ggaccggctg gccccatctg gaagactagt gattttgttg                    40

<210> SEQ ID NO 313
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 313
agattagagt ggctgtggtc tagtgctgtg tggaagacta                    40
```

<210> SEQ ID NO 314
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 314
tggaagacta gtgattttgt tgttctgatg tactacgaca                               40

<210> SEQ ID NO 315
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 315
tctttggtta tctagctgta tgagtggtgt ggagtcttca                               40

<210> SEQ ID NO 316
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 316
taaagctaga taaccgaaag taaaaataac cccatacact                               40

<210> SEQ ID NO 317
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 317
gaagcgagtt gttatctttg gttatctagc tgtatgagtg                               40

<210> SEQ ID NO 318
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 318
gagtgtattg gtcttcataa agctagataa ccgaaagtaa                               40

<210> SEQ ID NO 319
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 319
gggaggcccg tttctctctt tggttatcta gctgtatgag                               40

<210> SEQ ID NO 320
<211> LENGTH: 40
<212> TYPE: DNA
<213> ORGANISM: Artificial Sequence
<220> FEATURE:
<223> OTHER INFORMATION: oligonucleotide probe -continued

<400> SEQUENCE: 320
gtgccacaga gccgtcataa agctagataa ccgaaagtag                    40

<210> SEQ ID NO 321
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 321
gtctgtcttc tgtatatacc ctgtagatcc gaatttgtgt                    40

<210> SEQ ID NO 322
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 322
gtggtcacaa attcgtatct agggaatat gtagttgaca                     40

<210> SEQ ID NO 323
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 323
taccctgtag aaccgaattt gtgtggtatc cgtatagtca                    40

<210> SEQ ID NO 324
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 324
gtcacagatt cgattctagg ggaatatatg gtcgatgcaa                    40

<210> SEQ ID NO 325
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 325
ccttggagta aagtagcagc acataatggt ttgtggattt                    40

<210> SEQ ID NO 326
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 326
tttgtggatt ttgaaaaggt gcaggccata ttgtgctgcc                    40

<210> SEQ ID NO 327
<211> LENGTH: 40
<212> TYPE: DNA

```
<213> ORGANISM: Artificial Sequence
<220> FEATURE:
<223> OTHER INFORMATION: oligonucleotide probe

<400> SEQUENCE: 327
ggccttaaag tactgtagca gcacatcatg gtttacatgc                              40

<210> SEQ ID NO 328
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 328
tgctacagtc aagatgcgaa tcattatttg ctgctctaga                              40

<210> SEQ ID NO 329
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 329
caatgtcagc agtgccttag cagcacgtaa atattggcgt                              40

<210> SEQ ID NO 330
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 330
gttccactct agcagcacgt aaatattggc gtagtgaaat                              40

<210> SEQ ID NO 331
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 331
gcatctactg cagtgaaggc acttgtagca ttatggtgac                              40

<210> SEQ ID NO 332
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 332
gtcagaataa tgtcaaagtg cttacagtgc aggtagtgat                              40

<210> SEQ ID NO 333
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 333
taaggtgcat ctagtgcaga tagtgaagta gattagcatc                              40
```

<210> SEQ ID NO 334
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 334
tgtagttgtg caaatctatg caaaactgat ggtggcctgc                    40

<210> SEQ ID NO 335
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 335
ttctgctgtg caaatccatg caaaactgac tgtggtagtg                    40

<210> SEQ ID NO 336
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 336
gtggctgtgc aaatccatgc aaaactgatt gtgataatgt                    40

<210> SEQ ID NO 337
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 337
taaagtgctt atagtgcagg tagtgtttag ttatctactg                    40

<210> SEQ ID NO 338
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 338
gtcgggtagc ttatcagact gatgttgact gttgaatctc                    40

<210> SEQ ID NO 339
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 339
ttcaacagtc aacatcagtc tgataagcta cccgacaagg                    40

<210> SEQ ID NO 340
<211> LENGTH: 40
<212> TYPE: DNA
<213> ORGANISM: Artificial Sequence
<220> FEATURE:
<223> OTHER INFORMATION: oligonucleotide probe

```
<400> SEQUENCE: 340
tgtcctgacc cagctaaagc tgccagttga agaactgttg                              40

<210> SEQ ID NO 341
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 341
tcctgtcaca aatcacattg ccagggattt ccaaccgacc                              40

<210> SEQ ID NO 342
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 342
aatcacattg ccagggatta ccacgcaacc acgaccttgg                              40

<210> SEQ ID NO 343
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 343
ttttacacac tggctcagtt cagcaggaac aggagtcgag                              40

<210> SEQ ID NO 344
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 344
tccggtgcct actgagctga tatcagttct cattttacac                              40

<210> SEQ ID NO 345
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 345
agttggtttg tgtacactgg ctcagttcag caggaacagg                              40

<210> SEQ ID NO 346
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 346
acgctgccct gggcattgca cttgtctcgg tctgacagtg                              40

<210> SEQ ID NO 347
<211> LENGTH: 40
<212> TYPE: DNA
```

<213> ORGANISM: Artificial Sequence
<220> FEATURE:
<223> OTHER INFORMATION: oligonucleotide probe

<400> SEQUENCE: 347
ttcaagtaat ccaggatagg ctgtgcaggt cccaatggcc                                40

<210> SEQ ID NO 348
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 348
tcccaatggc ctatcttggt tacttgcacg gggacgcggg                                40

<210> SEQ ID NO 349
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 349
ttcaagtaat tcaggatagg ttgtgtgctg tccagcctgt                                40

<210> SEQ ID NO 350
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 350
gtccacacca agtcgtgttc acagtggcta agttccgccc                                40

<210> SEQ ID NO 351
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 351
ccgctttgtt cacagtggct aagttctgca cctgaagaga                                40

<210> SEQ ID NO 352
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 352
aaggagctca cagtctattg agttaccttt ctgactttcc                                40

<210> SEQ ID NO 353
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 353
ctagcaccat ctgaaatcgg ttataatgat tggggaagag                                40

<210> SEQ ID NO 354
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 354 cccttagag gatgactgat ttcttttggt gttcagagtc        40

<210> SEQ ID NO 355
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 355
agtgattgtc tagcaccatt tgaaatcagt gttcttgggg        40

<210> SEQ ID NO 356
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 356
ttttgtctag caccatttga aatcggttat gatgtagggg        40

<210> SEQ ID NO 357
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 357
gcgactgtaa acatcctcga ctggaagctg tgaagccaca        40

<210> SEQ ID NO 358
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 358
cacagatggg ctttcagtcg gatgtttgca gctgcctact        40

<210> SEQ ID NO 359
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 359
tgtaaacatc ctacactcag ctgtaataca tggattggct        40

<210> SEQ ID NO 360
<211> LENGTH: 40
<212> TYPE: DNA
<213> ORGANISM: Artificial Sequence
<220> FEATURE:
<223> OTHER INFORMATION: oligonucleotide probe

```
<400> SEQUENCE: 360
atggattggc tgggaggtgg atgtttactt cagctgactt                    40

<210> SEQ ID NO 361
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 361
tactgtaaac atcctacact ctcagctgtg gaaagtaaga                    40

<210> SEQ ID NO 362
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 362
taagacacag ctaagctttc agtcagatgt ttgctgctac                    40

<210> SEQ ID NO 363
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 363
ttgtaaacat ccccgactgg aagctgtaag acacagctaa                    40

<210> SEQ ID NO 364
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 364
ggcaagatgc tggcatagct gttgaactgg gaacctgcta                    40

<210> SEQ ID NO 365
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 365
tgtcacggcc tcaatgcaat ttagtgtgtg tgatattttc                    40

<210> SEQ ID NO 366
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 366
ggagatattg cacattacta agttgcatgt tgtcacggcc                    40

<210> SEQ ID NO 367
<211> LENGTH: 40
<212> TYPE: DNA
```

```
<213> ORGANISM: Artificial Sequence
<220> FEATURE:
<223> OTHER INFORMATION: oligonucleotide probe

<400> SEQUENCE: 367
gtgcattgct gttgcattgc acgtgtgtga ggcgggtgca                    40

<210> SEQ ID NO 368
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 368
gtggtgcatt gtagttgcat tgcatgttct ggtggtaccc                    40

<210> SEQ ID NO 369
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 369
gagtgtttct ttggcagtgt cttagctggt tgttgtgagc                    40

<210> SEQ ID NO 370
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 370
agtaaggaag caatcagcaa gtatactgcc ctagaagtgc                    40

<210> SEQ ID NO 371
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 371
acaggttggg atcggttgca atgctgtgtt tctgtatggt                    40

<210> SEQ ID NO 372
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 372
tctgtatggt attgcacttg tcccggcctg ttgagtttgg                    40

<210> SEQ ID NO 373
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 373
gttctatata aagtattgca cttgtcccgg cctgtggaag                    40
```

<210> SEQ ID NO 374
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 374
ccaaagtgct gttcgtgcag gtagtgtgat tacccaacct                              40

<210> SEQ ID NO 375
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 375
cgttacattc aacgggtatt tattgagcac ccactctgtg                              40

<210> SEQ ID NO 376
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 376
ctccgctctg agcaatcatg tgcagtgcca atatgggaaa                              40

<210> SEQ ID NO 377
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 377
tggccgattt tggcactagc acattttgc ttgtgtctct                               40

<210> SEQ ID NO 378
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 378
tgaggtagta agttgtattg ttgtggggta gggatattag                              40

<210> SEQ ID NO 379
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 379
gccttcgccg cacacaagct cgtgtctgtg ggtccgtgtc                              40

<210> SEQ ID NO 380
<211> LENGTH: 40
<212> TYPE: DNA
<213> ORGANISM: Artificial Sequence
<220> FEATURE:
<223> OTHER INFORMATION: oligonucleotide probe -continued

```
<400> SEQUENCE: 380
cacccgtaga accgaccttg cggggccttc gccgcacaca                           40

<210> SEQ ID NO 381
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 381
ataaacccgt agatccgatc ttgtggtgaa gtggaccgca                           40

<210> SEQ ID NO 382
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 382
tgaggcctgt tgccacaaac ccgtagatcc gaacttgtgg                           40

<210> SEQ ID NO 383
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 383
ccctggctca gttatcacag tgctgatgct gtctattcta                           40

<210> SEQ ID NO 384
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 384
tacagtactg tgataactga aggatggcag ccatcttacc                           40

<210> SEQ ID NO 385
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 385
gctgtatatc tgaaaggtac agtactgtga taactgaaga                           40

<210> SEQ ID NO 386
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 386
tctttgtatc tagcaccatt tgaaatcagt gttttaggag                           40

<210> SEQ ID NO 387
<211> LENGTH: 40
<212> TYPE: DNA
```

```
<213> ORGANISM: Artificial Sequence
<220> FEATURE:
<223> OTHER INFORMATION: oligonucleotide probe

<400> SEQUENCE: 387
gtagcattca ggtcaagcaa cattgtacag ggctatgaaa                                40

<210> SEQ ID NO 388
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 388
tatggatcaa gcagcattgt acagggctat gaaggcattg                                40

<210> SEQ ID NO 389
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 389
atcgtggtca aatgctcaga ctcctgtggt ggctgctcat                                40

<210> SEQ ID NO 390
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 390
ccttggccat gtaaaagtgc ttacagtgca ggtagctttt                                40

<210> SEQ ID NO 391
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 391
ggcatggagt tcaagcagca ttgtacaggg ctatcaaagc                                40

<210> SEQ ID NO 392
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 392
ccttagcaga gctgtggagt gtgacaatgg tgtttgtgtc                                40

<210> SEQ ID NO 393
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 393
gacgggacat tattactttt ggtacgcgct gtgacacttc                                40
```

```
<210> SEQ ID NO 394
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 394
tgtgacactt caaactcgta ccgtgagtaa taatgcgccg                    40

<210> SEQ ID NO 395
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 395
atacaattaa ggcacgcggt gaatgccaag aatggggctg                    40

<210> SEQ ID NO 396
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 396
ttaaggcacg cggtgaatgc caagagcgga gcctacggct                    40

<210> SEQ ID NO 397
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 397
ttaaggcacg cggtgaatgc caagagaggc gcctccgccg                    40

<210> SEQ ID NO 398
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 398
tctaggtccc tgagacccctt taacctgtga ggacatccag                    40

<210> SEQ ID NO 399
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 399
cagggtcaca ggtgaggttc ttgggagcct ggcgtctggc                    40

<210> SEQ ID NO 400
<211> LENGTH: 40
<212> TYPE: DNA
<213> ORGANISM: Artificial Sequence
<220> FEATURE:
<223> OTHER INFORMATION: oligonucleotide probe
```

<210> SEQ ID NO 400
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 400
tccctgagac cctaacttgt gatgtttacc gtttaaatcc          40

<210> SEQ ID NO 401
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 401
tagtaacatc acaagtcagg ctcttgggac ctaggcggag          40

<210> SEQ ID NO 402
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 402
accagacttt tcctagtccc tgagacccta acttgtgagg          40

<210> SEQ ID NO 403
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 403
tcggatccgt ctgagcttgg ctggtcggaa gtctcatcat          40

<210> SEQ ID NO 404
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 404
ttggattcgg ggccgtagca ctgtctgaga ggtttacatt          40

<210> SEQ ID NO 405
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 405
acatttctca cagtgaaccg gtctcttttt cagctgcttc          40

<210> SEQ ID NO 406
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 406
tcacagtgaa ccggtctctt tccctactgt gtcacactcc          40

<210> SEQ ID NO 407
<211> LENGTH: 40
<212> TYPE: DNA

<213> ORGANISM: Artificial Sequence
<220> FEATURE:
<223> OTHER INFORMATION: oligonucleotide probe

<400> SEQUENCE: 407
gggggccgat acactgtacg agagtgagta gcaggtctca				40

<210> SEQ ID NO 408
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 408
tggatctttt tgcggtctgg gcttgctgtt cctctcaaca				40

<210> SEQ ID NO 409
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 409
cctctcaaca gtagtcagga agcccttacc ccaaaaagta				40

<210> SEQ ID NO 410
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 410
ccagagctct tttcacattg tgctactgtc tgcacctgtc				40

<210> SEQ ID NO 411
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 411
tgtctgcacc tgtcactagc agtgcaatgt taaaagggca				40

<210> SEQ ID NO 412
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 412
tgtgggaact ggaggtaaca gtctacagcc atggtcgccc				40

<210> SEQ ID NO 413
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 413
tccagggcaa ccgtggcttt cgattgttac tgtgggaact				40

<210> SEQ ID NO 414
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 414
cctcttcaat ggatttggtc cccttcaacc agctgtagct                             40

<210> SEQ ID NO 415
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 415
ttggtcccct tcaaccagct gtagctgtgc attgatggcg                             40

<210> SEQ ID NO 416
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 416
atgcactgtg ttcaccctgt gggccaccta gtcaccaacc                             40

<210> SEQ ID NO 417
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 417
gtgtgtgact ggttgaccag aggggcatgc actgtgttca                             40

<210> SEQ ID NO 418
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 418
gcctcgctgt tctctatggc tttttattcc tatgtgattc                             40

<210> SEQ ID NO 419
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 419
cactctagtg ctttatggct ttttattcct atgtgatagt                             40

<210> SEQ ID NO 420
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 420
atgctccatc atcgtctcaa atgagtcttc agagggttct                                40

<210> SEQ ID NO 421
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 421
tgagccctcg gaggactcca tttgttttga tgatggattc                                40

<210> SEQ ID NO 422
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 422
ggattacgtt gttattgctt aagaatacgc gtagtcgagg                                40

<210> SEQ ID NO 423
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 423
agctggtgtt gtgaatcagg ccgttgccaa tcagagaacg                                40

<210> SEQ ID NO 424
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 424
agctggtgtt gtgaatcagg ccgacgagca gcgcatcctc                                40

<210> SEQ ID NO 425
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 425
gtgtattcta cagtgcacgt gtctccagtg tggctcggag                                40

<210> SEQ ID NO 426
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 426
gccagtggtt ttaccctatg gtaggttacg tcatgctgtt                                40

<210> SEQ ID NO 427
<211> LENGTH: 40
<212> TYPE: DNA

```
<213> ORGANISM: Artificial Sequence
<220> FEATURE:
<223> OTHER INFORMATION: oligonucleotide probe

<400> SEQUENCE: 427
ttctaccaca gggtagaacc acggacagga taccggggca                              40

<210> SEQ ID NO 428
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 428
ttgtgaagct cctaacactg tctggtaaag atggctcccg                              40

<210> SEQ ID NO 429
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 429
atcttccagt acagtgttgg atggtctaat tgtgaagctc                              40

<210> SEQ ID NO 430
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 430
cccataaagt agaaagcact actaacagca ctggagggtg                              40

<210> SEQ ID NO 431
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 431
ctggtcagtt gggagtctga gatgaagcac tgtagctcag                              40

<210> SEQ ID NO 432
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 432
cgatgagaca ctacagtata gatgatgtac tagtccgggc                              40

<210> SEQ ID NO 433
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 433
ccctggctgg gatatcatca tatactgtaa gtttgcgatg                              40
```

```
<210> SEQ ID NO 434
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 434
cctcacggtc cagttttccc aggaatccct tagatgctaa                       40

<210> SEQ ID NO 435
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 435
tgagaactga attccatggg ttgtgtcagt gtcagacctc                       40

<210> SEQ ID NO 436
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 436
gactatggaa gccagtgtgt ggaaatgctt ctgctagatt                       40

<210> SEQ ID NO 437
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 437
tgagtatgat agaagtcagt gcactacaga actttgtctc                       40

<210> SEQ ID NO 438
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 438
cgagctctgg ctccgtgtct tcactcccgt gcttgtccga                       40

<210> SEQ ID NO 439
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 439
ctccccatgg ccctgtctcc caacccttgt accagtgctg                       40

<210> SEQ ID NO 440
<211> LENGTH: 40
<212> TYPE: DNA
<213> ORGANISM: Artificial Sequence
<220> FEATURE:
<223> OTHER INFORMATION: oligonucleotide probe
```

-continued

<400> SEQUENCE: 440
gtatgtctca tccctacta gactgaagct ccttgaggac    40

<210> SEQ ID NO 441
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 441
actcgggctc tggagcagtc agtgcatgac agaacttggg    40

<210> SEQ ID NO 442
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 442
ccccggccca ggttctgtga tacactccga ctcgggctct    40

<210> SEQ ID NO 443
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 443
cagttgcata gtcacaaaag tgatcattgg caggtgtggc    40

<210> SEQ ID NO 444
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 444
cacagctgcc agtgtcattg tcacaaaagt gatcattggc    40

<210> SEQ ID NO 445
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 445
gcccagttgc atagtcacaa aagtgatcat tggaaactgt    40

<210> SEQ ID NO 446
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 446
gtggtacttg aagataggtt atccgtgttg ccttcgcttt    40

<210> SEQ ID NO 447
<211> LENGTH: 40
<212> TYPE: DNA

```
<213> ORGANISM: Artificial Sequence
<220> FEATURE:
<223> OTHER INFORMATION: oligonucleotide probe

<400> SEQUENCE: 447
gccttcgctt tatttgtgac gaatcataca cggttgacct                    40

<210> SEQ ID NO 448
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 448
ttaatgctaa tcgtgatagg ggttttTgcc tccaactgac                    40

<210> SEQ ID NO 449
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 449
tcagaggact ccaaggaaca ttcaacgctg tcggtgagtt                    40

<210> SEQ ID NO 450
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 450
gaaaaaacca ctgaccgttg actgtaccTT ggggtcctta                    40

<210> SEQ ID NO 451
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 451
tgaggttgct tcagtgaaca ttcaacgctg tcggtgagtt                    40

<210> SEQ ID NO 452
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 452
accatcgacc gttgattgta ccctatggct aaccatcatc                    40

<210> SEQ ID NO 453
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 453
tgccaagggt ttgggggaac attcaacctg tcggtgagtt                    40
```

```
<210> SEQ ID NO 454
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 454
atcgaccgtt gagtggaccc tgaggcctgg aattgccatc                              40

<210> SEQ ID NO 455
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 455
aggtaacagg atccggtggt tctagacttg ccaactatgg                              40

<210> SEQ ID NO 456
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 456
ttggcaatgg tagaactcac actggtgagg taacaggatc                              40

<210> SEQ ID NO 457
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 457
gactcctgtt ctgtgtatgg cactggtaga attcactgtg                              40

<210> SEQ ID NO 458
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 458
gtctcagtca gtgaattacc gaagggccat aaacagagca                              40

<210> SEQ ID NO 459
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 459
gactgtaagt gttggacgga gaactgataa gggtaggtga                              40

<210> SEQ ID NO 460
<211> LENGTH: 40
<212> TYPE: DNA
<213> ORGANISM: Artificial Sequence
<220> FEATURE:
<223> OTHER INFORMATION: oligonucleotide probe
```

```
<400> SEQUENCE: 460
cgtcccctta tcactttcc agcccagctt tgtgactgta                              40

<210> SEQ ID NO 461
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 461
gcgagggatt ggagagaaag gcagttcctg atggtcccct                             40

<210> SEQ ID NO 462
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 462
cctccccagg ggctggcttt cctctggtcc ttccctccca                             40

<210> SEQ ID NO 463
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 463
cttgtaactt tccaaagaat tctccttttg ggctttctgg                             40

<210> SEQ ID NO 464
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 464
ctcgtgtctt gtgttgcagc cggagggacg caggtccgca                             40

<210> SEQ ID NO 465
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 465
tcaccatgac acagtgtgag actcgggcta caacacagga                             40

<210> SEQ ID NO 466
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 466
tcacatccct tgcatggtgg agggtgagct ttctgaaaac                             40

<210> SEQ ID NO 467
<211> LENGTH: 40
<212> TYPE: DNA
```

<213> ORGANISM: Artificial Sequence
<220> FEATURE:
<223> OTHER INFORMATION: oligonucleotide probe

<400> SEQUENCE: 467
gcaggcctct gtgtgatatg tttgatatat taggttgtta                           40

<210> SEQ ID NO 468
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 468
caacggaatc ccaaaagcag ctgttgtctc cagagcattc                           40

<210> SEQ ID NO 469
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 469
tctgacctat gaattgacag ccagtgctct cgtctcccct                           40

<210> SEQ ID NO 470
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 470
ccaattccat aggtcacagg tatgttcgcc tcaatgccag                           40

<210> SEQ ID NO 471
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 471
agatgagggt gtcggatcaa ctggcctaca aagtcccagt                           40

<210> SEQ ID NO 472
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 472
aggatgggag ctgagggctg ggtctttgcg ggcgagatga                           40

<210> SEQ ID NO 473
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 473
tgtaacagca actccatgtg gactgtgtac caatttccag                           40

```
<210> SEQ ID NO 474
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 474
ccaatttcca gtggagatgc tgttactttt gatggttacc                              40

<210> SEQ ID NO 475
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 475
tctagcagca cagaaatatt ggcacaggga agcgagtctg                              40

<210> SEQ ID NO 476
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 476
ctgctgagtg aattaggtag tttcatgttg ttgggcctgg                              40

<210> SEQ ID NO 477
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 477
acacaacaac attaaaccac ccgattcacg gcagttactg                              40

<210> SEQ ID NO 478
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 478
agaaactgcc tgagttacat cagtcggttt tcgtcgaggg                              40

<210> SEQ ID NO 479
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 479
gctgatctgt ggcttaggta gtttcatgtt gttgggattg                              40

<210> SEQ ID NO 480
<211> LENGTH: 40
<212> TYPE: DNA
<213> ORGANISM: Artificial Sequence
<220> FEATURE:
<223> OTHER INFORMATION: oligonucleotide probe
```

```
<400> SEQUENCE: 480
taagagctct tcaccCttca ccaccttctc cacccagcat                    40

<210> SEQ ID NO 481
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 481
tcattggtcc agagggaga taggttcctg tgattttttcc                    40

<210> SEQ ID NO 482
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 482
gccaacccag tgttcagact acctgttcag gaggctctca                    40

<210> SEQ ID NO 483
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 483
tcgccccagt gttcagacta cctgttcagg acaatgccgt                    40

<210> SEQ ID NO 484
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 484
gtctgcacat tggttaggct gggctgggtt agaccctcgg                    40

<210> SEQ ID NO 485
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 485
acctccactc cgtctaccca gtgtttagac tatctgttca                    40

<210> SEQ ID NO 486
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 486
gtctctaata ctgcctggta atgatgacgg cggagccctg                    40

<210> SEQ ID NO 487
<211> LENGTH: 40
<212> TYPE: DNA
```

```
<213> ORGANISM: Artificial Sequence
<220> FEATURE:
<223> OTHER INFORMATION: oligonucleotide probe

<400> SEQUENCE: 487
gatctggcct aaagaggtat agggcatggg aagatggagc                          40

<210> SEQ ID NO 488
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 488
gttctgtagc gcaattgtga aatgtttagg accactagac                          40

<210> SEQ ID NO 489
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 489
tgggtccagt ggttcttaac agttcaacag ttctgtagcg                          40

<210> SEQ ID NO 490
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 490
cgtggacttc cctttgtcat cctatgcctg agaatatatg                          40

<210> SEQ ID NO 491
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 491
aggctgggaa ggcaaaggga cgttcaattg tcatcactgg                          40

<210> SEQ ID NO 492
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 492
tccttcattc caccggagtc tgtctcatac ccaaccagat                          40

<210> SEQ ID NO 493
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 493
ttgctatgga atgtaaggaa gtgtgtggtt tcggcaagtg                          40
```

<210> SEQ ID NO 494
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 494
tgcttcccga ggccacatgc ttctttatat ccccatatgg                    40

<210> SEQ ID NO 495
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 495
acctgatgct cacgtataag acgagcaaaa agcttgttgg                    40

<210> SEQ ID NO 496
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 496
agacccactg tgcgtgtgac agcggctgat ctgtgcctgg                    40

<210> SEQ ID NO 497
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 497 ttcccttttgt catccttcgc ctagggctct gagcagggca                   40

<210> SEQ ID NO 498
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 498
gcagggacag caaagggtg ctcagttgtc acttcccaca                     40

<210> SEQ ID NO 499
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 499
cctcagtaac agtctccagt cacggccacc gacgcctggc                    40

<210> SEQ ID NO 500
<211> LENGTH: 40
<212> TYPE: DNA
<213> ORGANISM: Artificial Sequence
<220> FEATURE:
<223> OTHER INFORMATION: oligonucleotide probe

```
<400> SEQUENCE: 500
cggacagcgc gccggcacct tggctctaga ctgcttactg                              40

<210> SEQ ID NO 501
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 501
aacattcatt gctgtcggtg ggttgaactg tgtggacaag                              40

<210> SEQ ID NO 502
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 502
tgtggacaag ctcactgaac aatgaatgca actgtggccc                              40

<210> SEQ ID NO 503
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 503
tgtacagcag gcacagacag gcagtcacat gacaacccag                              40

<210> SEQ ID NO 504
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 504
caggaaaatg acctatgaat tgacagacaa tatagctgag                              40

<210> SEQ ID NO 505
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 505
catttcttta ggccaatatt ctgtatgact gtgctacttc                              40

<210> SEQ ID NO 506
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 506
ctgggattat gctaaacaga gcaatttcct agccctcacg                              40

<210> SEQ ID NO 507
<211> LENGTH: 40
<212> TYPE: DNA
```

<213> ORGANISM: Artificial Sequence
<220> FEATURE:
<223> OTHER INFORMATION: oligonucleotide probe

<400> SEQUENCE: 507
gatggctgtg agttggctta atctcagctg gcaactgtga                              40

<210> SEQ ID NO 508
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 508
gaatcagtca ccatcagttc ctaatgcatt gccttcagca                              40

<210> SEQ ID NO 509
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 509
tgtcgcagat actgcatcag gaactgattg gataagaatc                              40

<210> SEQ ID NO 510
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 510
gttgtgcttg atctaaccat gtggttgcga ggtatgagta                              40

<210> SEQ ID NO 511
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 511
tggtggaacg atggaaacgg aacatggttc tgtcaagcac                              40

<210> SEQ ID NO 512
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 512
tcgctgcggg gctttccttt gtgcttgatc taaccatgtg                              40

<210> SEQ ID NO 513
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 513
attgtccaaa cgcaattctc gagtctatgg ctccggccga                              40

```
<210> SEQ ID NO 514
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 514
tgtggcattg tagggctcca caccgtatct gacactttgg                                40

<210> SEQ ID NO 515
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 515
caacagctac attgtctgct gggtttcagg ctacctggaa                                40

<210> SEQ ID NO 516
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 516
ctttcgtaat cagcagctac atctggctac tgggtctctg                                40

<210> SEQ ID NO 517
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 517
gctgctggaa ggtgtaggta ccctcaatgg ctcagtagcc                                40

<210> SEQ ID NO 518
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 518
gagtgtcagt ttgtcaaata ccccaagtgc ggcacatgct                                40

<210> SEQ ID NO 519
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 519
ggctttcaag tcactagtgg ttccgtttag tagatgattg                                40

<210> SEQ ID NO 520
<211> LENGTH: 40
<212> TYPE: DNA
<213> ORGANISM: Artificial Sequence
<220> FEATURE:
<223> OTHER INFORMATION: oligonucleotide probe
```

```
<400> SEQUENCE: 520
ggccgcagca acctcggttc gtatccgagt cacggcacca                              40

<210> SEQ ID NO 521
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 521
tccggatgga gcgtgggttc gaatcccact tctgacacca                              40

<210> SEQ ID NO 522
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 522
atggtagagc gctcgctttg cttgcgagag gtagcgggat                              40

<210> SEQ ID NO 523
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 523
gatctaaagg tccctggttc gatcccgggt ttcggcacca                              40

<210> SEQ ID NO 524
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 524
agcagagtgg cgcagcggaa gcgtgctggg cccataaccc                              40

<210> SEQ ID NO 525
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 525
aacccagagg tcgatggatc gaaaccatcc tctgctacca                              40

<210> SEQ ID NO 526
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 526
caatcggtta gcgcgttcgg ctgttaaccg aaaggttggt                              40

<210> SEQ ID NO 527
<211> LENGTH: 40
<212> TYPE: DNA
```

```
<213> ORGANISM: Artificial Sequence
<220> FEATURE:
<223> OTHER INFORMATION: oligonucleotide probe

<400> SEQUENCE: 527
tctagcgaca gagtggttca attccacctt tcgggcgcca                             40

<210> SEQ ID NO 528
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 528
acgcgaaagg tccccggttc gaaaccgggc ggaaacacca                             40

<210> SEQ ID NO 529
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 529
ctgaggtagt agtttgtaca gtttgagggt ctatgatacc                             40

<210> SEQ ID NO 530
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 530
gctgaggtag tagtttgtgc tgttggtcgg gttgtgacat                             40

<210> SEQ ID NO 531
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 531
attcagtgct atggaatgta aagaagtatg tattttgggt                             40

<210> SEQ ID NO 532
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 532
ctgctaagct atggaatgta aagaagtatg tatttcaggc                             40

<210> SEQ ID NO 533
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 533
atctttggtt atctagctgt atgagtgtat tggtcttcat                             40
```

-continued

```
<210> SEQ ID NO 534
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 534
gagtgtattg gtcttcataa agctagataa ccgaaagtaa                40

<210> SEQ ID NO 535
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 535
taccctgtag aaccgaattt gtgtggtacc cacatagtca                40

<210> SEQ ID NO 536
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 536
ttgagattaa aatcacattg ccagggatta ccacgcaacc                40

<210> SEQ ID NO 537
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 537
ttggtttccg ctttgttcac agtggctaag ttctgcacct                40

<210> SEQ ID NO 538
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 538
taaatagtga ttgtctagca ccatttgaaa tcagtgttct                40

<210> SEQ ID NO 539
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 539
tgtaaacatc ctacactcag ctgtcataca tgcgttggct                40

<210> SEQ ID NO 540
<211> LENGTH: 40
<212> TYPE: DNA
<213> ORGANISM: Artificial Sequence
<220> FEATURE:
<223> OTHER INFORMATION: oligonucleotide probe
```

<400> SEQUENCE: 540
tgtaaacatc cttgactgga agctgtaagg tgttgagagg                             40

<210> SEQ ID NO 541
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 541
cataaacccg tagatccgat cttgtggtga agtggaccgc                             40

<210> SEQ ID NO 542
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 542
gccttcgccg cacacaagct cgtgtctgtg ggtccgtgtc                             40

<210> SEQ ID NO 543
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 543
cacccgtaga accgaccttg cggggccttc gccgcacaca                             40

<210> SEQ ID NO 544
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 544
tgccacaaac ccgtagatcc gaacttgtgc tgattctgca                             40

<210> SEQ ID NO 545
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 545
gctgtccatt ctaaaggtac agtactgtga taactgaagg                             40

<210> SEQ ID NO 546
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 546
gtgtccaaac catcaaacgc cattatcaca ctaaatagct                             40

<210> SEQ ID NO 547
<211> LENGTH: 40
<212> TYPE: DNA

<213> ORGANISM: Artificial Sequence
<220> FEATURE:
<223> OTHER INFORMATION: oligonucleotide probe

<400> SEQUENCE: 547
gctgtggagt gtgacaatgg tgtttgtgtc caaaccatca         40

<210> SEQ ID NO 548
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 548
cattattact tttggtacgc gctgtgacac ttcaaactcg         40

<210> SEQ ID NO 549
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 549
gacacttcaa actcgtaccg tgagtaataa tgcgcggtca         40

<210> SEQ ID NO 550
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 550
taatgtctat acaattaagg cacgcggtga atgccaagag         40

<210> SEQ ID NO 551
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 551
tccctgagac cctttaacct gtgaggacgt ccagggtcac         40

<210> SEQ ID NO 552
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 552
gcctagtccc tgagacccta acttgtgagg tattttagta         40

<210> SEQ ID NO 553
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 553
attttagtaa catcacaagt caggttcttg ggacctaggc         40

<210> SEQ ID NO 554
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 554
ttcagaaaga tcatcggatc cgtctgagct tggctggtcg          40

<210> SEQ ID NO 555
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 555
aggtttacat ttctcacagt gaaccggtct cttttttcagc          40

<210> SEQ ID NO 556
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 556
ttggattcgg ggccgtagca ctgtctgaga ggtttacatt          40

<210> SEQ ID NO 557
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 557 cttttttgcgg tctgggcttg ctgtacataa ctcaatagcc          40

<210> SEQ ID NO 558
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 558 cttttttgcgg tctgggcttg ctgttttctc gacagtagtc          40

<210> SEQ ID NO 559
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 559
gtctaacgtg taccgagcag tgcaatgtta aaagggcatc          40

<210> SEQ ID NO 560
<211> LENGTH: 40
<212> TYPE: DNA
<213> ORGANISM: Artificial Sequence
<220> FEATURE:
<223> OTHER INFORMATION: oligonucleotide probe -continued

```
<400> SEQUENCE: 560
agtggtgtgg agtcttcata aagctagata accgaaagta                    40

<210> SEQ ID NO 561
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 561
tgtgggaacc ggaggtaaca gtctacagcc atggtcgccc                    40

<210> SEQ ID NO 562
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 562
atcgcctctt caatggattt ggtccccttc aaccagctgt                    40

<210> SEQ ID NO 563
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 563
gcactctgtt caccctgtgg gccacctagt caccaaccct                    40

<210> SEQ ID NO 564
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 564
tgtgtgactg gttgaccaga ggggcgtgca ctctgttcac                    40

<210> SEQ ID NO 565
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 565
ctatggcttt ttattcctat gtgattctat tgctcgctca                    40

<210> SEQ ID NO 566
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 566
gaggactcca tttgttttga tgatggattc ttaagctcca                    40

<210> SEQ ID NO 567
<211> LENGTH: 40
<212> TYPE: DNA
```

```
<213> ORGANISM: Artificial Sequence
<220> FEATURE:
<223> OTHER INFORMATION: oligonucleotide probe

<400> SEQUENCE: 567
ggattacgtt gttattgctt aagaatacgc gtagtcgagg                              40

<210> SEQ ID NO 568
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 568
agctggtgtt gtgaatcagg ccgacgagca gcgcatcctc                              40

<210> SEQ ID NO 569
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 569
ttacgtcatg ctgttctacc acagggtaga accacggaca                              40

<210> SEQ ID NO 570
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 570
gaagtatgaa gctcctaaca ctgtctggta aagatggccc                              40

<210> SEQ ID NO 571
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 571
cccataaagt agaaagcact actaacagca ctggagggtg                              40

<210> SEQ ID NO 572
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 572
tggtcagttg ggagtctgag atgaagcact gtagctcagg                              40

<210> SEQ ID NO 573
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 573
gtttgtgatg agacactaca gtatagatga tgtactagtc                              40
```

<210> SEQ ID NO 574
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 574
acggtccagt tttcccagga atcccttgga tgctaagatg                    40

<210> SEQ ID NO 575
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 575
tgagaactga attccatggg ttatatcaat gtcagacctg                    40

<210> SEQ ID NO 576
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 576
gctctggctc cgtgtcttca ctcccgtgtt tgtccgagga                    40

<210> SEQ ID NO 577
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 577
tgtctcccaa cccttgtacc agtgctgtgc ctcagaccct                    40

<210> SEQ ID NO 578
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 578
tatgtctcct ccctactaga ctgaggctcc ttgagggaca                    40

<210> SEQ ID NO 579
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 579
actcgggctc tggagcagtc agtgcatgac agaacttggg                    40

<210> SEQ ID NO 580
<211> LENGTH: 40
<212> TYPE: DNA
<213> ORGANISM: Artificial Sequence
<220> FEATURE:
<223> OTHER INFORMATION: oligonucleotide probe -continued

```
<400> SEQUENCE: 580
taatatgagc ccagttgcat agtgacaaaa gtgatcattg                                40

<210> SEQ ID NO 581
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 581
agataggtta ccgtgttgc cttcgcttta ttcgtgacga                                 40

<210> SEQ ID NO 582
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 582
ttaatgctaa ttgtgatagg ggttttggcc tctgactgac                                40

<210> SEQ ID NO 583
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 583
ccatggaaca ttcaacgctg tcggtgagtt tgggattcaa                                40

<210> SEQ ID NO 584
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 584
tttggcaatg gtagaactca caccggtaag gtaatgggac                                40

<210> SEQ ID NO 585
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 585
aacagtctca gtcagtgaat taccgaaggg ccataaacag                                40

<210> SEQ ID NO 586
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 586
tatggcactg gtagaattca ctgtgaacag tctcagtcag                                40

<210> SEQ ID NO 587
<211> LENGTH: 40
<212> TYPE: DNA
```

<213> ORGANISM: Artificial Sequence
<220> FEATURE:
<223> OTHER INFORMATION: oligonucleotide probe

<400> SEQUENCE: 587
tgtgactcta agtgttggac ggagaactga taagggtagg                40

<210> SEQ ID NO 588
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 588
gggattggag agaaaggcag ttcctgatgg tcccctccca                40

<210> SEQ ID NO 589
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 589
caaagaattc tccttttggg ctttctcatt ttattttaag                40

<210> SEQ ID NO 590
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 590
gggcgctgct ctgacccctc gtgtcttgtg ttgcagccgg                40

<210> SEQ ID NO 591
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 591
tcacatccct tgcatggtgg agggtgagct ctctgaaaac                40

<210> SEQ ID NO 592
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 592
cggtgcctac tgagctgata tcagttctca tttcacacac                40

<210> SEQ ID NO 593
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 593
ctgtgtgata tgtttgatat attaggttgt tatttaatcc                40

<210> SEQ ID NO 594
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 594
caacggaatc ccaaaagcag ctgttgtctc cagagcattc        40

<210> SEQ ID NO 595
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 595
ctgacctatg aattgacagc cagtgctctc gtctcccctc        40

<210> SEQ ID NO 596
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 596
tgagagtgtc agttcaactg gcctacaaag tcccagtcct        40

<210> SEQ ID NO 597
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 597
atcgggtgta acagcaactc catgtggact gtgctcggat        40

<210> SEQ ID NO 598
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 598
tagcagcaca gaaatattgg catggggaag tgagtctgcc        40

<210> SEQ ID NO 599
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 599
gtaggtagtt tcatgttgtt gggcctggct ttctgaacac        40

<210> SEQ ID NO 600
<211> LENGTH: 40
<212> TYPE: DNA
<213> ORGANISM: Artificial Sequence
<220> FEATURE:
<223> OTHER INFORMATION: oligonucleotide probe

```
<400> SEQUENCE: 600
gaggctggga catgtacagt agtctgcaca ttggttaggc                           40

<210> SEQ ID NO 601
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 601
tagtgtctga tctctaatac tgcctggtaa tgatgacggc                           40

<210> SEQ ID NO 602
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 602
ccgtggccat cttactgggc agcattggat agtgtctgat                           40

<210> SEQ ID NO 603
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 603
taccttactc agtaaggcat tgttcttcta tattaataaa                           40

<210> SEQ ID NO 604
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 604
gatctggtct aaagaggtat agcgcatggg aagatggagc                           40

<210> SEQ ID NO 605
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 605
ggtccagtgg ttcttgacag ttcaacagtt ctgtagcaca                           40

<210> SEQ ID NO 606
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 606
gtagcacaat tgtgaaatgt ttaggaccac tagacccggc                           40

<210> SEQ ID NO 607
<211> LENGTH: 40
<212> TYPE: DNA
```

<213> ORGANISM: Artificial Sequence
<220> FEATURE:
<223> OTHER INFORMATION: oligonucleotide probe

<400> SEQUENCE: 607
ttccctttgt catcctatgc ctgagaatat atgaaggagg                40

<210> SEQ ID NO 608
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 608
gtccttcatt ccaccggagt ctgtcttatg ccaaccagat                40

<210> SEQ ID NO 609
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 609
tagatatctc agcactatgg aatgtaagga agtgtgtggt                40

<210> SEQ ID NO 610
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 610
gctgcggctt gcgcttctcc tggctctcct ccctctcctt                40

<210> SEQ ID NO 611
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 611
cttcagtaac agtctccagt cacggccacc gacgcctggc                40

<210> SEQ ID NO 612
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 612
agcgcgccgg caccttggct ctagactgct tactgcccgg                40

<210> SEQ ID NO 613
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 613
aacattcatt gctgtcggtg ggttgaactg tgtggacaag                40

<210> SEQ ID NO 614
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 614
tgtacagcag gcacagacag gcagtcacat gacaacccag            40

<210> SEQ ID NO 615
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 615
caggagaatg acctatgatt tgacagaccg tgcagctgtg            40

<210> SEQ ID NO 616
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 616
gagatgtccc tatcattcct cacagtggtc tctgggatta            40

<210> SEQ ID NO 617
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 617
atggctatga gttggtttaa tctcagctgg caactgtgag            40

<210> SEQ ID NO 618
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 618
gcagatactg catcaggaac tgactggata agacttaatc            40

<210> SEQ ID NO 619
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 619
ccccatcagt tcctaatgca ttgccttcag catctaaaca            40

<210> SEQ ID NO 620
<211> LENGTH: 40
<212> TYPE: DNA
<213> ORGANISM: Artificial Sequence
<220> FEATURE:
<223> OTHER INFORMATION: oligonucleotide probe -continued

<400> SEQUENCE: 620
gggctttcct ttgtgcttga tctaaccatg tggtggaacg                              40

<210> SEQ ID NO 621
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 621
gtggtggaac gatggaaacg gaacatggtt ctgtcaagca                              40

<210> SEQ ID NO 622
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 622
tcctgattgt ccaaacgcaa ttctcgagtc tctggctccg                              40

<210> SEQ ID NO 623
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 623
ctctggctcc ggccgagagt tgcgtctgga cgtcccgagc                              40

<210> SEQ ID NO 624
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 624
caacagctac attgtctgct gggtttcagg ctacctggaa                              40

<210> SEQ ID NO 625
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 625
ggcatacaat gtagattct gtgtttgtta ggcaacagct                               40

<210> SEQ ID NO 626
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 626
ttggtaatca gcagctacat ctggctactg ggtctctggt                              40

<210> SEQ ID NO 627
<211> LENGTH: 40
<212> TYPE: DNA

```
<213> ORGANISM: Artificial Sequence
<220> FEATURE:
<223> OTHER INFORMATION: oligonucleotide probe

<400> SEQUENCE: 627
agagtgtcag tttgtcaaat accccaagtg tggctcatgc                              40

<210> SEQ ID NO 628
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 628
taagtcacta gtggttccgt ttagtagatg gtctgtgcat                              40

<210> SEQ ID NO 629
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 629
tgcattgttt caaaatggtg ccctagtgac tacaaagccc                              40

<210> SEQ ID NO 630
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 630
tagactgaag atctaaaggt ccctggttcg atcccgggtt                              40

<210> SEQ ID NO 631
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 631
aatctgaagg tcgtgagttc gatcctcaca cggggcacca                              40

<210> SEQ ID NO 632
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 632
agcagagtgg cgcagcggaa gcgtgctggg cccataaccc                              40

<210> SEQ ID NO 633
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 633
cccataaccc agaggtcgat ggatcgaaac catcctctgc                              40
```

<210> SEQ ID NO 634
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 634
tgcgttgtgg ccgcagcaac ctcggttcga atccgagtca                           40

<210> SEQ ID NO 635
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 635
gctcgttggt ctagggtat gattctcgct ttgggtgcga                            40

<210> SEQ ID NO 636
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 636
agctgtttag cgacagagtg gttcaattcc acctttcggg                           40

<210> SEQ ID NO 637
<211> LENGTH: 40
<212> TYPE: DNA
<213> ORGANISM: Artificial Sequence
<220> FEATURE:
<223> OTHER INFORMATION: oligonucleotide probe

<400> SEQUENCE: 637
ttccgtagtg tagtggttat cacgctcgcc tgacacgcga                           40

<210> SEQ ID NO 638
<211> LENGTH: 32
<212> TYPE: DNA
<213> ORGANISM: Artificial Sequence
<220> FEATURE:
<221> NAME/KEY: misc_feature
<222> LOCATION: 25, 26, 27, 28, 29, 30, 31, 32
<223> OTHER INFORMATION: n = A,T,C or G
<220> FEATURE:
<223> OTHER INFORMATION: oligonucleotide probe

<400> SEQUENCE: 638
aaaaaaaaaa aaaaaaaaaa aaaannnnnn nn                                   32

<210> SEQ ID NO 639
<211> LENGTH: 11
<212> TYPE: DNA
<213> ORGANISM: Artificial Sequence
<220> FEATURE:
<221> NAME/KEY: misc_feature
<222> LOCATION: 4, 5, 6, 7, 8, 9, 10, 11
<223> OTHER INFORMATION: n = A,T,C or G
<220> FEATURE:
<223> OTHER INFORMATION: oligonucleotide probe

<400> SEQUENCE: 639
aaannnnnnn n                                                          11

```
<210> SEQ ID NO 640
<211> LENGTH: 46
<212> TYPE: DNA
<213> ORGANISM: Artificial Sequence
<220> FEATURE:
<221> NAME/KEY: misc_feature
<222> LOCATION: 39, 40, 41, 42, 43, 44, 45, 46
<223> OTHER INFORMATION: n = A,T,C or G
<220> FEATURE:
<223> OTHER INFORMATION: oligonucleotide probe

<400> SEQUENCE: 640
gccagtgaat tgtaatacga ctcactatag ggaggcggnn nnnnnn            46

<210> SEQ ID NO 641
<211> LENGTH: 99
<212> TYPE: DNA
<213> ORGANISM: Homo sapiens

<400> SEQUENCE: 641
gtcagcagtg ccttagcagc acgtaaatat tggcgttaag attctaaaat tatctccagt    60
attaactgtg ctgctgaagt aaggttgacc atactctac                          99

<210> SEQ ID NO 642
<211> LENGTH: 99
<212> TYPE: DNA
<213> ORGANISM: Homo sapiens

<400> SEQUENCE: 642
gtcagcagtg ccttagcagc acgtaaatat tggcgttaag attctaaaat tatctccagt    60
attaactgtg ctgctgaagt aaggttgacc atactttac                          99

<210> SEQ ID NO 643
<211> LENGTH: 94
<212> TYPE: DNA
<213> ORGANISM: Homo sapiens

<400> SEQUENCE: 643
cctgttgcca caaacccgta gatccgaact tgtggtatta gtccgcacaa gcttgtatct    60
ataggtatgt gtctgttagg caatctcacg gacc                               94

<210> SEQ ID NO 644
<211> LENGTH: 94
<212> TYPE: DNA
<213> ORGANISM: Homo sapiens

<400> SEQUENCE: 644
cctgttgcca caaacccgta gatccgaact tgtggtatta gtccgcacaa gcttgtatct    60
ataggtatgt gtctgttagg caatctcaca gacc                               94

<210> SEQ ID NO 645
<211> LENGTH: 150
<212> TYPE: DNA
<213> ORGANISM: Homo sapiens

<400> SEQUENCE: 645
acctctctaa caaggtgcag agcttagctg attggtgaac agtgattggt ttccgctttg    60
ttcacagtgg ctaagttctg cacctgaaga gaaggtgaga tggggacagt taagttggag   120
ccgctggggc agaggccgtt gctgacgggc                                    150

<210> SEQ ID NO 646
```

```
<211> LENGTH: 150
<212> TYPE: DNA
<213> ORGANISM: Homo sapiens

<400> SEQUENCE: 646
acctctctaa caaggtgcag agcttagctg attggtgaac agtgattggt ttccgctttg     60
ttcacagtgg ctaagttctg cacctgaaga aaggtgaga tggggacagt taagttggag    120
ccgctggggc agaggccgtt gctgacaggc                                     150

<210> SEQ ID NO 647
<211> LENGTH: 86
<212> TYPE: DNA
<213> ORGANISM: Homo sapiens

<400> SEQUENCE: 647
tgcttcccga ggccacatgc ttctttatat ccccatatgg attactttgc tatggaatgt     60
aaggaagtgt gtggtttcgg caagtg                                          86

<210> SEQ ID NO 648
<211> LENGTH: 97
<212> TYPE: DNA
<213> ORGANISM: Homo sapiens

<400> SEQUENCE: 648
gtgctcggtt tgtaggcagt gtcattagct gattgtactg tggtggttac aatcactaac     60
tccactgcca tcaaaacaag gcacagcatc accgccg                              97

<210> SEQ ID NO 649

<400> SEQUENCE: 649

000

<210> SEQ ID NO 650
<211> LENGTH: 97
<212> TYPE: DNA
<213> ORGANISM: Homo sapiens

<400> SEQUENCE: 650
gtgctcggtt tgtaggcagt gtcattagct gattgtactg tggtggttac aatcactaac     60
tccactgcca tcaaaacaag gcacagcatc accaccg                              97

<210> SEQ ID NO 651
<211> LENGTH: 294
<212> TYPE: DNA
<213> ORGANISM: Homo sapiens

<400> SEQUENCE: 651
cttctggaag ctggtttcac atggtggctt agattttttcc atctttgtat ctagcaccat    60
ttgaaatcag tgttttagga gtaagaattg cagcacagcc aagggtggac tgcagaggaa   120
ctgctgctca tggaactggc tcctctcctc ttgccacttg agtctgttcg agaagtccag   180
ggaagaactt gaagagcaaa atacactctt gagtttgttg ggttttggga gaggtgacag   240
tagagaaggg ggttgtgttt aaaataaaca cagtggcttg agcaggggca gagg         294

<210> SEQ ID NO 652
<211> LENGTH: 294
<212> TYPE: DNA
<213> ORGANISM: Homo sapiens

<400> SEQUENCE: 652
```

-continued

```
cttctggaag ctggtttcac atggtggctt agatttttcc atctttgtat ctagcaccat    60
ttgaaatcag tgttttagga gtaagaattg cagcacagcc aagggtggac tgcagaggaa   120
ctgctgctca tggaactggc tcctctcctc ttgccacttg agtctgttcg agaagtccag   180
ggaagaactt gaagagcaaa atacactctt gagtttgttg ggttttggga gaggtgacag   240
tagagaaggg ggttgtgttt aaaataaaca cagtggcttg agcaggggca gaag         294
```

<210> SEQ ID NO 653
<211> LENGTH: 295
<212> TYPE: DNA
<213> ORGANISM: Homo sapiens

<400> SEQUENCE: 653

```
cttctggaag ctggtttcac atggtggctt agatttttcc atctttgtat ctagcaccat    60
ttgaaatcag tgttttagga gtaagaattg cagcacagcc aagggtggac tgcagaggaa   120
ctgctgctca tggaactggc tcctctcctc ttgccacttg agtctgttcg agaagtccag   180
ggaagaaact tgaagagcaa atacactctt gagtttgtt gggttttggg agaggtgaca   240
gtagagaagg gggttgtgtt taaaataaac acagtggctt gagcaggggc agagg        295
```

<210> SEQ ID NO 654
<211> LENGTH: 183
<212> TYPE: DNA
<213> ORGANISM: Homo sapiens

<400> SEQUENCE: 654

```
ggtcgggctc accatgacac agtgtgagac ctcgggctac aacacaggac ccgggcgctg    60
ctctgacccc tcgtgtcttg tgttgcagcc ggagggacgc aggtccgcag cagagcctgc   120
tccgcttgtc ctgagggact cgacacaggg gactgcacag agaccatggg aaagtccagg   180
ctc                                                                 183
```

<210> SEQ ID NO 655
<211> LENGTH: 183
<212> TYPE: DNA
<213> ORGANISM: Homo sapiens

<400> SEQUENCE: 655

```
ggtcgggctc accatgacac agtgtgagac ctcgggctac aacacaggac ccgggcgctg    60
ctctgacccc tcgtgtcttg tgttgcagcc ggagggacgc aggtccgcag cagagcctgc   120
tccgcttgtc ctgagggact cgacacaggg gactgcacag agaccatggg aaagtccagg   180
ccc                                                                 183
```

<210> SEQ ID NO 656
<211> LENGTH: 183
<212> TYPE: DNA
<213> ORGANISM: Homo sapiens

<400> SEQUENCE: 656

```
ggtcgggctc accatgacac agtgtgagac tcgagctaca acacaggacc cggggcgctg    60
ctctgacccc tcgtgtcttg tgttgcagcc ggagggacgc aggtccgcag cagagcctgc   120
tccgcttgtc ctgagggact cgacacaggg gactgcacag agaccatggg aaagtccagg   180
ctc                                                                 183
```

<210> SEQ ID NO 657
<211> LENGTH: 203

```
<212> TYPE: DNA
<213> ORGANISM: Homo sapiens

<400> SEQUENCE: 657
gatttaggat gagttgagat cccagtgatc ttctcgctaa gagtttcctg cctgggcaag      60
gaggaaagat gctacaagtg gcccacttct gagatgcggg ctgcttctgg atgacactgc     120
ttcccgaggc cacatgcttc tttatatccc catatggatt actttgctat ggaatgtaag     180
gaagtgtgtg gtttcggcaa gtg                                             203

<210> SEQ ID NO 658
<211> LENGTH: 203
<212> TYPE: DNA
<213> ORGANISM: Homo sapiens

<400> SEQUENCE: 658
gatttaggat gagttgagat cccagtgatc ttctcgctaa gagtttcctg cctgggcaag      60
gaggaaagat gctacaagtg gcccacttct gagatgcggg ctgcttctgg atgacactgc     120
ttcccgaggc cacatgcttc tttatatccc catatggatt acttttctat ggaatgtaag     180
gaagtgtgtg gtttcggcaa gtg                                             203

<210> SEQ ID NO 659
<211> LENGTH: 203
<212> TYPE: DNA
<213> ORGANISM: Homo sapiens

<400> SEQUENCE: 659
gttttaggat gagttgagat cccagtgatc ttctcgctaa gagtttcctg cctgggcaag      60
gaggaaagat gctacaagtg gcccacttct gagatgcggg ctgcttctgg atgacactgc     120
ttcccgaggc cacatgcttc tttatatccc catatggatt acttttctat ggaatgtaag     180
gaagtgtgtg gtttcggcaa gtg                                             203

<210> SEQ ID NO 660
<211> LENGTH: 120
<212> TYPE: DNA
<213> ORGANISM: Homo sapiens

<400> SEQUENCE: 660
cgaggtgcag accctgggag caccactggc ccatctctta cacaggctga ccgatttctc      60
ctggtgttca gagtctgttt ttgtctagca ccatttgaaa tcggttatga tgtaggggga     120

<210> SEQ ID NO 661
<211> LENGTH: 120
<212> TYPE: DNA
<213> ORGANISM: Homo sapiens

<400> SEQUENCE: 661
caaggtgcag accctgggag caccactggc ccatctctta cacaggctga ccgatttctc      60
ctggtgttca gagtctgttt ttgtctagca ccatttgaaa tcggttatga tgtaggggga     120

<210> SEQ ID NO 662
<211> LENGTH: 85
<212> TYPE: DNA
<213> ORGANISM: Homo sapiens

<400> SEQUENCE: 662
ccttagcaga gctgtggagt gtgacaatgg tgtttgtgtc taaactatca aacgccatta      60
tcacactaaa tagctactgc taggc                                            85
```

```
<210> SEQ ID NO 663
<211> LENGTH: 85
<212> TYPE: DNA
<213> ORGANISM: Homo sapiens

<400> SEQUENCE: 663
ccttagcaga gctgtggagt gtgacaatgg tgtttgtgtc taaactatca aatgccatta      60
tcacactaaa tagctactgc taggc                                           85

<210> SEQ ID NO 664
<211> LENGTH: 81
<212> TYPE: DNA
<213> ORGANISM: Homo sapiens

<400> SEQUENCE: 664
cttcaggaag ctggtttcat atggtggttt agatttaaat agtgattgtc tagcaccatt      60
tgaaatcagt gttcttgggg g                                               81
```

DIAGNOSIS AND TREATMENT OF CANCERS WITH MICRORNA LOCATED IN OR NEAR CANCER-ASSOCIATED CHROMOSOMAL FEATURES

RELATED APPLICATIONS

This application is a divisional of U.S. application Ser. No. 12/767,279, filed Apr. 26, 2010, now abandoned, which is a continuation of U.S. application Ser. No. 11/194,055, filed Jul. 29, 2005, now U.S. Pat. No. 7,723,030, which is a continuation-in-part of International Application No. PCT/US2005/004865, filed Feb. 9, 2005, which claims the benefit of U.S. Provisional Application No. 60/543,119, filed Feb. 9, 2004, U.S. Provisional Application No. 60/542,929, filed Feb. 9, 2004, U.S. Provisional Application No. 60/542,963, filed Feb. 9, 2004, U.S. Provisional Application No. 60/542,940, filed Feb. 9, 2004, U.S. Provisional Application No. 60/580,959, filed Jun. 18, 2004, and U.S. Provisional Application No. 60/580,797, filed Jun. 18, 2004. The entire teachings of the above applications are incorporated herein by reference.

GOVERNMENT SUPPORT

The invention described herein was supported in part by grant nos. P01CA76259, P01CA81534, and P30CA56036 from the National Cancer Institute. The U.S. government has certain rights in this invention

INCORPORATION BY REFERENCE OF MATERIAL IN ASCII TEXT FILE

This application incorporates by reference the Sequence Listing contained in the following ASCII text file being submitted concurrently herewith:
   a) File name: 35891018015 SEQUENCELISTING.txt; created Aug. 21, 2013, 128 KB in size.

FIELD OF THE INVENTION

The invention relates to the diagnosis of cancers, or the screening of individuals for the predisposition to cancer, by evaluating the status of at least one miR gene located in close proximity to chromosomal features, such as cancer-associated genomic regions, fragile sites, human papilloma virus integration sites, and homeobox genes and gene clusters. The invention also relates to the treatment of cancers by altering the amount of gene product produced from miR genes located in close proximity to these chromosomal features. The invention further provides methods of diagnosing CLL and other cancers by screening for mutations in miR genes.

BACKGROUND OF THE INVENTION

Taken as a whole, cancers are a significant source of mortality and morbidity in the U.S. and throughout the world. However, cancers are a large and varied class of diseases with diverse etiologies. Researchers therefore have been unable to develop treatments or diagnostic tests which cover more than a few types of cancer.

For example, cancers are associated with many different classes of chromosomal features. One such class of chromosomal features are perturbations in the genomic structure of certain genes, such as the deletion or mutation of tumor suppressor genes. The activation of proto-oncogenes by gene amplification or promoter activation (e.g., by viral integration), epigenetic modifications (e.g., a change in DNA methylation) and chromosomal translocations can also cause cancerigenesis. Such perturbations in the genomic structure which are involved in the etiology of cancers are called "cancer-associated genomic regions" or "CAGRs."

Chromosomal fragile sites are another class of chromosomal feature implicated in the etiology of cancers. Chromosomal fragile sites are regions of genomic DNA which show an abnormally high occurrence of gaps or breaks when DNA synthesis is perturbed during metaphase. These fragile sites are categorized as "rare" or "common." As their name suggests, rare fragile sites are uncommon. Such sites are associated with di- or tri-nucleotide repeats, can be induced in metaphase chromosomes by folic acid deficiency, and segregate in a Mendelian manner. An exemplary rare fragile site is the Fragile X site.

Common fragile sites are revealed when cells are grown in the presence of aphidocolin or 5-azacytidine, which inhibit DNA polymerase. At least eighty-nine common fragile sites have been identified, and at least one such site is found on every human chromosome. Thus, while their function is poorly understood, common fragile sites represent a basic component of the human chromosome structure.

Induction of fragile sites in vitro leads to increased sister-chromatid exchange and a high rate of chromosomal deletions, amplifications and translocations, while fragile sites have been colocalized with chromosome breakpoints in vivo. Also, most common fragile sites studied in tumor cells contain large, intra-locus deletions or translocations, and a number of tumors have been identified with deletions in multiple fragile sites. Chromosomal fragile sites are therefore mechanistically involved in producing many of the chromosomal lesions commonly seen in cancer cells.

Cervical cancer, which is the second leading cause of female cancer mortality worldwide, is highly associated with human papillomavirus (HPV) infection. Indeed, sequences from the HPV 16 or HPV 18 viruses are found in cells from nearly every cervical tumor cell examined. In malignant forms of cervical cancer, the HPV genome is found integrated into the genome of the cancer cells. HPV preferentially integrates in or near common chromosomal fragile sites. HPV integration into a host cell genome can cause large amplification, deletions or rearrangements near the integration site. Expression of cellular genes near the HPV integration site can therefore be affected, which may contribute to the oncogenesis of the infected cell. These sites of HPV integration into a host cell genome are therefore considered another class of chromosomal feature that is associated with a cancer.

Homeobox genes are a conserved family of regulatory genes that contain the same 183-nucleotide sequence, called the "homeobox." The homeobox genes encode nuclear transcription factors called "homeoproteins," which regulate the expression of numerous downstream genes important in development. The homeobox sequence itself encodes a 61 amino acid "homeodomain" that recognizes and binds to a specific DNA binding motif in the target developmental genes. Homeobox genes are categorized as "class I" or "clustered" homeobox genes, which regulate antero-posterior patterning during embryogenesis, or "class II" homeobox genes, which are dispersed throughout the genome. Altogether, the homeobox genes account for more than 0.1% of the vertebrate genome.

The homeobox genes are believed to "decode" external inductive stimuli that signal a given cell to proceed down a particular developmental lineage. For example, specific homeobox genes might be activated in response to various growth factors or other external stimuli that activate signal transduction pathways in a cell. The homeobox genes then activate and/or repress specific programs of effector or developmental genes (e.g., morphogenetic molecules, cell-cycle regulators, pro- or anti-apoptotic proteins, etc.) to induce the phenotype "ordered" by the external stimuli. The homeobox system is clearly highly coordinated during embryogenesis and morphogenesis, but appears to be dysregulated during oncogenesis. Such dysregulation likely occurs because of disruptions in the genomic structure or chromosomal architecture surrounding the homeobox genes or gene clusters. The homeobox genes or gene clusters are therefore considered yet another chromosomal feature which are associated with cancers.

Micro RNAs (miRs) are naturally-occurring 19 to 25 nucleotide transcripts found in over one hundred distinct organisms, including fruit flies, nematodes and humans. The miRs are typically processed from 60- to 70-nucleotide foldback RNA precursor structures, which are transcribed from the miR gene. The miR precursor processing reaction requires Dicer RNase III and Argonaute family members (Sasaki et al. (2003), *Genomics* 82, 323-330). The miR precursor or processed miR products are easily detected, and an alteration in the levels of these molecules within a cell can indicate a perturbation in the chromosomal region containing the miR gene.

To date, at least 222 separate miR genes have been identified in the human genome. Two miR genes (miR15a and miR16a) have been localized to a homozygously deleted region on chromosome 13 that is correlated with chronic lymphocytic leukemia (Calin et al. (2002), *Proc. Natl. Acad. Sci. USA* 99:15524-29), and the miR-143/miR145 gene cluster is downregulated in colon cancer (Michael et al. (2003), *Mol. Cancer. Res.* 1:882-91). However, the distribution of miR genes throughout the genome, and the relationship of the miR genes to the diverse chromosomal features discussed herein, has not been systematically studied.

A method for reliably and accurately diagnosing, or for screening individuals for a predisposition to, cancers associated with such diverse chromosomal features as CAGRs, fragile sites, HPV integration sites and homeobox genes is needed. A method of treating cancers associated with these diverse chromosomal features is also highly desired.

SUMMARY OF THE INVENTION

It has now been discovered that miR genes are commonly associated with chromosomal features involved in the etiology of different cancers. The perturbations in the genomic structure or chromosomal architecture of a cell caused by a cancer-associated chromosomal feature can affect the expression of the miR gene(s) located in close proximity to that chromosomal feature. Evaluation of miR gene expression can therefore be used to indicate the presence of a cancer-causing chromosomal lesion in a subject. As the change in miR gene expression level caused by a cancer-associated chromosomal feature may also contribute to cancerigenesis, a given cancer can be treated by restoring the level of miR gene expression to normal.

The invention therefore provides a method of diagnosing cancer in a subject. The cancer can be any cancer associated with a cancer-associated chromosomal feature. As used herein, a cancer-associated chromosomal feature includes, but is not limited to, a cancer-associated genomic region, a chromosomal fragile site, a human papillomavirus integration site on a chromosome of the subject, and a homeobox gene or gene cluster on a chromosome of the subject. The cancer can also be any cancer associated with one or more adverse prognostic markers, including cancers associated with positive ZAP-70 expression, an unmutated $IgV_H$ gene, positive CD38 expression, deletion at chromosome 11q23, and loss or mutation of TP53. In one embodiment, the diagnostic method comprises the following steps. In a sample obtained from a subject suspected of having a cancer associated with a cancer-associated chromosomal feature, the status of at least one miR gene located in close proximity to the cancer-associated chromosomal feature is evaluated by measuring the level of at least one miR gene product from the miR gene in the sample, provided the miR genes are not miR-15, miR-16, miR-143 or miR-145. An alteration in the level of miR gene product in the sample relative to the level of miR gene product in a control sample is indicative of the presence of the cancer in the subject. In a related embodiment, the diagnostic method comprises evaluating in a sample obtained from a subject suspected of having a cancer associated with a cancer-associated chromosomal feature, the status of at least one miR gene located in close proximity to the cancer-associated chromosomal feature, provided the miR gene is not miR-15 or miR-16, by measuring the level of at least one miR gene product from the miR gene in the sample. An alteration in the level of miR gene product in the sample relative to the level of miR gene product in a control sample is indicative of the presence of the cancer in the subject.

The status of the at least one miR gene in the subject's sample can also be evaluated by analyzing the at least one miR gene for a deletion, mutation and/or amplification. The detection of a deletion, mutation and/or amplification in the miR gene relative to the miR gene in a control sample is indicative of the presence of the cancer in the subject. The status of the at least one miR gene in the subject's sample can also be evaluated by measuring the copy number of the at least one miR gene in the sample, wherein a copy number other than two for miR genes located on any chromosome other than a Y chromosome, and other than one for miR genes located on a Y chromosome, is indicative of the subject either having or being at risk for having a cancer. In one embodiment, the diagnostic method comprises analyzing at least one miR gene in the sample for a deletion, mutation and/or amplification, wherein detection of a deletion, mutation and/or amplification in the miR gene relative to the miR gene in a control sample is indicative of the presence of the cancer in the subject. In a related embodiment, the diagnostic method comprises analyzing at least one miR gene in the sample for a deletion, mutation or amplification, provided the miR gene is not miR-15 or miR-16, wherein detection of a deletion, mutation and/or amplification in the miR gene relative to the miR gene in a control sample is indicative of the presence of the cancer in the subject. In a further embodiment, the diagnostic method comprises analyzing the miR-16 gene in the sample for a specific mutation, depicted in SEQ ID NO. 642, wherein detection of the mutation in the miR-16 gene relative to a miR-16 gene in a control sample is indicative of the presence of the cancer in the subject.

The invention also provides a method of screening subjects for a predisposition to develop a cancer associated with a cancer-associated chromosomal feature, by evaluating the status of at least one miR gene located in close proximity to the cancer-associated chromosomal feature in the same manner described herein for the diagnostic method. The cancer can be any cancer associated with a cancer-associated chromosomal feature.

In one embodiment, the level of the at least one miR gene product from the sample is measured by quantitatively reverse transcribing the miR gene product to form a complementary target oligodeoxynucleotide, and hybridizing the target oligodeoxynucleotide to a microarray comprising a probe oligonucleotide specific for the miR gene product. In another embodiment, the levels of multiple miR gene products in a sample are measured in this fashion, by quantitatively reverse transcribing the miR gene products to form complementary target oligodeoxynucleotides, and hybridizing the target oligodeoxynucleotides to a microarray comprising probe oligonucleotides specific for the miR gene products. In another embodiment, the multiple miR gene products are simultaneously reverse transcribed, and the resulting set of target oligodeoxynucleotides are simultaneously exposed to the microarray.

In a related embodiment, the invention provides a method of diagnosing cancer in a subject, comprising reverse transcribing total RNA from a sample from the subject to provide a set of labeled target oligodeoxynucleotides; hybridizing the target oligodeoxynucleotides to a microarray comprising miRNA-specific probe oligonucleotides to provide a hybridization profile for the sample; and comparing the sample hybridization profile to the hybridization profile generated from a control sample, an alteration in the profile being indicative of the subject either having, or being at risk for developing, a cancer. The microarray of miRNA-specific probe oligonucleotides preferably comprises miRNA-specific probe oligonucleotides for a substantial portion of the human miRNome, the full complement of microRNA genes in a cell. The microarray more preferably comprises at least about 60%, 70%, 80%, 90%, or 95% of the human miRNome. In one embodiment, the cancer is associated with a cancer-associated chromosomal feature, such as a cancer-associated genomic region or a chromosomal fragile site. In another embodiment, the cancer is associated with one or more adverse prognostic markers. In a particular embodiment, the cancer is B-cell chronic lymphocytic leukemia. In a further embodiment, the cancer is a subset of B-cell chronic lymphocytic leukemia that is associated with one or more adverse prognostic markers. As used herein, an adverse prognostic marker is any indicator, such as a specific genetic alteration or a level of expression of a gene, whose presence suggests an unfavorable prognosis concerning disease progression, the severity of the cancer, and/or the likelihood of developing the cancer.

The invention further provides a method of treating a cancer associated with a cancer-associated chromosomal feature in a subject. The cancer can be any cancer associated with a cancer-associated chromosomal feature, for example, cancers associated with a cancer-associated genomic region, a chromosomal fragile site, a human papillomavirus integration site on a chromosome of the subject, or a homeobox gene or gene cluster on a chromosome of the subject. Furthermore, the cancer is a cancer associated with a cancer-associated chromosomal feature in which at least one isolated miR gene product from a miR gene located in close proximity to the cancer-associated chromosomal feature is down-regulated or up-regulated in cancer cells of the subject, as compared to control cells. When the at least one isolated miR gene product is down regulated in the subject's cancer cells, the method comprises administering to the subject, an effective amount of at least one isolated miR gene product from the at least one miR gene, such that proliferation of cancer cells in the subject is inhibited. When the at least one isolated miR gene product is up-regulated in the cancer cells, an effective amount of at least one compound for inhibiting expression of the at least one miR gene is administered to the subject, such that proliferation of cancer cells in the subject is inhibited.

The invention further provides a method of treating cancer associated with a cancer-associated chromosomal feature in a subject, comprising the following steps. The amount of miR gene product expressed from at least one miR gene located in close proximity to the cancer-associated chromosomal region in cancer cells from the subject is determined relative to control cells. If the amount of the miR gene product expressed in the cancer cells is less than the amount of the miR gene product expressed in control cells, the amount of miR gene product expressed in the cancer cells is altered by administering to the subject an effective amount of at least one isolated miR gene product from the miR gene, such that proliferation of cancer cells in the subject is inhibited. If the amount of the miR gene product expressed in the cancer cells is greater than the amount of the miR gene product expressed in control cells, the amount of miR gene product expressed in the cancer cells is altered by administering to the subject an effective amount of at least one compound for inhibiting expression of the at least one miR gene, such that proliferation of cancer cells in the subject is inhibited.

The invention further provides pharmaceutical compositions comprising a pharmaceutically acceptable carrier and at least one miR gene product, or a nucleic acid expressing at least one miR gene product, from an miR gene located in close proximity to a cancer-associated chromosomal feature, provided the miR gene product is not miR-15 or miR-16.

The invention still further provides for the use of at least one miR gene product, or a nucleic acid expressing at least one miR gene product, from an miR gene located in close proximity to a cancer-associated chromosomal feature for the manufacture of a medicament for the treatment of a cancer associated with a cancer-associated chromosomal region.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7A is a schematic depicting the locations of mutations affecting various miRNAs. The mutated (below chromosome) and normal (above chromosome) nucleotide base is presented for each mutation/polymorphism. The figure is not drawn to scale.

FIG. 7B depicts the RT-PCR amplification products of primary transcripts corresponding to various mutant miR gene products for which mutations have been identified in B-CLL cells, as well as the length of the amplified genomic DNA (G). GAPDH levels were used for normalization; RT+=reverse transcription, RT-=control without reverse transcription, G=genomic control.

DETAILED DESCRIPTION OF THE INVENTION

Figure 1:
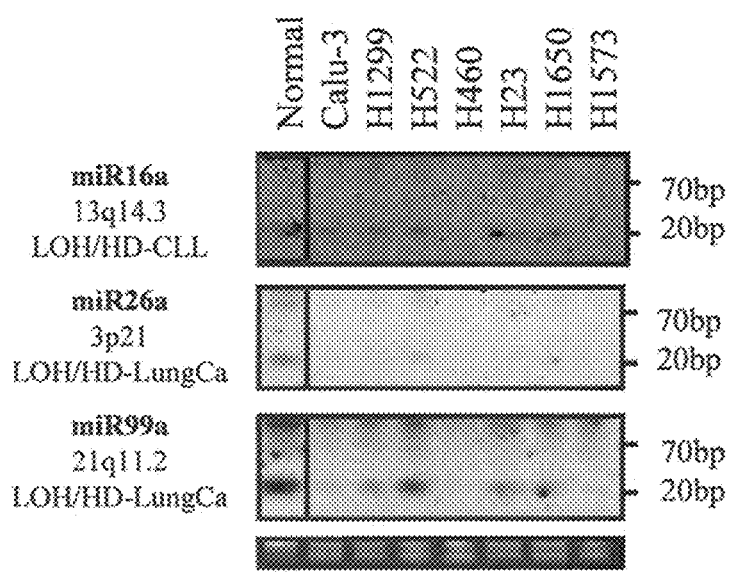
FIG. 1 is an image of a Northern blot analysis of the expression of miR-16a (upper panel), miR-26a (middle panel), and miR-99a (lower panel) in normal human lung (lane 1) and human lung cancer cells (lanes 2-8). Below the three blots is an image of an ethidium bromide-stained gel indicating the 5S RNA lane loading control. The genomic location and the type of alteration are indicated.

All nucleic acid sequences herein are given in the 5' to 3' direction. In addition, genes are represented by italics, and gene products are represented by normal type; e.g., mir-17 is the gene and miR-17 is the gene product.

It has now been discovered that the genes that comprise the miR gene complement of the human genome (or "miR-Nome") are non-randomly distributed throughout the genome in relation to each other. For example, of 222 human miR genes, at least ninety are located in thirty-six gene clusters, typically with two or three miR genes per cluster (median=2.5). The largest cluster is composed of six genes located on chromosome 13 at 13q31; the miR genes in this cluster are miR-17/miR-18/miR-19a/miR-20/miR-19b1/miR-92-1.

The human miR genes are also non-randomly distributed across the human chromosomal complement. For example, chromosome 4 has a less-than-expected rate of miRs, and chromosomes 17 and 19 contain significantly more miR genes than expected based on chromosome size. Indeed, six of the thirty-six miR gene clusters (17%), containing 16 of 90 clustered genes (18%), are located on chromosomes 17 and 19, which account for only 5% of the entire human genome.

The sequences of the gene products of 187 miR genes are provided in Table 1. The location and distribution of these 187 miR genes in the human genome is given in Tables 2 and 3; see also Example 1. All Tables are located in the Examples section below. As used herein, an "miR gene product" or "miRNA" means the unprocessed or processed RNA transcript from an miR gene. As the miR gene products are not translated into a protein, the term "miR gene products" does not include proteins.

A used herein, "probe oligonucleotide" refers to an oligonucleotide that is capable of hybridizing to a target oligonucleotide. "Target oligonucleotide" or "target oligodeoxynucleotide" refers to a molecule to be detected (e.g., in a hybridization). By "miR-specific probe oligonucleotide" or "probe oligonucleotide specific for an miR" is meant a probe oligonucleotide that has a sequence selected to hybridize to a specific miR gene product, or to a reverse transcript of the specific miR gene product.

The unprocessed miR gene transcript is also called an "miR precursor," and typically comprises an RNA transcript of about 70 nucleotides in length. The miR precursor can be processed by digestion with an RNAse (such as, Dicer, Argonaut, or RNAse III, e.g., E. coli RNAse III)) into an active 19-25 nucleotide RNA molecule. This active 19-25 nucleotide RNA molecule is also called the "processed miR gene transcript."

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAase III). It is understood that the active 19-25 nucleotide RNA molecule can also be produced directly by biological or chemical syntheses, without having been processed from the miR precursor. For ease of discussion, such a directly produced active 19-25 nucleotide RNA molecule is also referred to as a "processed miR gene product."

As used herein, "miR gene expression" refers to the production of miR gene products from an miR gene, including processing of the miR precursor into a processed miR gene product.

The human miR genes are closely associated with different classes of chromosomal features that are themselves associated with cancer. As used herein, a "cancer-associated chromosomal feature" refers to a region of a given chromosome, which, when perturbed, is correlated with the occurrence of at least one human cancer. As used herein, a chromosomal feature is "correlated" with a cancer when the feature and the cancer occur together in individuals of a study population in a manner not expected on the basis of chance alone.

A region of a chromosome is "perturbed" when the chromosomal architecture or genomic DNA sequence in that region is disturbed or differs from the normal architecture or sequence in that region. Exemplary perturbations of chromosomal regions include, e.g., chromosomal breakage and translocation, mutations, deletions or amplifications of genomic DNA, a change in the methylation pattern of genomic DNA, the presence of fragile sites, and the presence of viral integration sites. One skilled in the art would recognize that other chromosomal perturbations associated with a cancer are possible.

It is understood that a cancer-associated chromosomal feature can be a chromosomal region where perturbations are known to occur at a higher rate than at other regions in the genome, but where the perturbation has not yet occurred. For example, a common chromosomal breakpoint or fragile site is considered a cancer-associated chromosomal feature, even if a break has not yet occurred. Likewise, a region in the genomic DNA known as a mutational "hotspot" can be a cancer-associated chromosomal feature, even if no mutations have yet occurred in the region.

One class of cancer-associated chromosomal feature which is closely associated with miR genes in the human genome is a "cancer-associated genomic region" or "CAGR" (see Table 4). As used herein, a "CAGR" includes any region of the genomic DNA that comprises a genetic or epigenetic change (or the potential for a genetic or epigenetic change) that differs from normal DNA, and which is correlated with a cancer. Exemplary genetic changes include single- and double-stranded breaks (including common breakpoint regions in or near possible oncogenes or tumor-suppressor genes); chromosomal translocations; mutations, deletions, insertions (including viral, plasmid or transposon integrations) and amplifications (including gene duplications) in the DNA; minimal regions of loss-of-heterozygosity (LOH) suggestive of the presence of tumor-suppressor genes; and minimal regions of amplification suggestive of the presence of oncogenes. Exemplary epigenetic changes include any changes in DNA methylation patterns (e.g., DNA hyper- or hypo-methylation, especially in promoter regions). As used herein, "cancer-associated genomic region" or "CAGR" specifically excludes chromosomal fragile sites or human papillomavirus insertion sites.

Many of the known miR genes in the human genome are in or near CAGRs, including 80 miR genes that are located exactly in minimal regions of LOH or minimal regions of amplification correlated to a variety of cancers. Other miR genes are located in or near breakpoint regions, deleted areas, or regions of amplification. The distribution of miR genes in the human genome relative to CAGRs is given in Tables 6 and 7 and in Example 4A below.

As used herein, an miR gene is "associated" with a given CAGR when the miR gene is located in close proximity to the CAGR; i.e., when the miR is located within the same chromosomal band or within 3 megabases (3 Mb) of the CAGR. See Tables 6 and 7 and Example 4A below for a description of cancers which are correlated with CAGRs, and a description of miRs associated with those CAGRs.

For example, cancers associated with CAGRs include leukemia (e.g., AML, CLL, pro-lymphocytic leukemia), lung cancer (e.g., small cell and non-small cell lung carcinoma), esophageal cancer, gastric cancer, colorectal cancer, brain cancer (e.g., astrocytoma, glioma, glioblastoma, medulloblastoma, meningioma, neuroblastoma), bladder cancer, breast cancer, cervical cancer, epithelial cancer, nasopharyngeal cancer (e.g., oral or laryngeal squamous cell carcinoma), lymphoma (e.g., follicular lymphoma), uterine cancer (e.g., malignant fibrous histiocytoma), hepatic cancer (e.g., hepatocellular carcinoma), head-and-neck cancer (e.g., head-and-neck squamous cell carcinoma), renal cancer, male germ cell tumors, malignant mesothelioma, myelodysplastic syndrome, ovarian cancer, pancreatic or biliary cancer, prostate cancer, thyroid cancer (e.g., sporadic follicular thyroid tumors), and urothelial cancer.

Examples of miR genes associated with CAGRs include miR-153-2, let-7i, miR-33a, miR-34a-2, miR34a-1, let-7a-1, let-7d; let-7f-1, miR-24-1, miR-27b, miR-23b, miR-181a; miR-199b, miR-218-1, miR-31, let-7a-2, let-7g, miR-21, miR-32a-1, miR-33b, miR-100, miR-101-1, miR-125b-1, miR-135-1, miR-142 as, miR-142s; miR-144, miR-301, miR-297-3, miR-155(BIC), miR-26a, miR-17, miR-18, miR-19a, miR-19b1, miR-20, miR-92-1, miR-128a, miR-7-3, miR-22, miR-123, miR-132, miR-149, miR-161; miR-177, miR-195, miR-212, let-7c, miR-99a, miR-125b-2, miR-210, miR-135-2, miR-124a-1, miR-208, miR-211, miR-180, miR-145, miR-143, miR-127, miR-136, miR-138-1, miR-154, miR-134, miR-299, miR-203, miR-34, miR-92-2, miR-19b-2, miR-108-1, miR-193, miR-106a, miR-29a, miR-29b, miR-129-1, miR-182s, miR-182as, miR-96, miR-183, miR-32, miR-159-1, miR-192 and combinations thereof.

Specific groupings of miR gene(s) that are associated with a particular cancer are evident from Tables 6 and 7, and are preferred. For example, acute myeloid leukemia (AML) is associated with miR-153-2, and adenocarcinoma of the lung or esophagus is associated with let-7i. Where more than one miR gene is listed in Tables 6 and 7, it is understood that the cancer associated with those genes can be diagnosed by evaluating any one of the listed miR genes, or by evaluating any combination of the listed miR genes. Subgenera of CAGRs or associated with miR gene(s) would also be evident to one of ordinary skill in the art from Tables 6 and 7.

Another class of cancer-associated chromosomal feature which is closely associated with miR genes in the human genome is a "chromosomal fragile site" or "FRAs" (see Table 4 and Example 2). As used herein, a "FRA" includes any rare or common fragile site in a chromosome; e.g., one that can be induced by subjecting a cell to stress during DNA replication. For example, a rare FRA can be induced by subjecting the cell to folic acid deficiency during DNA replication. A common FRA can be induced by treating the cell with aphidocolin or 5-azacytidine during DNA replication. The identification or induction of chromosomal fragile sites is within the skill in the art; see, e.g., Arlt et al. (2003), *Cytogenet. Genome Res.* 100:92-100 and Arlt et al. (2002), *Genes, Chromosomes and Cancer* 33:82-92, the entire disclosures of which are herein incorporated by reference.

Approximately 20% of the known human miR genes are located in (13 miRs) or within 3 Mb (22 miRs) of cloned FRAs. Indeed, the relative incidence of miR genes inside fragile sites occurs at a rate 9.12 times higher than in non-fragile sites. Moreover, after studying 113 fragile sites in a human karyotype, it was found that 61 miR genes are located in the same chromosomal band as a FRA. The distribution of miR genes in the human genome relative to FRAs is given in Table 5 and in Example 2.

As used herein, an miR gene is "associated" with a given FRA when the miR gene is located in close proximity to the FRA; i.e., when the miR is located within the same chromosomal band or within 3 megabases (3 Mb) of the FRA. See Table 5 and Example 2 for a description of cancers which are correlated with FRAs, and a description of miRs associated with those FRAs.

For example, cancers associated with FRAs include bladder cancer, esophageal cancer, lung cancer, stomach cancer, kidney cancer, cervical cancer, ovarian cancer, breast cancer, lymphoma, Ewing sarcoma, hematopoietic tumors, solid tumors and leukemia.

Examples of miR genes associated with FRAs include miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, miR-175 and combinations thereof.

Specific groupings of miR gene(s) that are associated with a particular cancer and FRA are evident from Table 5, and are preferred. For example, FRA7H is correlated with esophageal cancer, and is associated with miR-29b, miR-29a, miR-96, miR-182s, miR-182 as, miR-183, and miR-129-1. FRA9D is correlated with bladder cancer, and is associated with let7a-1, let-7d, let-7f-1, miR-23b, miR-24-1, and miR-27b. Where more than one miR gene is listed in Table 5 in association with a FRA, it is understood that the cancer associated with those miR genes can be diagnosed by evaluating any one of the listed miR genes, or by evaluating any combination of the listed miR genes. Subgenera of CAGRs and/or associated with miR gene(s) would also be evident to one of ordinary skill in the art from Table 5.

Another class of cancer-associated chromosomal feature which is closely associated with miR genes in the human genome is a "human papillomavirus (HPV) integration site" (see Table 4 and Example 3). As used herein, an "HPV integration site" includes any site in a chromosome of a subject where some or all of an HPV genome can insert into the genomic DNA, or any site where some or all of an HPV genome has inserted into the genomic DNA. HPV integration sites are often associated with common FRAs, but are distinct from FRAs for purposes of the present invention. Any species or strain of HPV can insert some or all of its genome into an HPV integration site. However, the most common strains of HPV which insert some or all of their genomes into an HPV integration site are HPV 16 and HPV 18. The identification of HPV integration sites in the human genome is within the skill in the art; see, e.g., Thorland et al. (2000), Cancer Res. 60:5916-21, the entire disclosure of which is herein incorporated by reference.

Thirteen miR genes (7%) are located within 2.5 Mb of seven of the seventeen (45%) cloned integration sites in the human genome. The relative incidence of miRs at HPV 16 integration sites occurred at a rate 3.22 times higher than in the rest of the genome. Indeed, four miR genes (miR-21, miR-301, miR-142s and miR-142 as) were located within one cluster of integration sites at chromosome 17q23, in which there are three HPV 16 integration events spread over roughly 4 Mb of genomic sequence.

As used herein, an miR gene is "associated" with a given HPV integration site when the miR gene is located in close proximity to the HPV integration site; i.e., when the miR is located within the same chromosomal band or within 3 megabases (3 Mb), preferably within 2.5 Mb, of the HPV integration site. See Table 5 and Example 3 for a description of miRs associated with HPV integration sites.

Insertion of HPV sequences into the genome of subject is correlated with the occurrence of cervical cancer. Examples of miR genes associated with HPV integration sites on human chromosomes include miR-21, miR-301, miR-142 as, miR-142s, miR-194, miR-215, miR-32 and combinations thereof.

Specific groupings of miR gene(s) that are associated with a particular HPV integration site are evident from Table 5, and are preferred. For example, the HPV integration site located in or near FRA9E is associated with miR-32. The HPV integration site located in or near FRA1H is associated with miR-194 and miR-215. The HPV integration site located in or near FRA17B is associated with miR-21, miR-301, miR-142s, and miR-142 as. Where more than one miR gene is listed in Table 5 in relation to an HPV integration site, it is understood that the cancer associated with those miR genes can be diagnosed by evaluating any one of the listed miR genes, or by evaluating any combination of the listed miR genes.

Another class of cancer-associated chromosomal feature which is closely associated with miR genes in the human genome is a "homeobox gene or gene cluster" (see Table 4 and Example 5). As used herein, a "homeobox gene or gene cluster" is a single gene or a grouping of genes, characterized in that the gene or genes have been classified by sequence or function as a class I or class II homeobox gene or contain the 183-nucleotide "homeobox" sequence. Identification and characterization of homeobox genes or gene clusters are within the skill in the art; see, e.g., Cillo et al. (1999), Exp. Cell Res. 248:1-9 and Pollard et al. (2000), Current Biology 10:1059-62, the entire disclosures of which are herein incorporated by reference.

Of the four known class I homeobox gene clusters in the human genome, three contain miR genes: miR-10a and miR-196-1 are in the HOX B cluster on 17q21; miR-196-2 is in the HOX C cluster at 12q13; and miR-10b is in the HOX D cluster at 2q31. Three other miRs (miR-148, miR-152 and miR-148b) are located within 1 Mb of a HOX gene cluster. miR genes are also found within class II homeobox gene clusters; for example, seven microRNAs (miR-129-1, miR-153-2, let-7a-1, let-7f-1, let-7d, miR-202 and miR-139) are located within 0.5 Mb of class II homeotic genes. See Example 5 and FIG. 2 for a description of miRs associated with homeobox genes or gene clusters in the human genome.

Examples of homeobox genes associated with miR genes in the human genome include genes in the HOXA cluster, genes in the HOXB cluster, genes in the HOXC cluster, genes in the HOXD cluster, NK1, NK3, NK4, Lbx, Tlx, Emx, Vax, Hmx, NK6, Msx, Cdx, Xlox, Gsx, En, HB9, Gbx, Msx-1, Msx-2, GBX2, HLX, HEX PMX1, DLX, LHX2 and CDX2. Examples of homeobox gene clusters associated with miR genes in the human genome include HOXA, HOXB, HOXC, HOXD, extended Hox, NKL, ParaHox, and EHGbox, PAX, PBX, MEIS, REIG and PREP/KNOX1.

Examples of cancers associated with homeobox genes or gene clusters include renal cancer, Wilm's tumor, colorectal cancer, small cell lung cancer, melanoma, breast cancer, prostate cancer, skin cancer, osteosarcoma, neuroblastoma, leukemia (acute lymphocytic leukemia, acute myeloid leukemia, chronic lymphocytic leukemia), glioblastoma multiform, medulloblastoma, lymphoplasmacytoid lymphoma, thyroid cancer, rhabdomyosarcoma and solid tumors.

Examples of miR genes associated with homeobox genes or gene clusters include miR-148, miR-10a, miR-196-1, miR-152, miR-196-2, miR-148b, miR-10b, miR-129-1, miR-153-2, miR-202, miR-139, let-7a, let-7f, let-7d and combinations thereof.

Figure 2:
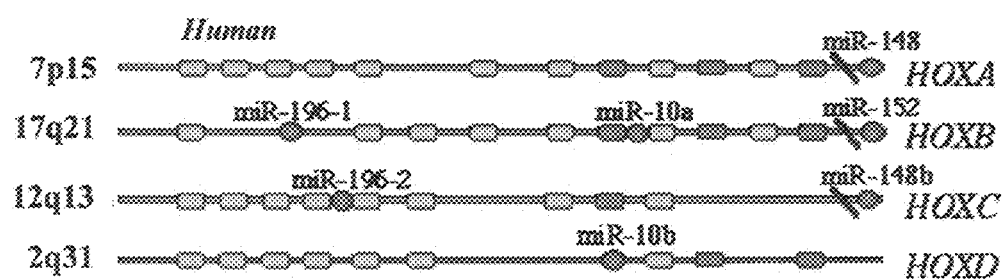
FIG. 2 is a schematic representation demonstrating the position of various miR genes on human chromosomes in relation to HOX gene clusters.

Specific groupings of miR gene(s) that are associated with particular homeobox genes or gene cluster are evident from Example 5 and FIG. 2, and are preferred. For example, homeobox gene cluster HOXA is associated with miR-148. Homeobox gene cluster HOXB is associated with miR-148, miR-10a, miR-196-1, miR-152 and combinations thereof. Homeobox gene cluster HOXC is associated with miR-196-2, miR-148b or a combination thereof. Homeobox gene cluster HOXD, is associated with miR-10b. Where more than one miR gene is associated with a homeobox gene or gene cluster, it is understood that the cancer associated with those genes can be diagnosed by evaluating any one of the miR genes, or by evaluating any combination of the miR genes. In one embodiment, the miR gene or gene product that is measured or analyzed is not miR-15, miR-16, miR-143 and/or miR-145.

Without wishing to be bound by any theory, it is believed that perturbations in the genomic structure or chromosomal architecture of a cell which comprise the cancer-associated chromosomal feature can affect the expression of the miR gene(s) associated with the feature in that cell. For example, a CAGR can comprise an amplification of the region containing an miR gene(s), causing an up-regulation of miR gene expression. Likewise, the CAGR can comprise a chromosomal breakpoint or a deletion that disrupts gene expression, and results in a down-regulation of miR gene expression.

HPV integrations and FRAs can cause deletions, amplifications or rearrangement of the surrounding DNA, which can also affect the structure or expression of any associated miR genes. The factors which cause the collected dysregulation of homeobox genes or gene clusters would cause similar disruptions to any associated miR genes. A change in the status of at least one of the miR genes associated with a cancer-associated chromosomal feature in a tissue or cell sample from a subject, relative to the status of that miR gene in a control sample, therefore is indicative of the presence of a cancer, or a susceptability to cancer, in a subject.

Without wishing to be bound by any theory, it is also believed that a change in status of miR genes associated with a cancer-associated chromosomal feature can be detected prior to, or in the early stages of, the development of transformed or neoplastic phenotypes in cells of a subject. The invention therefore also provides a method of screening subjects for a predisposition to developing a cancer associated with a cancer-associated chromosomal feature, by evaluating the status of at least one miR gene associated with a cancer-associated chromosomal feature in a tissue or cell sample from a subject, relative to the status of that miR gene in a control sample. Subjects with a change in the status of one or more miR genes associated with a cancer-associated chromosomal feature are candidates for further testing to determine or confirm that the subjects have cancer. Such further testing can comprise histological examination of blood or tissue samples, or other techniques within the skill in the art.

As used herein, the "status of an miR gene" refers to the condition of the miR gene in terms of its physical sequence or structure, or its ability to express a gene product. Thus, the status of an miR gene in cells of a subject can be evaluated by any technique suitable for detecting genetic or epigenetic changes in the miR gene, or by any technique suitable for detecting the level of miR gene product produced from the miR gene.

For example, the level of at least one miR gene product produced from an miR gene can be measured in cells of a biological sample obtained from the subject. An alteration in the level (i.e., an up- or down-regulation) of miR gene product in the sample obtained from the subject relative to the level of miR gene product in a control sample is indicative of the presence of the cancer in the subject. As used herein, a "subject" is any mammal suspected of having a cancer associated with a cancer-associated chromosomal feature. In one embodiment, the subject is a human suspected of having a cancer associated with a cancer-associated chromosomal feature. As used herein, expression of an miR gene is "up-regulated" when the amount of miR gene product produced from that gene in a cell or tissue sample from a subject is greater than the amount produced from the same gene in a control cell or tissue sample. Likewise, expression of an miR gene is "down-regulated" when the amount of miR gene product produced from that gene in a cell or tissue sample from a subject is less than the amount produced from the same gene in a control cell or tissue sample.

Methods for determining RNA expression levels in cells from a biological sample are within the level of skill in the art. For example, tissue sample can be removed from a subject suspected of having cancer associated with a cancer-associated chromosomal feature by conventional biopsy techniques. In another example, a blood sample can be removed from the subject, and white blood cells isolated for DNA extraction by standard techniques. The blood or tissue sample is preferably obtained from the subject prior to initiation of radiotherapy, chemotherapy or other therapeutic treatment. A corresponding control tissue or blood sample can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample.

For example, the relative miR gene expression in the control and normal samples can be conveniently determined with respect to one or more RNA expression standards. The standards can comprise, for example, a zero miR gene expression level, the miR gene expression level in a standard cell line, or the average level of miR gene expression previously obtained for a population of normal human controls.

Suitable techniques for determining the level of RNA transcripts of a particular gene in cells are within the skill in the art. According to one such method, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters by, e.g., the so-called "Northern" blotting technique. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes for Northern blot hybridization of a given miR gene product can be produced from the nucleic acid sequences provided in Table 1. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are herein incorporated by reference.

For example, the nucleic acid probe can be labeled with, e.g., a radionuclide such as $^3H$, $^{32}P$, $^{33}P$, $^{14}C$, or $^{35}S$; a heavy metal; or a ligand capable of functioning as a specific binding pair member for a labeled ligand (e.g., biotin, avidin or an antibody), a fluorescent molecule, a chemiluminescent molecule, an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are herein incorporated by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA blotting hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in Table 1, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). The methods for quantitative RT-PCR and variations thereof are within the skill in the art.

In some instances, it may be desirable to simultaneously determine the expression level of a plurality of different of miR genes in a sample. In certain instances, it may be desirable to determine the expression level of the transcripts of all known miR genes correlated with cancer. Assessing cancer-specific expression levels for hundreds of miR genes is time consuming and requires a large amount of total RNA (at least 20 μg for each Northern blot) and autoradiographic techniques that require radioactive isotopes. To overcome these limitations, an oligolibrary in microchip format may be constructed containing a set of probe oligonucleotides specific for a set of miR genes. In one embodiment, the oligolibrary contains probes corresponding to all known miRs from the human genome. The microchip oligolibrary may be expanded to include additional miRNAs as they are discovered.

The microchip is prepared from gene-specific oligonucleotide probes generated from known miRNAs. According to one embodiment, the array contains two different oligonucleotide probes for each miRNA, one containing the active sequence and the other being specific for the precursor of the miRNA. The array may also contain controls such as one or more mouse sequences differing from human orthologs by only a few bases, which can serve as controls for hybridization stringency conditions. tRNAs from both species may also be printed on the microchip, providing an internal, relatively stable positive control for specific hybridization. One or more appropriate controls for non-specific hybridization may also be included on the microchip. For this purpose, sequences are selected based upon the absence of any homology with any known miRNAs.

The microchip may be fabricated by techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g. 6×SSPE/30% formamide at 25° C. for 18 hours, followed by washing in 0.75× TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Images intensities of each spot on the array are proportional to the abundance of the corresponding miR in the patient sample.

The use of the array has several advantages for miRNA expression detection. First, the global expression of several hundred genes can be identified in a same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 μg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures may be associated with established disease markers, or directly with a disease state. As described hereinafter in Example 11, two distinct clusters of human B-cell chronic lymphocytic leukemia (CLL) samples are associated with the presence or the absence of Zap-70 expression, a predictor of early disease progression. As described in Examples 11 and 12, two miRNA signatures were associated with the presence of absence of prognostic markers of disease progression, including Zap-70 expression, mutations in the expressed immunoglobulin variable-region gene $IgV_H$ and deletions at 13q14. Therefore, miR gene expression profiles can be used for diagnosing the disease state of a cancer, such as whether a cancer is malignant or benign, based on whether or not a given profile is representative of a cancer that is associated with one or more established adverse prognostic markers. Prognostic markers that are suitable for this method include ZAP-70 expression, unmutated IgV$_H$ gene, CD38 expression, deletion at chromosome 11q23, loss or mutation of TP53, and any combination thereof.

According to the expression profiling method in one embodiment, total RNA from a sample from a subject suspected of having a cancer is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, i.e., noncancerous, control sample. An alteration in the signal is indicative of the presence of the cancer in the subject.

Other techniques for measuring miR gene expression are also within the skill in the art, and include various techniques for measuring rates of RNA transcription and degradation.

The status of an miR gene in a cell of a subject can also be evaluated by analyzing at least one miR gene or gene product in the sample for a deletion, mutation or amplification, wherein detection of a deletion, mutation or amplification in the miR gene or gene product relative to the miR gene or gene product in a control sample is indicative of the presence of the cancer in the subject. As used herein, a mutation is any alteration in the sequence of a gene of interest that results from one or more nucleotide changes. Such changes include, but are not limited to, allelic polymorphisms, and may affect gene expression and/or function of the gene product.

A deletion, mutation or amplification in an miR gene or gene product can be detected by determining the structure or sequence of an miR gene or gene product in cells from a biological sample from a subject suspected of having cancer associated with a cancer-associated chromosomal feature, and comparing this with the structure or sequence of a corresponding gene or gene product in cells from a control sample. Subject and control samples can be obtained as described herein. Especially suitable candidate miR genes for this type of analysis include, but are not limited to, miR-16-1, miR-27b, miR-206, miR-29b-2 and miR-187. As described in Examples 13 and 14 herein, specific mutations in these five miR genes have been identified in samples from CLL patients.

In certain embodiments, the present invention provides methods for diagnosing whether a subject has, or is at risk for developing, a cancer, comprising analyzing a miR gene or gene product in a test sample from the subject, wherein the detection of a mutation in the miR gene or gene product in the test sample, relative to a control sample, is indicative of the subject having, or being at risk for developing, cancer. In one embodiment, the method comprises analyzing the status of a miR-16-1 gene or gene product. In a particular embodiment, the method comprises analyzing the status of a miR-16-1 gene for the presence of a mutation, wherein the mutation is a C to T nucleotide substitution at +7 base pairs 3' of the miR-16-1 precursor coding region (see, e.g., SEQ ID NOS: 641 and 642). Suitable cancers to be diagnosed by this method include CLL, among others. In another embodiment, the method comprises analyzing the status of a miR-27b gene or gene product. In a particular embodiment, the method comprises analyzing the status of a miR-27b gene for the presence of a mutation, wherein the mutation is a G to A nucleotide substitution at +50 base pairs 3' of the miR-27b precursor coding region (see, e.g., SEQ ID NOS:645 and 646). Suitable cancers to be diagnosed by this method include, but are not limited to, CLL, throat cancer, and lung cancer. In an additional embodiment, the method comprises analyzing the status of a miR-206 gene or gene product. In a particular embodiment, the method comprises analyzing the status of a miR-206 gene for the presence of a mutation, wherein the mutation is a G to T nucleotide substitution at position 49 of the miR-206 precursor coding region (see, e.g., SEQ ID NOS:657 and 658). In a related embodiment, the method comprises analyzing the status of a miR-206 gene for the presence of a mutation, wherein the mutation is an A to T substitution at −116 base pairs 5' of the miR-206 precursor coding region (see, e.g., SEQ ID NOS:657 and 659). Suitable cancers to be diagnosed by this method include, but are not limited to, CLL and other leukemias, esophageal cancer, prostate cancer and breast cancer. In yet another embodiment the method comprises analyzing the status of a miR-29b-2 gene or gene product. In a particular embodiment, the method comprises analyzing the status of a miR-29b-2 gene for the presence of a mutation, wherein the mutation is a G to A nucleotide substitution at +212 base pairs 3' of the miR-29b-2 precursor coding region (see, e.g., SEQ ID NOS:651 and 652). In a related embodiment, the method comprises analyzing the status of a miR-206 gene for the presence of a mutation, wherein the mutation is an A nucleotide insertion at +107 base pairs 3' of the miR-29b-2 precursor coding region (see, e.g., SEQ ID NOS:651 and 653). Suitable cancers to be diagnosed by this method include, but are not limited to, CLL and other leukemias, as well as breast cancer. In a further embodiment, the method comprises analyzing the status of a miR-187 gene or gene product. In a particular embodiment, the method comprises analyzing the status of a miR-187 gene for the presence of a mutation, wherein the mutation is a T to C nucleotide substitution at +73 base pairs 3' of the miR-187 precursor coding region (see, e.g., SEQ ID NOS:654 and 655). Suitable cancers to be diagnosed by this method include, CLL, among others.

Any technique suitable for detecting alterations in the structure or sequence of genes can be used in the practice of the present method. For example, the presence of miR gene deletions, mutations or amplifications can be detected by Southern blot hybridization of the genomic DNA from a subject, using nucleic acid probes specific for miR gene sequences.

Southern blot hybridization techniques are within the skill in the art. For example, genomic DNA isolated from a subject's sample can be digested with restriction endonucleases. This digestion generates restriction fragments of the genomic DNA that can be separated by electrophoresis, for example, on an agarose gel. The restriction fragments are then blotted onto a hybridization membrane (e.g., nitrocellulose or nylon), and hybridized with labeled probes specific for a given miR gene or genes. A deletion or mutation of these genes is indicated by an alteration of the restriction fragment patterns on the hybridization membrane, as compared to DNA from a control sample that has been treated identically to the DNA from the subject's sample. Probe labeling and hybridization conditions suitable for detecting alterations in gene structure or sequence can be readily determined by one of ordinary skill in the art. The miR gene nucleic acid probes for Southern blot hybridization can be designed based upon the nucleic acid sequences provided in Table 1, as described herein. Nucleic acid probe hybridization can then be detected by exposing hybridized filters to photographic film, or by employing computerized imaging systems, such the Molecular Dynamics 400-B 2D Phosphorimager available from Amersham Biosciences, Piscataway, N.J.

Deletions, mutations and/or amplifications of an miR gene can also be detected by amplifying a fragment of these genes by polymerase chain reaction (PCR), and analyzing the amplified fragment by sequencing or by electrophoresis to determine if the sequence and/or length of the amplified fragment from the subject's DNA sample is different from that of a control DNA sample. Suitable reaction and cycling conditions for PCR amplification of DNA fragments can be readily determined by one of ordinary skill in the art.

Deletions of an miR gene can also be identified by detecting deletions of chromosomal markers that are closely linked to the miR gene. Mutations in an miR gene can also be detected by the technique of single strand conformational polymorphism (SSCP), for example, as described in Orita et al. (1989), *Genomics* 5:874-879 and Hayashi (1991), *PCR Methods and Applic.* 1:34-38, the entire disclosures of which are herein incorporated by reference. The SSCP technique consists of amplifying a fragment of the gene of interest by PCR; denaturing the fragment and electrophoresing the two denatured single strands under non-denaturing conditions. The single strands assume a complex sequence-dependent intrastrand secondary structure that affects the strands electrophoretic mobility.

The status of an miR gene in cells of a subject can also be evaluated by measuring the copy number of the at least one miR gene in the sample, wherein a gene copy number other than two for miR genes on somatic chromosomes and sex chromosomes in a female, or other than one for miR genes on sex chromosomes in a male, is indicative of the presence of the cancer in the subject.

Any technique suitable for detecting gene copy number can be used in the practice of the present method, including the Southern blot and PCR amplification techniques described above. An alternative method of determining the miR gene copy number in a sample of tissue relies on the fact that many miR genes or gene clusters are closely linked to chromosomal markers or other genes. The loss of a copy of an miR gene in an individual who is heterozygous at a marker or gene closely linked to the miR gene can be inferred from the loss of heterozygosity in the closely linked marker or gene. Methods for determining loss of heterozygosity of chromosomal markers are within the skill in the art.

As discussed above, the human miR genes are closely associated with different classes of chromosomal features that are themselves associated with cancer. These cancers are likely caused, in part, by the perturbation in the chromosome or genomic DNA caused by the cancer-associated chromosomal feature, which can affect expression of oncogenes or tumor-suppressor genes located near the site of perturbation. Without wishing to be bound by any theory, it is believed that the perturbations caused by the cancer-associated chromosomal features also affect the expression level of miR genes associated with the feature, and that this also may also contribute to cancerigenesis. Therefore, a given cancer can be treated by restoring the level of miR gene expression associated with that cancer to normal. For example, if the level of miR gene expression is down-regulated in cancer cells of a subject, then the cancer can be treated by raising the miR expression level. Likewise, if the level of miR gene expression is up-regulated in cancer cells of a subject, then the cancer can be treated by reducing the miR expression level.

The cancers associated with different cancer-associated chromosomal features, and the miR genes associated with these features, are described above and in Tables 5, 6 and 7 and FIG. 2. In the practice of the present method, expression the appropriate miR gene or genes associated with a particular cancer and/or cancer-associated chromosomal features is altered by the compositions and methods described herein. As before, specific groupings of miR gene(s) that are associated with a particular cancer-associated chromosomal feature and/or cancer are evident from Tables 5, 6 and 7 and in FIG. 2, and are preferred. In one embodiment, the method of treatment comprising administering an miR gene product. In another embodiment, the method of treatment comprises administering an miR gene product, provided the miR gene product is not miR-15, miR-16, miR-143 and/or miR-145.

In one embodiment of the present method, the level of at least one miR gene product in cancer cells of a subject is first determined relative to control cells. Techniques suitable for determining the relative level of miR gene product in cells are described above. If miR gene expression is down-regulated in the cancer cell relative to control cells, then the cancer cells are treated with an effective amount of a compound comprising the isolated miR gene product from the miR gene which is down-regulated. If miR gene expression is up-regulated in cancer cells relative to control cells, then the cancer cells are treated with an effective amount of a compound that inhibits miR gene expression. In one embodiment, the level of miR gene product in a cancer cell is not determined beforehand, for example, in those cancers where miR gene expression is known to be up- or down-regulated.

Thus, in the practice of the present treatment methods, an effective amount of at least one isolated miR gene product can be administered to a subject. As used herein, an "effective amount" of an isolated miR gene product is an amount sufficient to inhibit proliferation of a cancer cell in a subject suffering from a cancer associated with a cancer-associated chromosomal feature. One skilled in the art can readily determine an effective amount of an miR gene product to be administered to a given subject, by taking into account factors such as the size and weight of the subject; the extent of disease penetration; the age, health and sex of the subject; the route of administration; and whether the administration is regional or systemic.

For example, an effective amount of isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be at least about 10 micrograms/gram of tumor mass, and is preferably between about 10-500 micrograms/gram of tumor mass. More preferably, the effective amount is at least about 60 micrograms/gram of tumor mass. Particularly preferably, the effective amount is at least about 100 micrograms/gram of tumor mass. It is preferred that an effective amount based on the weight of the tumor mass be injected directly into the tumor.

An effective amount of an isolated miR gene product can also be based on the approximate or estimated body weight of a subject to be treated. Preferably, such effective amounts are administered parenterally or enterally, as described herein. For example, an effective amount of the isolated miR gene product is administered to a subject can range from about 5-3000 micrograms/kg of body weight, and is preferably between about 700-1000 micrograms/kg of body weight, and is more preferably greater than about 1000 micrograms/kg of body weight.

One skilled in the art can also readily determine an appropriate dosage regimen for the administration of an isolated miR gene product to a given subject. For example, an miR gene product can be administered to the subject once (e.g., as a single injection or deposition). Alternatively, an miR gene product can be administered once or twice daily to a subject for a period of from about three to about twenty-eight days, more preferably from about seven to about ten days. In a preferred dosage regimen, an miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one which is synthesized, or altered or removed from the natural state through human intervention. For example, an miR gene product naturally present in a living animal is not "isolated." A synthetic miR gene product, or an miR gene product partially or completely separated from the coexisting materials of its natural state, is "isolated." An isolated miR gene product can exist in substantially purified form, or can exist in a cell into which the miR gene product has been delivered. Thus, an miR gene product which is deliberately delivered to, or expressed in, a cell is considered an "isolated" miR gene product. An miR gene product produced inside a cell by from an miR precursor molecule is also considered to be "isolated" molecule.

Isolated miR gene products can be obtained using a number of standard techniques. For example, the miR gene products can be chemically synthesized or recombinantly produced using methods known in the art. Preferably, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products which are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or can be expressed from the same recombinant plasmid. Preferably, the miR gene products are expressed as the RNA precursor molecules from a single plasmid, and the precursor molecules are processed into the functional miR gene product by a suitable processing system, including processing systems extant within a cancer cell.

Other suitable processing systems include, e.g., the in vitro *Drosophila* cell lysate system as described in U.S. published application 2002/0086356 to Tuschl et al. and the *E. coli* RNAse III system described in U.S. published patent application 2004/0014113 to Yang et al., the entire disclosures of which are herein incorporated by reference.

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol,* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are herein incorporated by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, for example, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J. E. et al. (2002), *J Virol* 76:791-801, the entire disclosure of which is herein incorporated by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therap.* 2:301-310; Eglitis (1988), *Biotechniques* 6:608-614; Miller (1990), *Hum. Gene Therap.* 1:5-14; and Anderson (1998), *Nature* 392:25-30, the entire disclosures of which are herein incorporated by reference.

Preferred viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is herein incorporated by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.,* 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference. Preferably, the miR gene products are expressed from a single recombinant AAV vector comprising the CMV intermediate early promoter.

In one embodiment, a recombinant AAV viral vector of the invention comprises a nucleic acid sequence encoding an miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In the practice of the present treatment methods, an effective amount of at least one compound which inhibits miR gene expression can also be administered to the subject. As used herein, "inhibiting miR gene expression" means that the production of miR gene product from the miR gene in the cancer cell after treatment is less than the amount produced prior to treatment. One skilled in the art can readily determine whether miR gene expression has been inhibited in a cancer cell, using for example the techniques for determining miR transcript level discussed above for the diagnostic method.

As used herein, an "effective amount" of a compound that inhibits miR gene expression is an amount sufficient to inhibit proliferation of a cancer cell in a subject suffering from a cancer associated with a cancer-associated chromosomal feature. One skilled in the art can readily determine an effective amount of an miR gene expression-inhibiting compound to be administered to a given subject, by taking into account factors such as the size and weight of the subject; the extent of disease penetration; the age, health and sex of the subject; the route of administration; and whether the administration is regional or systemic.

For example, an effective amount of the expression-inhibiting compound can be based on the approximate weight of a tumor mass to be treated. The approximate weight of a tumor mass can be determined by calculating the approximate volume of the mass, wherein one cubic centimeter of volume is roughly equivalent to one gram. An effective amount based on the weight of a tumor mass can be at least about 10 micrograms/gram of tumor mass, and is preferably between about 10-500 micrograms/gram of tumor mass. More preferably, the effective amount is at least about 60 micrograms/gram of tumor mass. Particularly preferably, the effective amount is at least about 100 micrograms/gram of tumor mass. It is preferred that an effective amount based on the weight of the tumor mass be injected directly into the tumor.

An effective amount of a compound that inhibits miR gene expression can also be based on the approximate or estimated body weight of a subject to be treated. Preferably, such effective amounts are administered parenterally or enterally, as described herein. For example, an effective amount of the expression-inhibiting compound administered to a subject can range from about 5□-3000 micrograms/kg of body weight, and is preferably between about 700-1000 micrograms/kg of body weight, and is more preferably greater than about 1000 micrograms/kg of body weight.

One skilled in the art can also readily determine an appropriate dosage regimen for administering a compound that inhibits miR gene expression to a given subject. For example, an expression-inhibiting compound can be administered to the subject once (e.g., as a single injection or deposition). Alternatively, an expression-inhibiting compound can be administered once or twice daily to a subject for a period of from about three to about twenty-eight days, more preferably from about seven to about ten days. In a preferred dosage regimen, an expression-inhibiting compound is administered once a day for seven days. Where a dosage regimen comprises multiple administrations, it is understood that the effective amount of the expression-inhibiting compound administered to the subject can comprise the total amount of compound administered over the entire dosage regimen.

Suitable compounds for inhibiting miR gene expression include double-stranded RNA (such as short- or small-interfering RNA or "siRNA"), antisense nucleic acids, and enzymatic RNA molecules such as ribozymes. Each of these compounds can be targeted to a given miR gene product and destroy or induce the destruction of the target miR gene product.

For example, expression of a given miR gene can be inhibited by inducing RNA interference of the miR gene with an isolated double-stranded RNA ("dsRNA") molecule which has at least 90%, for example 95%, 98%, 99% or 100%, sequence homology with at least a portion of the miR gene product. In a preferred embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target miR gene product.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in one embodiment, the siRNA comprises at least one 3' overhang of from 1 to about 6 nucleotides (which includes ribonucleotides or deoxyribonucleotides) in length, preferably from 1 to about 5 nucleotides in length, more preferably from 1 to about 4 nucleotides in length, and particularly preferably from about 2 to about 4 nucleotides in length. In a preferred embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. published patent application 2002/0173478 to Gewirtz and in U.S. published patent application 2004/0018176 to Reich et al., the entire disclosures of which are herein incorporated by reference.

Expression of a given miR gene can also be inhibited by an antisense nucleic acid. As used herein, an "antisense nucleic acid" refers to a nucleic acid molecule that binds to target RNA by means of RNA-RNA or RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, PNA) that generally comprise a nucleic acid sequence complementary to a contiguous nucleic acid sequence in an miR gene product. Preferably, the antisense nucleic acid comprises a nucleic acid sequence that is 50-100% complementary, more preferably 75-100% complementary, and most preferably 95-100% complementary to a contiguous nucleic acid sequence in an miR gene product. Nucleic acid sequences for the miR gene products are provided in Table 1. Without wishing to be bound by any theory, it is believed that the antisense nucleic acids activate RNase H or some other cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators such as acridine or the inclusion of one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are herein incorporated by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of an miR gene product, and which is able to specifically cleave the miR gene product. Preferably, the enzymatic nucleic acid substrate binding region is 50-100% complementary, more preferably 75-100% complementary, and most preferably 95-100% complementary to a contiguous nucleic acid sequence in an miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucl. Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are herein incorporated by reference.

Administration of at least one miR gene product, or at least one compound for inhibiting miR gene expression, will inhibit the proliferation of cancer cells in a subject who has a cancer associated with a cancer-associated chromosomal feature. As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibiting compounds. An inhibition of cancer cell proliferation can also be inferred if the absolute number of such cells increases, but the rate of tumor growth decreases.

The number of cancer cells in a subject's body can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The miR gene products or miR gene expression-inhibiting compounds can be administered to a subject by any means suitable for delivering these compounds to cancer cells of the subject. For example, the miR gene products or miR expression inhibiting compounds can be administered by methods suitable to transfect cells of the subject with these compounds, or with nucleic acids comprising sequences encoding these compounds. Preferably, the cells are transfected with a plasmid or viral vector comprising sequences encoding at least one miR gene product or miR gene expression inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy)

propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

An miR gene product or miR gene expression inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Preferred administration routes are injection, infusion and direct injection into the tumor.

In the present methods, an miR gene product or miR gene expression inhibiting compound can be administered to the subject either as naked RNA, in combination with a delivery reagent, or as a nucleic acid (e.g., a recombinant plasmid or viral vector) comprising sequences that express the miR gene product or expression inhibiting compound. Suitable delivery reagents include, e.g., the Mirus Transit TKO lipophilic reagent; lipofectin; lipofectamine; cellfectin; polycations (e.g., polylysine), and liposomes.

Recombinant plasmids and viral vectors comprising sequences that express the miR gene products or miR gene expression inhibiting compounds, and techniques for delivering such plasmids and vectors to cancer cells, are discussed above.

In a preferred embodiment, liposomes are used to deliver an miR gene product or miR gene expression-inhibiting compound (or nucleic acids comprising sequences encoding them) to a subject. Liposomes can also increase the blood half-life of the gene products or nucleic acids.

Liposomes suitable for use in the invention can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501, 728, 4,837,028, and 5,019,369, the entire disclosures of which are herein incorporated by reference.

The liposomes for use in the present methods can comprise a ligand molecule that targets the liposome to cancer cells. Ligands which bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), Proc. Natl. Acad. Sci., USA, 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression inhibition compounds (or nucleic acids comprising sequences encoding them) to tumor cells.

The miR gene products or miR gene expression inhibition compounds are preferably formulated as pharmaceutical compositions, sometimes called "medicaments," prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

The present pharmaceutical formulations comprise at least one miR gene product or miR gene expression inhibition compound (or at least one nucleic acid comprising sequences encoding them) (e.g., 0.1 to 90% by weight), or a physiologically acceptable salt thereof, mixed with a pharmaceutically-acceptable carrier. The pharmaceutical formulations of the invention can also comprise at least one miR gene product or miR gene expression inhibition compound (or at least one nucleic acid comprising sequences encoding them) which are encapsulated by liposomes and a pharmaceutically-acceptable carrier. In one embodiment, the pharmaceutical compositions comprise an miR gene or gene product that is not miR-15, miR-16, miR-143 and/or miR-145.

Preferred pharmaceutically-acceptable carriers are water, buffered water, normal saline, 0.4% saline, 0.3% glycine, hyaluronic acid and the like.

In a preferred embodiment, the pharmaceutical compositions of the invention comprise at least one miR gene product or miR gene expression inhibition compound (or at least one nucleic acid comprising sequences encoding them) which is resistant to degradation by nucleases. One skilled in the art can readily synthesize nucleic acids which are nuclease resistant, for example by incorporating one or more ribonucleotides that are modified at the 2'-position into the miR gene products. Suitable 2'-modified ribonucleotides include those modified at the 2'-position with fluoro, amino, alkyl, alkoxy, and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression inhibition compound (or at least one nucleic acid comprising sequences encoding them) encapsulated in a liposome as described above, and a propellant. A carrier can also be included as desired; e.g., lecithin for intranasal delivery.

The invention will now be illustrated by the following non-limiting examples.

EXAMPLES

The following techniques were used in the Examples.
General Methods:
The miR gene database
A set of 187 human miR genes was compiled (see Table 1). The set comprises 153 miRs identified in the miR Registry (maintained by the Wellcome Trust Sanger Institute, Cambridge, UK), and 36 other miRs manually curated from published papers (Lim et al., 2003, Science 299:1540; Lagos-Quintana et al., 2001, Science 294:853-858; Lau et al., 2001, Science 294:858-862; Lee et al., 2001, Science 294:862-864; Mourelatos et al., 2002, Genes Dev. 16:720-728; Lagos-Quintana et al., 2002, Curr. Biol. 12:735-739; Dostie et al., 2003, RNA 9:180-186; Houbaviy et al., 2003, Dev. Cell. 5:351-8) or found in the GenBank database accessed through the National Center for Biotechnology Information (NCBI) website, maintained by the National Institutes of Health and the National Library of Medicine Nineteen new human miRs (approximately 10% of the miR set) were found based on their homology with cloned miRs from other species (mainly mouse). For all miRs, the sequence of the precursor was identified using the M Zucker RNA folding program and selecting the precursor sequence that gave the best score for the hairpin structure. The program is available and is maintained by Michael Zucker of Rensselaer Polytechnic Institute.

TABLE 1

| Human miR Gene Product Sequences | | |
|---|---|---|
| Name | Precursor Sequence (5' to 3')* | SEQ ID NO. |
| has-let-7a-1-prec | CACTGTGGGATGAGGTAGTAGGTTGTATAGTTTTAGG GTCACACCCACCACTGGGAGATAACTATACAATCTAC TGTCTTTCCTAACGTG | 1 |
| hsa-let-7a-2-prec | AGGTTGAGGTAGTAGGTTGTATAGTTTAGAATTACAT CAAGGGAGATAACTGTACAGCCTCCTAGCTTTCCT | 2 |

TABLE 1-continued

Human miR Gene Product Sequences

| Name | Precursor Sequence (5' to 3')* | SEQ ID NO. |
|---|---|---|
| hsa-let-7a-3-prec | GGGTGAGGTAGTAGGTTGTATAGTTTGGGGCTCTGCC CTGCTATGGGATAACTATACAATCTACTGTCTTTCCT | 3 |
| hsa-let-7a-4-prec | GTGACTGCATGCTCCCAGGTTGAGGTAGTAGGTTGTA TAGTTTAGAATTACACAAGGGAGATAACTGTACAGCC TCCTAGCTTTCCTTGGGTCTTGCACTAAACAAC | 4 |
| hsa-let-7b-prec | GGCGGGGTGAGGTAGTAGGTTGTGTGGTTTCAGGGCA GTGATGTTGCCCCTCGGAAGATAACTATACAACCTAC TGCCTTCCCTG | 5 |
| hsa-let-7c-prec | GCATCCGGGTTGAGGTAGTAGGTTGTATGGTTTAGAG TTACACCCTGGGAGTTAACTGTACAACCTTCTAGCTTT CCTTGGAGC | 6 |
| hsa-let-7d-prec | CCTAGGAAGAGGTAGTAGGTTGCATAGTTTTAGGGCA GGGATTTTGCCCACAAGGAGGTAACTATACGACCTGC TGCCTTTCTTAGG | 7 |
| hsa-let-7d-v1-prec | CTAGGAAGAGGTAGTAGTTTGCATAGTTTTAGGGCAA AGATTTTGCCCACAAGTAGTTAGCTATACGACCTGCA GCCTTTTGTAG | 8 |
| hsa-let-7d-v2-prec | CTGGCTGAGGTAGTAGTTTGTGCTGTTGGTCGGGTTGT GACATTGCCCGCTGTGGAGATAACTGCGCAAGCTACT GCCTTGCTAG | 9 |
| hsa-let-7e-prec | CCCGGGCTGAGGTAGGAGGTTGTATAGTTGAGGAGGA CACCCAAGGAGATCACTATACGGCCTCCTAGCTTTCCC CAGG | 10 |
| hsa-let-7f-1-prec | TCAGAGTGAGGTAGTAGATTGTATAGTTGTGGGGTAG TGATTTTACCCTGTTCAGGAGATAACTATACAATCTAT TGCCTTCCCTGA | 11 |
| hsa-let-7f-2-prec | CTGTGGGATGAGGTAGTAGATTGTATAGTTGTGGGGT AGTGATTTTACCCTGTTCAGGAGATAACTATACAATCT ATTGCCTTCCCTGA | 12 |
| hsa-let-7f-2-prec | CTGTGGGATGAGGTAGTAGATTGTATAGTTTTAGGGT CATACCCCATCTTGGAGATAACTATACAGTCTACTGTC TTTCCCACGG | 13 |
| hsa-let-7g-prec | TTGCCTGATTCCAGGCTGAGGTAGTAGTTTGTACAGTT TGAGGGTCTATGATACCACCCGGTACAGGAGATAACT GTACAGGCCACTGCCTTGCCAGGAACAGCGCGC | 14 |
| hsa-let-7i-prec | CTGGCTGAGGTAGTAGTTTGTGCTGTTGGTCGGGTTGT GACATTGCCCGCTGTGGAGATAACTGCGCAAGCTACT GCCTTGCTAG | 15 |
| hsa-mir-001b-1-prec | ACCTACTCAGAGTACATACTTCTTTATGTACCCATATG AACATACAATGCTATGGAATGTAAAGAAGTATGTATT TTTGGTAGGC | 16 |
| hsa-mir-001b-1-prec | CAGCTAACAACTTAGTAATACCTACTCAGAGTACATA CTTCTTTATGTACCCATATGAACATACAATGCTATGGA ATGTAAAGAAGTATGTATTTTTGGTAGGCAATA | 17 |
| hsa-mir-001b-2-prec | GCCTGCTTGGGAAACATACTTCTTTATATGCCCATATG GACCTGCTAAGCTATGGAATGTAAAGAAGTATGTATC TCAGGCCGGG | 18 |
| hsa-mir-001b-prec | TGGGAAACATACTTCTTTATATGCCCATATGGACCTGC TAAGCTATGGAATGTAAAGAAGTATGTATCTCA | 19 |
| hsa-mir-001d-prec | ACCTACTCAGAGTACATACTTCTTTATGTACCCATATG AACATACAATGCTATGGAATGTAAAGAAGTATGTATT TTTGGTAGGC | 20 |
| hsa-mir-007-1 | TGGATGTTGGCCTAGTTCTGTGTGGAAGACTAGTGATT TTGTTGTTTTTAGATAACTAAATCGACAACAAATCACA GTCTGCCATATGGCACAGGCCATGCCTCTACA | 21 |

TABLE 1-continued

Human miR Gene Product Sequences

| Name | Precursor Sequence (5' to 3')* | SEQ ID NO. |
|---|---|---|
| hsa-mir-007-1-prec | TTGGATGTTGGCCTAGTTCTGTGTGGAAGACTAGTGAT TTTGTTGTTTTTAGATAACTAAATCGACAACAAATCAC AGTCTGCCATATGGCACAGGCCATGCCTCTACAG | 22 |
| hsa-mir-007-2 | CTGGATACAGAGTGGACCGGCTGGCCCCATCTGGAAG ACTAGTGATTTTGTTGTTGTCTTACTGCGCTCAACAAC AAATCCCAGTCTACCTAATGGTGCCAGCCATCGCA | 23 |
| hsa-mir-007-2-prec | CTGGATACAGAGTGGACCGGCTGGCCCCATCTGGAAG ACTAGTGATTTTGTTGTTGTCTTACTGCGCTCAACAAC AAATCCCAGTCTACCTAATGGTGCCAGCCATCGCA | 24 |
| hsa-mir-007-3 | AGATTAGAGTGGCTGTGGTCTAGTGCTGTGTGGAAGA CTAGTGATTTTGTTGTTCTGATGTACTACGACAACAAG TCACAGCCGGCCTCATAGCGCAGACTCCCTTCGAC | 25 |
| hsa-mir-007-3-prec | AGATTAGAGTGGCTGTGGTCTAGTGCTGTGTGGAAGA CTAGTGATTTTGTTGTTCTGATGTACTACGACAACAAG TCACAGCCGGCCTCATAGCGCAGACTCCCTTCGAC | 26 |
| hsa-mir-009-1 | CGGGGTTGGTTGTTATCTTTGGTTATCTAGCTGTATGA GTGGTGTGGAGTCTTCATAAAGCTAGATAACCGAAAG TAAAAATAACCCCA | 27 |
| hsa-mir-009-2 | GGAAGCGAGTTGTTATCTTTGGTTATCTAGCTGTATGA GTGTATTGGTCTTCATAAAGCTAGATAACCGAAAGTA AAAACTCCTTCA | 28 |
| hsa-mir-009-3 | GGAGGCCCGTTTCTCTCTTTGGTTATCTAGCTGTATGA GTGCCACAGAGCCGTCATAAAGCTAGATAACCGAAAG TAGAAATGATTCTCA | 29 |
| hsa-mir-010a-prec | GATCTGTCTGTCTTCTGTATATACCCTGTAGATCCGAA TTTGTGTAAGGAATTTTGTGGTCACAAATTCGTATCTA GGGGAATATGTAGTTGACATAAACACTCCGCTCT | 30 |
| hsa-mir-010b-prec | CCAGAGGTTGTAACGTTGTCTATATATACCCTGTAGAA CCGAATTTGTGTGGTATCCGTATAGTCACAGATTCGAT TCTAGGGGAATATATGGTCGATGCAAAAACTTCA | 31 |
| hsa-mir-015a-2-prec | GCGCGAATGTGTGTTTAAAAAAAATAAAACCTTGGAG TAAAGTAGCAGCACATAATGGTTTGTGGATTTTGAAA AGGTGCAGGCCATATTGTGCTGCCTCAAAAATAC | 32 |
| hsa-mir-015a-prec | CCTTGGAGTAAAGTAGCAGCACATAATGGTTTGTGGA TTTTGAAAAGGTGCAGGCCATATTGTGCTGCCTCAAA AATACAAGG | 33 |
| hsa-mir-015b-prec | CTGTAGCAGCACATCATGGTTTACATGCTACAGTCAA GATGCGAATCATTATTTGCTGCTCTAG | 34 |
| hsa-mir-015b-prec | TTGAGGCCTTAAAGTACTGTAGCAGCACATCATGGTTT ACATGCTACAGTCAAGATGCGAATCATTATTTGCTGCT CTAGAAATTTAAGGAAATTCAT | 35 |
| hsa-mir-016a-chr13 | GTCAGCAGTGCCTTAGCAGCACGTAAATATTGGCGTT AAGATTCTAAAATTATCTCCAGTATTAACTGTGCTGCT GAAGTAAGGTTGAC | 36 |
| hsa-mir-016b-chr3 | GTTCCACTCTAGCAGCACGTAAATATTGGCGTAGTGA AATATATATTAAACACCAATATTACTGTGCTGCTTTAG TGTGAC | 37 |
| hsa-mir-016-prec-13 | GCAGTGCCTTAGCAGCACGTAAATATTGGCGTTAAGA TTCTAAAATTATCTCCAGTATTAACTGTGCTGCTGAAG TAAGGT | 38 |
| hsa-mir-017-prec | GTCAGAATAATGTCAAAGTGCTTACAGTGCAGGTAGT GATATGTGCATCTACTGCAGTGAAGGCACTTGTAGCA TTATGGTGAC | 39 |
| hsa-mir-018-prec | TGTTCTAAGGTGCATCTAGTGCAGATAGTGAAGTAGA TTAGCATCTACTGCCCTAAGTGCTCCTTCTGGCA | 40 |

TABLE 1-continued

Human miR Gene Product Sequences

| Name | Precursor Sequence (5' to 3')* | SEQ ID NO. |
|---|---|---|
| hsa-mir-018-prec-13 | TTTTTGTTCTAAGGTGCATCTAGTGCAGATAGTGAAGT AGATTAGCATCTACTGCCCTAAGTGCTCCTTCTGGCAT AAGAA | 41 |
| hsa-mir-019a-prec | GCAGTCCTCTGTTAGTTTTGCATAGTTGCACTACAAGA AGAATGTAGTTGTGCAAATCTATGCAAAACTGATGGT GGCCTGC | 42 |
| hsa-mir-019a-prec-13 | CAGTCCTCTGTTAGTTTTGCATAGTTGCACTACAAGAA GAATGTAGTTGTGCAAATCTATGCAAAACTGATGGTG GCCTG | 43 |
| hsa-mir-019b-1-prec | CACTGTTCTATGGTTAGTTTTGCAGGTTTGCATCCAGC TGTGTGATATTCTGCTGTGCAAATCCATGCAAAACTGA CTGTGGTAGTG | 44 |
| hsa-mir-019b-2-prec | ACATTGCTACTTACAATTAGTTTTGCAGGTTTGCATTT CAGCGTATATATGTATATGTGGCTGTGCAAATCCATGC AAAACTGATTGTGATAATGT | 45 |
| hsa-mir-019b-prec-13 | TTCTATGGTTAGTTTTGCAGGTTTGCATCCAGCTGTGT GATATTCTGCTGTGCAAATCCATGCAAAACTGACTGT GGTAG | 46 |
| hsa-mir-019b-prec-X | TTACAATTAGTTTTGCAGGTTTGCATTTCAGCGTATAT ATGTATATGTGGCTGTGCAAATCCATGCAAAACTGAT TGTGAT | 47 |
| hsa-mir-020-prec | GTAGCACTAAAGTGCTTATAGTGCAGGTAGTGTTTAG TTATCTACTGCATTATGAGCACTTAAAGTACTGC | 48 |
| hsa-mir-021-prec | TGTCGGGTAGCTTATCAGACTGATGTTGACTGTTGAAT CTCATGGCAACACCAGTCGATGGGCTGTCTGACA | 49 |
| hsa-mir-021-prec-17 | ACCTTGTCGGGTAGCTTATCAGACTGATGTTGACTGTT GAATCTCATGGCAACACCAGTCGATGGGCTGTCTGAC ATTTTG | 50 |
| hsa-mir-022-prec | GGCTGAGCCGCAGTAGTTCTTCAGTGGCAAGCTTTAT GTCCTGACCCAGCTAAAGCTGCCAGTTGAAGAACTGT TGCCCTCTGCC | 51 |
| hsa-mir-023a-prec | GGCCGGCTGGGGTTCCTGGGGATGGGATTTGCTTCCT GTCACAAATCACATTGCCAGGGATTTCCAACCGACC | 52 |
| hsa-mir-023b-prec | CTCAGGTGCTCTGGCTGCTTGGGTTCCTGGCATGCTGA TTTGTGACTTAAGATTAAAATCACATTGCCAGGGATTA CCACGCAACCACGACCTTGGC | 53 |
| hsa-mir-023-prec-19 | CCACGGCCGGCTGGGGTTCCTGGGGATGGGATTTGCT TCCTGTCACAAATCACATTGCCAGGGATTTCCAACCG ACCCTGA | 54 |
| hsa-mir-024-1-prec | CTCCGGTGCCTACTGAGCTGATATCAGTTCTCATTTTA CACACTGGCTCAGTTCAGCAGGAACAGGAG | 55 |
| hsa-mir-024-2-prec | CTCTGCCTCCCGTGCCTACTGAGCTGAAACACAGTTGG TTTGTGTACACTGGCTCAGTTCAGCAGGAACAGGG | 56 |
| hsa-mir-024-prec-19 | CCCTGGGCTCTGCCTCCCGTGCCTACTGAGCTGAAACA CAGTTGGTTTGTGTACACTGGCTCAGTTCAGCAGGAA CAGGGG | 57 |
| hsa-mir-024-prec-9 | CCCTCCGGTGCCTACTGAGCTGATATCAGTTCTCATTT TACACACTGGCTCAGTTCAGCAGGAACAGCATC | 58 |
| hsa-mir-025-prec | GGCCAGTGTTGAGAGGCGGAGACTTGGGCAATTGCTG GACGCTGCCCTGGGCATTGCACTTGTCTCGGTCTGACA GTGCCGGCC | 59 |
| hsa-mir-026a-prec | AGGCCGTGGCCTCGTTCAAGTAATCCAGGATAGGCTG TGCAGGTCCCAATGGCCTATCTTGGTTACTTGCACGGG GACGCGGGCCT | 60 |

TABLE 1-continued

Human miR Gene Product Sequences

| Name | Precursor Sequence (5' to 3')* | SEQ ID NO. |
|---|---|---|
| hsa-mir-026b-prec | CCGGGACCCAGTTCAAGTAATTCAGGATAGGTTGTGT GCTGTCCAGCCTGTTCTCCATTACTTGGCTCGGGGACC GG | 61 |
| hsa-mir-027a-prec | CTGAGGAGCAGGGCTTAGCTGCTTGTGAGCAGGGTCC ACACCAAGTCGTGTTCACAGTGGCTAAGTTCCGCCCC CCAG | 62 |
| hsa-mir-027b-prec | AGGTGCAGAGCTTAGCTGATTGGTGAACAGTGATTGG TTTCCGCTTTGTTCACAGTGGCTAAGTTCTGCACCT | 63 |
| hsa-mir-027b-prec | ACCTCTCTAACAAGGTGCAGAGCTTAGCTGATTGGTG AACAGTGATTGGTTTCCGCTTTGTTCACAGTGGCTAAG TTCTGCACCTGAAGAGAAGGTG | 64 |
| hsa-mir-027-prec-19 | CCTGAGGAGCAGGGCTTAGCTGCTTGTGAGCAGGGTC CACACCAAGTCGTGTTCACAGTGGCTAAGTTCCGCCC CCAGG | 65 |
| hsa-mir-028-prec | GGTCCTTGCCCTCAAGGAGCTCACAGTCTATTGAGTTA CCTTTCTGACTTTCCCACTAGATTGTGAGCTCCTGGAG GGCAGGCACT | 66 |
| hsa-mir-029a-2 | CCTTCTGTGACCCCTTAGAGGATGACTGATTTCTTTTG GTGTTCAGAGTCAATATAATTTTCTAGCACCATCTGAA ATCGGTTATAATGATTGGGGAAGAGCACCATG | 67 |
| hsa-mir-029a-prec | ATGACTGATTTCTTTTGGTGTTCAGAGTCAATATAATT TTCTAGCACCATCTGAAATCGGTTAT | 68 |
| hsa-mir-029c-prec | ACCACTGGCCCATCTCTTACACAGGCTGACCGATTTCT CCTGGTGTTCAGAGTCTGTTTTTGTCTAGCACCATTTG AAATCGGTTATGATGTAGGGGGAAAAGCAGCAGC | 69 |
| hsa-mir-030a-prec | GCGACTGTAAACATCCTCGACTGGAAGCTGTGAAGCC ACAGATGGGCTTTCAGTCGGATGTTTGCAGCTGC | 70 |
| hsa-mir-030b-prec | ATGTAAACATCCTACACTCAGCTGTAATACATGGATT GGCTGGGAGGTGGATGTTTACGT | 71 |
| hsa-mir-030b-prec | ACCAAGTTTCAGTTCATGTAAACATCCTACACTCAGCT GTAATACATGGATTGGCTGGGAGGTGGATGTTTACTT CAGCTGACTTGGA | 72 |
| hsa-mir-030c-prec | AGATACTGTAAACATCCTACACTCTCAGCTGTGGAAA GTAAGAAAGCTGGGAGAAGGCTGTTTACTCTTTCT | 73 |
| hsa-mir-030d-prec | GTTGTTGTAAACATCCCCGACTGGAAGCTGTAAGACA CAGCTAAGCTTTCAGTCAGATGTTTGCTGCTAC | 74 |
| hsa-mir-031-prec | GGAGAGGAGGCAAGATGCTGGCATAGCTGTTGAACTG GGAACCTGCTATGCCAACATATTGCCATCTTTCC | 75 |
| hsa-mir-032-prec | GGAGATATTGCACATTACTAAGTTGCATGTTGTCACG GCCTCAATGCAATTTAGTGTGTGTGATATTTTC | 76 |
| hsa-mir-033b-prec | GGGGGCCGAGAGAGGCGGGCGGCCCCGCGGTGCATT GCTGTTGCATTGCACGTGTGTGAGGCGGGTGCAGTGC CTCGGCAGTGCAGCCCGGAGCCGGCCCCTGGCACCAC | 77 |
| hsa-mir-033-prec | CTGTGGTGCATTGTAGTTGCATTGCATGTTCTGGTGGT ACCCATGCAATGTTTCCACAGTGCATCACAG | 78 |
| hsa-mir-034-prec | GGCCAGCTGTGAGTGTTTCTTTGGCAGTGTCTTAGCTG GTTGTTGTGAGCAATAGTAAGGAAGCAATCAGCAAGT ATACTGCCCTAGAAGTGCTGCACGTTGTGGGGCCC | 79 |
| hsa-mir-091-prec-13 | TCAGAATAATGTCAAAGTGCTTACAGTGCAGGTAGTG ATATGTGCATCTACTGCAGTGAAGGCACTTGTAGCATT ATGGTGA | 80 |
| hsa-mir-092-prec-13 = 092-1 | CTTTCTACACAGGTTGGGATCGGTTGCAATGCTGTGTT TCTGTATGGTATTGCACTTGTCCCGGCCTGTTGAGTTT GG | 81 |

TABLE 1-continued

Human miR Gene Product Sequences

| Name | Precursor Sequence (5' to 3')* | SEQ ID NO. |
|---|---|---|
| hsa-mir-092-prec-X = 092-2 | TCATCCCTGGGTGGGGATTTGTTGCATTACTTGTGTTCTATATAAAGTATTGCACTTGTCCCGGCCTGTGGAAGA | 82 |
| hsa-mir-093-prec-7.1 = 093-1 | CTGGGGGCTCCAAAGTGCTGTTCGTGCAGGTAGTGTGATTACCCAACCTACTGCTGAGCTAGCACTTCCCGAGCCCCCGG | 83 |
| hsa-mir-093-prec-7.2 = 093-2 | CTGGGGGCTCCAAAGTGCTGTTCGTGCAGGTAGTGTGATTACCCAACCTACTGCTGAGCTAGCACTTCCCGAGCCCCCGG | 84 |
| hsa-mir-095-prec-4 | AACACAGTGGGCACTCAATAAATGTCTGTTGAATTGAAATGCGTTACATTCAACGGGTATTTATTGAGCACCCACTCTGTG | 85 |
| hsa-mir-096-prec-7 | TGGCCGATTTTGGCACTAGCACATTTTTGCTTGTGTCTCTCCGCTCTGAGCAATCATGTGCAGTGCCAATATGGGAAA | 86 |
| hsa-mir-098-prec-X | GTGAGGTAGTAAGTTGTATTGTTGTGGGGTAGGGATATTAGGCCCCAATTAGAAGATAACTATACAACTTACTACTTTCC | 87 |
| hsa-mir-099b-prec-19 | GGCACCCACCCGTAGAACCGACCTTGCGGGGCCTTCGCCGCACACAAGCTCGTGTCTGTGGGTCCGTGTC | 88 |
| hsa-mir-099-prec-21 | CCCATTGGCATAAACCCGTAGATCCGATCTTGTGGTGAAGTGGACCGCACAAGCTCGCTTCTATGGGTCTGTGTCAGTGTG | 89 |
| hsa-mir-100-1/2-prec | AAGAGAGAAGATATTGAGGCCTGTTGCCACAAACCCGTAGATCCGAACTTGTGGTATTAGTCCGCACAAGCTTGTATCTATAGGTATGTGTCTGTTAGGCAATCTCAC | 90 |
| hsa-mir-100-prec-11 | CCTGTTGCCACAAACCCGTAGATCCGAACTTGTGGTATTAGTCCGCACAAGCTTGTATCTATAGGTATGTGTCTGTTAGG | 91 |
| hsa-mir-101-1/2-prec | AGGCTGCCCTGGCTCAGTTATCACAGTGCTGATGCTGTCTATTCTAAAGGTACAGTACTGTGATAACTGAAGGATGGCAGCCATCTTACCTTCCATCAGAGGAGCCTCAC | 92 |
| hsa-mir-101-prec | TCAGTTATCACAGTGCTGATGCTGTCCATTCTAAAGGTACAGTACTGTGATAACTGA | 93 |
| hsa-mir-101-prec-1 | TGCCCTGGCTCAGTTATCACAGTGCTGATGCTGTCTATTCTAAAGGTACAGTACTGTGATAACTGAAGGATGGCA | 94 |
| hsa-mir-101-prec-9 | TGTCCTTTTTCGGTTATCATGGTACCGATGCTGTATATCTGAAAGGTACAGTACTGTGATAACTGAAGAATGGTG | 95 |
| hsa-mir-102-prec-1 | CTTCTGGAAGCTGGTTTCACATGGTGGCTTAGATTTTTCCATCTTTGTATCTAGCACCATTTGAAATCAGTGTTTTAGGAG | 96 |
| hsa-mir-102-prec-7.1 | CTTCAGGAAGCTGGTTTCATATGGTGGTTTAGATTTAAATAGTGATTGTCTAGCACCATTTGAAATCAGTGTTCTTGGGGG | 97 |
| hsa-mir-102-prec-7.2 | CTTCAGGAAGCTGGTTTCATATGGTGGTTTAGATTTAAATAGTGATTGTCTAGCACCATTTGAAATCAGTGTTCTTGGGGG | 98 |
| hsa-mir-103-2-prec | TTGTGCTTTCAGCTTCTTTACAGTGCTGCCTTGTAGCATTCAGGTCAAGCAACATTGTACAGGGCTATGAAAGAACCA | 99 |
| hsa-mir-103-prec-20 | TTGTGCTTTCAGCTTCTTTACAGTGCTGCCTTGTAGCATTCAGGTCAAGCAACATTGTACAGGGCTATGAAAGAACCA | 100 |
| hsa-mir-103-prec-5 = 103-1 | TACTGCCCTCGGCTTCTTTACAGTGCTGCCTTGTTGCATATGGATCAAGCAGCATTGTACAGGGCTATGAAGGCATTG | 101 |

TABLE 1-continued

Human miR Gene Product Sequences

| Name | Precursor Sequence (5' to 3')* | SEQ ID NO. |
|---|---|---|
| hsa-mir-104-prec-17 | AAATGTCAGACAGCCCATCGACTGGTGTTGCCATGAG ATTCAACAGTCAACATCAGTCTGATAAGCTACCCGAC AAGG | 102 |
| hsa-mir-105-prec-X.1 = 105-1 | TGTGCATCGTGGTCAAATGCTCAGACTCCTGTGGTGGC TGCTCATGCACCACGGATGTTTGAGCATGTGCTACGGT GTCTA | 103 |
| hsa-mir-105-prec-X.2 = 105-2 | TGTGCATCGTGGTCAAATGCTCAGACTCCTGTGGTGGC TGCTCATGCACCACGGATGTTTGAGCATGTGCTACGGT GTCTA | 104 |
| hsa-mir-106-prec-X | CCTTGGCCATGTAAAAGTGCTTACAGTGCAGGTAGCT TTTTGAGATCTACTGCAATGTAAGCACTTCTTACATTA CCATGG | 105 |
| hsa-mir-107-prec-10 | CTCTCTGCTTTCAGCTTCTTTACAGTGTTGCCTTGTGGC ATGGAGTTCAAGCAGCATTGTACAGGGCTATCAAAGC ACAGA | 106 |
| hsa-mir-122a-prec | CCTTAGCAGAGCTGTGGAGTGTGACAATGGTGTTTGT GTCTAAACTATCAAACGCCATTATCACACTAAATAGC TACTGCTAGGC | 107 |
| hsa-mir-122a-prec | AGCTGTGGAGTGTGACAATGGTGTTTGTGTCCAAACT ATCAAACGCCATTATCACACTAAATAGCT | 108 |
| hsa-mir-123-prec | ACATTATTACTTTTGGTACGCGCTGTGACACTTCAAAC TCGTACCGTGAGTAATAATGCGC | 109 |
| hsa-mir-124a-1-prec | tccttcctCAGGAGAAAGGCCTCTCTCTCCGTGTTCACAGC GGACCTTGATTTAAATGTCCATACAATTAAGGCACGC GGTGAATGCCAAGAATGGGGCT | 110 |
| hsa-mir-124a-1-prec | AGGCCTCTCTCTCCGTGTTCACAGCGGACCTTGATTTA AATGTCCATACAATTAAGGCACGCGGTGAATGCCAAG AATGGGGCTG | 111 |
| hsa-mir-124a-2-prec | ATCAAGATTAGAGGCTCTGCTCTCCGTGTTCACAGCG GACCTTGATTTAATGTCATACAATTAAGGCACGCGGT GAATGCCAAGAGCGGAGCCTACGGCTGCACTTGAAG | 112 |
| hsa-mir-124a-3-prec | CCCGCCCCAGCCCTGAGGGCCCCTCTGCGTGTTCACA GCGGACCTTGATTTAATGTCTATACAATTAAGGCACG CGGTGAATGCCAAGAGAGGCGCCTCCGCCGCTCCTT | 113 |
| hsa-mir-124a-3-prec | TGAGGGCCCCTCTGCGTGTTCACAGCGGACCTTGATTT AATGTCTATACAATTAAGGCACGCGGTGAATGCCAAG AGAGGCGCCTCC | 114 |
| hsa-mir-124a-prec | CTCTGCGTGTTCACAGCGGACCTTGATTTAATGTCTAT ACAATTAAGGCACGCGGTGAATGCCAAGAG | 115 |
| hsa-mir-124b-prec | CTCTCCGTGTTCACAGCGGACCTTGATTTAATGTCATA CAATTAAGGCACGCGGTGAATGCCAAGAG | 116 |
| hsa-mir-125a-prec | TGCCAGTCTCTAGGTCCCTGAGACCCTTTAACCTGTGA GGACATCCAGGGTCACAGGTGAGGTTCTTGGGAGCCT GGCGTCTGGCC | 117 |
| hsa-mir-125a-prec | GGTCCCTGAGACCCTTTAACCTGTGAGGACATCCAGG GTCACAGGTGAGGTTCTTGGGAGCCTGG | 118 |
| hsa-mir-125b-1 | ACATTGTTGCGCTCCTCTCAGTCCCTGAGACCCTAACT TGTGATGTTTACCGTTTAAATCCACGGGTTAGGCTCTT GGGAGCTGCGAGTCGTGCTTTTGCATCCTGGA | 119 |
| hsa-mir-125b-1 | TGCGCTCCTCTCAGTCCCTGAGACCCTAACTTGTGATG TTTACCGTTTAAATCCACGGGTTAGGCTCTTGGGAGCT GCGAGTCGTGCT | 120 |
| hsa-mir-125b-2-prec | ACCAGACTTTTCCTAGTCCCTGAGACCCTAACTTGTGA GGTATTTTAGTAACATCACAAGTCAGGCTCTTGGGAC CTAGGCGGAGGGGA | 121 |

TABLE 1-continued

Human miR Gene Product Sequences

| Name | Precursor Sequence (5' to 3')* | SEQ ID NO. |
|---|---|---|
| hsa-mir-125b-2-prec | CCTAGTCCCTGAGACCCTAACTTGTGAGGTATTTTAGTAACATCACAAGTCAGGCTCTTGGGACCTAGGC | 122 |
| hsa-mir-126-prec | CGCTGGCGACGGGACATTATTACTTTTGGTACGCGCTGTGACACTTCAAACTCGTACCGTGAGTAATAATGCGCCGTCCACGGCA | 123 |
| hsa-mir-126-prec | ACATTATTACTTTTGGTACGCGCTGTGACACTTCAAACTCGTACCGTGAGTAATAATGCGC | 124 |
| hsa-mir-127-prec | TGTGATCACTGTCTCCAGCCTGCTGAAGCTCAGAGGGCTCTGATTCAGAAAGATCATCGGATCCGTCTGAGCTTGGCTGGTCGGAAGTCTCATCATC | 125 |
| hsa-mir-127-prec | CCAGCCTGCTGAAGCTCAGAGGGCTCTGATTCAGAAAGATCATCGGATCCGTCTGAGCTTGGCTGGTCGG | 126 |
| hsa-mir-128a-prec | TGAGCTGTTGGATTCGGGGCCGTAGCACTGTCTGAGAGGTTTACATTTCTCACAGTGAACCGGTCTCTTTTTCAGCTGCTTC | 127 |
| hsa-mir-128b-prec | GCCCGGCAGCCACTGTGCAGTGGGAAGGGGGCCGATACACTGTACGAGAGTGAGTAGCAGGTCTCACAGTGAACCGGTCTCTTTCCCTACTGTGTCACACTCCTAATGG | 128 |
| hsa-mir-128-prec | GTTGGATTCGGGGCCGTAGCACTGTCTGAGAGGTTTACATTTCTCACAGTGAACCGGTCTCTTTTTCAGC | 129 |
| hsa-mir-129-prec | TGGATCTTTTTGCGGTCTGGGCTTGCTGTTCCTCTCAACAGTAGTCAGGAAGCCCTTACCCCAAAAAGTATCTA | 130 |
| hsa-mir-130a-prec | TGCTGCTGGCCAGAGCTCTTTTCACATTGTGCTACTGTCTGCACCTGTCACTAGCAGTGCAATGTTAAAAGGGCATTGGCCGTGTAGTG | 131 |
| hsa-mir-131-1-prec | gccaggaggcggGGTTGGTTGTTATCTTTGGTTATCTAGCTGTATGAGTGGTGTGGAGTCTTCATAAAGCTAGATAACCGAAAGTAAAAATAACCCCATACACTGCGCAG | 132 |
| hsa-mir-131-3-prec | CACGGCGCGGCAGCGGCACTGGCTAAGGGAGGCCCGTTTCTCTCTTTGGTTATCTAGCTGTATGAGTGCCACAGAGCCGTCATAAAGCTAgataaccgaaagtagaaatg | 133 |
| hsa-mir-131-prec | GTTGTTATCTTTGGTTATCTAGCTGTATGAGTGTATTGGTCTTCATAAAGCTAGATAACCGAAAGTAAAAAC | 134 |
| hsa-mir-132-prec | CCGCCCCCGCGTCTCCAGGGCAACCGTGGCTTTCGATTGTTACTGTGGGAACTGGAGGTAACAGTCTACAGCCATGGTCGCCCCGCAGCACGCCCACGCGC | 135 |
| hsa-mir-132-prec | GGGCAACCGTGGCTTTCGATTGTTACTGTGGGAACTGGAGGTAACAGTCTACAGCCATGGTCGCCC | 136 |
| hsa-mir-133a-1 | ACAATGCTTTGCTAGAGCTGGTAAAATGGAACCAAATCGCCTCTTCAATGGATTTGGTCCCCTTCAACCAGCTGTAGCTATGCATTGA | 137 |
| hsa-mir-133a-2 | GGGAGCCAAATGCTTTGCTAGAGCTGGTAAAATGGAACCAAATCGACTGTCCAATGGATTTGGTCCCCTTCAACCAGCTGTAGCTGTGCATTGATGGCGCCG | 138 |
| hsa-mir-133-prec | GCTAGAGCTGGTAAAATGGAACCAAATCGCCTCTTCAATGGATTTGGTCCCCTTCAACCAGCTGTAGC | 139 |
| hsa-mir-134-prec | CAGGGTGTGTGACTGGTTGACCAGAGGGGCATGCACTGTGTTCACCCTGTGGGCCACCTAGTCACCAACCCTC | 140 |
| hsa-mir-134-prec | AGGGTGTGTGACTGGTTGACCAGAGGGGCATGCACTGTGTTCACCCTGTGGGCCACCTAGTCACCAACCCT | 141 |
| hsa-mir-135-1-prec | AGGCCTCGCTGTTCTCTATGGCTTTTTATTCCTATGTGATTCTACTGCTCACTCATATAGGGATTGGAGCCGTGGCGCACGGCGGGGACA | 142 |

TABLE 1-continued

Human miR Gene Product Sequences

| Name | Precursor Sequence (5' to 3')* | SEQ ID NO. |
|---|---|---|
| hsa-mir-135-2-prec | AGATAAATTCACTCTAGTGCTT<u>TATGGCTTTTTATTCC TATGTGAT</u>AGTAATAAAGTCTCATGTAGGGATGGAAG CCATGAAATACATTGTGAAAAATCA | 143 |
| hsa-mir-135-prec | C<u>TATGGCTTTTTATTCCTATGTGATT</u>CTACTGCTCACTC ATATAGGGATTGGAGCCGTGG | 144 |
| hsa-mir-136-prec | TGAGCCCTCGGAGG<u>ACTCCATTTGTTTTGATGATGGAT</u> TCTTATGCTCCATCATCGTCTCAAATGAGTCTTCAGAG GGTTCT | 145 |
| hsa-mir-136-prec | GAGG<u>ACTCCATTTGTTTTGATGATGGA</u>TTCTTATGCTC CATCATCGTCTCAAATGAGTCTTC | 146 |
| hsa-mir-137-prec | CTTCGGTGACGGGTATTCTTGGGTGGATAATACGGATT ACGTTGT<u>TATTGCTTAAGAATACGCGTAGTCGAGG</u> | 147 |
| hsa-mir-138-1-prec | CCCTGGCATGGTGTGGTGGGGC<u>AGCTGGTGTTGTGAA TC</u>AGGCCGTTGCCAATCAGAGAACGGCTACTTCACAA CACCAGGGCCACACCACACTACAGG | 148 |
| hsa-mir-138-2-prec | CGTTGCTGC<u>AGCTGGTGTTGTGAATC</u>AGGCCGACGAG CAGCGCATCCTCTTACCCGGCTATTTCACGACACCAGG GTTGCATCA | 149 |
| hsa-mir-138-prec | C<u>AGCTGGTGTTGTGAATC</u>AGGCCGACGAGCAGCGCAT CCTCTTACCCGGCTATTTCACGACACCAGGGTTG | 150 |
| hsa-mir-139-prec | GTGTATT<u>CTACAGTGCACGTGTCT</u>CCAGTGTGGCTCGG AGGCTGGAGACGCGGCCCTGTTGGAGTAAC | 151 |
| hsa-mir-140 | TGTGTCTCTCTCTGTGTCCTGCCAGTGGTTTTACCCTAT GGTAGGTTACGTCATGCTGTTC<u>TACCACAGGGTAGAA CCACGGA</u>CAGGATACCGGGGCACC | 152 |
| hsa-mir-140as-prec | TCCTGCCAGTGGTTTTACCCTATGGTAGGTTACGTCAT GCTGTTC<u>TACCACAGGGTAGAACCACGGA</u>CAGGA | 153 |
| hsa-mir-140s-prec | CCTGCCAGTGGTTTTACCCTATGGTAGGTTACGTCATG CTGTTC<u>TACCACAGGGTAGAACCACGGA</u>CAGG | 154 |
| hsa-mir-141-prec | CGGCCGGCCCTGGGTCCATCTTCCAGTACAGTGTTGG ATGGTCTAATTGTGAAGCTCCT<u>AACACTGTCTGGTAAA GATGG</u>CTCCGGGTGGGTTC | 155 |
| hsa-mir-141-prec | GGGTCCATCTTCCAGTACAGTGTTGGATGGTCTAATTG TGAAGCTCCT<u>AACACTGTCTGGTAAAGATGG</u>CCC | 156 |
| hsa-mir-142as-prec | ACC<u>CATAAAGTAGAAAGCACTAC</u>TAACAGCACTGGAG GGTGTAGTGTTTCCTACTTTATGGATG | 157 |
| hsa-mir-142-prec | GACAGTGCAGTCACCC<u>ATAAAGTAGAAAGCACTACTA</u> ACAGCACTGGAGGGTGTAGTGTTTCCTACTTTATGGAT GAGTGTACTGTG | 158 |
| hsa-mir-142s-pres | ACC<u>CATAAAGTAGAAAGCACTAC</u>TAACAGCACTGGAG GGTGTAGTGTTTCCTACTTTATGGATG | 159 |
| hsa-mir-143-prec | GCGCAGCGCCCTGTCTCCCAGCCTGAGGTGCAGTGCT GCATCTCTGGTCAGTTGGGAGT<u>CTGAGATGAAGCACT GTAGCTC</u>AGGAAGAGAGAAGTTGTTCTGCAGC | 160 |
| hsa-mir-143-prec | CCTGAGGTGCAGTGCTGCATCTCTGGTCAGTTGGGAG TC<u>TGAGATGAAGCACTGTAGCTC</u>AGG | 161 |
| hsa-mir-144-prec | TGGGGCCCTGGCTGGGATATCATCATATACTGTAAGTT TGCGATGAGACAC<u>TACAGTATAGATGATGTACTAG</u>TC CGGGCACCCCC | 162 |
| hsa-mir-144-prec | GGCTGGGATATCATCATATACTGTAAGTTTGCGATGA GACAC<u>TACAGTATAGATGATGTACTAG</u>TC | 163 |

TABLE 1-continued

Human miR Gene Product Sequences

| Name | Precursor Sequence (5' to 3')* | SEQ ID NO. |
|---|---|---|
| hsa-mir-145-prec | CACCTTGTCCTCACGGTCCAGTTTTCCCAGGAATCCCT TAGATGCTAAGATGGGGATTCCTGGAAATACTGTTCTT GAGGTCATGGTT | 164 |
| hsa-mir-145-prec | CTCACGGTCCAGTTTTCCCAGGAATCCCTTAGATGCTA AGATGGGGATTCCTGGAAATACTGTTCTTGAG | 165 |
| hsa-mir-146-prec | CCGATGTGTATCCTCAGCTTTGAGAACTGAATTCCATG GGTTGTGTCAGTGTCAGACCTCTGAAATTCAGTTCTTC AGCTGGGATATCTCTGTCATCGT | 166 |
| hsa-mir-146-prec | AGCTTTGAGAACTGAATTCCATGGGTTGTGTCAGTGTC AGACCTGTGAAATTCAGTTCTTCAGCT | 167 |
| hsa-mir-147-prec | AATCTAAAGACAACATTTCTGCACACACACCAGACTA TGGAAGCCAGTGTGTGGAAATGCTTCTGCTAGATT | 168 |
| hsa-mir-148-prec | GAGGCAAAGTTCTGAGACACTCCGACTCTGAGTATGA TAGAAGTCAGTGCACTACAGAACTTTGTCTC | 169 |
| hsa-mir-149-prec | GCCGGCGCCCGAGCTCTGGCTCCGTGTCTTCACTCCCG TGCTTGTCCGAGGAGGGAGGGAGGGACGGGGCTGT GCTGGGGCAGCTGGA | 170 |
| hsa-mir-149-prec | GCTCTGGCTCCGTGTCTTCACTCCCGTGCTTGTCCGAG GAGGGAGGGAGGGAC | 171 |
| hsa-mir-150-prec | CTCCCCATGGCCCTGTCTCCCAACCCTTGTACCAGTGC TGGGCTCAGACCCTGGTACAGGCCTGGGGGACAGGGA CCTGGGGAC | 172 |
| hsa-mir-150-prec | CCCTGTCTCCCAACCCTTGTACCAGTGCTGGGCTCAGA CCCTGGTACAGGCCTGGGGGACAGGG | 173 |
| hsa-mir-151-prec | CCTGCCCTCGAGGAGCTCACAGTCTAGTATGTCTCATC CCCTACTAGACTGAAGCTCCTTGAGGACAGG | 174 |
| hsa-mir-152-prec | TGTCCCCCCCGGCCCAGGTTCTGTGATACACTCCGACT CGGGCTCTGGAGCAGTCAGTGCATGACAGAACTTGGG CCCGGAAGGACC | 175 |
| hsa-mir-152-prec | GGCCCAGGTTCTGTGATACACTCCGACTCGGGCTCTG GAGCAGTCAGTGCATGACAGAACTTGGGCCCCGG | 176 |
| hsa-mir-153-1-prec | CTCACAGCTGCCAGTGTCATTTTTGTGATCTGCAGCTA GTATTCTCACTCCAGTTGCATAGTCACAAAAGTGATCA TTGGCAGGTGTGGC | 177 |
| hsa-mir-153-1-prec | tctctctctccctcACAGCTGCCAGTGTCATTGTCACAAAAGTG ATCATTGGCAGGTGTGGCTGCTGCATG | 178 |
| hsa-mir-153-2-prec | AGCGGTGGCCAGTGTCATTTTTGTGATGTTGCAGCTAG TAATATGAGCCCAGTTGCATAGTCACAAAAGTGATCA TTGGAAACTGTG | 179 |
| hsa-mir-153-2-prec | CAGTGTCATTTTTGTGATGTTGCAGCTAGTAATATGAG CCCAGTTGCATAGTCACAAAAGTGATCATTG | 180 |
| hsa-mir-154-prec | GTGGTACTTGAAGATAGGTTATCCGTGTTGCCTTCGCT TTATTTGTGACGAATCATACACGGTTGACCTATTTTTC AGTACCAA | 181 |
| hsa-mir-154-prec | GAAGATAGGTTATCCGTGTTGCCTTCGCTTTATTTGTG ACGAATCATACACGGTTGACCTATTTTT | 182 |
| hsa-mir-155-prec | CTGTTAATGCTAATCGTGATAGGGGTTTTTGCCTCCAA CTGACTCCTACATATTAGCATTAACAG | 183 |
| hsa-mir-16-2-prec | CAATGTCAGCAGTGCCTTAGCAGCACGTAAATATTGG CGTTAAGATTCTAAAATTATCTCCAGTATTAACTGTGC TGCTGAAGTAAGGTTGACCATACTCTACAGTTG | 184 |

TABLE 1-continued

Human miR Gene Product Sequences

| Name | Precursor Sequence (5' to 3')* | SEQ ID NO. |
|---|---|---|
| hsa-mir-181a-prec | AGAAGGGCTATCAGGCCAGCCTTCAGAGGACTCCAAG<u>GAACATTCAACGCTGTCGGTGAGTTTGGGATTTGAAA</u>AAACCACTGACCGTTGACTGTACCTTGGGGTCCTTA | 185 |
| hsa-mir-181b-prec | TGAGTTTTGAGGTTGCTTCAGTG<u>AACATTCAACGCTGTCGGTGAGTTTGGAATTAAAATCAAAACCATCGACCGT</u>TGATTGTACCCTATGGCTAACCATCATCTACTCCA | 186 |
| hsa-mir-181c-prec | CGGAAAATTTGCCAAGGGTTTGGGG<u>AACATTCAACCTGTCGGTGAG</u>TTTGGGCAGCTCAGGCAAACCATCGACCGTTGAGTGGACCCTGAGGCCTGGAATTGCCATCCT | 187 |
| hsa-mir-182-as-prec | GAGCTGCTTGCCTCCCCCGTT<u>TTTGGCAATGGTAGAACTCACAC</u>TGGTGAGGTAACAGGATCCGGTGGTTCTAGACTTGCCAACTATGGGGCGAGGACTCAGCCGGCAC | 188 |
| hsa-mir-182-prec | T<u>TTTTGGCAATGGTAGAACTCACAC</u>TGGTGAGGTAACAGGATCCGGTGGTTCTAGACTTGCCAACTATGG | 189 |
| hsa-mir-183-prec | CCGCAGAGTGTGACTCCTGTTCTGTG<u>TATGGCACTGGTAGAATTCACTGTGAACAGTCTCAGTCAGTGAATTACC</u>GAAGGGCCATAAACAGAGCAGAGACAGATCCACGA | 190 |
| hsa-mir-184-prec | CCAGTCACGTCCCCTTATCACTTTTCCAGCCCAGCTTTGTGACTGTAAGTGTT<u>GGACGGAGAACTGATAAGGGTA</u>GGTGATTGA | 191 |
| hsa-mir-184-prec | CCTTATCACTTTTCCAGCCCAGCTTTGTGACTGTAAGTGTT<u>GGACGGAGAACTGATAAGGGTAGG</u> | 192 |
| hsa-mir-185-prec | AGGGGGCGAGGGAT<u>TGGAGAGAAAGGCAGTTC</u>CTGATGGTCCCCTCCCCAGGGGCTGGCTTTCCTCTGGTCCTTCCCTCCCA | 193 |
| hsa-mir-185-prec | AGGGAT<u>TGGAGAGAAAGGCAGTTC</u>CTGATGGTCCCCTCCCCAGGGGCTGGCTTTCCTCTGGTCCTT | 194 |
| hsa-mir-186-prec | TGCTTGTAACTTTC<u>CAAAGAATTCTCCTTTTGGGCTTT</u>CTGGTTTTATTTTAAGCCCAAAGGTGAATTTTTTGGGAAGTTTGAGCT | 195 |
| hsa-mir-186-prec | ACTTTC<u>CAAAGAATTCTCCTTTTGGGCTTT</u>CTGGTTTTATTTTAAGCCCAAAGGTGAATTTTTTGGGAAGT | 196 |
| hsa-mir-187-prec | GGTCGGGCTCACCATGACACAGTGTGAGACTCGGGCTACAACACAGGACCCGGGGCGCTGCTCTGACCCC<u>TCGTGTCTTGTGTTGCAGCCGG</u>AGGGACGCAGGTCCGCA | 197 |
| hsa-mir-188-prec | TGCTCCCTCTCTCACAT<u>CCCTTGCATGGTGGAGGGT</u>GAGCTTTCTGAAAACCCCTCCCACATGCAGGGTTTGCAGGATGGCGAGCC | 198 |
| hsa-mir-188-prec | TCTCACAT<u>CCCTTGCATGGTGGAGGGT</u>GAGCTTTCTGAAAACCCCTCCCACATGCAGGGTTTGCAGGA | 199 |
| hsa-mir-189-prec | CTGTCGATTGGACCCGCCCTCCG<u>GTGCCTACTGAGCTGATATCAGT</u>TCTCATTTTACACACTGGCTCAGTTCAGCAGGAACAGGAGTCGAGCCCTTGAGCAA | 200 |
| hsa-mir-189-prec | CTCCG<u>GTGCCTACTGAGCTGATATCAGT</u>TCTCATTTTACACACTGGCTCAGTTCAGCAGGAACAGGAG | 201 |
| hsa-mir-190-prec | TGCAGGCCTCTGTG<u>TGATATGTTTGATATATTAGGTTG</u>TTATTTAATCCAACTATATATCAAACATATTCCTACAGTGTCTTGCC | 202 |
| hsa-mir-190-prec | CTGT<u>GTGATATGTTTGATATATTAGGTT</u>GTTATTTAATCCAACTATATATCAAACATATTCCTACAG | 203 |
| hsa-mir-191-prec | CGGCTGGACAGCGGG<u>CAACGGAATCCCAAAAGCAGCT</u>GTTGTCTCCAGAGCATTCCAGCTGCGCTTGGATTTCGTCCCCTGCTCTCCTGCCT | 204 |

TABLE 1-continued

Human miR Gene Product Sequences

| Name | Precursor Sequence (5' to 3')* | SEQ ID NO. |
|---|---|---|
| hsa-mir-191-prec | AGCGGGCAACGGAATCCCAAAAGCAGCTGTTGTCTCC AGAGCATTCCAGCTGCGCTTGGATTTCGTCCCCTGCT | 205 |
| hsa-mir-192-2/3 | CCGAGACCGAGTGCACAGGGCTCTGACCTATGAATTG ACAGCCAGTGCTCTCGTCTCCCCTCTGGCTGCCAATTC CATAGGTCACAGGTATGTTCGCCTCAATGCCAG | 206 |
| hsa-mir-192-prec | GCCGAGACCGAGTGCACAGGGCTCTGACCTATGAATT GACAGCCAGTGCTCTCGTCTCCCCTCTGGCTGCCAATT CCATAGGTCACAGGTATGTTCGCCTCAATGCCAGC | 207 |
| hsa-mir-193-prec | CGAGGATGGGAGCTGAGGGCTGGGTCTTTGCGGGCGA GATGAGGGTGTCGGATCAACTGGCCTACAAAGTCCCA GTTCTCGGCCCCCG | 208 |
| hsa-mir-193-prec | GCTGGGTCTTTGCGGGCGAGATGAGGGTGTCGGATCA ACTGGCCTACAAAGTCCCAGT | 209 |
| hsa-mir-194-prec | ATGGTGTTATCAAGTGTAACAGCAACTCCATGTGGAC TGTGTACCAATTTCCAGTGGAGATGCTGTTACTTTTGA TGGTTACCAA | 210 |
| hsa-mir-194-prec | GTGTAACAGCAACTCCATGTGGACTGTGTACCAATTTC CAGTGGAGATGCTGTTACTTTTGAT | 211 |
| hsa-mir-195-prec | AGCTTCCCTGGCTCTAGCAGCACAGAAATATTGGCAC AGGGAAGCGAGTCTGCCAATATTGGCTGTGCTGCTCC AGGCAGGGTGGTG | 212 |
| hsa-mir-195-prec | TAGCAGCACAGAAATATTGGCACAGGGAAGCGAGTCT GCCAATATTGGCTGTGCTGCT | 213 |
| hsa-mir-196-1-prec | CTAGAGCTTGAATTGGAACTGCTGAGTGAATTAGGTA GTTTCATGTTGTTGGGCCTGGGTTTCTGAACACAACAA CATTAAACCACCCGATTCACGGCAGTTACTGCTCC | 214 |
| hsa-mir-196-1-prec | GTGAATTAGGTAGTTTCATGTTGTTGGGCCTGGGTTTC TGAACACAACAACATTAAACCACCCGATTCAC | 215 |
| hsa-mir-196-2-prec | TGCTCGCTCAGCTGATCTGTGGCTTAGGTAGTTTCATG TTGTTGGGATTGAGTTTTGAACTCGGCAACAAGAAAC TGCCTGAGTTACATCAGTCGGTTTTCGTCGAGGGC | 216 |
| hsa-mir-196-prec | GTGAATTAGGTAGTTTCATGTTGTTGGGCCTGGGTTTC TGAACACAACAACATTAAACCACCCGATTCAC | 217 |
| hsa-mir-197-prec | GGCTGTGCCGGGTAGAGAGGGCAGTGGGAGGTAAGA GCTCTTCACCCTTCACCACCTTCTCCACCCAGCATGGCC | 218 |
| hsa-mir-198-prec | TCATTGGTCCAGAGGGGAGATAGGTTCCTGTGATTTTT CCTTCTTCTCTATAGAATAAATGA | 219 |
| hsa-mir-199a-1-prec | GCCAACCCAGTGTTCAGACTACCTGTTCAGGAGGCTC TCAATGTGTACAGTAGTCTGCACATTGGTTAGGC | 220 |
| hsa-mir-199a-2-prec | AGGAAGCTTCTGGAGATCCTGCTCCGTCGCCCCAGTG TTCAGACTACCTGTTCAGGACAATGCCGTTGTACAGTA GTCTGCACATTGGTTAGACTGGGCAAGGGAGAGCA | 221 |
| hsa-mir-199b-prec | CCAGAGGACACCTCCACTCCGTCTACCCAGTGTTTAG ACTATCTGTTCAGGACTCCCAAATTGTACAGTAGTCTG CACATTGGTTAGGCTGGGCTGGGTTAGACCCTCGG | 222 |
| hsa-mir-199s-prec | GCCAACCCAGTGTTCAGACTACCTGTTCAGGAGGCTC TCAATGTGTACAGTAGTCTGCACATTGGTTAGGC | 223 |
| hsa-mir-200a-prec | GCCGTGGCCATCTTACTGGGCAGCATTGGATGGAGTC AGGTCTCTAATACTGCCTGGTAATGATGACGGC | 224 |
| hsa-mir-200b-prec | CCAGCTCGGGCAGCCGTGGCCATCTTACTGGGCAGCA TTGGATGGAGTCAGGTCTCTAATACTGCCTGGTAATG ATGACGGCGGAGCCCTGCACG | 225 |

TABLE 1-continued

Human miR Gene Product Sequences

| Name | Precursor Sequence (5' to 3')* | SEQ ID NO. |
|---|---|---|
| hsa-mir-202-prec | GTTCCTTTTTCCTATGCATATACTTCTTTGAGGATCTGG CCTAAA<u>GAGGGTATAGGGCATGGGAAGA</u>TGGAGC | 226 |
| hsa-mir-203-prec | GTGTTGGGGACTCGCGCGCTGGGTCCAGTGGTTCTTA ACAGTTCAACAGTTCTGTAGCGCAATT<u>GTGAAATGTTT</u> <u>AGGACCACTAGA</u>CCCGGCGGGCGCGGCGACAGCGA | 227 |
| hsa-mir-204-prec | GGCTACAGTCTTTCTTCATGTGACTCGTGGAC<u>TTCCCT</u> <u>TTGTCATCCTATGCCT</u>GAGAATATATGAAGGAGGCTG GGAAGGCAAAGGGACGTTCAATTGTCATCACTGGC | 228 |
| hsa-mir-205-prec | AAAGATCCTCAGACAATCCATGTGCTTCTCTTG<u>TCCTT</u> <u>CATTCCACCGGAGTCTGT</u>CTCATACCCAACCAGATTTC AGTGGAGTGAAGTTCAGGAGGCATGGAGCTGACA | 229 |
| hsa-mir-206-prec | TGCTTCCCGAGGCCACATGCTTCTTTATATCCCCATAT GGATTACTTTGCTA<u>TGGAATGTAAGGAAGTGTGTGGT</u> TTCGGCAAGTG | 230 |
| hsa-mir-206-prec | AGGCCACATGCTTCTTTATATCCCCATATGGATTACTT TGCTA<u>TGGAATGTAAGGAAGTGTGTGG</u>TTTT | 231 |
| hsa-mir-208-prec | TGACGGGCGAGCTTTTGGCCCGGGTTATACCTGATGCT CACGT<u>ATAAGACGAGCAAAAAGCTTGT</u>TGGTCA | 232 |
| hsa-mir-210-prec | ACCCGGCAGTGCCTCCAGGCGCAGGGCAGCCCCTGCC CACCGCACACTGCGCTGCCCCAGACCCA<u>CTGTGCGTG</u> <u>TGACAGCGGCTG</u>ATCTGTGCCTGGGCAGCGCGACCC | 233 |
| hsa-mir-211-prec | TCACCTGGCCATGTGACTTGTGGGC<u>TTCCCTTTGTCAT</u> <u>CCTTCGCCT</u>AGGGCTCTGAGCAGGGCAGGGACAGCAA AGGGGTGCTCAGTTGTCACTTCCCACAGCACGGAG | 234 |
| hsa-mir-212-prec | CGGGGCACCCCGCCCGGACAGCGCGCCGGCACCTTGG CTCTAGACTGCTTACTGCCCGGGCCGCCCTCAGT<u>AACA</u> <u>GTCTCCAGTCACGGCC</u>ACCGACGCCTGGCCCCGCC | 235 |
| hsa-mir-213-prec | CCTGTGCAGAGATTATTTTTAAAAGGTCACAATC<u>AAC</u> <u>ATTCATTGCTGTCGGTGGGT</u>TGAACTGTGTGGACAAG CTCACTGAACAATGAATGCAACTGTGGCCCCGCTT | 236 |
| hsa-mir-213-prec-LIM | GAGTTTTGAGGTTGCTTCAGTGAACATTCAACGCTGTC GGTGAGTTTGGAATTAAAATCAAAA<u>CCATCGACCGTT</u> <u>GATTGTACC</u>CTATGGCTAACCATCATCTACTCC | 237 |
| hsa-mir-214-prec | GGCCTGGCTGGACAGAGTTGTCATGTGTCTGCCTGTCT ACACTTGCTGTGCAGAACATCCGCTCACCTGT<u>ACAGC</u> <u>AGGCACAGACAGGCAG</u>TCACATGACAACCCAGCCT | 238 |
| hsa-mir-215-prec | ATCATTCAGAAATGGTATACAGGAAA<u>ATGACCTATGA</u> <u>ATTGACAGAC</u>AATATAGCTGAGTTTGTCTGTCATTTCT TTAGGCCAATATTCTGTATGACTGTGCTACTTCAA | 239 |
| hsa-mir-216-prec | GATGGCTGTGAGTTGGCT<u>TAATCTCAGCTGGCAACTGT</u> <u>GAGATGTT</u>CATACAATCCCTCACAGTGGTCTCTGGGAT TATGCTAAACAGAGCAATTTCCTAGCCCTCACGA | 240 |
| hsa-mir-217-prec | AGTATAATTATTACATAGTTTTTGATGTCGCAGA<u>TACT</u> <u>GCATCAGGAACTGATTGGAT</u>AAGAATCAGTCACCATC AGTTCCTAATGCATTGCCTTCAGCATCTAAACAAG | 241 |
| hsa-mir-218-1-prec | GTGATAATGTAGCGAGATTTTCTGT<u>TGTGCTTGATCTA</u> <u>ACCATGT</u>GGTTGCGAGGTATGAGTAAAACATGGTTCC GTCAAGCACCATGGAACGTCACGCAGCTTTCTACA | 242 |
| hsa-mir-218-2-prec | GACCAGTCGCTGCGGGGCTTTCCTT<u>TGTGCTTGATCTA</u> <u>ACCATGT</u>GGTGGAACGATGGAAACGGAACATGGTTCT GTCAAGCACCGCGGAAAGCACCGTGCTCTCCTGCA | 243 |
| hsa-mir-219-prec | CCGCCCCGGGCCGCGGCTCCTGA<u>TTGTCCAAACGCAA</u> <u>TTCT</u>CGAGTCTATGGCTCCGGCCGAGAGTTGAGTCTGG ACGTCCCGAGCCGCCGCCCCCAAACCTCGAGCGGG | 244 |

TABLE 1-continued

Human miR Gene Product Sequences

| Name | Precursor Sequence (5' to 3')* | SEQ ID NO. |
| --- | --- | --- |
| hsa-mir-220-prec | GACAGTGTGGCATTGTAGGGCTCCACACCGTATCTGACACTTTGGGCGAGGGCACCATGCTGAAGGTGTTCATGATGCGGTCTGGGAACTCCTCACGGATCTTACTGATG | 245 |
| hsa-mir-221-prec | TGAACATCCAGGTCTGGGGCATGAACCTGGCATACAATGTAGATTTCTGTGTTCGTTAGGCAACAGCTACATTGTCTGCTGGGTTTCAGGCTACCTGGAAACATGTTCTC | 246 |
| hsa-mir-222-prec | GCTGCTGGAAGGTGTAGGTACCCTCAATGGCTCAGTAGCCAGTGTAGATCCTGTCTTTCGTAATCAGCAGCTACATCTGGCTACTGGGTCTCTGATGGCATCTTCTAGCT | 247 |
| hsa-mir-223-prec | CCTGGCCTCCTGCAGTGCCACGCTCCGTGTATTTGACAAGCTGAGTTGGACACTCCATGTGGTAGAGTGTCAGTTTGTCAAATACCCCAAGTGCGGCACATGCTTACCAG | 248 |
| hsa-mir-224-prec | GGGCTTTCAAGTCACTAGTGGTTCCGTTTAGTAGATGATTGTGCATTGTTTCAAAATGGTGCCCTAGTGACTACAAAGCCC | 249 |
| hsA-mir-29b-1 = 102-prec1 | CTTCTGGAAGCTGGTTTCACATGGTGGCTTAGATTTTTCCATCTTTGTATCTAGCACCATTTGAAATCAGTGTTTTAGGAG | 250 |
| hsA-mir-29b-2 = 102prec7.1 = 7.2 | CTTCAGGAAGCTGGTTTCATATGGTGGTTTAGATTTAAATAGTGATTGTCTAGCACCATTTGAAATCAGTGTTCTTGGGGG | 251 |
| hsA-mir-29b-3 = 102prec7.1 = 7.2 | CTTCAGGAAGCTGGTTTCATATGGTGGTTTAGATTTAAATAGTGATTGTCTAGCACCATTTGAAATCAGTGTTCTTGGGGG | 252 |
| hsa-mir-30* = mir-097-prec-6 | GTGAGCGACTGTAAACATCCTCGACTGGAAGCTGTGAAGCCACAGATGGGCTTTCAGTCGGATGTTTGCAGCTGCCTACT | 253 |
| mir-033b | ACCAAGTTTCAGTTCATGTAAACATCCTACACTCAGCTGTAATACATGGATTGGCTGGGAGGTGGATGTTTACTTCAGCTGACTTGGA | 254 |
| mir-101-precursor-9 = mir-101-3 | TGCCCTGGCTCAGTTATCACAGTGCTGATGCTGTCTATTCTAAAGGTACAGTACTGTGATAACTGAAGGATGGCA | 255 |
| mir-108-1-small | ACACTGCAAGAACAATAAGGATTTTTAGGGGCATTATGACTGAGTCAGAAAACACAGCTGCCCCTGAAAGTCCCTCATTTTTCTTGCTGT | 256 |
| mir-108-2-small | ACTGCAAGAGCAATAAGGATTTTTAGGGGCATTATGATAGTGGAATGGAAACACATCTGCCCCCAAAAGTCCCTCATTTT | 257 |
| mir-123-prec = mir-126-prec | CGCTGGCGACGGGACATTATTACTTTTGGTACGCGCTGTGACACTTCAAACTCGTACCGTGAGTAATAATGCGCCGTCCACGGCA | 258 |
| mir-123-prec = mir-126-prec | ACATTATTACTTTTGGTACGCGCTGTGACACTTCAAACTCGTACCGTGAGTAATAATGCGC | 259 |
| mir-129-1-prec | TGGATCTTTTTGCGGTCTGGGCTTGCTGTTCCTCTCAACAGTAGTCAGGAAGCCCTTACCCCAAAAAGTATCTA | 260 |
| mir-129-small-2 = 129b? | TGCCCTTCGCGAATCTTTTTGCGGTCTGGGCTTGCTGTACATAACTCAATAGCCGGAAGCCCTTACCCCAAAAAGCATTTGCGGAGGGCG | 261 |
| mir-133b-small | GCCCCCTGCTCTGGCTGGTCAAACGGAACCAAGTCCGTCTTCCTGAGAGGTTTGGTCCCCTTCAACCAGCTACAGCAGGG | 262 |
| mir-135-small- | AGATAAATTCACTCTAGTGCTTTATGGCTTTTTATTCCTATGTGATAGTAATAAAGTCTCATGTAGGGATGGAAGCCATGAAATACATTGTGAAAAATCA | 263 |

TABLE 1-continued

Human miR Gene Product Sequences

| Name | Precursor Sequence (5' to 3')* | SEQ ID NO. |
|---|---|---|
| mir-148b-small | AAGCACGATTAGCATTTGAGGTGAAGTTCTGTTATAC ACTCAGGCTGTGGCTCTCTGAAAGTCAGTGCAT | 264 |
| mir-151-prec | CCTGTCCTCAAGGAGCTTCAGTCTAGTAGGGGATGAG ACATACTAGACTGTGAGCTCCTCGAGGGCAGG | 265 |
| mir-155-prec(BIC) | CTGT<u>TTAATGCTAATCGTGATAGGGG</u>TTTTTGCCTCCAA CTGACTCCTACATATTAGCATTAACAG | 266 |
| mir-156 = mir-157 = overlap mir-141 | CCTAACACTGTCTGGTAAAGATGGCTCCCGGGTGGGT TCTCTCGGCAGTAACCTTCAGGGAGCCCTGAAGACCA TGGAGGAC | 267 |
| mir-158-small = mir-192 | GCCGAGACCGAGTGCACAGGGC<u>TCTGACCTATGAATT GACAGCC</u>AGTGCTCTCGTCTCCCCTCTGGCTGCCAATT CCATAGGTCACAGGTATGTTCGCCTCAATGCCAGC | 268 |
| mir-159-1-small | TCCCGCCCCCTGTAACAGCAACTCCATGTGGAAGTGC CCACTGGTTCCAGTGGGGCTGCTGTTATCTGGGGCGA GGGCCA | 269 |
| mir-161-small | AAAGCTGGGTTGAGAGGGCGAAAAAGGATGAGGTGA CTGGTCTGGGCTACGCTATGCTGCGGCGCTCGGG | 270 |
| mir-163-1b-small | CATTGGCCTCCTAAGCCAGGGATTGTGGGTTCGAGTC CCACCCGGGGTAAAGAAAGGCCGAATT | 271 |
| mir-163-3-small | CCTAAGCCAGGGATTGTGGGTTCGAGTCCCACCTGGG GTAGAGGTGAAAGTTCCTTTTACGGAATTTTTT | 272 |
| mir-175-small = mir-224 | GGGCTTTCAAGTCACTAGTGGTTCCGTTTAGTAGATGA TTGTGCATTGTTTCAAAATGGTGCCCTAGTGACTACAA AGCCC | 273 |
| mir-177-small | ACGCAAGTGTCCTAAGGTGAGCTCAGGGAGCACAGAA ACCTCCAGTGGAACAGAAGGGCAAAAGCTCATT | 274 |
| mir-180-small | CATGTGTCACTTTCAGGTGGAGTTTCAAGAGTCCCTTC CTGGTTCACCGTCTCCTTTGCTCTTCCACAAC | 275 |
| mir-187-prec | GGTCGGGCTCACCATGACACAGTGTGAGACTCGGGCT ACAACACAGGACCCGGGGCGCTGCTCTGACCCC<u>TCGT GTCTTGTGTTGCAGCCGGAGGGACGCAGGTCCGCA</u> | 276 |
| mir-188-prec | TGCTCCCTCTCTCACAT<u>CCCTTGCATGGTGGAGGG</u>TGA GCTTTCTGAAAACCCCTCCCACATGCAGGGTTTGCAG GATGGCGAGCC | 277 |
| mir-190-prec | TGCAGGCCTCTGTGTGATATGTTTGATATATTAGGTTG TTATTTAATCCAACTATATATCAAACATATTCCTACAG TGTCTTGCC | 278 |
| mir-197-2 | GTGCATGTGTATGTATGTGTGCATGTGCATGTGTATGT GTATGAGTGCATGCGTGTGTGC | 279 |
| mir-197-prec | GGCTGTGCCGGGTAGAGAGGGCAGTGGGAGGTAAGA GCTCTTCACCC<u>TTCACCACCTTCTCCACCCAGCATGGCC</u> | 280 |
| mir-202-prec | GTTCCTTTTTCCTATGCATATACTTCTTTGAGGATCTGG CCTAA<u>AGAGGTATAGGGCATGGGAAGA</u>TGGAGC | 281 |
| mir-294-1 (chr16) | CAATCTTCCTTTATCATGGTATTGATTTTTCAGTGCTTC CCTTTTGTGTGAGAGAAGATA | 282 |
| mir-hes1 | ATGGAGCTGCTCACCCTGTGGGCCTCAAATGTGGAGG AACTATTCTGATGTCCAAGTGGAAAGTGCTGCGACAT TTGAGCGTCACCGGTGACGCCCATATCA | 283 |
| mir-hes2 | GCATCCCCTCAGCCTGTGGCACTCAAACTGTGGGGGC ACTTTCTGCTCTCGGTGAAAGTGCCGCCATCTTTTGA GTGTTACCGCTTGAGAAGACTCAACC | 284 |
| mir-hes3 | CGAGGAGCTCATACTGGGATACTCAAAATGGGGCGC TTTCCTTTTTGTCTGTTACTGGGAAGTGCTTCGATTTTG GGGTGTCCCTGTTTGAGTAGGGCATC | 285 |

TABLE 1-continued

Human miR Gene Product Sequences

| Name | Precursor Sequence (5' to 3')* | SEQ ID NO. |
|---|---|---|
| hsa-mir-29b-1 | CTTCAGGAAGCTGGTTTCATATGGTGGTTTAGATTTAAATAGTGATTGTCTAGCACCATTTGAAATCAGTGTTCTTGGGGG | 664 |

* An underlined sequence within a precursor sequence represents a processed miR transcript. All sequences are human.

Genome Analysis

The BUILD 33 and BUILD 34 Version 1 of the *Homo sapiens* genome, available at the NCBI website (see above), was used for genome analysis. For each human miR present in the miR database, a BLAST search was performed using the default parameters against the human genome to find the precise location, followed by mapping using the maps available at the Human Genome Resources at the NCBI website. See also Altschul et al. (1990), J. Mol. Biol. 215:403-10 and Altschul et al. (1997), Nucleic Acids Res. 25:3389-3402, the entire disclosures of which are herein incorporated by reference, for a discussion of the BLAST search algorithm Also, as a confirmation of the data, the human clone corresponding to each miR was identified and mapped to the human genome (see Table 2). Perl scripts for the automatic submission of BLAST jobs and for the retrieval of the search results were based on the LPW, HTML, and HTPP Perl modules and BioPerl modules.

Fragile Site Database

This database was constructed using the Virtual Gene Nomenclature Workshop, maintained by the HUGO Gene Nomenclature Committee at University College, London. For each FRA locus, the literature was screened for publications reporting the cloning of the locus. In ten cases, genomic positions for both centromeric and telomeric ends were found. The total genomic length of these FRA loci is 26.9 Mb. In twenty-nine cases, only one anchoring marker was identified. It was determined, based on the published data, that 3 Mb can be used as the median length for each FRA locus. Therefore, 3 Mb was used as a guideline or window length for considering whether miR were in close proximity to the FRA sites.

The human clones for seventeen HPV16 integration sites (IS) were also precisely mapped on the human genome. By analogy with the length of a FRA, in the case of HPV16 integration sites, "close" vicinity was defined to be a distance of less than 2 Mb.

PubMed Database

The PubMed database was screened on-line for publications describing cancer-related abnormalities such as minimal regions of loss-of-heterozygosity (minimal LOH) and minimal regions of amplification (minimal amplicons) using the words "LOH and genome-wide," "amplification and genome-wide" and "amplicon and cancer." The PubMed database is maintained by the NCBI and was accessed via its website. The data obtained from thirty-two papers were used to screen for putative CAGRs, based on markers with high frequency of LOH/amplification. As a second step, a literature search was performed to determine the presence or absence of the above three types of alterations and to determine the precise location of miRs with respect to CAGRs (see above). Search phrases included the combinations "minimal regions of LOH AND cancer", and "minimal region amplification AND cancer." A total of 296 publications were found and manually curated to find regions defined by both telomeric and centromeric markers. One hundred fifty-four minimally deleted regions (median length-4.14 Mb) and 37 minimally amplified regions (median length-2.45 Mb) were identified with precise genomic mapping for both telomeric and centromeric ends involving all human chromosomes except Y. To identify common breakpoint regions, PubMed was searched with the combination "translocation AND cloning AND breakpoint AND cancer." The search yielded 308 papers, which were then manually curated. Among these papers, 45 translocations with at least one breakpoint precisely mapped were reported.

Statistical Analyses

The incidence of miR genes and their association with specific chromosomes and chromosome regions, such as FRAs and amplified or deleted regions in cancer, was analyzed with random effect Poisson regression models. Under these models, "events" are defined as the number of miR genes, and non-overlapping lengths of the region of interest defined exposure "time" (i.e., fragile site versus non-fragile site, etc.). The "length" of a region was exactly ±1 Mb, if known, or estimated as ±1 Mb if unknown. The random effect used was chromosomal location, in that data within a chromosome were assumed to be correlated. The fixed effect in each model consisted of an indicator variable(s) for the type of region. This model provided the incidence rate ratio (IRR), 2-sided 95% confidence interval of the IRR, and 2-sided p-values for testing the hypothesis that the IRR is 1.0. An IRR significantly greater than 1 indicates an increase in the number of miR genes within a region.

Each model was repeated considering the distribution of miR genes only in the transcriptionally active portion of the genome (about 43% of the genome using the published data), rather than the entire chromosome length, and similar results were obtained. Considering the distribution of miRs only in the transcriptionally active portion of the genome is more conservative, and takes into account the phenomenon of clustering that was observed for the miR genes' genomic location. All computations were completed using STATA v7.0.

Patient Samples and Cell Lines

Patient samples were obtained from twelve chronic lymphocytic leukemia (CLL) patients, and mononuclear cells were isolated through Ficoll-Hypaque gradient centrifugation (Amersham Pharmacia Biotech, Piscataway, N.J.), as previously described (Calin et al., Proc. Natl. Acad. Sci. USA 2002, 99:15524-15529). Samples were then processed for RNA and DNA extraction according to standard protocols as described in Sambrook J et al. (1989), *Molecular cloning: A Laboratory Manual* (Cold Spring Harbor Laboratory Press, Cold Spring Harbor, N.Y.), the entire disclosure of which is herein incorporated by reference.

Seven human lung cancer cell lines were obtained from the American Type Culture Collection (ATCC; Manassas, Va.)

and maintained according to ATCC instructions. These cell lines were: Calu-3, H1299, H522, H460, H23, H1650 and H1573.

Northern Blotting

Total RNA isolation from patient samples and cell lines described above was performed using the Tri-Reagent protocol (Molecular Research Center, Inc). RNA samples (30 µg each) were run on 15% acryl amide denaturing (urea) Criterion recast gels (Bio-Red Laboratories, Hercules, Calif.) and then transferred onto Hyoid-N+ membrane (Amersham Pharmacia Biotech), as previously described (Calin et al., Proc. Natl. Acad. Sci. USA 2002, 99:15524-15529). Hybridization with gamma-$^{32}$P ATP labeled probes was performed at 42° C. in 7% SDS, 0.2 M Na$_2$PO$_4$, pH 7.0 overnight. Membranes were washed at 42° C., twice in 2×SSPE, 0.1% SDS and twice with 0.5×SSPE, 0.1% SDS. Blots were stripped by boiling in 0.1% aqueous SDS/0.1×SSC for 10 minutes, and were reprobed several times. As a gel loading control, 5S rRNA was also loaded and was stained with ethidium bromide. Lung tissue RNA was utilized as the normal control; normal lung total RNA was purchased from Clontech (Palo Alto, Calif.).

Example 1 miR Genes are Non-Randomly Distributed in the Human Genome

One hundred eighty-six human genes representing known or predicted miR genes were mapped, based on mouse homology or computational methods, as described above in the General Methods. The results are presented in Table 2. The names were as in the miRNA Registry; for new miR genes, sequential names were assigned. miR 213 from Sanger database is different from miR 213 described in Lim et al. (2003, Science 299:1540). MiR genes in clusters are separated by a forward slash "/". The approximate location in Mb of each clone is presented in the last column.

TABLE 2 miR Database: Chromosome Location and Clustering

| Name | Chromosome location | Genes in Cluster | Loc (Mb) (built 33) |
|---|---|---|---|
| let-7a-1 | 09q22.2 | let-7a-1/let-7f-1/let-7d | 90.2-.3 |
| let-7a-2 | 11q24.1 | miR-125b-1/let-7a-2/miR-100 | 121.9-122.15 |
| let-7a-3 | 22q13.3 | let-7a-3/let-7b | 44.7-.8 |
| let-7b | 22q13.3 | let-7a-3/let-7b | 44.7-.8 |
| let-7c | 21q11.2 | miR-99a/let-7c/miR-125b-2 | 16.7-.9 |
| let-7d | 09q22.2 | let-7a-1/let-7f-1/let7d | 90.2-.3 |
| let-7e | 19q13.4 | miR-99b/let-7e/miR-125a | 56.75-57 |
| let-7f-1 | 09q22.2 | let-7a-1/let-7f-1/let7d | 90.2-.3 |
| let-7f-2 | Xp11.2 | miR-98/let-7f-2 | 52.2-.3 |
| let-7g | 03p21.3 | let-7g/miR-135-1 | 52.1-.3 |
| let-7i | 12q14.1 | | 62.7-.9 |
| miR-001b-2 | 20q13.3 | miR-133a-2/miR-1b-2 | 61.75-.8 |
| miR-001d | 18q11.1 | miR-133a-1/miR-1d | 19.25-.4 |
| miR-007-1 | 09q21.33 | | 80-80.1 |
| miR-007-2 | 15q25 | | 86.7-.8 |
| miR-007-3 | 19p13.3 | | 4.7-.75 |
| miR-009-1 (= miR-131-1) | 01q22 | | 153.1-.2 |
| miR-009-2 (= miR-131-2) | 05q14 | | 87.85-88 |
| miR-009-3 (= miR-131-3) | 15q25.3 | | 87.5 |
| miR-010a | 17q21.3 | miR-196-1/miR-10a | 46.95-47.05 |
| miR-010b | 02q31 | | 176.85-177 |
| miR-015a | 13q14 | miR-16a/miR-15a | 49.5-.8 |
| miR-015b | 03q26.1 | miR-15b/miR-16b | 161.35-.5 |
| miR-016a | 13q14 | miR-16a/miR-15a | 49.5-.8 |
| miR-016b | 03q26.1 | miR-15b/miR-16b | 161.35-.5 |
| miR-017 (= miR-91) | 13q31 | miR-17/miR-18/miR-19a/miR-20/miR-19b-1/miR-92-1 | 90.82 |
| miR-018 | 13q31 | miR-17/miR-18/miR-19a/miR-20/miR-19b-1/miR-92-1 | 90.82 |
| miR-019a | 13q31 | miR-17/miR-18/miR-19a/miR-20/miR-19b-1/miR-92-1 | 90.82 |
| miR-019b-1 | 13q31 | miR-17/miR-18/miR-19a/miR-20/miR-19b-1/miR-92-1 | 90.82 |
| miR-019b-2 | Xq26.2 | miR-92-2/miR-19b-2/miR-106a | 131.2-.3 |
| miR-020 | 13q31 | miR-17/miR-18/miR-19a/miR-20/miR-19b-1/miR-92-1 | 90.82 |
| miR-021 (= miR104-as) | 17q23.2 | | 58.25-.35 |

TABLE 2-continued miR Database: Chromosome Location and Clustering

| Name | Chromosome location | Genes in Cluster | Loc (Mb) (built 33) |
|---|---|---|---|
| miR-022 | 17p13.3 | | 1.4-.6 |
| miR-023a | 19p13.2 | miR-24-2/miR-27a/miR-23a/miR-181c | 13.75-.95 |
| miR-023b | 09q22.1 | miR-24-1/miR27b/miR-23b | 90.8-91 |
| miR-024-1 (= miR-189) | 09q22.1 | miR-24-1/miR27b/miR-23b | 90.8-91 |
| miR-024-2 | 19p13.2 | miR-24-2/miR-27a/miR-23a/miR-181c | 13.75-.95 |
| miR-025 | 07q22 | miR-106b/miR-25/miR-93-1 | 99.25-.4 |
| miR-026a | 03p21 | | 37.8-.9 |
| miR-026b | 02q35 | | 219.1-.3 |
| miR-027a | 19p13.2 | miR-24-2/miR-27a/miR-23a/miR-181c | 13.75-.95 |
| miR-027b | 09q22.1 | miR-24-1/miR27b/miR-23b | 90.8-91 |
| miR-028 | 03q28 | | 189.65-.85 |
| miR-029a | 07q32 | miR-29a/miR29b | 129.9-130.1 |
| miR-029b (= miR-102-7.1) | 07q32 | miR-29a/miR29b | 129.9-130.1 |
| miR-029c | 01q32.2-32.3 | miR-29c/miR-102 | 204.6-.7 |
| miR-030a-as | 06q12-13 | | 72.05-.2 |
| miR-030a-s (= miR-097) | 06q12-13 | | 72.05-.2 |
| miR-030b | 08q24.2 | miR-30d/miR-30b | 135.5 |
| miR-030c | 06q13 | | 71.95-72.1 |
| miR-030d | 08q24.2 | miR-30d/miR-30b | 135.5 |
| miR-031 | 09p21 | | 21.3-.5 |
| miR-032 | 09q31.2 | | 105.1-.3 |
| miR-033a | 22q13.2 | | 40.5-.8 |
| miR-033b | 17p11.2 | | 17.6-.7 |
| miR-034 (= miR-170) | 01p36.22 | | 8.8 |
| miR-034a-1 | 11q23 | miR-34a-2/miR 34-1 | 111.3-.5 |
| miR-034a-2 | 11q23 | miR-34a-2/miR 34-1 | 111.3-.5 |
| miR-092-1 | 13q31 | miR-17/miR-18/miR-19a/miR-20/miR-19b-1/miR-92-1 | 90.82 |
| miR-092-2 | Xq26.2 | miR-92-2/miR-19b-2/miR-106a | 131.2-.3 |
| miR-093-1 | 07q22 | miR-106b/miR-25/miR-93-1 | 99.25-.4 |
| miR-095 | 04p16 | | 8-.2 |
| miR-096 | 07q32 | miR-182s/miR-182as/miR-96/miR-183 | 128.9-129 |
| miR-098 | Xp11.2 | miR-98/let-7f-2 | 52.2-.3 |
| miR-099a | 21q11.2 | miR-99a/let-7c/miR-125b-2 | 16.7-.9 |
| miR-099b | 19q13.4 | miR-99b/let-7e/miR-125a | 56.75-57 |
| miR-100 | 11q24.1 | miR-125b-1/let-7a-2/miR-100 | 121.9-122.15 |
| miR-101-1 | 01p31.3 | | 64.85-95 |
| miR-101-2 | 09p24 | | 4.8-5 |
| miR-102 | 01q32.2-32.3 | miR-29c/miR-102 | 204.5-.7 |
| miR-103-1 | 05q35.1 | | 167.8-.95 |
| miR-103-2 | 20p13 | | 3.82-.90 |
| miR-105-1 | Xq28 | | 149.3-.4 |
| miR-106b (= miR-94) | 07q22 | miR-106b/miR-25/miR-93-1 | 99.25-.4 |
| miR-106a | Xq26.2 | miR-92-2/miR-19b-2/miR-106a | 131.2-.3 |
| miR-107 | 10q23.31 | | 91.45-.6 |
| miR-108-1 | 17q11.1 | miR-108-1/miR-193 | 29.6-.8 |
| miR-108-2 | 16q13.1 | | 14.3-.5 |
| miR-122a | 18q21 | | 55.85-56 |
| miR-123 (= miR-126) | 09q34 | | 132.9-133.05 |
| miR-124a-1 | 08p23 | | 9.5-.65 |
| miR-124a-2 | 08q12.2 | | 64.9-65.1 |
| miR-124a-3 | 20q13.33 | | 62.4-.55 |
| miR-125a | 19q13.4 | miR-99b/let-7e/miR-125a | 56.75-57 |
| miR-125b-1 | 11q24.1 | miR-125b1/let-7a-2/miR-100 | 121.9-122.1 |
| miR-125b-2 | 21q11.2 | miR-99a/let-7c/miR-125b-2 | 16.7-.9 |
| miR-127 | 14q32 | miR-127/miR-136 | 99.2-.4 |
| miR-128a | 02q21 | | 136.3-.5 |
| miR-128b | 03p22 | | 35.45-.6 |

TABLE 2-continued miR Database: Chromosome Location and Clustering

| Name | Chromosome location | Genes in Cluster | Loc (Mb) (built 33) |
|---|---|---|---|
| miR-129-1 | 07q32 | | 127.25-.4 |
| miR-129-2 | 11p11.2 | | 43.65-.75 |
| miR-130a | 11q12 | | 57.6-.7 |
| miR-130b | 22q11.1 | | 20.2-.4 |
| miR-132 | 17p13.3 | miR-212/miR-132 | 1.85-2 |
| miR-133a-1 | 18q11.1 | miR-133a-1/miR-1d | 19.25-.4 |
| miR-133a-2 | 20q13.3 | miR-133a-2/miR-1b-2 | 61.75-.8 |
| miR-133b | 06p12 | miR-206/miR-133b | 51.9-52 |
| miR-134 | 14q32 | miR-154/miR-134/miR-299 | 99.4-.6 |
| miR-135-1 | 03p21.3 | let-7g/miR-135-1 | 52.1-.3 |
| miR-135-2 | 12q23 | | 97.85-98 |
| miR-136 | 14q32 | miR-127/miR-136 | 99.2-.4 |
| miR-137 | 01p21-22 | | 97.75 |
| miR-138-1 | 03p21 | | 43.85-.95 |
| miR-138-2 | 16q12-13 | | 56.55-.7 |
| miR-139 | 11q13 | | 72.55-.7 |
| miR-140as | 16q22.1 | | 69.6-.8 |
| miR-140s | 16q22.1 | | 69.6-.8 |
| miR-141 (= overlap miR-156) | 12p13 | overlap miR-156-cluster | 6.9-7.05 |
| miR-142-as | 17q23 | | 56.75-.9 |
| miR-142-s | 17q23 | | 56.75-.9 |
| miR-143 | 05q32-33 | miR-145/miR-143 | 148.65-.8 |
| miR-144 | 17q11.2 | | 27.05 |
| miR-145 | 05q32-33 | miR-145/miR-143 | 148.65-.8 |
| miR-146 | 05q34 | | 159.8-.9 |
| miR-147 | 09q33 | | 116.35-.55 |
| miR-148 | 07p15 | | 25.6-.8 |
| miR-148b | 12q13 | | 54.35-.45 |
| miR-149 | 02q37.3 | | 241.3-.4 |
| miR-150 | 19q13 | | 54.6-.8 |
| miR-151 | 08q24.3 | | 141.4-.5 |
| miR-152 | 17q21 | | 46.4-.5 |
| miR-153-1 | 02q36 | | 220.1-.2 |
| miR-153-2 | 07q36 | | 156.5-.7 |
| miR-154 | 14q32 | miR-154/miR-134/miR-299 | 99.4-.6 |
| miR-155 (BIC) | 21q21 | | 25.85 |
| miR-156 (= miR-157) | 12p13 | overlap miR-141-cluster | 6.9-7.05 |
| miR-159-1 | 11q13 | miR-159-1/miR-192 | 64.9-65 |
| miR-161 | 08p21 | | 21.8-.9 |
| miR-175 (= miR-224) | Xq28 | | 148.8-.9 |
| miR-177 | 08p21 | | 21.25-.35 |
| miR-180 | 22q11.21-12.2 | | 26.45 |
| miR-181a (= miR-178-2) | 09q33.1-34.13 | | 120.85-.95 |
| miR-181b (= miR-178 = miR-213-LIM) | 01q31.2-q32.1 | miR-213 S/miR-181b | 195.2-.35 |
| miR-181c | 19p13.3 | miR-24-2/miR-27a/miR-23a/miR-181c | 13.75-.95 |
| miR-182-as | 07q32 | miR-182s/miR-182as/miR-96/miR-183 | 128.9-129 |
| miR-182-s | 07q32 | miR-182s/miR-182as/miR-96/miR-183 | 128.9-129 |
| miR-183 (= miR-174) | 07q32 | miR-182s/miR-182as/miR-96/miR-183 | 128.9-129 |
| miR-184 | 15q24 | | 76.9-77.1 |
| miR-185 | 22q11.2 | | 18.35-.45 |
| miR-186 | 01p31 | | 70.9-71 |
| miR-187 | 18q12.1 | | 33.25-.4 |
| miR-188 | Xp11.23-p11.2 | | 48.35-.5 |
| miR-190 | 15q21 | | 60.6-.8 |
| miR-191 | 03p21 | | 48.85-.95 |

TABLE 2-continued miR Database: Chromosome Location and Clustering

| Name | Chromosome location | Genes in Cluster | Loc (Mb) (built 33) |
|---|---|---|---|
| miR-192 (= miR-158) | 11q13 | miR-159-1/miR-192 | 64.9-65 |
| miR-193 | 17q11.2 | miR-108-1/miR-193 | 29.6-.8 |
| miR-194 (= miR-159-2) | 01q41 | miR-215/miR-194 | 216.7-.8 |
| miR-195 | 17p13 | | 6.75-.85 |
| miR-196-1 | 17q21 | miR-196-1/miR-10a | 46.9-47.1 |
| miR-196-2 | 12q13 | | 54-54.15 |
| miR-197 | 01p13 | | 109.2-.3 |
| miR-198 | 03q13.3 | | 121.3-.4 |
| miR-199a-1 (= miR-199s) | 19p13.2 | | 10.75-.8 |
| miR-199a-2 | 01q23.3 | miR-214/miR-199a-2 | 168.7-.8 |
| miR-199as (= antisense miR-199a-1) | 19p13.2 | | 10.75-.8 |
| miR-199b (= miR-164) | 09q34 | | 124.3-.5 |
| miR-200 | 01p36.3 | | 0.9-1 |
| miR-202 | 10q26.3 | | 135 |
| miR-203 | 14q32.33 | | 102.4-.6 |
| miR-204 | 09q21.1 | | 66.9-67 |
| miR-205 | 01q32.2 | | 206.2-.3 |
| miR-206 | 06p12 | miR-206/miR-133b | 51.9-52 |
| miR-208 | 14q11.2 | | 21.8-22 |
| miR-210 | 11p15 | | 0.55-0.75 |
| miR-211 | 15q11.2-q12 | | 28.9-29.1 |
| miR-212 | 17p13.3 | miR-212/miR-132 | 1.9-2.1 |
| miR-213-SANGER | 01q31.3-q32.1 | miR-213 S/miR-181b | 195.2-.35 |
| miR-214 | 01q23.3 | miR-214/miR-199a-2 | 168.7-.8 |
| miR-215 | 01q41 | miR-215/miR-194 | 216.7-.8 |
| miR-216 | 02p16 | miR-217/miR-216 | 56.2-.4 |
| miR-217 | 02p16 | miR-217/miR-216 | 56.2-.4 |
| miR-218-1 | 04p15.32 | | 20.15-.35 |
| miR-218-2 | 05q35.1 | | 168-.15 |
| miR-219 | 06p21.2-21.31 | | 33.1-.25 |
| miR-220 | Xq25 | | 120.6-.8 |
| miR-221 | Xp11.3 | miR-222/miR-221 | 44.35-.45 |
| miR-222 | Xp11.3 | miR-222/miR-221 | 44.35-.45 |
| miR-223 | Xq12-13.3 | | 63.4-.5 |
| miR-294-1 | 16q22 | | 65.1-.3 |
| miR-297-3 | 20q13.2 | | 52.25-.35 |
| miR-299 | 14q32 | miR-154/miR-134/miR-299 | 99.4-.6 |
| miR-301 | 17q23 | | 57.5-.7 |
| miR-302 | 04q25 | | 113.9-114 |
| miR-hes1 | 19q13.4 | miR-hes1/miR-hes2/miR-hes3 | 58.9-59.05 |
| miR-hes2 | 19q13.4 | miR-hes1/miR-hes2/miR-hes3 | 58.9-59.05 |
| miR-hes3 | 19q13.4 | miR-hes1/miR-hes2/miR-hes3 | 58.9-59.05 |

The distribution of the 186 human miR genes was found to be non-random. Ninety miR genes were located in 36 clusters, usually with two or three genes per cluster (median=2.5). The largest cluster found comprises six genes (miR-17/miR-18/miR-19a/miR-20/miR-19b1/miR-92-1) and is located at 13q31 (Table 2). A significant association of the incidence of miR genes with specific chromosomes was found. Chromosome 4 was found to have a lower than expected rate of miR genes (IRR=0.27; p=0.035). Chromosomes 17 and 19 were found to have significantly more miR genes than expected, based on chromosome size (IRR=2.97, p=0.002 and IRR=3.39, p=0.001, respectively). Six of the 36 miR gene clusters (17%), which contain 16 of 90 clustered genes (18%), are located on these two small chromosomes, which account for only 5% of the entire genome.

Similar results were obtained using a model considering the distribution of miR genes only in the transcriptionally active portion of the genome (see Table 3).

Chromosome 1 is used as the baseline in the model with a rate of miR gene incidence of ~0.057, which is approximately equal to the overall rate of miR gene incidence across the genome.

TABLE 3

Location of miRs by chromosome and results of mixed effects Poisson regression model.

| Chromosome | Length | # of miRs | IRR | p |
|---|---|---|---|---|
| 1 | 279 | 16 | — | — |
| 2 | 251 | 7 | 0.49 | 0.112 |
| 3 | 221 | 10 | 0.79 | 0.557 |
| 4 | 197 | 3 | 0.27 | 0.035 |
| 5 | 198 | 6 | 0.53 | 0.183 |
| 6 | 176 | 6 | 0.59 | 0.277 |
| 7 | 163 | 13 | 1.39 | 0.377 |
| 8 | 148 | 6 | 0.71 | 0.469 |
| 9 | 140 | 15 | 1.87 | 0.082 |
| 10 | 143 | 2 | 0.24 | 0.060 |
| 11 | 148 | 11 | 1.29 | 0.508 |
| 12 | 142 | 6 | 0.74 | 0.523 |
| 13 | 118 | 8 | 0 | 1.000 |
| 14 | 107 | 7 | 1.14 | 0.771 |
| 15 | 100 | 5 | 0.87 | 0.789 |
| 16 | 104 | 5 | 0.84 | 0.731 |
| 17 | 88 | 15 | 2.97 | 0.002 |
| 18 | 86 | 4 | 0.81 | 0.708 |
| 19 | 72 | 14 | 3.39 | 0.001 |
| 20 | 66 | 5 | 1.32 | 0.587 |
| 21 | 45 | 4 | 1.55 | 0.433 |
| 22 | 48 | 6 | 2.09 | 0.123 |
| X | 163 | 12 | 1.28 | 0.513 |
| Y | 51 | 0 | 0 | 1.000 |

Example 2 miR Genes are Located in or Near Fragile Sites

Thirty-five of 186 miRs (19%) were found in (13 miR genes), or within 3 Mb (22 miR genes) of cloned fragile sites (FRA). A set of 39 fragile sites with available cloning information was used in the analysis. Data were available for the exact dimension (mean 2.69 Mb) and position of ten of these cloned fragile sites (see General Methods above). The relative incidence of miR genes inside fragile sites occurred at a rate 9.12 times higher than in non-fragile sites (p<0.001, using mixed effect Poisson regression models; see Tables 3 and 4). The same very high statistical significance was also found when only the 13 miRs located exactly inside a FRA or exactly in the vicinity of the "anchoring" marker mapped for a FRA were considered (IRR=3.21, p<0.001). Among the four most active common fragile sites (FRA3B, FRA16D, FRA6E, and FRA7H), the data demonstrate seven miRs in (miR-29a and miR-29b) or close (miR-96, miR-182s, miR-182 as, miR-183, and miR-129-1) to FRA7H, the only fragile site where no candidate tumor suppressor (TS) gene has been found. The other three of the four most active sites contain known or candidate TS genes; i.e., FHIT, WWOX and PARK2, respectively (Ohta et al., 1996, Cell 84:587-597; Paige et al., 2001, Proc. Natl. Acad. Sci. USA 98:11417-11422; Cesari et al., 2003, Proc. Natl. Acad. Sci. USA 100: 5956-5961).

Analysis of 113 fragile sites scattered in the human karyotype showed that 61 miR genes are located in the same cytogenetic positions with FRAs. Thirty-five miR genes were located inside twelve cloned FRAs. These data indicate that more miRs are located in or near FRAs, and that the results described herein represent an underestimation of miR gene/FRA association, likely because the mapping of these unstable regions is not complete.

TABLE 4

Mixed Effect Poisson Regression Results for the Association Between microRNAs and Several Types of Regions of Interest

| Region of interest | Incidence Rate Ratio (IRR) | 95% CI IRR | p |
|---|---|---|---|
| Cloned Fragile sites vs. non-fragile sites | 9.12 | 6.22, 13.38 | <0.001 |
| HPV16 insertion vs. all other | 3.22 | 1.55, 6.68 | <0.002 |
| Deleted region vs. all other | 4.08 | 2.99, 5.56 | <0.001 |
| Amplified region vs. all other | 3.97 | 2.31, 6.83 | <0.001 |
| HOX Clusters vs. all other | 15.77 | 7.39, 33.62 | <0.001 |
| Homeobox genes vs. all other | 2.95 | 1.63, 5.34 | <0.001 |

Note:
"all other" means all the genome except the regions of interest.

Example 3 miR Genes are Located in or Near Human Papilloma Virus (HPV) Integration Sites

Because common fragile sites are preferential targets for HPV16 integration in cervical tumors, and infection with HPV 16 or HPV 18 is the major risk factor for developing cervical cancer, the association between miR gene locations and HPV 16 integration sites in cervical tumors was analyzed. The data indicate that thirteen miR genes (7%) are located within 2.5 Mb of seven of seventeen (45%) cloned integration sites. The relative incidence of miRs at HPV16 integration sites occurred at a rate 3.22 times higher than in the rest of the genome (p<0.002) (Tables 4 and 5). In one cluster of integration sites at chromosome 17q23, where three HPV 16 integration sites are spread over roughly 4 Mb of genomic sequence, four miR genes (miR-21, miR-301, miR-142s and miR-142 as) were found.

TABLE 5

Analyzed FRA Sites, Cancer Correlation and HPV Integration Sites

| Symbol | Chromosome | Cancer correlation | Type | Location (Mb) | Closest miR (s) | Distance miR-FRA (Mb) | HPV16 integration* |
|---|---|---|---|---|---|---|---|
| FRA1A | 1p36 | | | | | | |
| FRA1C | 1p31 | | aphidicolin type, common | 67.87 | miR-186; miR-101-1 | 3; 3 | |
| FRA1F | 1q21 | bladder | | | | | |
| FRA1H | 1q42.1 | cervical | 5-azacytidine, common | 216.5 | miR-194; miR-215 | exact | YES |
| FRA2G | 2q31 | RCC | | | | | |
| FRA2I | 2q33 | chronic myelogenous leukemia | | | | | |

TABLE 5-continued

Analyzed FRA Sites, Cancer Correlation and HPV Integration Sites

| Symbol | Chromosome | Cancer correlation | Type | Location (Mb) | Closest miR (s) | Distance miR-FRA (Mb) | HPV16 integration* |
|---|---|---|---|---|---|---|---|
| FRA3B | 3p14.2 | esophageal carcinoma, lung, stomach, kidney, cervical cancer | | | | | |
| FRA4B | 4q12 | | | | | | |
| FRA4C | 4q31.1 | | | | | | |
| FRA5C | 5q31.1 | | | | | | |
| FRA5E | 5p14 | | | | | | |
| FRA6E | 6q26 | ovarian | | | | | |
| FRA6F | 6q21 | leukemias and solid tumors | | | | | |
| FRA7E | 7q21.2 or 21.11 | | | | | | |
| FRA7F | 7q22 | | aphidicolin type, common | 100.2-107 | miR-106b; miR-25; miR-93 | less than 1 | |
| FRA7G | 7q31.2 | ovarian | | | | | |
| FRA7H | 7q32.3 | esophageal | aphidicolin type, common | 129.8-130.4 | miR-29b; miR-29a; miR-96; miR-182s; miR-182as; miR-183; miR-129-1 | exact; 1 and 2.5 | |
| FRA7I | 7q35 | breast | | | | | |
| FRA8B | 8q22.1 | | | | | | |
| FRA8E | 8q24.1 | | | | | | |
| FRA9D | 9q22.1 | bladder | aphidicolin type, common | 89.5-92 | let7a-1; let-7d; let-7f-1 miR-23b; miR-24-1; miR-27b | exact | |
| FRA9E | 9q32-33.1 | ovarian, bladder, cervical | aphidicolin type, common | 101.3-111.9 | miR-32 | exact | YES |
| FRA10B | 10q25.2 | | | | | | |
| FRA10C | 10q21 | | | | | | |
| FRA10D | 10q22.1 | | | | | | |
| FRA11A | 11q13.3 | hematopoietic and solid tumors | folic acid type, rare | 66.18-66.9 | miR-159-1; miR-192 | 1.2 | |
| FRA11B | 11q23.3 | | folic acid type, rare | 119.1-.2 | miR-125b-1; let-7a-2; miR-100 | 2 | |
| FRA12A | 12q13.1 | | folic acid type, rare | 53.55 | miR-196-2; miR-148b | 1 | |
| FRA13C | 13q21.2 | | | | | | |
| FRA15A | 15q22 | | aphidicolin type, common | 60.93 | miR-190 | exact | |
| FRA16D | 16q23.2 | gastric adenocarcinoma, adenocarcinomas of stomach, colon, lung and ovary | | | | | |
| FRA16E | 16p12.1 | | | | | | |
| FRA17B | 17q23.1 | | aphidicolin type, common | 58.25-58.35 | miR-21 miR-301 miR-142s; miR-142as | exact 0.5 1.5 | YES |
| FRA18A | 18q12.2 | esophageal carcinoma | | | | | |
| FRA22A | 22q13 | | | | | | |
| FRAXA | Xq27.31 | | | | | | |
| FRAXB | Xp22.3 | | | | | | |
| FRAXE | Xq28 | | | | | | |
| FRAXF | Xq28 | | | 146.58 | miR-105-1; miR-175 | 2.2 | |

Note:
*other microRNAs located close to HPV16 integration sites were found in relation to FRA5C, FRA11C, FRA12B and FRA12E.
Positions are indicated according to Build 33 of the Human Genome.

Example 4A miR Genes are Located in or Near Cancer Associated Genomic Regions

Because the miR-FRA-HPV16 association has significance for cancer pathogenesis, miR genes might be involved in malignancies through other mechanisms, such as deletion, amplification, or epigenetic modifications. Thus, a search was performed for reported genomic alterations in human cancers, located in regions containing miR genes. PubMed was searched for reports of CAGR such as minimal regions of loss-of-heterozygosity (LOH) suggestive of the presence of tumor-suppressor genes (TSs), minimal regions of amplification suggestive of the presence of oncogenes (OGs), and common breakpoint regions in or near possible OGs or TSs (see General Methods above). Overall, 98 of 187 (52.5%) miR genes were found to be located in CAGRs (see Tables 6 and 7). Eighty of the miR genes (43%) were found to be located exactly within minimal regions of LOH or minimal regions of amplification described in a variety of tumors, such as lung, breast, ovarian, colon, gastric and hepatocellular carcinoma, as well as leukemias and lymphomas (see Tables 6 and 7).

The analysis showed that on chromosome 9, eight of fifteen mapped miR genes (including six located in clusters), were located inside two regions of deletion on 9q (Simoneau et al., 1999, Oncogene 7:157-163): the clusters let-7a-1/let-7f-1/let-7d and miR-23b/miR-27b/miR-24-1 inside region B at 9q22.3 and miR-181a and miR-199b inside region D at 9q33-34.1 (Table 6). Furthermore, five other miR genes were located less than 2 Mb from the markers with the highest rate of LOH: miR-31 near IFNA, miR-204 near D9S15, miR-181 and miR-147 near GSN, and miR-123 near D9S67.

In breast carcinomas, two different regions of loss at 11q23, independent from the ATM locus, have been studied extensively: the first spans about 2 Mb between loci D11S1347 and D11S927; the second is located between loci D11S1345 and D11S1316 and is estimated at about 1 Mb (di Iasio et al., 1999, Oncogene 25:1635-1638). Despite extensive effort, the only candidate TS gene found was the PPP2R1B gene, involved in less than 10% of reported cases (Calin et al., 2002, Proc. Natl. Acad. Sci. USA 99:15524-15529; Wang et al., 1998, Science 282:284-7). Both of these minimal LOH regions contained numerous microRNAs: the cluster miR-34-a1/miR-34-a2 in the first and the cluster miR-125b1/let-7a-2/miR-100 in the second.

High frequency LOH at 17p13.3 and relatively low TP53 mutation frequency in cases of hepatocellular carcinomas (HCC), lung cancers and astrocytomas indicate the presence of other TSs involved in the development of these tumors. One minimal LOH region correlated with HCC, and located telomeric to TP53 between markers D17S1866 and D17S1574 on chromosome 17, contained three miR genes: miR-22, miR-132, and miR-212. miR-195 is located between ENO3 and TP53 on chromosome 17.

Homozygous deletions (HD) in cancer can indicate the presence of TSs (Huebner et al., 1998, Annu. Rev. Genet. 32:7-31), and several miR genes are located in homozygously deleted regions without known TSs. In addition to miR-15a and miR-16a located at 13q14 HD region in B-CLL, the cluster miR-99a/let-7c/miR-125b-2 mapped in a 21p11.1 region of HD in lung cancers and miR-32 at 9q31.2 in a region of HD in various types of cancer. Among the seven regions of LOH and HD on the short arm of chromosome 3, three of the regions harbor miRs: miR-26a in region AP20, miR-138-1 in region 5 at 3p21.3 and the cluster let-7g/miR-135-1 in region 3 at 3p21.1-p21.2. The locations of the miR genes/gene clusters are not likely to be random, because it was found that overall, the relative incidence of miRs in both deleted and amplified regions is highly significant (IRR=4.08, $p<0.001$ and IRR=3.97, $p=0.001$, respectively) (Table 4). Thus, these miRs expand the spectrum of candidate TSs.

TABLE 6

Examples of microRNAs Located in Minimal Deleted Regions, Minimal Amplified Regions, and Breakpoint Regions Involved in Human Cancers*

| Chromosome | Location (defining markers) | Size Mb | MiR Gene | Histotype | Known OG/TS |
|---|---|---|---|---|---|
| 3p21.1-21.2-D | ARP-DRR1 | 7 | let-7g/miR-135-1 | lung, breast cancer | — |
| 3p21.3(AP20)-D | GOLGA4-VILL | 0.75 | miR-26a | epithelial cancer | — |
| 3p23-21.31 (MDR2)-D | D3S1768-D3S1767 | 12.32 | miR-26a; miR-138-1 | nasopharyngeal cancer | — |
| 5q32-D | ADRB2-ATX1 | 2.92 | miR-145/miR-143 | myelodysplastic syndrome | — |
| 9q22.3-D | D9S280-D9S1809 | 1.46 | miR-24-1/mir-27b/miR-23b; let-7a-1/let-7f-1/let-7d | urothelial cancer | PTC, FANCC |
| 9q33-D | D9S1826-D9S158 | 0.4 | miR-123 | NSCLC | — |
| 11q23-q24-D | D11S927-D11S1347 | 1.994 | miR-34a-1/miR-34a-2 | breast, lung cancer | PPP2R1B |
| 11q23-q24-D | D11S1345-D11S1328 | 1.725 | miR-125b-1/let-7a-2/miR-100 | breast, lung, ovary, cervix cancer | — |
| 13q14.3-D | D13S272-D13S25 | 0.54 | miR-15a/miR-16a | B-CLL | — |
| 13q32-33-A | stSG15303-stSG31624 | 7.15 | miR-17/miR-18/miR-19a/miR-20/miR-19b-1/miR-92-1 | follicular lymphoma | — |
| 17p13.3-D | D17S1866-D17S1574 | 1.899 | miR-22; miR-132; miR-212 | HCC | — |
| 17p13.3-D | ENO3-TP53 | 2.275 | miR-195 | lung cancer | TP53 |
| 17q22-t(8; 17) | miR-142s/c-MYC | | miR-142s; miR-142as | prolymphocytic leukemia | c-MYC |
| 17q23-A | CLTC-PPM1D | 0.97 | miR-21 | neuroblastoma | — |
| 20q13-A | FLJ33887-ZNF217 | 0.55 | miR-297-3 | colon cancer | — |

TABLE 6-continued

Examples of microRNAs Located in Minimal Deleted Regions, Minimal Amplified Regions, and Breakpoint Regions Involved in Human Cancers*

| Chromosome | Location (defining markers) | Size Mb | MiR Gene | Histotype | Known OG/TS |
|---|---|---|---|---|---|
| 21q11.1-D | D21S1911-ANA | 2.84 | miR-99a/let-7c/miR-125b | lung cancer | — |

Note:
*OG—oncogene; TS—tumor suppressor gene; D—deleted region; A—amplified region; NSCLC—Non-Small Cell Lung Cancer; HCC—Hepatocellular carcinoma; B-CLL—B-Chronic Lymphocytic Leukemia; PTC—patched homolog (*Drosophila*); FANCC—Fanconi anemia, complementation group C; PPP2R1B—protein phosphatase 2, regulatory subunit A (PR 65), β isoform. miR genes in a cluster are separated by a slash.

TABLE 7

MicroRNAs Located in Minimal Deleted Regions, Minimal Amplified Regions and Breakpoint Regions Involved in Human Cancers

| Chromosome | Type of region (name) | Marker 1 | Position (Mb) | Marker 2 | Position (Mb) | Size/Distance (Mb) | Histotype | Closest miR | miR Location (Mb) |
|---|---|---|---|---|---|---|---|---|---|
| 01p31 | D | D1S2638 | 62.92 | ARHI | 67.885 | 4.96 | ovarian and breast cancer | miR-101-1 | 64.9 |
| 01p36.3 | D | D1S468 | 3.36 | D1s2697 | 15.23 | 0 | Non Small Cell Lung Ca. | miR-34 | 8.8 |
| 02q21 | D | D2S1334 | 136.66 | | | 0.1 | gastric ca. | miR-128a | 136.55 |
| 02q37 | D | D2S125 | 241.5 | | | 0.2 | hepatocellular carcinoma (HCC) | miR-149 | 241.65 |
| 03p21.1-21.2 | D | ARP | 51.5 | DRR1 | 58.5 | 7 | lung, breast ca. | let-7g/miR-135-1 | 52.3 |
| 03p21.3 | D (AP20) | GOLGA4 | 37.25 | VILL | 38 | 0.75 | epithelial malignancies | miR-26a | 38 |
| 03p23-21.31 | D (MDR2) | D3S1768 | 34.59 | D3S1767 | 46.91 | 12.32 | nasopharyngeal carcinoma | miR-26a; miR-138-1 | 38; 44 |
| 03q27 | t (3; 11) (q27; q23.1) | LAZ3/BCL6 | 188.75 | BOB1/OBF1 | 110.78 | | B cell leukemia line (Karpas 231) | miR-34a-2/miR-34a-1 | 110.9 |
| 04p15.3 | D | D4S1608 | 18.83 | D4S404 | 23.98 | 5.15 | primary bladder ca. | miR-218-1 | 20.25 |
| 05q31-33 | D | D5S1480 | 144.17 | D5S820 | 156.1 | 11.93 | prostate ca. aggressiveness | miR-145/miR-143 | 148.7 |
| 05q32 | D | ADRB2 | 148.23 | ATX1 | 151.15 | 2.92 | myelodysplastic syndrome | miR-145/miR-143 | 148.7 |
| 07q32 | D | D7S3061 | 122.84 | D7S1804 | 131.25 | 8.41 | prostate ca. (aggressiveness) | miR-129-1; miR-182s/miR-182as/miR-96/miR-183; miR29a/miR-29b | 127.3; 129; 130 |
| 07q32-q33 | D | D7S2531 | 130.35 | D7S1804 | 131.69 | 1.34 | prostate ca. (aggressiveness) | miR-29a/miR-29b | 130 |
| 08p21 | D (MRL1) | D8S560 | 21.61 | D8S1820 | 28.02 | 6.41 | HCC | miR-161; miR-177 | 22; 21.5 |
| 08p21 | D | D8S282 | 21.42 | | | 0.1 | HCC | miR-177 | 21.5 |
| 08p22 | D | D8S254 | 16.62 | SFTP2 | 22.05 | 5.43 | oral and laryngeal squamous carcinoma. | miR-161; miR-177 | 22; 21.5 |
| 08p23.1 | A | D8S1819 | 6.737 | D8S550 | 10.919 | 4.18 | malignant fibrous histiocytomas (MFHs) | miR-124a-1 | 9.75 |
| 09p21 | D (LOH) | IFNA | 21.2 | D9S171/S1814 | 22.07 | 0.87 | primary bladder tumor | miR-31 | 21.4 |
| 09p21 | D | IFNA | 21.5 | | | 0 | lung adenocarcinoma | miR-31 | 21.4 |
| 09p21 | D | IFNA | 21.5 | | | 0 | gastric ca. | miR-31 | 21.4 |
| 09p21 | D | CDKN2A, CDKN2B | 21.9 | | | 0.5 | breast ca. | miR-31 | 21.4 |
| 09q22 | D | D9S280 | 92.47 | D9S1809 | 93.93 | 1.46 | urothelial ca. | miR-24-1/miR-27b/miR-23b; let-7a-1/let-7f1/let-7d | 92.9; 92.3 |
| 09q22.3 | D (reg B) | D9S12 | 91.21 | D9S180 R | 96.03 | 4.82 | bladder ca. | let-7a-1/let-7f1/let-7d; miR-24-1/miR-27b/miR-23b | 92.3; 92.9 |

TABLE 7-continued

MicroRNAs Located in Minimal Deleted Regions, Minimal Amplified Regions and Breakpoint Regions Involved in Human Cancers

| Chromosome | Type of region (name) | Marker 1 | Position (Mb) | Marker 2 | Position (Mb) | Size/ Distance (Mb) | Histotype | Closest miR | miR Location (Mb) |
|---|---|---|---|---|---|---|---|---|---|
| 09q32 | D | D9S1677 | 107.35 | | | 0.2 | Small Cell Lung Ca., Non-Small Cell Lung Ca. | miR-32 | 107.15 |
| 09q33 | D | D9S1826 | 133.88 | D9S158 | 134.53 | 0.4 | NSCLC | miR-123 | 134.95 |
| 09q33-34.1 | D (reg D) | GSN | 119.45 | D9S260 | 127.09 | 7.64 | bladder ca. | miR-181a; miR-199b | 122.85; 126.3 |
| 09q34 | D | D9S158 | 134.54 | | | 0.4 | HCC | miR-123 | 134.95 |
| 11p15 | D | D11S2071 | 0.23 | | | 0.4 | ovarian ca. | miR-210 | 0.6 |
| 11p15.5 | D (LOH11B) | HRAS | 0.52 | D11S1363 | 1.05 | 0.53 | lung ca. | miR-210 | 0.6 |
| 11q13 | D | D11S4946 | 64.35 | D11S4939 | 64.54 | 0.19 | sporadic follicular thyroid tumor | miR-159-1/miR-192 | 64.45 |
| 11q22 | D | D11S940/S1782 | 100.65 | CD3D/D11S4104 | 118.7 | 18.05 | lung adenocarcinoma | miR-34a-1/miR-34a-2 | 111 |
| 11q22.1-23.2 | D (MDR3) | D11S2017 | 107.05 | D11S965 | 111.3 | 4.25 | nasopharyngeal carcinoma | miR-34a-1/miR-34a-2 | 111 |
| 11q22.3-q25 | D | D11S1340 | 116.12 | D11S912 | 128.16 | 12.04 | ovarian ca. | miR125b-1/let-7a-2/miR-100 | 121.5 |
| 11q22-q23 | D | D11S2106/S2220 | 108.76 | D11S1356 | 117.454 | 8.7 | chronic lymphocytic leukemia | miR-34a-1/miR-34a-2 | 111 |
| 11q23 | D | D11S1647 | 110.34 | NCAM2/NCAM1 | 112.5 | 2.16 | lung ca. | miR-34a-1/miR-34a-2 | 111 |
| 11q23 | D | D11S1345 | 121.83 | D11S1328 | 123.56 | 1.73 | lung adenocarcinoma | miR125b-1/let-7a-2/miR-100 | 121.5 |
| 11q23 | D | D11S1345 | 121.83 | D11S1328 | 123.56 | 1.73 | lung adenocarcinoma | miR125b-1/let-7a-2/miR-100 | 121.5 |
| 11q23.1-23.2 | D (LOH) | D11S4167 | 121.68 | D11S4144 | 122.96 | 1.28 | cervical ca. | miR125b-1/let-7a-2/miR-100 | 121.5 |
| 11q23-q24 | D (LOH11CR1) | D11S927 | 109.676 | D11S1347 | 111.67 | 1.994 | breast, lung ca. | miR-34a-1/miR-34a-2 | 111 |
| 11q23-q24 | D (LOH11CR2) | D11S1345 | 121.835 | D11S1328 | 123.56 | 1.725 | breast, lung, ovary, cervix ca. | miR125b-1/let-7a-2/miR-100 | 121.5 |
| 12p13 | t (7; 12) (q36; p13) | TEL (ETV6) | 11.83 | near HLXB9 | 156.21 | | acute myeloid leukemia (AML) | miR-153-2 | 156.6 |
| 12q13-q14 | A | DGKA | 54.6 | BLOV1 | 67.4 | 12.8 | adenocarcinomas of lung and esophagus | let-7i | 61.35 |
| 12q13-q15 | A | GLI | 56.15 | MDM2 | 67.5 | 11.35 | bladder ca. | let-7i | 61.3-.45 |
| 12q22 | D | D12S1716 | 95.45 | P382A8AG/D12S296 | 97.47 | 2.02 | male germ cell tumors | miR-135-2 | 96.5 |
| 12q22 | D | D12S377/D12S101 | 94.1 | D12S296 | 97.47 | 3.37 | male germ cell tumors. | miR-135-2 | 96.5 |
| 13q14.3 | D | D13S319/D13S272 | 48.5 | D13S25 | 49.04 | 0.54 | B-Chronic Lymphocytic Leuk (B-CLL) | miR-15a/miR-16a | 48.5 |
| 13q14 | D | D13S260 | 30.23 | AFMa301wb5 | 48.62 | 18.39 | adult lymphoblastic leukemia | miR-15a/miR-16a | 48.5 |
| 13q14 | D | Rb1 | 46.77 | BCMS (DLEU-1) | 48.46 | 1.69 | lipoma | miR-15a/miR16a | 48.5 |
| 13q14.3 | D (RMD) | D13S272 | 48.5 | AF077401 | 48.765 | 0.265 | CLL | miR-15a/miR-16a | 48.5 |
| 13q14.3 | D (Reg II) | D13S153 | 46.68 | D13S1289 | 62.43 | 15.75 | head-and-neck squamous-cell carcinoma | miR-15a/miR-16a | 48.5 |
| 13q14.3 | D | D13S273 | 48.11 | D13S176 | 58.31 | 10.2 | oral ca. | miR-15a/miR-16a | 48.5 |
| 13q14.3 | D | D13S1168 | 48.28 | D13S25 | 49.04 | 0.76 | B-CLL | miR-15a/miR-16a | 48.5 |
| 13q32-33 | A | stSG15303 | 89.7 | stSG31624 | 96.85 | 7.15 | follicular lymphoma | miR-17/miR-18/miR-19a/miR-20/miR-19b-1/miR-92-1 | 89.7 |
| 14q11.1-q12 | D | D14S283 | 20.67 | D14S64 | 22.55 | 1.88 | malignant mesothelioma | miR-208 | 21.8 |
| 14q32 | D | D14S51 | 95.56 | telomere | 105.2 | 9.64 | nasopharyngeal carcinoma | miR-127/miR-136; miR-154/miR-134/miR-299; miR-203 | 99.3; 99.5; 102.5 |
| 15q11.1-15 | D | D15S128 | 22.67 | D15S1012 | 36.72 | 14.05 | malignant mesothelioma. | miR-211 | 29 |

TABLE 7-continued

MicroRNAs Located in Minimal Deleted Regions, Minimal Amplified Regions and Breakpoint Regions Involved in Human Cancers

| Chromosome | Type of region (name) | Marker 1 | Position (Mb) | Marker 2 | Position (Mb) | Size/ Distance (Mb) | Histotype | Closest miR | miR Location (Mb) |
|---|---|---|---|---|---|---|---|---|---|
| 17p11.2 | A | PNMT | 17.351 | | | 0.5 | breast ca | miR-33b | 17.8 |
| 17p11.2 | D | D17S1857 | 16.61 | D17S805/ S959 | 20.79 | 4.18 | kidney ca (Birt-Hogg-Dube sy) | miR-33b | 17.9 |
| 17p11.2 | D | D117S1857 | 16.61 | D17S805/ S959 | 20.79 | 4.18 | medulloblastoma (Smith-Magenis syndrome) | miR-33b | 17.9 |
| 17p13 | D | D17S578 | 7.025 | | | 0 | HCC | miR-195 | 7 |
| 17p13.3 | D | D17S1866 | 0.121 | D17S1574 | 2.02 | 1.9 | HCC | miR-22; miR-132; miR-212 | 1.75; 2.2 |
| 17p13.3 | D | ENO3 | 5.5 | TP53 | 7.775 | 2.275 | lung ca. | miR-195 | 7 |
| 17p13.3 | D | D17S1574 | 2.02 | D17S379 | 2.46 | 0.44 | lung ca. | miR-132; miR-212 | 2.2 |
| 17q11.1 | D | NF1 | 29.7 | | | 0.3 | ovarian ca. | miR-108-1 | 30 |
| 17q11.1 | D | NF1 | 29.7 | | | 0.3 | ovarian ca. | miR-193 | 30 |
| 17q11.2 | A | MLN 62 (TRAF4) | 27.22 | | | 0.1 | primary breast ca. | miR-144 | 27.35 |
| 17q11.2 | D (NF1 locus) | CYTOR4 | 29.25 | WI-12393 | 30.52 | 1.27 | NF1 microdeletion | miR-108-1/miR-193 | 30; 30 |
| 17q22 | t (8; 17) | "BCL3" | 56.95 | c-MYC | 128.7 | | prolymphocytic leukemia | miR-142s/miR-142as | 56.95 |
| 17q23 | A | RAD51C | 57.116 | | | 0.25 | breast ca. | miR-142s/miR-142as | 56.95 |
| 17q23 | A | RAD51C | 57.116 | | | 0.5 | breast ca. | miR-301 | 57.7 |
| 17q23 | A | CLTC | 58.21 | PPM1D | 59.18 | 0.97 | neuroblastoma | miR-21 | 58.45 |
| 17q25 | A (SRO2) | D17S1306 | 53.76 | D17S1604 | 58.45 | 4.69 | breast ca. | miR-142s; miR-142as; miR-301; miR-21 | 56.95; 57.7; 58.45 |
| 19p13.3 | D | D19S886 | 0.95 | D19S216 | 4.9 | 3.95 | lung adenocarcinoma | miR-7-3 | 4.75 |
| 19p13.3 | D (LOH) | D19S216 | 4.9 | D19S549 | 5.44 | 0.54 | gynecological tumor in Peutz-Jegher's sy | miR-7-3 | 4.75 |
| 19p13.3 | D (HZYG) | D19S894 | 4.34 | D19S395 | 7.32 | 2.98 | gynecological tumor in Peutz-Jegher's sy | miR-7-3 | 4.75 |
| 19p13.3 | D (LOH) | D19S886 | 0.95 | D19S216 | 4.9 | 3.95 | pancreatic and biliary ca | miR-7-3 | 4.75 |
| 20q13 | A | FLJ33887 | 52.2 | ZNF217 | 52.75 | 0.55 | colon ca | miR-297-3 | 52.35 |
| 20q13.1 | A | ZNF217 | 52.285 | | | 0 | ovarian | miR-297-3 | 52.35 |
| 20q13.2 | A | D20S854 | 52.68 | D20S120 | 53.69 | 1.01 | gastric adenocarcinoma | miR-297-3 | 52.35 |
| 20q13.2 | A | ZNF217 | 52.85 | | | 0.5 | head/neck squamous carcinoma | miR-297-3 | 52.35 |
| 21q11.1 | D | D21S120/ S1911 | 15.06 | ANA | 17.9 | 2.84 | lung ca. (cell line MA17) | miR-99a/let-7c/miR-125b-2 | 16.8 |
| 21q21 | A | BIC | 25.8 | BIC | 25.9 | 0.1 | colon ca. | miR-155(BIC) | 25.85 |
| 22q12.2-q13.33 | D | D22S280 | 31.53 | D22S274 | 43.54 | 12.01 | colorectal ca. | miR-33a | 40.6 |
| 22q12.3-q13.33 | D | D22S280 | 31.53 | D22S282 | 42.1 | 10.57 | astrocytomas | miR-33a | 40.6 |
| 22q12.1 | t (4; 22) | | | MN1 | 26.5 | | meningioma | miR-180 | 26.45 |
| Xq25-26.1 | D | DXS1206 | 125.08 | HPRT | 132.31 | 7.23 | advanced ovarian ca. | miR-92-2/miR-19b-2/miR-106a | 132 |

Note:
D—deletion;
A—amplification;
ca.—cancer;
sy—syndrome.
The distance (in Mb) from the markers used in genome-wide analysis is shown.
miRs in clusters are separated by a slash.
Positions are according to BUILD 34, version 1, of the Human Genome Example 4B Effect of Genomic Location on miR Gene Expression In order to investigate whether the genomic location in deleted regions influences miR gene expression, a set of lung cancer cell lines was analyzed. miR-26a and miR-99a, located at 3p21 and 21q1.2, respectively, are not expressed or are expressed at low levels in lung cancer cell lines. The locations of miR-26a and miR-99a correlate with regions of LOH/HD in lung tumors. However, the expression of miR-16a (located at 13q14) was unchanged in the majority of lung tumor cell lines as compared to normal lung (see FIG. 1).

Several miR genes are located near breakpoint regions, including miR-142s at 50 nt from the t(8;17) translocation involving chromosome 17 and MYC, and miR-180 at 1 kb from the MN1 gene involved in a t(4;22) translocation in meningioma (Table 6). The t(8;17) translocation brings the MYC gene near the miR gene promoter, with consequent MYC over-expression, while the t(4;22) translocation inactivates the MN1 gene, and possibly inactivates the miR gene located in the same position. Other miR genes are located relatively close to chromosomal breakpoints, such as the cluster miR34a-1/34a-2 and miR-153-2 (see Table 7). Further supporting a role for miR-122a in cancer, it was found herein that human miR-122a is located in the minimal amplicon around MALT1 in aggressive marginal zone lymphoma (MZL), and was found to be about 160 kb from the breakpoint region of translocation t(11;18) in mucosa-associated lymphoid tissue (MALT) lymphoma (Sanchez-Izquierdo et al., 2003, Blood 101:4539-4546). Apart from miR-122a, several other miR genes were located in regions particularly prone to cancer-specific abnormalities, such as miR-142s and miR-142 as, located at 17q23 close to a t(8;17) breakpoint in B cell acute leukemia, and also located within the minimal amplicon in breast cancer and near the FRA17B site, which is also a target for HPV16 integration in cervical tumors (see Tables 5 and 7).

Example 5

MicroRNAs are Located in or Near HOX Gene Clusters

Homeobox-containing genes are a family of transcription factor genes that play crucial roles during normal development and in oncogenesis. HOXB4, HOXB5, HOXC9, HOXC10, HOXD4 and HOXD8, all with miR gene neighbors, are deregulated in a variety of solid and hematopoietic cancers (Cillo et al., 1999, Exp. Cell Res. 248:1-9; Owebs et al., 2002, Stem Cells 20:364-379). A strong correlation was found between the location of specific miR genes and homeobox (HOX) genes. The miR-10a and miR-196-1 genes are located within the HOX B cluster on 17q21, while miR-196-2 is within the HOX C cluster at 12q13, and miR-10b maps to the HOX D cluster at 2q31 (see FIG. 2). Moreover, three other miRs (miR-148, miR-152 and miR-148b) are close to HOX clusters (less than 1 Mb; see FIG. 2). The 1 Mb distance was selected because some form of long-range coordinated regulation of gene expression was shown to expand up to one megabase to HOX clusters (Kamath et al., 2003, Nature 421:231-7). Such proximity of miR genes to HOX gene clusters is unlikely to have occurred by chance (IRR=15.77; p<0.001) (Table 4). Because collinear expression of, and cooperation between, HOX genes is well demonstrated, these data indicated that miRs are altered along with the HOX genes in human cancers.

Next, it was determined whether miR genes were located within class II HOX gene clusters as well. Fourteen additional human HOX gene clusters (Pollard et al., 2000, Current Biology 10:1059-1062) were analyzed, and seven miR genes (miR-129-1, miR-153-2, let-7a-1, let-7f-1, let-7d, miR-202 and miR-139) were located within 0.5 Mb of class II homeotic genes, a result which was highly unlikely to occur by chance (IRR=2.95, p<0.001) (Table 4).

Example 6

Expression of miR Gene Products in Human Cells

The cDNA sequence encoding the entire miR precursor transcript of an miR gene is separately cloned into the context of an irrelevant mRNA expressed under the control of the cytomegalovirus immediate early (CMV-IE) promoter, according to the procedure of Zeng et al., 2002, Mol. Cell. 9:1327-1333, the entire disclosure of which is herein incorporated by reference.

Briefly, Xho I linkers are placed on the end of double-stranded cDNA sequences encoding an miR precursor, and this construct is separately cloned into the Xho I site present in the pBC12/CMV plasmid. The pBC12/CMV plasmid is described in Cullen, 1986, Cell 46:973-982, the entire disclosure of which is herein incorporated by reference.

pCMV plasmid containing the miR precursor coding sequence is transfected into cultured human 293T cells by standard techniques using the FuGene 6 reagent (Roche). Total RNA is extracted as described above, and the presence of the processed miR transcript is detected by Northern blot analysis with an miR probe specific for the miR transcript.

pCMV-miR is also transfected into cultured human normal cells or cells with proliferative disorders, such as cancer cells. For example, the proliferative disease or cancer cell types include ovarian cancer, breast cancer, small cell lung cancer, sporadic follicular thyroid tumor, chronic lymphocytic leukemia, cervical cancer, acute myeloid leukemia, adenocarcinomas, male germ cell tumor, non-small cell lung cancer, gastric cancer, hepatocellular carcinoma, lung cancer, nasopharyngeal cancer, B-chronic lymphocytic leukemia, lipoma, mesothelioma, kidney cancer, NF1 microdeletion, neuroblastoma, medulloblastoma, pancreatic cancer, biliary cancer, colon cancer, gastric adenocarcinoma, head/neck squamous carcinoma, astrocytoma, meningioma, B cell leukemia, primary bladder cancer, prostate cancer, myelodysplastic syndrome, oral cavity carcinoma, laryngeal squamous carcinoma, and urothelial cancer. Total RNA is extracted as described above, and the presence of processed miR transcripts in the cancer cells is detected by Northern blot analysis with miR specific probes. The transfected cells are also evaluated for changes in morphology, the ability to overcome contact inhibition, and other markers indicative of a transformed phenotype.

Example 7

Preparation of Liposomes Encapsulating miR Gene Products

Liposome Preparation 1—Liposomes composed of lactosyl cerebroside, phosphatidylglycerol, phosphatidylcholine, and cholesterol in molar ratios of 1:1:4:5 are prepared by the reverse phase evaporation method described in U.S. Pat. No. 4,235,871, the entire disclosure of which is herein incorporated by reference. The liposomes are prepared in an aqueous solution of 100 µg/ml processed miR transcripts or 500 µg/ml pCMV-microRNA. The liposomes thus prepared encapsulate either the processed microRNA, or the pCMV-microRNA plasmids.

The liposomes are then passed through a 0.4 polycarbonate membrane and suspended in saline, and are separated from non-encapsulated material by column chromatography in 135 mM sodium chloride, 10 mM sodium phosphate (pH 7.4). The liposomes are used without further modification, or are modified as described herein.

A quantity of the liposomes prepared above are charged to an appropriate reaction vessel to which is added, with stirring, a solution of 20 mM sodium metaperiodate, 135 mM sodium chloride and 10 mM sodium phosphate (pH 7.4). The resulting mixture is allowed to stand in darkness for 90 minutes at a temperature of about 20° C. Excess periodate is removed by dialysis of the reaction mixture against 250 ml of buffered saline (135 mM sodium chloride, 10 mM sodium phosphate, pH 7.4) for 2 hours. The product is a liposome having a surface modified by oxidation of carbohydrate hydroxyl groups to aldehyde groups. Targeting groups or opsonization inhibiting moieties are conjugated to the liposome surface via these aldehyde groups.

Liposome Preparation 2—A second liposome preparation composed of maleimidobenzoyl-phosphatidylethanolamine (MBPE), phosphatidylcholine and cholesterol is obtained as follows. MBPE is an activated phospholipid for coupling sulfhydryl-containing compounds, including proteins, to the liposomes.

Dimyristoylphosphatidylethanolamine (DMPE) (100 mmoles) is dissolved in 5 ml of anhydrous methanol containing 2 equivalents of triethylamine and 50 mg of m-maleimidobenzoyl N-hydroxysuccinimide ester, as described in Kitagawa et al. (1976), J. Biochem. 79:233-236, the entire disclosure of which is herein incorporated by reference. The resulting reaction is allowed to proceed under a nitrogen gas atmosphere overnight at room temperature, and is subjected to thin layer chromatography on Silica gel H in chloroform/methanol/water (65/25/4), which reveals quantitative conversion of the DMPE to a faster migrating product. Methanol is removed under reduced pressure and the products re-dissolved in chloroform. The chloroform phase is extracted twice with 1% sodium chloride and the maleimidobenzoyl-phosphatidylethanolamine (MBPE) purified by silicic acid chromatography with chloroform/methanol (4/1) as the solvent. Following purification, thin-layer chromatography indicates a single phosphate containing spot that is ninhydrin negative.

Liposomes are prepared with MBPE, phosphatidylcholine and cholesterol in molar ratios of 1:9:8 by the reverse phase evaporation method of U.S. Pat. No. 4,235,871, supra, in an aqueous solution of 100 µg/ml processed microRNA or a solution of 500 µg/ml pCMV-miR (see above). Liposomes are separated from non-encapsulated material by column chromatography in 100 mM sodium chloride-2 mM sodium phosphate (pH 6.0).

Example 8

Attachment of Anti-Tumor Antibodies to Liposomes

An appropriate vessel is charged with 1.1 ml (containing about 10 mmoles) of Liposome Preparation 1 (see above) carrying reactive aldehyde groups, or Liposome Preparation 2 (see above). 0.2 ml of a 200 mM sodium cyanoborohydride solution and 1.0 ml of a 3 mg/ml solution of a monoclonal antibody directed against a tumor cell antigen is added to the preparation, with stirring. The resulting reaction mixture is allowed to stand overnight while maintained at a temperature of 4° C. The reaction mixture is separated on a Biogel A5M agarose column (Biorad, Richmond, Calif.; 1.5×37 cm).

Example 9

Inhibition of Human Tumor Growth In Vivo with miR Gene Products

A cancer cell line, such as one of the lung cancer cell lines described above or a tumor-derived cell, is inoculated into nude mice, and the mice are divided into treatment and control groups. When tumors in the mice reach 100 to 250 cubic millimeters, processed miR transcripts encapsulated in liposomes are injected directly into the tumors of the test group. The tumors of the control group are injected with liposomes encapsulating carrier solution only. Tumor volume is measured throughout the study.

Example 10

Oligonucleotide Microchip for Genome-Wide miRNA Profiling

Introduction

A micro-chip microarray was prepared as follows, containing 368 gene-specific oligonucleotide probes generated from 248 miRNAs (161 human, 84 mouse, and 3 arabidopsis) and 15 tRNAs (8 human and 7 mouse). These sequences correspond to human and mouse miRNAs found in the miRNA Registry (June 2003) (Griffiths-Jones, S. (2004) *Nucleic Acids Res.* 32, D109-D111) or collected from published literature (Lagos-Quintana, M., Rauhut, R., Lendeckel, W. & Tuschl, T. (2001) *Science* 294, 853-858; Lim, L. P., Glasner, M. E., Yekta, S., Burge, C. B. & Bartel, D. P. (2003) *Science* 299, 1540; Mourelatos, Z., Dostie, J., Paushkin, S., Sharma, A., Charroux, B., Abel, L., Rappsilber, J., Mann, M. & Dreyfuss, G. (2002) *Genes Dev* 16, 720-728). For 76 miRNAs, two different oligonucleotide probes were designed, one containing the active sequence and the other specific for the precursor. Using these distinct sequences, we were able to separately analyze the expression of miRNA and pre-miRNA transcripts for the same gene.

Various specificity controls were used to validate data. For intra-assay validation, individual oligonucleotide-probes were printed in triplicate. Fourteen oligonucleotides had a total of six replicates because of identical mouse and human sequences and therefore were spotted on both human and mouse sections of the array. Several mouse and human orthologs differ only in few bases, serving as controls for the hybridization stringency conditions. tRNAs from both species were also printed on the microchip, providing an internal, relatively stable positive, control for specific hybridization, while *Arabidopsis* sequences were selected, based on the absence of any homology with known miRNAs from other species, and used as controls for non-specific hybridization.

Materials and Methods

The following materials and methods were employed in designing and testing the microchip.

miRNA Oligonucleotide Probe Design. A total of 281 miRNA precursor sequences (190 *Homo sapiens*, 88 *Mus musculus*, and 3 *Arabidopsis thaliana*) with annotated active sites were selected for oligonucleotide design. These correspond to human and mouse miRNAs found in the miRNA Registry or collected from published literature. All of the sequences were confirmed by BLAST alignment with the corresponding genome and the hairpin structures were analyzed. When two precursors with different length or slightly different base composition for the same miRNAs were found, both sequences were included in the database and the one that satisfied the highest number of design criteria was used. The sequences were clustered by organism using the LEADS platform (Sorek, R., Ast, G. & Graur, D. (2002) *Genome Research* 12, 1060-1067), resulting in 248 clusters (84 mouse, 161 human, and 3 arabidopsis). For each cluster, all 40-mer oligonucleotides were evaluated for their cross-homology to all genes of the relevant organism, number of bases in alignment to a repetitive element, amount of low-complexity sequence, maximum homopolymeric stretch, global and local G+C content, and potential hairpins (self 5-mers). The best oligonucleotide was selected that contained each active site of each miRNA. This produced a total of 259 oligonucleotides; there were 11 clusters with multiple annotated active sites. Next, we attempted to design an oligonucleotide that did not contain the active site for each cluster, when it was possible to choose such an oligonucleotide that did not overlap the selected oligonucleotide(s) by more than 10 nt. To design each of these additional oligonucleotides, we required <75% global cross-homology and <20 bases in any 100% alignment to the relevant organism, <16 bases in alignments to repetitive elements, <16 bases of low-complexity, homopolymeric stretches of no more than 6 bases, G+C content between 30-70% and no more than 11 windows of size 10 with G+C content outside 30-70%, and no self 5-mers. A total of 76 additional oligonucleotides were designed. In addition, we designed oligonucleotides for 7 mouse tRNAs and 8 human tRNAs, using similar design criteria. We selected a single oligonucleotide for each, with the exception of the human and mouse initiators, Met-tRNA-i, for which we selected two oligonucleotides each (Table 8).

TABLE 8

Oligonucleotides used for the miRNA microarray chip and correspondence with specific human and mouse microRNAs.

| Oligonucleotide name | Corresponding miRNA | Oligonucleotide sequence | Covers active site? | Notes | SEQ ID NO. |
|---|---|---|---|---|---|
| ath-miR156a-#1 | ath-miR156a | TGACAGAAGAGAGTGAGCACACAAAGGCAATTTGCATATC | yes | | 286 |
| ath-miR156a-#2 | ath-miR156a | CATTGACTTGCTTCTCTTGCCTGCTCACTGCTCTTTCTG | no | | 287 |
| ath-miR157a-#1 | ath-miR157a | GTGTTGACAGAAGATAGAGAGCACAGATGATGAGATACAA | yes | | 288 |
| ath-miR157a-#2 | ath-miR157a | CATCTTACTCCTTTGTGCTCTCTAGCCTTCTGTCATCACC | no | | 289 |
| ath-miR180a-#1 | ath-miR180 | GATGGACGGTGGTGATTCACTCTCCACAAAGTTCTCTATG | no | | 290 |
| ath-miR180a-#2 | ath-miR180 | TGAGAATCTTGATGATGCTGCATCGGCAATCAACGACTAT | yes | | 291 |
| hsa-let-7a-1-prec | let-7a-1 | TGAGGTAGTAGGTTGTATAGTTTTAGGGTCACACCCACCA | yes | | 292 |
| hsa-let-7a-2-prec-#1 | let-7a-2 | TACAGCCTCCTAGCTTTCCTTGGGTCTTTGCACTAAACAAC | no | | 293 |
| hsa-let-7a-2-prec-#2 | let-7a-2 | ACTGCATGCTCCCAGGTTGAGGTAGTAGGTTGTATAGTTT | yes | | 294 |
| hsa-let-7a-3-prec | let-7a-3 | GGGTGAGGTAGTAGGTTGTATAGTTTGGGGCTCTGCCCTG | yes | | 295 |
| hsa-let-7b-prec | let-7b | TGAGGTAGTAGGTTGTGTGGTTTCAGGGCAGTGATGTTGC | yes | | 296 |
| hsa-let-7c-prec | let-7c | GCATCCGGGTTGAGGTAGTAGGTTGTATGGTTTAGAGTTA | yes | | 297 |
| hsa-let-7d-prec | let-7d | CCTAGGAAGAGGTAGTAGGTTGCATAGTTTTAGGGCAGGG | yes | | 298 |
| hsa-let-7d-v1-prec | let-7d (=7d-v1) | CTAGGAAGAGGTAGTAGTTTGCATAGTTTTAGGGCAAAGA | yes | | 299 |
| hsa-let-7d-v2-prec-#1 | let-7i (=let-7d-v2) | TTGTCGGGTTGTGACATTGCCCGCTGTGGAGATAACTGC | no | | 300 |
| hsa-let-7d-v2-prec-#2 | let-7i (=let-7d-v2) | GCTGAGGTAGTAGTTTGTGCTGTTGGTCGGGTTGTGACAT | yes | idem mmu-let-7i-prec | 301 |
| hsa-let-7e-prec | let-7e | GGCTGAGGTAGGAGGTTGTATAGTTGAGGAGGACACCCAA | yes | | 302 |
| hsa-let-7f-1-prec-#1 | let-7f-1 | GGTAGTGATTTTACCCTGTTCAGGAGATAACTATACAATC | no | | 303 |
| hsa-let-7f-1-prec-#2 | let-7f-1 | GGGATGAGGTAGTAGATTGTATAGTTGTGGGGTAGTGATT | yes | | 304 |
| hsa-let-7f-2-prec | let-7f-2 | TGAGGTAGTAGATTGTATAGTTTTAGGGTCATACCCCATC | yes | | 305 |
| hsa-let-7g-prec-#1 | let-7g | CTGATTCCAGGCTGAGGTAGTAGTTTGTACAGTTTGAGGG | yes | | 306 |
| hsa-let-7g-prec-#2 | let-7g | TTGAGGGTCTATGATACCACCCGGTACAGGAGATAACTGT | no | | 307 |
| hsa-miR-001b-1-prec1 | miR-001 | AATGCTATGCAATGTAAAGAAGTATGTATTTTGGTAGGC | yes | | 308 |

TABLE 8-continued

Oligonucleotides used for the miRNA microarray chip and correspondence with specific human and mouse microRNAs.

| Oligonucleotide name | Corresponding miRNA | Oligonucleotide sequence | Covers active site? | Notes | SEQ ID NO. |
|---|---|---|---|---|---|
| hsa-miR-001b-2-prec | miR-001 | TAAGCTATGGAATGTAAAGAAGTATGTATCTCAGGCCGGG | yes | | 309 |
| hsa-miR-007-1-prec | miR-007-1 | TGTTGGCCTAGTTCTGTGTGGAAGACTAGTGATTTTGTTG | yes | | 310 |
| hsa-miR-007-2-prec-#1 | miR-007-2 | TACTGCGCTCAACAACAAATCCCAGTCTACCTAATGGTGC | no | | 311 |
| hsa-miR-007-2-prec-#2 | miR-007-2 | GGACCGGCTGGCCCATCGGAAGACTAGTGATTTTGTTG | yes | | 312 |
| hsa-miR-007-3-prec-#1 | miR-007-3 | AGATTAGAGTGGCTGTGTCTAGTGCTGTGTGAAGACTA | no | | 313 |
| hsa-miR-007-3-prec-#2 | miR-007-3 | TGGAAGACTAGTGATTTTGTTCTGATGTACTACGACA | yes | | 314 |
| hsa-miR-009-1-#1 | miR-009-1 (miR-131-1) | TCTTTGGTTATCTAGCTGTATGAGTGGTGTGGAGTCTTCA | yes | | 315 |
| hsa-miR-009-1-#2 | miR-009-1 (miR-131-1) | TAAAGCTAGATAACCGAAAGTAAAAATAACCCATACACT | yes | | 316 |
| hsa-miR-009-2-#1 | miR-009-2 (miR-131-2) | GAAGCGAGTGTTATCTTTGGTTATCTAGCTGTATGAGTG | yes | | 317 |
| hsa-miR-009-2-#2 | miR-009-2 (miR-131-2) | GAGTGTATTGGTCTTCATAAAGCTAGATAACCGAAAGTAA | yes | idem mmu-miR-009-prec-#2 | 318 |
| hsa-miR-009-3-#1 | miR-009-3 (miR-131-3) | GGGAGGCCCGTTTCTCTCTTTGGTTATCTAGCTGTATGAG | yes | | 319 |
| hsa-miR-009-3-#2 | miR-009-3 (miR-131-3) | GTGCCAAGAGAGCCGTCATAAAGCTAGATAACCGAAAGTAG | yes | | 320 |
| hsa-miR-010a-prec-#1 | miR-010a | GTCTGTCTTCTGTATATACCCTGTAGATCCGAATTTGTGT | yes | | 321 |
| hsa-miR-010a-prec-#2 | miR-010a | GTGGTCACAAATTCGTATCTAGGGGAATATGTAGTTGACA | no | | 322 |
| hsa-miR-010b-prec-#1 | miR-010b | TACCCTGTAGAACCGAATTTGTGTGGTATCCGTATAGTCA | yes | | 323 |
| hsa-miR-010b-prec-#2 | miR-010b | GTCACAGATTCGATTCTAGGGGAATATATGGTTCGATGCAA | no | | 324 |
| hsa-miR-015a-2-prec-#1 | miR-15-a | CCTTGGAGTAAAGTAGCAGCACATAATGGTTTGTGGATTT | yes | | 325 |
| hsa-miR-015a-2-prec-#2 | miR-15-a | TTTGTGGATTTTGAAAAGGTGCAGGCCATATTGTGCTGCC | no | | 326 |
| hsa-miR-015b-prec-#1 | miR-015-b | GGCCTTAAAGTACTGTAGCAGCACATCATGTTTACATGC | yes | | 327 |
| hsa-miR-015b-prec-#2 | miR-015-b | TGCTACAGTCAAGATGCGAATCATTATTTGCTGCTCTAGA | no | | 328 |
| hsa-miR-016a-chr13 | miR-016-1 | CAATGTCAGTGCAGTGCCTTAGCAGCACGTAAATATTGGCGT | yes | | 329 |
| hsa-miR-016b-chr3 | miR-016-2 | GTTCCACTCTAGCAGCACGTAAATATTGGCGTAGTGAAAT | yes | | 330 |
| hsa-miR-017-prec-#1 | miR-017 (miR-091) | GCATCTACTGCAGTGAAGGCACTTGTAGCATTATGGTGAC | yes | | 331 |

TABLE 8-continued

Oligonucleotides used for the miRNA microarray chip and correspondence with specific human and mouse microRNAs.

| Oligonucleotide_name | Corresponding miRNA | Oligonucleotide sequence | Covers active site? | Notes | SEQ ID NO. |
|---|---|---|---|---|---|
| hsa-miR-017-prec-#2 | miR-017 (miR-091) | GTCAGAATAATGTCAAAGTGCTTACAGTGCAGTAGTGAT | yes | | 332 |
| hsa-miR-018-prec | miR-018 | TAAGGTGCATCTAGTGCAGATAGTGAAGTGATTAGCATC | yes | | 333 |
| hsa-miR-019a-prec | miR-019a | TGTAGTTGTGCAAATCTATGCAAAACTGATGGTGGCCTGC | yes | | 334 |
| hsa-miR-019b-1-prec | miR-019b-1 | TTCTGCTGTGCAAATCCATGCAAAACTGACTGTGGTAGTG | yes | | 335 |
| hsa-miR-019b-2-prec | miR-019b-2 | GTGGCTGTGCAAATCCATGCAAAACTGATTGTGATAATGT | yes | | 336 |
| hsa-miR-020-prec | miR-020 | TAAAGTGCTTATAGTGCAGGTAGTGTTTAGTTATCTACTG | yes | | 337 |
| hsa-miR-021-prec-17-#1 | miR-021 | GTCGGGTAGCTTATCAGACTGATGTTGACTGTTGAATCTC | yes | | 338 |
| hsa-miR-021-prec-17-#2 | miR-021 | TTCAACAGTCAACATCAGTCTGATAAGCTACCCGACAAGG | yes | | 339 |
| hsa-miR-022-prec | miR-022 | TGTCCTGACCCGCAGCTAAAGCTGCCAGTTGAAGAACTGTTG | yes | | 340 |
| hsa-miR-023a-prec | miR-023a | TCCTGTCACAAATCACATTGCCAGGGATTTCCAACCGACC | yes | | 341 |
| hsa-miR-023b-prec | miR-023b | AATCACATTGCCAGGGATTACCACGCAACCACGACCTTGG | yes | | 342 |
| hsa-miR-024-1-prec-#1 | miR-024-1 | TTTTACACACTGGCTCAGTTCAGCAGGAACAGGAGTCGAG | yes | | 343 |
| hsa-miR-024-1-prec-#2 | miR-024-1 | TCCGGTGCCTACTGAGCTGATATCAGTTCTCATTTTACAC | yes | | 344 |
| hsa-miR-024-2-prec | miR-024-2 | AGTTGGTTTGTGTACACTGGCTCAGTTCAGCAGGAACAGG | yes | | 345 |
| hsa-miR-025-prec | miR-025 | ACGCTGCCCTGGGCATTGCACTTGTCTCGGTCTGACAGTG | yes | | 346 |
| hsa-miR-026a-prec-#1 | miR-026a | TTCAAGTAATCCAGGATAGGCTGTGCAGGTCCCAATGCCC | yes | | 347 |
| hsa-miR-026a-prec-#2 | miR-026a | TCCCAATGGCCTATCTTGGTTACTTGCACGGGGACGCGGG | no | | 348 |
| hsa-miR-026b-prec | miR-026b | TTCAAGTAATTCAGGATAGGTTGTGTGCTGTCCAGCCTGT | yes | | 349 |
| hsa-miR-027a-prec | miR-027a | GTCCACACCAAGTCGTGTTCACAGTGGCTAAGTTCCGCCC | yes | | 350 |
| hsa-miR-027b-prec | miR-027b | CCGCTTTGTTCACAGTGGCTAAGTTCTGCACCTGAAGAGA | yes | | 351 |
| hsa-miR-028-prec | miR-028 | AAGGAGCTCACAGTCTATTGAGTTACCTTTCTGACTTTCC | yes | | 352 |
| hsa-miR-029a-2-#1 | miR-029a | CTAGCACCATCTGAAATCGGTTATAATGATTGGGGAAGAG | yes | | 353 |
| hsa-miR-029a-2-#2 | miR-029a | CCCCTTAGAGGATGACTGATTTCTTTTGGTGTTCAGAGTC | no | | 354 |
| hsa-miR-029b-2 = 102prec7.2 | miR-029b (=miR-102-7.1 = 7.2) | AGTGATTGTCTAGCACCATTTGAAATCAGTGTTCTTGGGG | yes | | 355 |

TABLE 8-continued

Oligonucleotides used for the miRNA microarray chip and correspondence with specific human and mouse microRNAs.

| Oligonucleotide_name | Corresponding miRNA | Oligonucleotide sequence | Covers active site? | Notes | SEQ ID NO. |
|---|---|---|---|---|---|
| hsa-miR-029c-prec | miR-029c | TTTGTCTAGCACCATTTGAAATCGGTTATGATGTAGGGG | yes | | 356 |
| hsa-miR-030a-prec-#1 | miR-030a-as | GCGACTGTAAACATCCTCGACTGGAAGCTGTGAAGCCACA | yes | | 357 |
| hsa-miR-030a-prec-#2 | miR-030a-s | CACAGATGGGCTTTCAGTCGGATGTTTGCAGCTGCCTACT | yes | | 358 |
| hsa-miR-030b-prec-#1 | miR-030b | TGTAAACATCCTACACTCAGCTGTAATACATGATTGGCT | yes | | 359 |
| hsa-miR-030b-prec-#2 | miR-030b | ATGGATTGGCTGGGAGGTGGATGTTTACTTCAGCTGACTT | no | | 360 |
| hsa-miR-030c-prec | miR-030c | TACTGTAAACATCCTACACTCTCAGCTGTGGAAAGTAAGA | yes | | 361 |
| hsa-miR-030d-prec-#1 | miR-030d | TAAGACACAGCTAAGCTTTCAGTCAGATGTTTGCTGCTAC | no | | 362 |
| hsa-miR-030d-prec-#2 | miR-030d | TTGTAAACATCCCCGACTGGAAGCTGTAAGACACAGCTAA | yes | | 363 |
| hsa-miR-031-prec | miR-031 | GGCAAGATGCTGGCATAGCTGTTGAACTGGGAACCTGCTA | yes | | 364 |
| hsa-miR-032-prec-#1 | miR-032 | TGTCACGGCCTCAATGCAATTTAGTGTGTGTGATATTTTC | no | | 365 |
| hsa-miR-032-prec-#2 | miR-032 | GGAGATATTGCACATTACTAAGTTGCATGTTGTCACGGCC | yes | | 366 |
| hsa-miR-033b-prec | miR-033b | GTGCATTGCTGTTGCATTGCACGTGTGAGGCGGGTGCA | yes | | 367 |
| hsa-miR-033-prec | miR-33 | GTGGTGCATTGTAGTTGCATTGCATGTTCTGGTGGTACCC | yes | | 368 |
| hsa-miR-034-prec-#1 | miR-034 (=miR-170) | GAGTGTTTCTTTGGCAGTGTCTTAGCTGGTTGTTGTGAGC | yes | | 369 |
| hsa-miR-034-prec-#2 | miR-034 (=miR-170) | AGTAAGGAAGCAATCAGCAAGTATACTGCCCTAGAAGTGC | no | | 370 |
| hsa-miR-092-prec-#1<br>13 = 092-1 | miR-092-1 | ACAGGTTGGGATCGGTTGCAATGCTGTGTTTCTGTATGGT | no | | 371 |
| hsa-miR-092-prec-#2<br>13 = 092-1 | miR-092-1 | TCTGTATGGTATTGCACTTGTCCCGGCCTGTTGAGTTTGG | yes | | 372 |
| hsa-miR-092-prec-2<br>X = 092-2 | miR-092-2 | GTTCTATATAAAGTATTGCACTTGTCCCGGCCTGTGGAAG | yes | | 373 |
| hsa-miR-093-prec-1<br>7.1 = 093-1 | miR-093-1 | CCAAAGTGCTGTTCGTGCAGGTAGTGTGATTACCCAACCT | yes | | 374 |
| hsa-miR-095-prec-4 | miR-095 | CGTTACATTCAACGGGTATTATTGAGCACCCACTCTGTG | yes | | 375 |
| hsa-miR-096-prec-7-#1 | miR-096 | CTCCGCTCTGAGCAATCATGTCAGTGCCAATATGGGAAA | no | | 376 |
| hsa-miR-096-prec-7-#2 | miR-096 | TGGCCGATTTTGCACTAGCACATTTTGCTGTGTCTCT | yes | | 377 |

TABLE 8-continued

Oligonucleotides used for the miRNA microarray chip and correspondence with specific human and mouse microRNAs.

| Oligonucleotide name | Corresponding miRNA | Oligonucleotide sequence | Covers active site? | Notes | SEQ ID NO. |
|---|---|---|---|---|---|
| hsa-miR-098-prec-X | miR-098 | TGAGGTAGTAAGTTGTATTGTTGTGGGTAGGGATATTAG | yes | | 378 |
| hsa-miR-099b-prec-19-#1 | miR-099b | GCCTTCGCCGCACCAAGCTCGTCTGTCTGTGGGTCCGTGTC | no | idem mmu-miR-099b-prec-#1 | 379 |
| hsa-miR-099b-prec-19-#2 | miR-099b | CACCCGTAGAACCGACCTTGCGGGGCCTTCGCCGCACACA | yes | idem mmu-miR-099b-prec-#2 | 380 |
| hsa-miR-099-prec-21 | miR-099a (=miR-099-prec21) | ATAAACCCGTAGATCCGATCTTGTGGTGAAGTGGACCGCA | yes | | 381 |
| hsa-miR-100-1/2-prec | miR-100 | TGAGGCCTGTTGCCACAAACCCTAGATCCGAACTTGTGG | yes | | 382 |
| hsa-miR-101-1/2-prec-#1 | miR-101-1 | CCCTGGCTCAGTTATCACAGTGCTGATGCTGTCTATTCTA | no | | 383 |
| hsa-miR-101-1/2-prec-#2 | miR-101-1 | TACAGTACTGTGATAACTGAAGGATGCAGCCATCTTACC | yes | | 384 |
| hsa-miR-101-prec-9 | miR-101-2 | GCTGTATATCTGAAAGGTACAGTACTGTGATAACTGAAGA | yes | | 385 |
| hsa-miR-102-prec-1 | miR-102 | TCTTTGTATCTAGCACCATTGAAATCAGTGTTTTAGGAG | yes | | 386 |
| hsa-miR-103-2-prec | miR-103-2 | GTAGCATTCAGGTCAAGCAACATTGTACAGGGCTATGAAA | yes | | 387 |
| hsa-miR-103-prec-5 = 103-1 | miR-103-1 (=miR-103-5) | TATGGATCAAGCAGCATTGTACAGGGCTATGAAGGCATTG | yes | | 388 |
| hsa-miR-105-prec-X.1 = 105-1 | miR-105-1 (=miR-105-prec-X) | ATCGTGTCAAATGCTCAGACTCCTGTGTGGCTGCTCAT | yes | | 389 |
| hsa-miR-106-prec-X | miR-106a | CCTTGGCCATGTAAAAGTGCTTACAGTGCAGGTAGCTTTT | yes | | 390 |
| hsa-miR-107-prec-10 | miR-107 | GGCATGGAGTTCAAGCAGCATTGTACAGGGCTATCAAAGC | yes | | 391 |
| hsa-miR-122a-prec | miR-122a | CCTTAGCAGAGCTGTGGAGTGTGACAATGGTGTTTGTGTC | yes | | 392 |
| hsa-miR-123-prec-#1 | miR-123 = miR-126 | GACGGGACATTATTACTTTTGGTACGCGCTGTGACACTTC | yes | | 393 |
| hsa-miR-123-prec-#2 | miR-123 = miR-126 | TGTGACACTTCAAACTCTACCGTGAGTAATAATGCGCCG | yes | | 394 |
| hsa-miR-124a-1-prec1 | miR-124a-1 | ATACAATTAAGGCACGCGGTGAATGCCAAGAATGGGGCTG | yes | | 395 |
| hsa-miR-124a-2-prec | miR-124a-2 | TTAAGGCACGCGGTGAATGCCAAGAGCGGAGCCTACGGCT | yes | | 396 |
| hsa-miR-124a-3-prec | miR-124a-3 | TTAAGGCACGCGGTGAATGCCAAGAGAGAGGCGCCTCCGCCG | yes | | 397 |
| hsa-miR-125a-prec-#1 | miR-125a | TCTAGGTCCCTGAGACCCTTTAACCTGTGAGGACATCCAG | yes | | 398 |

TABLE 8-continued

Oligonucleotides used for the miRNA microarray chip and correspondence with specific human and mouse microRNAs.

| Oligonucleotide_name | Corresponding miRNA | Oligonucleotide sequence | Covers active site? | Notes | SEQ ID NO. |
|---|---|---|---|---|---|
| hsa-miR-125a-prec-#2 | miR-125a | CAGGGTCACAGGTGAGGTTCTTGGGAGCCTGGCGTCTGGC | no | | 399 |
| hsa-miR-125b-1 | miR-125b-1 | TCCCTGAGACCCTAACTTGTGATGTTTACCGTTTAAATCC | yes | | 400 |
| hsa-miR-125b-2-prec-#1 | miR-125b-2 | TAGTAACATCACAAGTCAGGCTCTTGGGACCTAGGCGGAG | no | | 401 |
| hsa-miR-125b-2-prec-#2 | miR-125b-2 | ACCAGACTTTTCCTAGTCCCTGAGACCTAACTTGTGAGG | yes | | 402 |
| hsa-miR-127-prec | miR-127 | TCCGATCCGTCTGAGCTTGGCTGTCGGTCGAAGTCTCATCAT | yes | | 403 |
| hsa-miR-128a-prec-#1 | miR-128a | TTGGATTCGGGGCCGTAGCACTGTCTGAGAGGTTTACATT | no | idem mmu-miR-128-prec-#2 | 404 |
| hsa-miR-128a-prec-#2 | miR-128a | ACATTTCACAGTGAACCGGTCTCTTTTTCAGCTGCTTC | yes | | 405 |
| hsa-miR-128b-prec-#1 | miR-128b | TCACAGTGAACCGGTCTCTTTCCCTACTGTGTCACACTCC | yes | | 406 |
| hsa-miR-128b-prec-#2 | miR-128b | GGGGGCCGATACACTGTACGAGAGTGAGTAGCAGGTCTCA | no | | 407 |
| hsa-miR-129-prec-#1 | miR-129-1/2 | TGGATCTTTTTGCGGTCTGGGCTTGCTGTTCCTCTCAACA | yes | | 408 |
| hsa-miR-129-prec-#2 | miR-129-1/2 | CCTCTCACAGTAGTCAGGAAGCCCTTACCCCAAAAGTA | no | | 409 |
| hsa-miR-130a-prec-#1 | miR-130a | CCAGAGCTCTTTTCACATTGTGCTACTGTCTGCACCTGTC | no | | 410 |
| hsa-miR-130a-prec-#2 | miR-130a | TGTCTGCACCTGTCACTAGCAGTGCAATGTTAAAAGGGCA | yes | | 411 |
| hsa-miR-132-prec-#1 | miR-132 | TGTGGGAACTGGAGGTAACACTACAGCTGGTTGACCATGG | yes | | 412 |
| hsa-miR-132-prec-#2 | miR-132 | TCCAGGGCAACCGTGGCTTTCGATTGTTACTGTGGGAACT | no | | 413 |
| hsa-miR-133a-1 | miR-133a-1 (=miR-133c) | CCTCTTCAATGAGGATTTGGTCCCCTTCAACCAGCTGTAGCT | yes | | 414 |
| hsa-miR-133a-2 | miR-133a-2 (=miR-133d) | TTGGTCCCCTTCAACCAGCTGTAGCTGTGCATTGATGCG | yes | | 415 |
| hsa-miR-134-prec-#1 | miR-134 | ATGCACTGTGTTCACCCTGTGGGCCACCTAGTCACCAACC | no | | 416 |
| hsa-miR-134-prec-#2 | miR-134 | GTGTGTGACTGGTTGACCAGAGGGGCATGCACTGTGTTCA | yes | | 417 |
| hsa-miR-135-1-prec | miR-135-1 (=miR-135) | GCCTCGCTGTTCTCTATGGCTTTTTATTCCTATGTGATTC | yes | | 418 |
| hsa-miR-135-2-prec | miR-135-2 | CACTCTAGTGCTTTATGCTTTTTATTCCTATGTGATAGT | yes | | 419 |
| hsa-miR-136-prec-#1 | miR-136 | ATGCTCCATCATCGTCTCAAATGAGTCTTCAGAGGGTTCT | no | | 420 |
| hsa-miR-136-prec-#2 | miR-136 | TGAGCCCTCGGAGGACTCCATTTGTTTTGATGATGGATTC | yes | | 421 |

TABLE 8-continued

Oligonucleotides used for the miRNA microarray chip and correspondence with specific human and mouse microRNAs.

| Oligonucleotide_name | Corresponding miRNA | Oligonucleotide sequence | Covers active site? | Notes | SEQ ID NO. |
|---|---|---|---|---|---|
| hsa-miR-137-prec | miR-137 | GGATTACGTTGTTATTGCTTAAGAATACGCGTAGTCGAGG | yes | idem mmu-miR-137-prec | 422 |
| hsa-miR-138-1-prec | miR-138-1 | AGCTGGTGTTGTGAATCAGGCCGTTGCCAATCAGAGAACG | yes | | 423 |
| hsa-miR-138-2-prec | miR-138-2 | AGCTGGTGTTGTGAATCAGGCCGACGAGCAGCCGCATCCTC | yes | idem mmu-miR-138-prec | 424 |
| hsa-miR-139-prec | miR-139 | GTCTATTCTACAGTGCACGTGTCTCCAGTGTGGCTCGAG | yes | | 425 |
| hsa-miR-140-#1 | miR-140-as | GCCAGTGGTTTTACCCTATGGTAGGTTACGTCATGCTGTT | no | | 426 |
| hsa-miR-140-#2 | miR-140-as | TTCTACCACAGGGTAGAACCACGGACCAGGATACCGGGGCA | yes | | 427 |
| hsa-miR-141-prec-#1 | miR-141 | TTGTGAAGCTCCTAACACTGTCTGGTAAAGATGGCTCCCG | yes | | 428 |
| hsa-miR-141-prec-#2 | miR-141 | ATCTTCCAGTACAGTGTTGGATGGTCTAATTGTGAAGCTC | no | | 429 |
| hsa-miR-142-prec | miR-142-as | CCCATAAAGTAGAAAGCACTACTAACAGCACTGGAGGGTG | yes | idem mmu-miR-142-prec | 430 |
| hsa-miR-143-prec | miR-143 | CTGGTCAGTTGGGAGTCTGAGATGAAGCACTGTAGCTCAG | yes | | 431 |
| hsa-miR-144-prec-#1 | miR-144 | CGATGAGACACTACAGTATAGATGATGTACTAGTCCGGGC | yes | | 432 |
| hsa-miR-144-prec-#2 | miR-144 | CCCTGGCTGGGATATCATCATATACTGTAAGTTTGCGATG | no | | 433 |
| hsa-miR-145-prec | miR-145 | CCTCACGGTCCAGTTTTCCCAGGAATCCCTTAGATGCTAA | yes | | 434 |
| hsa-miR-146-prec | miR-146 | TGAGAACTGAATTCCATGGGTTGTGTCAGTGTCAGACCTC | yes | | 435 |
| hsa-miR-147-prec | miR-147 | GACTATGGAAGCCAGTGTGTGGAAATGCTTCTGCTAGATT | yes | | 436 |
| hsa-miR-148-prec | miR-148 | TGAGTATGATAGAAGTCAGTGCACTACAGAACTTTGTCTC | yes | | 437 |
| hsa-miR-149-prec | miR-149 | CGAGCTCTGGCTCCGTGTCTTCACTCCCGTGCTTGTCCGA | yes | | 438 |
| hsa-miR-150-prec | miR-150 | CTCCCCATGGCCCTGTCCTCCCAACCCTTGTACCAGTGCTG | yes | | 439 |
| hsa-miR-151-prec | miR-151 | GTATGTCTCATCCCCTACTAGACTGAAGCTCCTTGAGGAC | yes | | 440 |
| hsa-miR-152-prec-#1 | miR-152 | ACTCGGGCTCTGGAGCAGTCAGTGCATGACAGAACTTGGG | yes | idem mmu-miR-152-prec | 441 |
| hsa-miR-152-prec-#2 | miR-152 | CCCCGGCCCAGGTTCTGTGATACACTCCGACTCGGGCTCT | no | | 442 |
| hsa-miR-153-1-prec1 | miR-153-1 | CAGTTGCATAGTCACAAAAGTGATCATTGGCAGGTGTGGC | yes | | 443 |

TABLE 8-continued

Oligonucleotides used for the miRNA microarray chip and correspondence with specific human and mouse microRNAs.

| oligonucleotide_name | Corresponding miRNA | Oligonucleotide sequence | Covers active site? Notes | SEQ ID NO. |
|---|---|---|---|---|
| hsa-miR-153-1-prec2 | miR-153-1 | CACAGCTGCCAGTGCTCATTGTCACAAAAGTGATCATTGGC | yes | 444 |
| hsa-miR-153-2-prec | miR-153-2 | GCCCAGTTGCATAGTCACAAAAGTGATCATTGAAACTGT | yes | 445 |
| hsa-miR-154-prec1-#1 | miR-154 | GTGGTACTTGAAGATAGTTATCCGTGTTGCCTTCGCTTT | yes | 446 |
| hsa-miR-154-prec1-#2 | miR-154 | GCCTTCGCTTTATTTGTGACGAATCATACACCGTTGACCT | no | 447 |
| hsa-miR-155-prec | miR-155(BIC) | TTAATGCTAATCGTGATAGGGGTTTTGCCTCCAACTGAC | yes | 448 |
| hsa-miR-181a-prec-#1 | miR-181a (=miR-178-2) | TCAGAGGACTCCAAGGAACATTCAACGCTGTCGGTGAGTT | yes | 449 |
| hsa-miR-181a-prec-#2 | miR-181a (=miR-178-2) | GAAAAAACCACTGACCGTTGACTGTACCTTGGGGTCCTTA | no | 450 |
| hsa-miR-181b-prec-#1 | miR-181b (=miR-178) | TGAGGTTGCTTCAGTGAACATTCAACGCTGTCGGTGAGTT | yes | 451 |
| hsa-miR-181b-prec-#2 | miR-181b (=miR-178) | ACCATCGACCGTTGATTGTACCCTATGCTAACCATCATC | yes | 452 |
| hsa-miR-181c-prec-#1 | miR-181c | TGCCAAGGGTTTGGGGAACATTCAACCTGTCGGTGAGTT | yes | 453 |
| hsa-miR-181c-prec-#2 | miR-181c | ATCGACCGTTGAGTGACCCTGAGGCCTGGAATTGCCATC | no | 454 |
| hsa-miR-182-s-prec-#1 | miR-182-s | AGGTAACAGGATCCGGTGGTTCTAGACTTGCCAACTATGG | no | 455 |
| hsa-miR-182-s-prec-#2 | miR-182-s | TTGGCAATGGTAGAACTCACACTGGTGAGGTAACAGGATC | yes | 456 |
| hsa-miR-183-prec-#1 | miR-183 (=miR-174) | GACTCCTGTTCTGTGTATGGCACTGGTAGAATTCACTGTG | yes | 457 |
| hsa-miR-183-prec-#2 | miR-183 (=miR-174) | GTCTCAGTCAGTGAATTACCGAAGGGCCATAAACAGAGCA | no | 458 |
| hsa-miR-184-prec-#1 | miR-184 | GACTGTAAGTGTTGGACCGAGAACTGATAAGGGTAGGTGA | yes | 459 |
| hsa-miR-184-prec-#2 | miR-184 | CGTCCCCCTTATCACTTTTCCAGCCCAGCTTTGTGACTGTA | no | 460 |
| hsa-miR-185-prec-#1 | miR-185 | GCCGAGGGATTGGAGAGAAAGGCAGTTCCTGATGGTCCCCT | yes | 461 |
| hsa-miR-185-prec-#2 | miR-185 | CCTCCCCAGGGGCTGGCTTTCCTCTGGTCCTTCCCTCCCA | no | 462 |
| hsa-miR-186-prec | miR-186 | CTTGTAACTTTCCAAAGAATTCTCCTTTTGGGCTTTCTGG | yes | 463 |
| hsa-miR-187-prec-#1 | miR-187 | CTCGTGTCTTGTGTTGCAGCCGGACCCGAGGGACCAGGTCCGCA | yes | 464 |
| hsa-miR-187-prec-#2 | miR-187 | TCACCATGACACAGTGTGAGACTCGGGCTACACACAGGA | no | 465 |
| hsa-miR-188-prec | miR-188 | TCACATCCCTTGCATGGTGGAGGGTGAGCTTTCTGAAAAC | yes | 466 |
| hsa-miR-190-prec | miR-190 | GCAGGCCTCTGTGTGATATGTTTGATATATTAGGTTGTTA | yes | 467 |

TABLE 8-continued

Oligonucleotides used for the miRNA microarray chip and correspondence with specific human and mouse microRNAs.

| Oligonucleotide_name | Corresponding miRNA | Oligonucleotide sequence | Covers active site? | Notes | SEQ ID NO. |
|---|---|---|---|---|---|
| hsa-miR-191-prec | miR-191 | CAACGGAATCCCAAAAGCAGCTGTTGTCTCCAGAGCATTC | yes | idem mmu-miR-191-prec | 468 |
| hsa-miR-192-2/3-#1 | miR-192 | TCTGACCTATGAATTGACAGCCAGTGCTCTCGTCTCCCT | yes | | 469 |
| hsa-miR-192-2/3-#2 | miR-192 | CCAATTCCATAGTCACAGGTATGTTCGCCTCACAATGCCAG | no | | 470 |
| hsa-miR-193-prec-#1 | miR-193 | AGATGAGGGTGTCGGATCAACTGGCCTACAAAGTCCCAGT | yes | | 471 |
| hsa-miR-193-prec-#2 | miR-193 | AGGATGGGAGCTGAGGGCTGGGTCTTTGCGGGCGAGATGA | no | | 472 |
| hsa-miR-194-prec-#1 | miR-194 | TGTAACAGCAACTCCATGTGGACTGTGTACCAATTTCCAG | yes | | 473 |
| hsa-miR-194-prec-#2 | miR-194 | CCAATTTCCAGTGGAGATGCTGTTACTTTTGATGGTTACC | no | | 474 |
| hsa-miR-195-prec | miR-195 | TCTAGCAGCACAGAAATATTGGCACAGGGAAGCGAGTCTG | yes | | 475 |
| hsa-miR-196-1-prec-#1 | miR-196-1 | CTGCTGAGTGAATTAGGTAGTTTCATGTTGTTGGGCCTGG | yes | | 476 |
| hsa-miR-196-1-prec-#2 | miR-196-1 | ACACAACAACATTAAACCACCCGATTCACGGCAGTTACTG | no | | 477 |
| hsa-miR-196-2-prec-#1 | miR-196-2 | AGAAACTGCCTGAGTTACATCAGTCGGTTTTCGTGAGGG | no | | 478 |
| hsa-miR-196-2-prec-#2 | miR-196-2 | GCTGATCTGTGGCTTAGGTAGTTTCATGTTGTTGGGATTG | yes | | 479 |
| hsa-miR-197-prec | miR-197 | TAAGAGCTCTTCACCCTTCACCACCTTCTCCACCCAGCAT | yes | | 480 |
| hsa-miR-198-prec | miR-198 | TCATTGGTCCAGAGGGGAGATAGGTTTCCTGTGATTTTTCC | yes | | 481 |
| hsa-miR-199a-1-prec | miR-199a-1 (=199s) | GCCAACCAGTGTTCAGACTACCTGTTCAGGAGGCTCTCA | yes | | 482 |
| hsa-miR-199a-2-prec | miR-199a-2 | TCGCCCCAGTGTTCAGACTACCTGTTCAGGACAATGCCGT | yes | | 483 |
| hsa-miR-199b-prec-#1 | miR-199b | GTCTGCACATTGTAGGCTGGTCTGGGCTGGGTTAGACCCTCGG | no | | 484 |
| hsa-miR-199b-prec-#2 | miR-199b | ACCTCCACTCCGTCTACCCAGTGTTTAGACTATCTGTTCA | yes | | 485 |
| hsa-miR-200a-prec | miR-200a | GTCTCTAATACTGCCTGGTAATGATGACGGCGGAGCCCTG | yes | | 486 |
| hsa-miR-202-prec | miR-202 | GATCTGGCCTAAAGAGGTATAGGGCATGGGAAGATGGAGC | yes | | 487 |
| hsa-miR-203-prec-#1 | miR-203 | GTTCTGTAGCGCAATTGTGAAATGTTTAGGACCACTAGAC | yes | | 488 |
| hsa-miR-203-prec-#2 | miR-203 | TGGGTCCAGTGTTCTTAACAGTTCAACAGTTCTGTAGCG | no | | 489 |
| hsa-miR-204-prec-#1 | miR-204 | CGTGGACTTCCCTTTGTCATCCTATGCCTGAGAATATATG | yes | | 490 |

TABLE 8-continued

Oligonucleotides used for the miRNA microarray chip and correspondence with specific human and mouse microRNAs.

| Oligonucleotide name | Corresponding miRNA | Oligonucleotide sequence | Covers active site? | Notes | SEQ ID NO. |
|---|---|---|---|---|---|
| hsa-miR-204-prec-#2 | miR-204 | AGGCTGGGAAGGCAAAGGGACGTTCAATTGTCATCACTGG | no | | 491 |
| hsa-miR-205-prec | miR-205 | TCCTTCATTCCACCGGAGTCTGTCTCATACCCAACCAGAT | yes | | 492 |
| hsa-miR-206-prec-#1 | miR-206 | TTGCTATGGAATGTAAGGAAGTGTGTGGTTTCGGCAAGTG | yes | | 493 |
| hsa-miR-206-prec-#2 | miR-206 | TGCTTCCCGAGGCCACATGCTTCTTTATATCCCCATATGG | no | | 494 |
| hsa-miR-208-prec | miR-208 | ACCTGATGCTCACGTATAAGACAGCAAAAGCTTGTTGG | yes | | 495 |
| hsa-miR-210-prec | miR-210 | AGACCCACTGTGCGTGTGACAGCGGCTGATCTGTGCCTGG | yes | | 496 |
| hsa-miR-211-prec-#1 | miR-211 | TTCCCTTTGTCATCCTTCGCCTAGGGCTCTGAGCAGGGCA | yes | | 497 |
| hsa-miR-211-prec-#2 | miR-211 | GCAGGGACAGCAAAGGGGTGCTCAGTTGTCACTTCCCACA | no | | 498 |
| hsa-miR-212-prec-#1 | miR-212 | CCTCAGTAACAGTCTCCAGTCACGGCCACCGACGCCTGGC | yes | | 499 |
| hsa-miR-212-prec-#2 | miR-212 | CGGACAGCGCGCCGGCACCTTGGCTCTAGACTGCTTACTG | no | | 500 |
| hsa-miR-213-prec-#1 | miR-213 | AACATTCATTGCTGTCGTGGGTTGAACTGTGTGGACAAG | yes | idem mmu-miR-213-prec | 501 |
| hsa-miR-213-prec-#2 | miR-213 | TGTGGACAAGCTCACTGAACAATGAATGCAACTGTGGCCC | no | | 502 |
| hsa-miR-214-prec | miR-214 | TGTACAGCAGGCACAGACAGGCAGTCACATGACAACCCAG | yes | idem mmu-miR-214-prec | 503 |
| hsa-miR-215-prec-#1 | miR-215 | CAGGAAAATGACCTATGAATTGACAGACAATATAGCTGAG | yes | | 504 |
| hsa-miR-215-prec-#2 | miR-215 | CATTTCTTTAGGCCAATATTCTGTATGACTGTGCTACTTC | no | | 505 |
| hsa-miR-216-prec-#1 | miR-216 | CTGGGATTATGCTAAACAGAGACAATTCCTAGCCCTCACG | no | | 506 |
| hsa-miR-216-prec-#2 | miR-216 | GATGGCTGTGAGTTGGCTTAAATCTCAGCTGGCAACTGTGA | yes | | 507 |
| hsa-miR-217-prec-#1 | miR-217 | GAATCAGTCACCATCAGTTCCTAATGCATTGCCTTCAGCA | no | | 508 |
| hsa-miR-217-prec-#2 | miR-217 | TGTCGCAGATACTGCATCAGGAACTGATTGGATAAGAATC | yes | | 509 |
| hsa-miR-218-1-prec | miR-218-1 | GTTGTGCTTGATCTAACCATGTGGTTGCGAGGTATGAGTA | yes | | 510 |
| hsa-miR-218-2-prec-#1 | miR-218-2 | TGGTGGAACGATGGAAACGGAACATGGTTCTGTCAAGCAC | no | | 511 |
| hsa-miR-218-2-prec-#2 | miR-218-2 | TCGCTGCGGGCTTTCCTTTGCTTGATCTAACCATGTG | yes | | 512 |
| hsa-miR-219-prec | miR-219 | ATTGTCCAAACGAATTCTCGAGTCTATGCCTCCGGCCGA | yes | | 513 |

TABLE 8-continued

Oligonucleotides used for the miRNA microarray chip and correspondence with specific human and mouse microRNAs.

| Oligonucleotide name | Corresponding miRNA | Oligonucleotide sequence | Covers active site? | Notes | SEQ ID NO. |
|---|---|---|---|---|---|
| hsa-miR-220-prec | miR-220 | TGTGGCATTGTAGGGCTCCACACCGTATCTGACACTTTGG | yes | | 514 |
| hsa-miR-221-prec | miR-221 | CAACAGCTACATTGTCTGCTGGGTTTCAGGCTACCTGAAA | yes | idem mmu-miR-221-prec-#1 | 515 |
| hsa-miR-222-prec-#1 | miR-222 | CTTTCGTAATCAGCAGCTACATCTGGCTACTGGGTCTCTG | yes | | 516 |
| hsa-miR-222-prec-#2 | miR-222 | GCTGCTGGAAGGTGTAGGTACCCTCAATGGCTCAGTAGCC | no | | 517 |
| hsa-miR-223-prec | miR-223 | GAGTGTCAGTTTGTCAAATACCCCAAGTGCGGCACATGCT | yes | | 518 |
| hsa-miR-224-prec | miR-224 | GGCTTTCAAGTCACTAGTGGTTCCGTTTAGTAGATGATTG | yes | | 519 |
| HSHELA01 | — | GGCCGCAGCAACCTCGGTTCGTATCCGAGTCACGGCACCA | — | | 520 |
| HSTRNL | — | TCCGGATGGAGCGTGGGTTCGAATCCCACTTCTGACACCA | — | | 521 |
| HUMTRAB | — | ATGTAGAGCGCTCGCTTTGCTTGCGAGAGGTAGCGGGAT | — | | 522 |
| HUMTRF | — | GATCTAAAGGTCCCTGGTTCGATCCCGGGTTTCGGCACCA | — | | 523 |
| HUMTRMI-#1 | — | AGCAGAGTGGCGCAGCGGAAGCGTGCTGGGCCCATAACCC | — | idem MUSTRMI-#1 | 524 |
| HUMTRMI-#2 | — | AACCCAGAGGTCGATGGATCGAAACATCCTCTGCTACCA | — | | 525 |
| HUMTRN | — | CAATCGGTTAGCGCGTTCGGCTGTTAACCGAAAGGTTGGT | — | | 526 |
| HUMTRS | — | TCTAGCGACAGAGTGGTTCAATTCCACCTTTCGGGCGCCA | — | | 527 |
| HUMTRV1A | — | ACGCGAAAGGTCCCCGGTTCGAAACCGGGCGGAAACACCA | — | | 528 |
| mmu-let-7g-prec | mmu-let-7g | CTGAGGTAGTAGTTTGTACAGTTTGAGGGTTCTATGATACC | yes | | 529 |
| mmu-let-7i-prec | mmu-let-7i | GCTGAGGTAGTAGTTTGTGCTGTTGGTCGGGTTGTGACAT | yes | idem hsa-let-7d-v2-prec-#2 | 530 |
| mmu-miR-001b-prec | mmu-miR-001b | ATTCAGTGCTATGGAATGTAAAGAAGTATGTATTTTGGGT | yes | | 531 |
| mmu-miR-001d-prec | mmu-miR-001d | CTGCTAAGCTATGGAATGTAAAGAAGTATGTATTTCAGGC | yes | | 532 |
| mmu-miR-009-prec-#1 | mmu-miR-009 | ATCTTTGGTTATCTAGCTGTATGAGTGTATTGGTCTTCAT | yes | | 533 |
| mmu-miR-009-prec-#2 | mmu-miR-009- | GAGTGTATTGGTCTTCATAAAGCTAGATAACCGAAAGTAA | yes | idem hsa-miR-009-2-#2 | 534 |
| mmu-miR-010b-prec | mmu-miR-010b | TACCCTGTAGAACCGAATTTGTGTGGTACCCACATAGTCA | yes | | 535 |

TABLE 8-continued

Oligonucleotides used for the miRNA microarray chip and correspondence with specific human and mouse microRNAs.

| Oligonucleotide_name | Corresponding miRNA | Oligonucleotide sequence | Covers active site? | Notes | SEQ ID NO. |
|---|---|---|---|---|---|
| mmu-miR-023b-prec | mmu-miR-023b | TTGAGATTAAAATCACATTGCCAGGGATTACCACGCAACC | yes | | 536 |
| mmu-miR-027b-prec | mmu-miR-027b | TTGGTTTCCGCTTTGTTCACAGTGGCTAAGTTCTGCACCT | yes | | 537 |
| mmu-miR-029b-prec | mmu-miR-029b | TAAATAGTGATTGTCTAGCACCATTTGAAATCAGTGTTCT | yes | | 538 |
| mmu-miR-030b-prec | mmu-miR-030b | TGTAAACATCCTACACTCAGCTGTCATACATGCGTTGGCT | yes | | 539 |
| mmu-miR-030e-prec | mmu-miR-030e | TGTAAACATCCTTGACTGGAAGCTGTAAGGTGTTGAGAGG | yes | | 540 |
| mmu-miR-099a-prec | mmu-miR-099a | CATAAACCCGTAGATCCGATCTTGTGGTGAAGTGGACCGC | yes | | 541 |
| mmu-miR-099b-prec-#1 | mmu-miR-099b | GCCTTCGCCGCACACAAGCTCGTGTCTGTGGGTCCGTGTC | no | idem hsa-miR-099b-prec-19-#1 | 542 |
| mmu-miR-099b-prec-#2 | mmu-miR-099b | CACCCGTAGAACCGACCTTGCGGGGCCTTCGCCGCACACA | yes | idem hsa-miR-099b-prec-19-#2 | 543 |
| mmu-miR-100-prec | mmu-miR-100 | TGCCACAAACCCGTAGATCCGAACTTGTGCTGATTCTGCA | yes | | 544 |
| mmu-miR-101-prec | mmu-miR-101 | GCTGTCCATTCTAAAGGTACAGTACTGTGATAACTGAAGG | yes | | 545 |
| mmu-miR-122a-prec-#1 | mmu-miR-122a | GTGTCCAAACCATCAAACGCCATTATCACACTAAATAGCT | no | | 546 |
| mmu-miR-122a-prec-#2 | mmu-miR-122a | GCTGTGGAGTGTGACAATGGTGTTTGTGTCCAAACCATCA | yes | | 547 |
| mmu-miR-123-prec-#1 | mmu-miR-123 | CATTATTACTTTTGGTACGGCTGTGAGTAATAATGCGGTCG | yes | | 548 |
| mmu-miR-123-prec-#2 | mmu-miR-123 | GACACTTCAAACTCGTACCGTGAGTAATAATGCGGGTCA | yes | | 549 |
| mmu-miR-124a-prec | mmu-miR-124a | TAATGTCTATACAATTAAGGCACGCGGTGAATGCCAAGAG | yes | | 550 |
| mmu-miR-125a-prec | mmu-miR-125a | TCCCTGAGACCCTTTAACCTGTGAGGACGTCAGGGTCAC | yes | | 551 |
| mmu-miR-125b-prec-#1 | mmu-miR-125b | GCCTAGTCCCTGAGACCCTAACTTGTGAGGTATTTTAGTA | yes | | 552 |
| mmu-miR-125b-prec-#2 | mmu-miR-125b | ATTTTAGTAACATCACAAGTCAGGTTCTTGGGACCTAGGC | no | | 553 |
| mmu-miR-127-prec | mmu-miR-127 | TTCAGAAAGATCATCGGATCCGTCCTGAGCTTGGCTGTCG | yes | | 554 |
| mmu-miR-128-prec-#1 | mmu-miR-128 | AGGTTTACATTTCTCACAGTGAACCGGTTCTCTTTTTCAGC | yes | | 555 |
| mmu-miR-128-prec-#2 | mmu-miR-128 | TTGGATTCGGGGCCGTAGCACTGTCTGAGAGGTTTACATT | no | idem hsa-miR-128a-prec-#1 | 556 |
| mmu-miR-129b-prec | mmu-miR-129b | CTTTTTGCGGTCTGGGCTTGCTGTGTACATAACTCAATAGCC | yes | | 557 |
| mmu-miR-129-prec | mmu-miR-129 | CTTTTTGCGGTCTGGGCTTGCTGTTTTCTCGACAGTAGTC | yes | | 558 |

TABLE 8-continued

Oligonucleotides used for the miRNA microarray chip and correspondence with specific human and mouse microRNAs.

| Oligonucleotide_name | Corresponding miRNA | Oligonucleotide sequence | Covers active site? | Notes | SEQ ID NO. |
|---|---|---|---|---|---|
| mmu-miR-130-prec | mmu-miR-130 | GTCTAACGTGTACCGAGCAGTGCAATGTTAAAAGGGCATC | yes | | 559 |
| mmu-miR-131-3-prec | mmu-miR-131-3 | AGTGGTGTGGAGTCTTCATAAAGCTAGATAACCGAAAGTA | yes | | 560 |
| mmu-miR-132-prec | mmu-miR-132 | TGTGGGAACCGGAGGTAACAGTCTACAGCATGGTCGCCC | yes | | 561 |
| mmu-miR-133-prec | mmu-miR-133 | ATCGCCCTTCATGGATTTGTCCCCTTCAACCAGTGT | yes | | 562 |
| mmu-miR-134-prec-#1 | mmu-miR-134 | GCACTCTGTTCACCCTGTGGGCACCTAGTCACCAACCCT | no | | 563 |
| mmu-miR-134-prec-#2 | mmu-miR-134 | TGTGTGACTGGTTGACCAGAGAGGGCGTGCACTCTGTTCAC | yes | | 564 |
| mmu-miR-135-prec | mmu-miR-135 | CTATGGCTTTTATTCCTATGTGATTCTATTGCTCGCTCA | yes | | 565 |
| mmu-miR-136-prec | mmu-miR-136 | GAGGACTCCATTTGTTTTGATGATGATTCTTAAGCTCCA | yes | | 566 |
| mmu-miR-137-prec | mmu-miR-137 | GGATTACCTTGTTATTGCTTAAGAATACGCGTAGTCGAGG | yes | idem hsa-miR-137-prec | 567 |
| mmu-miR-138-prec | mmu-miR-138 | AGTCGGTTGTGAATCAGGCCGACGAGCAGCGCATCCTC | yes | idem hsa-miR-138-2-prec | 568 |
| mmu-miR-140s-prec | mmu-miR-140s | TTACGTCATGCTGTTCTACCAGGGTAGAACCACGGACA | yes | | 569 |
| mmu-miR-141-prec | mmu-miR-141 | GAAGTATGAAGCTCCTAACACTGTCTGTAAAGATGGCCC | yes | | 570 |
| mmu-miR-142-prec | mmu-miR-142 | CCCATAAAGTAGAAAGCACTACTAACAGCACTGGAGGTG | yes | idem hsa-miR-142-prec | 571 |
| mmu-miR-143-prec | mmu-miR-143 | TGGTCAGTTGGGAGTCTGAGATGAAGCACTGTAGCTCAGG | yes | | 572 |
| mmu-miR-144-prec | mmu-miR-144 | GTTTGTGATGAGACACTACAGTATAGATGATGTACTAGTC | yes | | 573 |
| mmu-miR-145-prec | mmu-miR-145 | ACGGTCCAGTTTTCCCAGGAATCCCTTGGATGCTAAGATG | yes | | 574 |
| mmu-miR-146-prec | mmu-miR-146 | TGAGAACTGAATTCCATGGGTTATATCAATGTCAGACCTG | yes | | 575 |
| mmu-miR-149-prec | mmu-miR-149 | GCTCTGGCTCCGTGTCTTCACTCCCGTGTTTGTCCGAGGA | yes | | 576 |
| mmu-miR-150-prec | mmu-miR-150 | TGTCTCCCAACCCTTGTACCAGTGCTGTGCCTCAGACCCT | yes | | 577 |
| mmu-miR-151-prec | mmu-miR-151 | TATGTCTCCTCCTACTAGACTGAGGCTCCTTGAGGACA | yes | | 578 |
| mmu-miR-152-prec | mmu-miR-152 | ACTCGGGACTCTGGAGCAGTCAGTGCATGACAGAACTTGGG | yes | idem hsa-miR-152-prec-#1 | 579 |
| mmu-miR-153-prec | mmu-miR-153 | TAATATGAGCCCAGTTGCATAGTGACAAAGTGATCATTG | yes | | 580 |

TABLE 8-continued

Oligonucleotides used for the miRNA microarray chip and correspondence with specific human and mouse microRNAs.

| Oligonucleotide_name | Corresponding miRNA | Oligonucleotide sequence | Covers active site? | Notes | SEQ ID NO. |
|---|---|---|---|---|---|
| mmu-miR-154-prec | mmu-miR-154 | AGATAGGTTATCCGTGTGCCTTCGCTTATTCGTGACGA | yes | | 581 |
| mmu-miR-155-prec | mmu-miR-155 | TTAATGCTAATTGTGATAGGGGTTTTGGCCTCTGACTGAC | yes | | 582 |
| mmu-miR-181-prec | mmu-miR-181 | CCATGGACATTCAACGCTGTCGGTGAGTTTGGGATTCAA | yes | | 583 |
| mmu-miR-182-prec | mmu-miR-182 | TTTGGCAATGGTAGAACTCACACCGGTAAGGTAATGGGAC | yes | | 584 |
| mmu-miR-183-prec-#1 | mmu-miR-183 | AACAGTCTCAGTCAGTGAATTACCGAAGGGCCATAAACAG | no | | 585 |
| mmu-miR-183-prec-#2 | mmu-miR-183 | TATGGCACTGGTAGAATTCACTGTGAACAGTCTCAGTCAG | yes | | 586 |
| mmu-miR-184-prec | mmu-miR-184 | TGTGACTCTAAGTGTTGGACGGAGAACTGATAAGGGTAGG | yes | | 587 |
| mmu-miR-185-prec | mmu-miR-185 | GGGATTGGAGAGAAAGGCAGTTCCTGATGGTCCCCTCCCA | yes | | 588 |
| mmu-miR-186-prec | mmu-miR-186 | CAAAGAATTCTCCTTTTGGGCTTTGTGTCTTTGTTGCAGCCGG | yes | | 589 |
| mmu-miR-187-prec | mmu-miR-187 | GGGCGCTGCTCTGACCCCTCGTGTCTTGTGTTGCAGCCGG | yes | | 590 |
| mmu-miR-188-prec | mmu-miR-188 | TCACATCCCTTGCATGGTGGAGGGTGAGCTCTCTGAAAAC | yes | | 591 |
| mmu-miR-189-prec | mmu-miR-189 | CGGTGCCTACTGAGCTGATATCAGTTCTCATTTCACACAC | yes | | 592 |
| mmu-miR-190-prec | mmu-miR-190 | CTGTGTGATATGTTTGATATATTAGGTTGTTATTAATCC | yes | | 593 |
| mmu-miR-191-prec | mmu-miR-191 | CAACGGAATCCCAAAAGCAGCTGTTGTCTCCAGAGCATTC | yes | idem hsa-miR-191-prec | 594 |
| mmu-miR-192-2/3-prec | mmu-miR-192-2/3 | CTGACCTATGAATTGAACAGCCAGTGCTCTCGTCTCCCCTC | yes | | 595 |
| mmu-miR-193-prec | mmu-miR-193 | TGAGAGTGTCAGTTCAACTGGCCTACAAAGTCCCAGTCCT | yes | | 596 |
| mmu-miR-194-prec | mmu-miR-194 | ATCGGGGTAAACAGCAACTCCATGTGGACTGTGCTCGGAT | yes | | 597 |
| mmu-miR-195-prec | mmu-miR-195 | TAGCAGCACAGAAATATTGGCATGGGGAAGTGAGTCTGCC | yes | | 598 |
| mmu-miR-196-prec | mmu-miR-196 | GTAGGTAGTTTCATGTTGTTGGGCCTGGCTTTCTGAACAC | yes | | 599 |
| mmu-miR-199as-prec | mmu-miR-199as | GAGGCTGGGACATGTACAGTAGTCTGCACATTGGTTAGGC | yes | | 600 |
| mmu-miR-200a-prec-#1 | mmu-miR-200a | TAGTGTCTGATCTCTAATACTGCCTGGTAATGATGACGGC | yes | | 601 |
| mmu-miR-200a-prec-#2 | mmu-miR-200a | CCGTGGCCATCTTACTGGGCAGCATTGGATAGTGTCTGAT | no | | 602 |
| mmu-miR-201-prec | mmu-miR-201 | TACCTTACTCAGTAAGGCATTGTTCTTCTATATTAATAAA | yes | | 603 |

TABLE 8-continued

Oligonucleotides used for the miRNA microarray chip and correspondence with specific human and mouse microRNAs.

| oligonucleotide_name | Corresponding miRNA | Oligonucleotide sequence | Covers active site? | Notes | SEQ ID NO. |
|---|---|---|---|---|---|
| mmu-miR-202-prec | mmu-miR-202 | GATCTGGTCTAAAGAGGTATAGCGCATGGGAAGATGGAGC | yes | | 604 |
| mmu-miR-203-prec-#1 | mmu-miR-203 | GGTCCAGTGGTTCTTGACAGTTCAACAGTTCTGTAGCACA | no | | 605 |
| mmu-miR-203-prec-#2 | mmu-miR-203 | GTAGCACAATTGTGAAATGTTTAGGACCACTAGACCCGGC | yes | | 606 |
| mmu-miR-204-prec | mmu-miR-204 | TTCCCTTTGTCATCCTATGCCTGAGAATATATGAAGGAGG | yes | | 607 |
| mmu-miR-205-prec | mmu-miR-205 | GTCCTTCATTCCACCGGAGTCTGTCTTATGCCAACCAGAT | yes | | 608 |
| mmu-miR-206-prec | mmu-miR-206 | TAGATATCTCAGCACTATGGAATGTAAGGAAGTGTGTGGT | yes | | 609 |
| mmu-miR-207-prec | mmu-miR-207 | GCTGCGGCTTGCCGTTCCCTGGCTCTCCTCCCTCTCCTT | yes | | 610 |
| mmu-miR-212-prec-#1 | mmu-miR-212 | CTTCAGTAACAGTCTCCAGTCACGGCCACCGACGCCTGGC | yes | | 611 |
| mmu-miR-212-prec-#2 | mmu-miR-212 | AGCGCGCCGGCACCTTGGCTCTAGACTGCTTACTGCCCGG | no | | 612 |
| mmu-miR-213-prec | mmu-miR-213 | AACATTCATTGCTGTCGGTGGGTTGAACTGTGTGGACAAG | yes | idem hsa-miR-213-prec-#1 | 613 |
| mmu-miR-214-prec | mmu-miR-214 | TGTACAGCAGGCACAGAGAGGCAGTCACATGACAACCCAG | yes | idem hsa-miR-214-prec | 614 |
| mmu-miR-215-prec | mmu-miR-215 | CAGGAGAATGACCTATGATTTGACAGACCGTCAGCTGTG | yes | | 615 |
| mmu-miR-216-prec-#1 | mmu-miR-216 | GAGATGTCCCTATCATTCCTCACAGTGTCTCTGGGATTA | no | | 616 |
| mmu-miR-216-prec-#2 | mmu-miR-216 | ATGGCTATGAGTTGGTTTAATCTCAGTGGCAACTGTGAG | yes | | 617 |
| mmu-miR-217-prec-#1 | mmu-miR-217 | GCAGATACTGCATCAGGAACTGACTGGATAAGACTTAATC | yes | | 618 |
| mmu-miR-217-prec-#2 | mmu-miR-217 | CCCCATCAGTTCCTAATGCATTGCCTTCAGCATCTAAACA | no | | 619 |
| mmu-miR-218-2-prec-#1 | mmu-miR-218-2 | GGGCTTTCCTTTGTCTTGATCTAACCATGTGTGGAACG | yes | | 620 |
| mmu-miR-218-2-prec-#2 | mmu-miR-218-2 | GTGGTGGAACGATGGAAACGGAACATGTTCTGTCAAGCA | no | | 621 |
| mmu-miR-219-prec-#1 | mmu-miR-219 | TCCTGATTGTCCAAACGGCAATTCTCGAGTCTCTGGCTCCG | yes | | 622 |
| mmu-miR-219-prec-#2 | mmu-miR-219 | CTCTGGCTCCGGCCGAGAGTTGCGTCTGGACCTCCCGAGC | no | | 623 |
| mmu-miR-221-prec-#1 | mmu-miR-221 | CAACAGCTACATTGTCTGCTGGGTTTCAGGCTACCTGAA | yes | idem hsa-miR-221-prec | 624 |
| mmu-miR-221-prec-#2 | mmu-miR-221 | GGCATACAATGTAGATTTCTGTGTTGTTAGGCAACAGCT | no | | 625 |
| mmu-miR-222-prec | mmu-miR-222 | TTGGTAATCAGCAGCTACATCTGGCTACTGGGTCTCTGT | yes | | 626 |

TABLE 8-continued

Oligonucleotides used for the miRNA microarray chip and correspondence with specific human and mouse microRNAs.

| Oligonucleotide_name | Corresponding miRNA | Oligonucleotide sequence | Covers active site? | Notes | SEQ ID NO. |
|---|---|---|---|---|---|
| mmu-miR-223-prec | mmu-miR-223 | AGAGTGTCAGTTTGTCAAATACCCCAAGTGTGGCTCATGC | yes | | 627 |
| mmu-miR-224-precformer175-#1 | mmu-miR-224-(miR-175) | TAAGTCACTAGTGGTTCCGTTTAGTAGATGGTCTGTGCAT | yes | | 628 |
| mmu-miR-224-precformer175-#2 | mmu-miR-224-(miR-175) | TGCATTGTTTCAAAATGTGCCCTAGTGACTACAAAGCCC | no | | 629 |
| MUSTRF | — | TAGACTGAAGATCTAAAGGTCCCTGGTTCGATCCCGGGTT | — | | 630 |
| MUSTRM4 | — | AATCGAAGGTCGTGAGTTCGATCCTCACACGGGGCACCA | — | | 631 |
| MUSTRMI-#1 | — | AGCAGAGTGGCGCAGCGGAAGCGTGCTGGGCCCATAACCC | — | idem HUMTRMI-#1 | 632 |
| MUSTRMI-#2 | — | CCCATAACCCAGAGGTCGATGGATCGAAACCATCCTCTGC | — | | 633 |
| MUSTRNAH | — | TGCCTTGTGGCCCGCAGCAACCTCGGTTCGAATCCGAGTCA | — | | 634 |
| MUSTRP2 | — | GCTCGTTGGTCTAGGGGTATGATTCTCGCTTTGGGTGCGA | — | | 635 |
| MUSTRS | — | AGTGTTTAGCGACAGAGTGGTTCAATTCCACCTTTCGG | — | | 636 |
| MUSTRV1MN | — | TTCCGTAGTGTAGTGGTTATCACGCTCGCCTGACACGCGA | — | | 637 |
| Oligonucleotide primer #1 | — | 5' biotin-AAA-AAA-AAA-AAA-AAA-(biotin)AAA-AAA-AAA-AAA-NNN-NNN-NN 3' | — | | 638 |
| Oligonucleotide primer #2 | — | 5' biotin-(biotin)-AAA-NNN-NNN-NN 3' | — | | 639 |
| Oligonucleotide primer #3 | — | 5' GCC-AGT-GAA-TTG-TAA-TAC-GAC-TCA-CTA-TAG-GGA-GGC-GGN-NNN-NNN-N 3' | — | | 640 | miRNA Microarray Fabrication. 40-mer 5' amine modified C6 oligonucleotides were resuspended in 50 mM phosphate buffer pH 8.0 at 20 mM concentration. The individual oligonucleotide-probe was printed in triplicate on Amersham CodeLink™ activated slides under 45% humidity by GeneMachine OmniGrid™ 100 Microarrayer in 2×2 pin configuration and 20×20 spot configuration of each subarray. The spot diameter was 100 μm and distance from center to center was 200 μm. The printed miRNA microarrays were further chemically covalently-coupled under 70% humidity overnight. The miRNA microarrays were ready for sample hybridization after additional blocking and washing steps.

Target Preparation. Five μg of total RNA were separately added to a reaction mix in a final volume of 12 containing 1 μg of [3'(N)8-(A)12-biotin-(A)12-biotin 5'] oligonucleotide primer. The mixture was incubated for 10 min at 70° C. and chilled on ice. With the mixture remaining on ice, 4 μl of 5× first-strand buffer, 2 ml 0.1 M DTT, 1 μl of 10 mM dNTP mix and 1 μl Superscript™ II RNaseH⁻ reverse transcriptase (200 U/μl) was added to a final volume of 20 μl, and the mixture incubated for 90 min in a 37° C. water bath. After incubation for first strand cDNA synthesis, 3.5 μl of 0.5 M NaOH/50 mM EDTA was added into 20 μl of first strand reaction mix and incubated at 65° C. for 15 min to denature the RNA/DNA hybrids and degrade RNA templates. Then 5 μl of 1 M Tris-HCl, pH 7.6 (Sigma) was added to neutralize the reaction mix and labeled targets were stored in 28.5 μl at −80° C. until chip hybridization.

Array Hybridization. Labeled targets from 5 μg of total RNA were used for hybridization on each KCC/TJU miRNA microarray containing 368 probes in triplicate, corresponding to 245 human and mouse miRNA genes. All probes on these microarrays were 40-mer oligonucleotides spotted by contacting technologies and covalently attached to a polymeric matrix. The microarrays were hybridized in 6×SSPE/30% formamide at 25° C. for 18 hours, washed in 0.75×TNT at 37° C. for 40 min, and processed using direct detection of the biotin-containing transcripts by Streptavidin-Alexa647 conjugate. Processed slides were scanned using a Perkin Elmer ScanArray® XL5K Scanner with the laser set to 635 nm, at Power 80 and PMT 70 setting, and a scan resolution of 10 microns.

Data Analysis. Images were quantified by QuantArray® Software (PerkinElmer). Signal intensities for each spot were calculated by subtracting local background (based on the median intensity of the area surrounding each spot) from total intensities. Raw data were normalized and analyzed using the GeneSpring® software version 6.1.1 (Silicon Genetics, Redwood City, Calif.). GeneSpring generates an average value of the three spot replicates of each miRNA. Following data transformation (to convert any negative value to 0.01), normalization was performed by using a per-chip 50th percentile method that normalizes each chip on its median allowing comparison among chips. Hierarchical clustering for both genes and conditions were then generated by using standard correlation as a measure of similarity. To highlight genes that characterize each tissue, a per-gene on median normalization was performed, which normalizes the expression of every miRNA on its median among samples.

Samples. HeLa cells were purchased from ATCC and grown as recommended. Mouse macrophage cell line RAW264.7 (established from BALB/c mice) was also used (Dumitru, C. D., Ceci, J. D., Tsatsanis, C., Kontoyiannis, D., Stamatakis, K., Lin, J. H., Patriotis, C., Jenkins, N. A., Copeland, N. G., Kollias, G. & Tsichlis, P. N. (2000) *Cell* 103, 1071-83). RNA from 20 normal human tissues, including 18 of adult origin (7 hematopoietic: bone marrow, lymphocytes B, T, and CD5+ cells from 2 individuals, peripheral blood leukocytes derived from three healthy donors, spleen, and thymus; and 11 solid tissues, including brain, breast, ovary, testis, prostate, lung, heart, kidney, liver, skeletal muscle, and placenta) and 2 of fetal origin (fetal liver and fetal brain) were assessed for miRNA expression. Each RNA was labeled and hybridized in duplicate and the average expression was calculated. For all the normal tissues, except lymphocytes B, T and CD5+ cells, total RNA was purchased from Ambion (Austin, Tex.).

Cell Preparation. Mononuclear cells (MNC) from peripheral blood of normal donors were separated by Ficoll-Hypaque density gradients. T cells were purified from these MNC by rosetting with neuraminidase treated SRBC and depletion of contaminant monocytes (Cd11b+), natural killer cells (CD16+) and B lymphocytes (CD19+) were purified using magnetic beads (Dynabeads, Unipath, Milano, Italy) and specific monoclonal antibodies (Becton Dickinson, San Jose, Calif.). Total B cells and CD5+ B cells were prepared from tonsils as described (Dono, M., Zupo, S., Leanza, N., Melioli, G., Fogli, M., Melagrana, A., Chiorazzi, N. & Ferrarini, M. (2000) *J. Immunol.* 164, 5596-604). Briefly, tonsils were obtained from patients in the pediatric age group undergoing routine tonsillectomies, after informed consent. Purified B cells were prepared by rosetting T cells from MNC cells with neuraminidase treated SRBC. In order to obtain CD5+ B cells, purified B cells were incubated with anti CD5 monoclonal antibody followed by goat anti mouse Ig conjugated with magnetic microbeads. CD5+ B cells were positively selected by collecting the cells retained on the magnetic column MS by Mini MACS system (Miltenyi Biotec, Auburn, Calif.). The degree of purification of the cell preparations was higher than 95%, as assessed by flow cytometry.

RNA Extraction and Northern Blots. Total RNA isolation and blots were performed as described (Calin, et al., (2002) *Proc Natl Acad Sc USA*. 99, 15524-15529). After RNA isolation, the washing step with ethanol was not performed, or if performed, the tube walls were rinsed with 75% ethanol without perturbing the RNA pellet (Lagos-Quintana, et al., (2001) *Science* 294, 853-858). For reuse, blots were stripped by boiling in 0.1% aqueous SDS/0.1×SSC for 10 min, and were reprobed. 5S rRNA stained with ethidium bromide served as a loading control.

Quantitative RT-PCR for miRNA Precursors. Quantitative RT-PCR was performed as described (Schmittgen, T. D., Jiang, J., Liu, Q. & Yang, L. (2004) *Nucleic Acid Research* 32, 43-53). Briefly, RNA was reverse transcribed to cDNA with gene-specific primers and Thermoscript, and the relative amount of each miRNA to both U6 RNA and tRNA for initiator methionine was described using the equation $2^{-dC}T$, where $dC_T=(C_{TmiRNA}-C_{TU6\ or\ HUMTMI\ RNA})$. The miRNAs analyzed included miR-15a, miR-16-1, miR-18, miR-20, miR-21, miR-28-2, miR-30d, miR-93-1, miR-105, miR-124a-2, miR-147, miR-216, miR-219, and miR-224. The primers used were as published (Schmittgen, T. D., Jiang, J., Liu, Q. & Yang, L. (2004) *Nucleic Acid Research* 32, 43-53).

Microarray Data Submission. All data were submitted using MIAMExpress to Array Express database and each of the 44 samples described here received an ID number ranging from SAMPLE169150SUB621 to SAMPLE 169193SIUB621.

Results

Hybridization Sensitivity. The hybridization sensitivity of the miRNA microarray was tested using various quantities of total RNA from HeLa cells, starting from 2.5 μg up to 20 μg. The coefficients of correlation between the 5 μg experiment versus the 2.5, 10 and 20 μg experiments, were 0.98, 0.99 and 0.97 respectively. These results clearly show high inter-assay reproducibility, even in the presence of large differences in RNA quantities. In addition, standard deviation calculated for miRNA triplicates was below 10% for the vast majority (>95%) of oligonucleotides. All other experiments described here were performed with 5 µg of total RNA.

Microarray specificity. To test the specificity of the microchip, miRNA expression in human blood leukocytes from three healthy donors and 2 samples of mouse macrophages was analyzed. Samples derived from the same type of tissue presented homogenous patterns of miRNA expression. Furthermore, the pattern of hybridization is different for the two species. To confirm microarray results, the same RNA samples from mouse macrophages and HeLa cells were also analyzed by quantitative RT-PCR for a randomly selected set of 14 miRNAs (Schmittgen, T. D., Jiang, J., Liu, Q. & Yang, L. (2004) *Nucleic Acid Research* 32, 43-53). When we were able to amplify a miRNA precursor for which a correspondent oligonucleotide was present on the chip (hsa-miR-15a, hsa-mir-30d, mmu-miR-219 and mmu-miR-224) the concordance between the two techniques was 100%. Furthermore, it has been reported that expression levels of the active miRNA and the precursor pre-miRNA are different in the same sample (Calin, et al. (2002) *Proc Natl Acad Sc USA.* 99, 15524-15529; Mourelatos, et al. (2002) *Genes Dev* 16, 720-728; Lagos-Quintana, et al. (2002) *Curr Biol* 12, 735-739); in fact, for another 10 miRNAs for which only the oligonucleotide corresponding to the active version was present on the chip, no concordance with quantitative real-time PCR results was observed for the precursor.

The stringency of hybridization was, in several instances, sufficient to distinguish nucleotide mismatches for members of closely related miRNA families and very similar sequences gave distinct expression profiles (for example let-7a-1 and let-7f-2 which are 89% similar in an 88 nucleotide sequence). Therefore, each quantified result represents the specific expression of a single miRNA member and not the combined expression of the entire family. In other cases, when a portion of oligonucleotide was 100% identical for two probes (for example, the 23mer of active molecule present in the 40-mer oligonucleotides for both mir-16 sequences from chromosome 13 and chromosome 3), very similar profiles were observed. Therefore, both sequence similarity and secondary structure influence the cross-hybridization between different molecules on this type of microarray.

miRNA Expression in Normal Human Tissues. To further validate reliability of the microarray, we analyzed a panel of 20 RNAs from human normal tissues, including 18 of adult origin (7 hematopoietic and 11 solid tissues) and 2 of fetal origin (fetal liver and brain). For 15 of them, at least two different RNA samples or two replicates from the same preparation were used (for a detailed list of samples see the above Methods). The results demonstrated that different tissues have distinctive patterns of miRNome expression (defined as the full complement of miRNAs in a cell) with each tissue presenting a specific signature. Using unsupervised hierarchical clustering, the same types of tissue from different individuals clustered together. The hematopoietic tissues presented two distinct clusters, the first one containing CD5+ cells, T lymphocytes, and leukocytes and the second cluster containing bone marrow, fetal liver and B lymphocytes. Of note, RNA of fetal or adult type from the same tissue origin (brain) present different miRNA expression pattern. The results demonstrated that some miRNAs are highly expressed in only one or few tissues, such as miR-1b-2 or miR-99b in brain, and the closely related members miR-133a and miR-133b in skeletal muscle, heart and prostate. The types of normalization of the GeneSpring software (on 50% with or without a per-gene on median normalization) did not influence these results.

To verify these data, Northern blot analysis was performed on total RNA used in the microarray experiments, using four miRNA probes: miR-16-1, miR-26a, miR-99a and miR-223. In each case, the concordance between the two techniques was high: in all instances the highest and the lowest expression levels were concordant. For example high levels of miR-223 expression were found by both techniques in spleen, for miR-16-1 in CD5+ cells, while very low levels were found in brain for both miRNAs. Moreover, in several instances (for example miR-15a), we were able to identify the same pattern of expression for the precursor and the active miR with both microchip and Northern blots.

We also compared the published expression data for cloned human and mouse miRNAs by Northern blot analyses against the microarray results. We found that the concordance with the chip data is high for both pattern and intensity of expression. For example, miR-133 was reported to be strongly expressed only in the skeletal muscle and heart (Sempere, et al. (2003) *Genome Biol.* 5, R13), precisely as was found with the microarray, while miR-125 and mir-128 were reported to be highly expressed in brain (Sempere, et al. (2003) *Genome Biol.* 5, R13), a finding confirmed on the microchip.

Example 11 miRNA Profiling of B-Cell Chronic Lymphocytic Leukemia Samples

Introduction

The miRNome expression in 38 individual human B-cell chronic lymphocytic leukemia (CLL) cell samples was determined utilizing the microchip of Example 10. One normal lymph node sample and 5 samples from healthy donors, including two tonsillar CD5+ B lymphocyte samples and three blood mononuclear cell (MNC) samples, were included for comparison. As hereinafter demonstrated, two distinct clusters of CLL samples associated with the presence or the absence of Zap-70 expression, a predictor of early disease progression. Two miRNA signatures were associated with presence or absence of mutations in the expressed immunoglobulin variable-region genes or with deletions at 13q14 respectively.

Materials and Methods

The following methods were employed in the miRNome expression study.

Tissue Samples and CLL Samples. 47 samples were used for this study, including 41 samples from 38 patients with CLL, and 6 normal samples, including one lymph node, tonsillar CD5+ B cells from two normal donors and blood mononuclear cells from three normal donors. For three cases, two independent samples were collected and processed. CLL samples were obtained after informed consent from patients diagnosed with CLL at the CLL Research Consortium institutions. Briefly, blood was obtained from CLL patients, mononuclear cells were isolated through Ficoll/Hypaque gradient centrifugation (Amersham Pharmacia Biotech) and processed for RNA extraction according to described protocols (M. Lagos-Quintana, R. Rauhut, W. Lendeckel, T. Tuschl, *Science* 294, 853-858 (2001)). For the majority of samples clinical and biological information, such as age at diagnosis, sex, Rai stage, presence/absence of treatment, ZAP-70 expression, $IgV_H$ gene mutation status were available, as provided in Table 9:

TABLE 9

Clinical and biological data for the patients in the two CLL clusters*

| Semnification | Dx Age | Sex | % Zap | VH gene | Mut |
|---|---|---|---|---|---|
| CLL cluster 1 | 50.68 | F | 30.4 | VH4-04 | Neg |
| CLL cluster 1 | 57.4 | F | 50.6 | VH3-33 | Pos |
| CLL cluster 1 | 67.49 | M | 0.5 | VH3-23 | Pos |
| CLL cluster 1 | 59.74 | M | 31.5 | VH3-09 | Pos |
| CLL cluster 1 | 77.49 | F | 0.3 | VH5-51 | Pos |
| CLL cluster 1 | 58.19 | F | 3.6 | VH3-30/3-30.5 | Pos |
| CLL cluster 1 | 43 | M | 41.9 | VH4-30.1/4-31 | Neg |
| CLL cluster 1 | 61.82 | M | 83.2 | VH1-03 | Neg |
| CLL cluster 1 | 48.44 | F | 69.3 | VH1-69 | Neg |
| CLL cluster 2 | 72.59 | M | 2.2 | VH3-72 | Pos |
| CLL cluster 2 | 45.19 | M | 7.3 | VH1-69 | Pos |
| CLL cluster 2 | 56.39 | F | 0.6 | VH3-15 | Pos |
| CLL cluster 2 | 61.85 | F | 0.1 | VH3-30 | Neg |
| CLL cluster 2 | 60.89 | F | 0.1 | VH2-05 | Pos |
| CLL cluster 2 | 62.66 | M | 1 | VH3-07 | Pos |
| CLL cluster 2 | 49.85 | M | 3.6 | VH3-74 | Pos |
| CLL cluster 2 | 70.62 | M | 0.2 | VH3-13 | Pos |
| CLL cluster 2 | 68.02 | F | 0.9 | VH3-30.3 | Pos |
| CLL cluster 2 | 46.84 | M | 62.2 | VH3-30/3-30.5 | Neg |
| CLL cluster 2 | 51.31 | F | 91.9 | VH4-59 | Neg |
| CLL cluster 2 | 52.6 | F | 10.6 | VH3-07 | Pos |
| CLL cluster 2 | 56.04 | F | 0.4 | VH3-72 | Pos |
| CLL cluster 2 | 61.67 | M | 77.9 | VH3-74 | Neg |
| CLL cluster 2 | 62.14 | F | 46 | VH1-02 | Pos |
| CLL cluster 2 | 39.29 | F | 10.1 | VH3-07 | Neg |

*data for ZAP-70 expression were available for 25 patients (25/38, 66%).

Cell Preparation. Mononuclear cells (MNC) from peripheral blood of normal donors were separated by Ficoll-Hypaque density gradients. T cells were purified from these MNC by rosetting with neuraminidase-treated sheep red blood cells (SRBC) and depletion of contaminant monocytes (Cd11b+), natural killer cells (CD 16+) and B lymphocytes (CD 19+) were purified using magnetic beads (Dynabeads, Unipath, Milano, Italy) and specific monoclonal antibodies (Becton Dickinson, San Jose, Calif.). Total B cells and CD5+ B cells were prepared from tonsillar lymphocytes as described (M. Dono et al., *J. Immunol.* 164, 5596-604. (2000)). Briefly, tonsils were obtained from patients in the pediatric age group undergoing routine tonsillectomies, after informed consent. Purified B cells were prepared by rosetting T cells from MNC cells with neuraminidase treated SRBC. In order to obtain CD5+ B cells, purified B cells were incubated with anti CD5 monoclonal antibody followed by goat anti mouse Ig conjugated with magnetic microbeads. CD5+ B cells were positively selected by collecting the cells retained on the magnetic column MS by Mini MACS system (Miltenyi Biotec, Auburn, Calif.). The degree of purification of the cell preparations was higher than 95%, as assessed by flow cytometry.

RNA Extraction and Northern Blots. Total RNA isolation and blots were performed as described (G. A. Calin et al., *Proc Natl Acad Sc USA.* 99, 15524-15529 (2002)). After RNA isolation, the washing step with ethanol was not performed, or if performed, the tube walls were rinsed with 75% ethanol without perturbing the RNA pellet (M. Lagos-Quintana, R. Rauhut, W. Lendeckel, T. Tuschl, *Science* 294, 853-858 (2001)). For reuse, blots were stripped by boiling in 0.1% aqueous SDS/0.1×SSC for 10 minutes, and were reprobed. 5S rRNA stained with ethidium bromide served as a sample loading control.

Microarray Experiments. RNA blot analysis was performed as described in Example 10, utilizing the microchip of Example 10. Briefly, labeled targets from 5 μg of total RNA was used for hybridization on each miRNA microarray chip containing 368 probes in triplicate, corresponding to 245 human and mouse miRNA genes. The microarrays were hybridized in 6×SSPE/30% formamide at 25° C. for 18 hrs, washed in 0.75×TNT at 37° C. for 40 min, and processed using a method of direct detection of the biotin-containing transcripts by Streptavidin-Alexa647 conjugate. Processed slides were scanned using a Perkin Elmer ScanArray® XL5K Scanner, with the laser set to 635 nm, at Power 80 and PMT 70 setting, and a scan resolution of 10 microns.

Data Analysis. Expression profiles were analyzed in duplicate independent experiments starting from the same cell sample. Raw data were normalized and analyzed in GeneSpring® software version 6.1.1 (Silicon Genetics, Redwood City, Calif.). GeneSpring generated an average value of the three spot replicates of each miRNA. Following data transformation (to convert any negative value to 0.01), normalization was performed by using a per-chip on median normalization method and a normalization to specific samples, expressly to the two CD5+ B cell samples, used as common reference for miRNA expression. Hierarchical clustering for both genes and conditions were generated by using standard correlation as a measure of similarity. To identify genes with statistically significant differences between sample groups (i.e. CLL cells and CD5+ B cells, CLL and MNC, CLL samples with or without IgV$_H$ mutations or CLL cases with or without 13q14.3 deletion), a Welch's approximate t-test for two groups (variances not assumed equal) with a p-value cutoff of 0.05 and Benjamini and Hochberg False Discovery Rate as multiple testing correction were performed.

Real Time PCR. Quantitative real-time PCR was performed as described by T. D. Schmittgen, J. Jiang, Q. Liu, L. Yang, *Nucleic Acid Research* 32, 43-53 (2004). Briefly, RNA was reverse transcribed to cDNA with gene-specific primers and Thermoscript and the relative amount of each miRNA to tRNA for initiator methionine was described, using the equation $2^{-dC}T$, where $dC_T = (C_{TmiRNA} - C_{TU6\ or\ HUMTMI\ RNA})$. The set of analyzed miRNAs included miR-15a, miR-16-1, miR-18, miR-20, and miR-21. The primers used were as published (Id).

Western Blotting. Protein lysates were prepared from the leukemia cells of 7 CLL patients and from isolated tonsillar CD5+ B cells. Western blot analysis was performed with a polyclonal Pten antibody (Cell Signaling Technology, Beverly, Mass.) and was normalized using an anti-actin antibody (Sigma, St. Louis, Mo.).

Microarray Data Submission. All data were submitted using MIAMExpress to the Array Express database and each of the 39 CLL samples described here received an ID number ranging from SAMPLE 169194SUB621 to SAMPLE 169234SIUB621.

Results

Comparison of miRNA expression in CLL cells vs. normal CD5+ B cells and normal blood mononuclear cells. Normal CD5+ B cells utilized in this study are considered as normal cell counterparts to CLL B cells. As described in Table 10, two groups of differentially expressed miRNAs, the first composed of 55 genes and the second of 29 genes, had statistically significant differences in expression levels between the various groups (p<0.05 using Welch t-test as described in Materials and Methods, above). Only 6 miRNA are shared between the two lists, confirming the results of Example 10 showing distinct miRNome signatures in CD5+ B cells and leukocytes. When both pre-miRNA and mature miRNA were observed to be dysregulated (such as for miR-123, miR-132 or miR-136), the same type of variation in CLL samples with respect to CD5 or MNC was noted in every case. Also, for some miRNA genomic clusters all members were aberrantly regulated (such as the up-regulated 7q32 group encompassing miR-96- miR182-miR183), while for others only some members were abnormally expressed (such as the 13q31 genomic cluster where two out of six members, miR-19 and miR-92-1, were strongly up-regulated and two, miR-17 and miR-20, were moderately down-regulated). Without wishing to be bound by any theory, the results illustrate the complexity of the patterns of miRNA expression in CLL and indicate the existence of mechanisms regulating individual miRNA genes that map in the same chromosome region. In confirmation of the accuracy of the data, miR-223, reported to be expressed at high levels in granulocytes (M. Lagos-Quintana et al., Curr Biol 12, 735-739 (2002)), was expressed at significantly lower levels in the CLL samples than in the MNC, but at about the same level as that noted for CD5$^+$ B cells (which generally constitute less than a few percent of blood MNC).

TABLE 10

Differentially expressed miRNAs in CLLs versus CD5+ cells or CLLs versus MNC (bold)*

| Oligonucleotide probe | microRNA | Chr location | FRA associated | P-value | Type |
|---|---|---|---|---|---|
| hsa-let-7a-2-precNo1 | let-7a-2 | 11q24.1 | | 0.014 | Down |
| hsa-let-7d-v2-precNo2 | let-7d-v2-prec | 12q14.1 | | 4.29E−04 | Down |
| hsa-let-7f-1-precNo1 | let-7f-1 | 09q22.2 | FRA9D | 3.09E−29 | Down |
| hsa-mir-009-2No1 | miR-9-2 | 5q14 | | 0.013 | up |
| hsa-mir-010a-precNo2 | miR-10a-prec | 17q21.3 | | 0.007 | up |
| hsa-mir-010b-precNo1 | mir-10b | 02q31 | | 1.10E−15 | up |
| hsa-mir-015b-precNo2 | mir-15b-prec | 03q26.1 | | 5.79E−14 | up |
| hsa-mir-017-precNo2 | mir-17-prec | 13q31 | | 0.042 | Down |
| hsa-mir-017-precNo2 | mir-17-prec | 13q31 | | 0.049 | Down |
| hsa-mir-019a-prec | mir-19a | 13q31 | | 5.16E−17 | up |
| hsa-mir-020-prec | mir-20a | 13q31 | | 0.038 | Down |
| hsa-mir-021-prec-17No2 | mir-21-prec | 17q23.2 | FRA17B | 0.044 | up |
| hsa-mir-022-prec | mir-22 | 17p13.3 | | 7.16E−04 | up |
| hsa-mir-023a-prec | mir-23a | 19p13.2 | | 0.011 | Down |
| hsa-mir-024-1-precNo1 | mir-24-1 | 09q22.1 | FRA9D | 0.002 | Down |
| hsa-mir-024-1-precNo2 | mir-24-1-prec | 09q22.1 | FRA9D | 7.35E−20 | up |
| hsa-mir-024-2-prec | mir-24-2 | 19p13.2 | | 5.69E−17 | Down |
| hsa-mir-025-prec | mir-25 | 07q22 | FRA7F | 9.52E−04 | Down |
| hsa-mir-027b-prec | mir-27b | 09q22.1 | FRA9D | 0.046 | Down |
| hsa-mir-029a-2No1 | mir-29a-2 | 07q32 | FRA7H | 0.013 | up |
| hsa-mir-029a-2No2 | mir-29a-2-prec | 07q32 | FRA7H | 0.001 | up |
| hsa-mir-029c-prec | mir-29c | 01q32.2-32.3 | | 0.002 | up |
| hsa-mir-030a-precNo1 | mir-30a | 06q12-13 | | 0.004 | Down |
| hsa-mir-030a-precNo2 | mir-30a-prec | 06q12-13 | | 0.034 | Down |
| hsa-mir-030d-precNo2 | mir-30d-prec | 08q24.2 | | 0.008 | Down |
| hsa-mir-033-prec | mir-33 | 22q13.2 | | 1.56E−18 | up |
| hsa-mir-034precNo1 | mir-34 | 01p36.22 | | 6.00E−06 | up |
| hsa-mir-092-prec-13 = 092-1No1 | mir-92-1 | 13q31 | | 1.70E−12 | up |
| hsa-mir-092-prec-13 = 092-1No2 | mir-92-prec | 13q31 | | 0.021 | Down |
| hsa-mir-092-prec-X = 092-2 | mir-92-2 | Xq26.2 | | 3.38E−04 | Down |
| hsa-mir-092-prec-X = 092-2 | mir-92-2 | Xq26.2 | | 0.042 | Down |
| hsa-mir-096-prec-7No1 | mir-96 | 07q32 | FRA7H | 1.79E−04 | up |
| hsa-mir-099-prec-21 | mir-99 | 21q11.2 | | 0.001 | Down |
| hsa-mir-101-1/2-precNo1 | mir-101 | 01p31.3 | FRA1C | 1.26E−08 | up |
| hsa-mir-101-1/2-precNo2 | mir-101-prec | 01p31.3 | | 0.017 | up |
| hsa-mir-103-prec-5 = 103-1 | mir-103-1 | 05q35.1 | | 0.002 | Down |
| hsa-mir-103-prec-5 = 103-1 | mir-103-1 | 05q35.1 | | 0.007 | Down |
| hsa-mir-105-prec-X.1 = 105-1 | mir-105-1 | Xq28 | FRAXF | 1.55E−05 | up |
| hsa-mir-107-prec-10 | mir-107 | 10q23.31 | | 0.002 | Down |
| hsa-mir-123-precNo1 | mir-123 | 09q34 | | 2.80E−16 | up |
| hsa-mir-123-precNo1 | mir-123 | 09q34 | | 0.021 | Down |
| hsa-mir-123-precNo2 | mir-123-prec | 09q34 | | 0.021 | Down |
| hsa-mir-124a-2-prec | mir-124a-2 | 08q12.2 | | 4.33E−06 | up |
| hsa-mir-128b-precNo1 | mir-128b | 03p22 | | 5.05E−07 | Down |
| hsa-mir-128b-precNo2 | mir-128-prec | 03p22 | | 0.007 | up |
| hsa-mir-130a-precNo2 | mir-130a-prec | 11q12 | | 0.010 | Down |
| hsa-mir-130a-precNo2 | mir-130a-prec | 11q12 | | 0.050 | up |
| hsa-mir-132-precNo1 | mir-132 | 11q12 | | 1.68E−07 | up |
| hsa-mir-132-precNo2 | mir-132-prec | 17p13.3 | | 8.62E−04 | up |
| hsa-mir-134-precNo1 | mir-134 | 14q32 | | 6.01E−08 | up |
| hsa-mir-136-precNo1 | mir-136 | 14q32 | | 0.003 | up |
| hsa-mir-136-precNo2 | mir-136-prec | 14q32 | | 7.44E−04 | up |
| hsa-mir-137-prec | mir-137 | 01p21-22 | | 0.013 | up |
| hsa-mir-138-1-prec | mir-138-1 | 03p21 | | 2.53E−04 | up |
| hsa-mir-140No1 | mir-140 | 16q22.1 | | 2.41E−16 | up |
| hsa-mir-141-precNo1 | mir-141 | 12p13 | | 7.91E−08 | up |
| hsa-mir-141-precNo2 | mir-141-prec | 12p13 | | 1.39E−08 | up |
| hsa-mir-142-prec | mir-142 | 17q23 | FRA17B | 0.004 | Down |
| hsa-mir-145-prec | mir-145 | 05q32-33 | | 0.021 | Down |
| hsa-mir-146-prec | mir-146 | 05q34 | | 1.03E−08 | Down |
| hsa-mir-148-prec | mir-148 | 07p15 | | 3.48E−05 | up |
| hsa-mir-152-precNo1 | mir-152 | 17q21 | | 0.003 | up |
| hsa-mir-152-precNo2 | mir-152-prec | 17q21 | | 3.35E−05 | up |
| hsa-mir-153-1-prec1 | mir-153 | 02q36 | | 0.005 | up |

TABLE 10-continued

Differentially expressed miRNAs in CLLs versus CD5+ cells or CLLs versus MNC (bold)*

| Oligonucleotide probe | microRNA | Chr location | FRA associated | P-value | Type |
|---|---|---|---|---|---|
| hsa-mir-153-1-prec2 | mir-153-prec | 02q36 | | 1.48E–08 | up |
| hsa-mir-154-prec1No1 | mir-154 | 14q32 | | 1.14E–10 | up |
| hsa-mir-155-prec | mir-155 | 21q21 | | 0.029 | up |
| hsa-mir-181b-precNo2 | mir-181b-prec | 01q31.2-q32.1 | | 3.26E–06 | up |
| hsa-mir-181c-precNo2 | mir-181c-prec | 19p13.3 | | 0.003 | up |
| hsa-mir-182-precNo2 | mir-182-prec | 07q32 | FRA7H | 0.001 | up |
| hsa-mir-183-precNo2 | mir-183-prec | 07q32 | FRA7H | 1.26E–23 | up |
| hsa-mir-184-precNo1 | mir-184 | 15q24 | | 0.007 | up |
| hsa-mir-188-prec | mir-188 | Xp11.23-p11.2 | | 6.08E–11 | up |
| hsa-mir-190-prec | mir-190 | 15q21 | FRA15A | 1.48E–20 | up |
| hsa-mir-191-prec | mir-191 | 03p21 | | 9.14E–05 | Down |
| hsa-mir-192-2/3No1 | mir-192 | 11q13 | | 2.00E–07 | Down |
| hsa-mir-193-precNo2 | mir-193-prec | 17q11.2 | | 9.14E–05 | up |
| hsa-mir-194-precNo1 | mir-194 | 01q41 | FRA1H | 0.002 | up |
| hsa-mir-196-2-precNo1 | mir-196-2 | 12q13 | FRA12A | 4.94E–08 | up |
| hsa-mir-196-2-precNo2 | mir-196-2-prec | 12q13 | FRA12A | 0.040 | up |
| hsa-mir-197-prec | mir-197 | 01p13 | | 0.003 | Down |
| hsa-mir-200a-prec | mir-200a | 01p36.3 | | 9.14E–05 | up |
| hsa-mir-204-precNo2 | mir-204-prec | 09q21.1 | | 8.55E–04 | up |
| hsa-mir-206-precNo1 | mir-206 | 06p12 | | 0.003 | Down |
| hsa-mir-210-prec | mir-210 | 11p15 | | 0.009 | Down |
| hsa-mir-212-precNo1 | mir-212 | 17p13.3 | | 0.045 | Down |
| hsa-mir-213-precNo1 | mir-213 | 01q31.3-q32.1 | | 1.47E–33 | Down |
| hsa-mir-217-precNo2 | mir-217 | 02p16 | | 3.85E–09 | up |
| hsa-mir-220-prec | mir-220 | Xq25 | | 2.14E–09 | Down |
| hsa-mir-220-prec | mir-220 | Xq25 | | 3.16E–05 | Down |
| hsa-mir-221-prec | mir-221 | Xp11.3 | | 1.39E–05 | Down |
| hsa-mir-223-prec | mir-223 | Xq12-13.3 | | 9.04E–04 | Down |

*The correlation with fragile sites (FRA) location is as published in Calin et al., Proc Natl Acad Sci USA. 101, 2999-3004 (2004).

As indicated in the CLL vs. CD5+ B cell list of Table 10, several miRNAs located exactly inside fragile sites (miR-183 at FRA7H, miR-190 at FRA15A and miR-24-1 at FRA9D) and miR-213. The mature miR-213 molecule is expressed at lower levels in all the CLL samples, and the precursor miR-213 is reduced in expression in 62.5% of the samples. miR-16-1, at 13q14.3, which we previously reported to be down-regulated in the majority of CLL cases by microarray analysis (G. A. Calin et al., Proc Natl Acad Sc USA. 99, 15524-15529 (2002), was expressed at low levels in 45% of CLL samples. An identical mature miR-16 exists on chromosome 3; because the 40-mer oligonucleotide for both miR-16 sequences from chromosome 13 (miR-16-1) and chromosome 3 (miR-16-2) exhibit the same 23-mer mature sequence, very similar profiles were observed. However, since we observed very low levels of miR-16-2 expression in CLL samples by Northern blot, the expression observed is mainly contributed by miR-16-1. The other miRNA of 13q14.3, miR-15a, was expressed at low levels in ~25% of CLL cases. Overall, these data demonstrate that CLL is a malignancy with extensive alterations of miRNA expression.

Validation of the microarray data was supplied for four miRNAs by Northern blot analyses: miR-16-1, located within the region of deletion at 13q14.3, miR-26a, on chromosome 3 in a region not involved in the pathogeneses of CLL, and miR-206 and miR-223 that are down-regulated (see above) in the majority of samples. For all four miRNAs, the Northern blot analyses confirmed the data obtained using the microarray. We also performed real-time PCR to measure expression levels of precursor molecules for five genes (miR-15a, miR-16-1, miR-18, miR-21, and miR-30d) and we found results concordant with the chip data.

Figure 3:
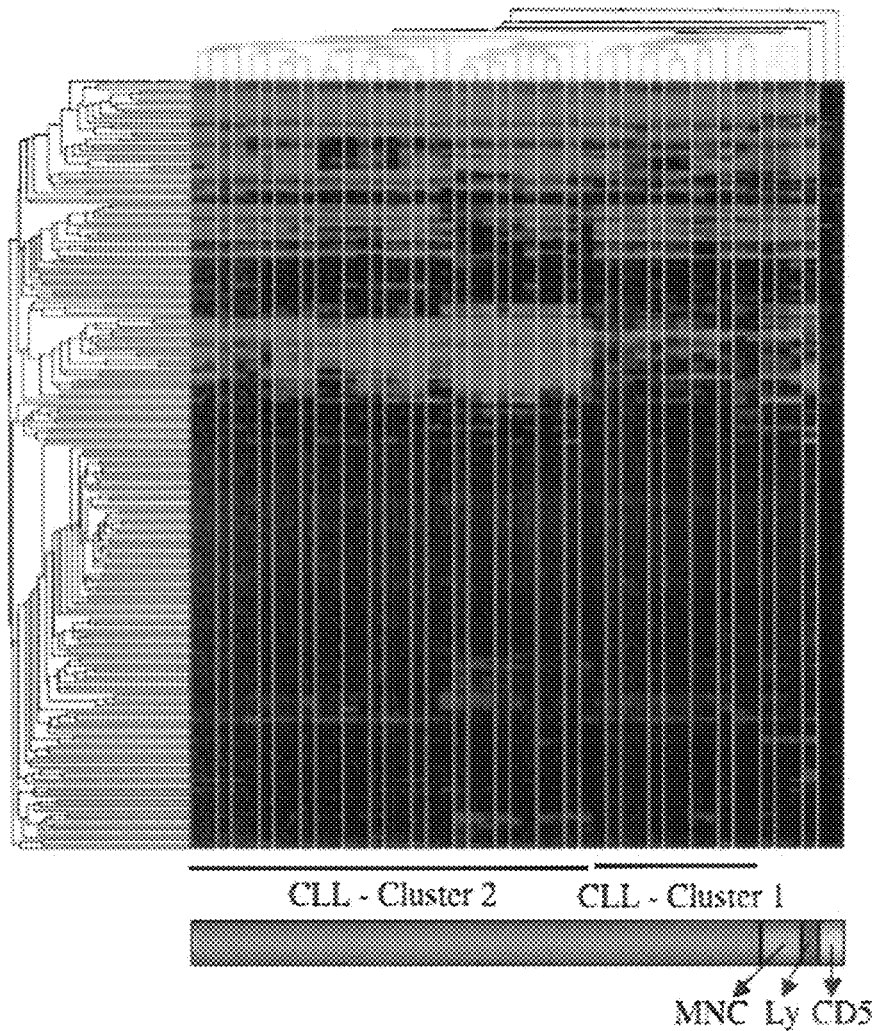
FIG. 3 shows an miRNome expression analysis of 38 individual CLL samples. The main miR-associated CLL clusters are presented. The control samples are: MNC, mononuclear cells; Ly, Diffuse large B cell lymphoma; CD5, selected CD5+B lymphocytes.
Figure 4:
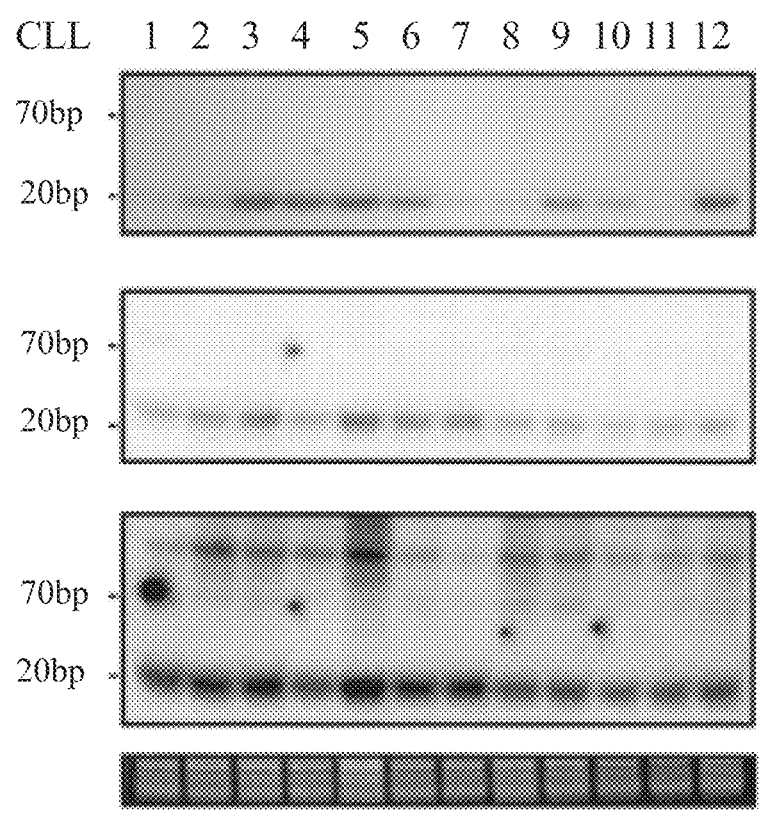
FIG. 4 is an image of a Northern blot analysis of the expression of miR-16a (upper panel), miR-26a (middle panel), and miR-99a (lower panel) in 12 B-CLL samples. Below the three blots is an image of an ethidium bromide-stained gel indicating the 5S RNA lane loading control. miR-16a expression levels varied in these B-CLL cases, and were either low or absent in several of the samples tested. However, the expression levels of miR-26a and miR-99a, both regions not involved in B-CLL, were relatively constant in the tested samples.

Unsupervised hierarchical clustering generated two clearly distinguishable miRNA signatures within the set of CLL samples, one closer to the miRNA expression profile observed in human leukocytes and the other clearly different (FIG. 3). A list of the microRNAs differentially expressed between the two main CLL clusters is given in Table 11. The name of each miRNA is as in the miRNA Registry. The disregulation of either active molecule or precursor is specified in the name. The location in minimally deleted or minimally amplified or breakpoint regions or in fragile sites is presented. The top 25 differentially expressed miRNA in these two signatures (at p<0.001) include genes known or suggested to be involved in cancer. The precursor of miR-155 is over-expressed in the majority of childhood Burkitt's lymphoma (M. Metzler, M. Wilda, K. Busch, S. Viehmann, A. Borkhardt, Genes Chromosomes Cancer. 39, 167-9. (2004)), miR-21 is located at the fragile site FRA17B (G. A. Calin et al., Proc Natl Acad Sci USA. 101, 2999-3004. (2004)), miR-26a is at 3p21.3, a region frequently deleted region in epithelial cancers, while miR-92-1 and miR-17 are at 13q32, a region amplified in follicular lymphoma (Id.).

TABLE 11 microRNAs differentially expressed between the two main CLL clusters*.

| Oligonucleotide | miRNA | Chr location | P-value | Cancer-associated genomic regions |
|---|---|---|---|---|
| hsa-miR-017-precNo2 | miR-17-prec | 13q31 | 0.00000000 | Amp - Folicular Ly/Del - HCC |
| hsa-miR-020-prec | miR-20 | 13q31 | 0.00000000 | Amp - Folicular Ly/Del - HCC |
| hsa-miR-103-2-prec | miR-103-2 | 20p13 | 0.00000001 | |

TABLE 11-continued microRNAs differentially expressed between the two main CLL clusters*.

| Oligonucleotide | miRNA | Chr location | P-value | Cancer-associated genomic regions |
|---|---|---|---|---|
| hsa-miR-030d-precNo2 | miR-30d-prec | 08q24.2 | 0.00000002 | |
| hsa-miR-106-prec-X | miR-106 | Xq26.2 | 0.00000006 | Del - advanced ovarian ca. |
| hsa-miR-026b-prec | miR-26b | 02q35 | 0.00000006 | |
| hsa-miR-103-prec-5 = 103-1 | miR-103-1 | 05q35.1 | 0.00000006 | |
| hsa-miR-025-prec | miR-25 | 07q22 | 0.00000007 | FRA7F |
| hsa-miR-030a-precNo1 | miR-30a | 06q12-13 | 0.00000008 | |
| hsa-miR-021-prec-17No1 | miR-21 | 17q23.2 | 0.00000008 | Amp - Neuroblastoma; FRA17B |
| hsa-miR-107-prec-10 | miR-107 | 10q23.31 | 0.00000008 | |
| hsa-miR-092-prec-13 = 092-1No2 | miR-92-1-prec | 13q31 | 0.00000024 | Amp - Follicular Ly. |
| hsa-miR-027a-prec | miR-27a | 19p13.2 | 0.00000024 | |
| hsa-miR-023a-prec | miR-23a | 19p13.2 | 0.00000032 | |
| hsa-miR-092-prec-X = 092-2 | miR-92-2 | Xq26.2 | 0.00000040 | Del - Advanced Ovarian ca. |
| hsa-miR-030b-precNo1 | miR-30b | 08q24.2 | 0.000004 | |
| hsa-miR-026a-precNo1 | miR-26a | 03p21 | 0.000009 | Del - Epithelial malignancies |
| hsa-miR-093-prec-7.1 = 093-1 | miR-93-1 | 07q22 | 0.000009 | Amp - Folicular Ly/Del - HCC; FRA7F |
| hsa-miR-194-precNo1 | miR-194 | 01q41 | 0.000015 | FRA1H |
| hsa-miR-155-prec | miR-155 | 21q21 | 0.000028 | Amp - Colon ca; Childhood Burkit Ly |
| hsa-miR-153-2-prec | miR-153-2 | 07q36 | 0.000028 | t(7; 12)(q36; p13) - Acute Myeloid Leukemia |
| hsa-miR-193-precNo2 | miR-193-prec | 17q11.2 | 0.000044 | Del - Ovarian ca. |
| hsa-miR-130a-precNo1 | miR-130a | 11q12 | 0.0001 | |
| hsa-miR-023b-prec | miR-23b | 09q22.1 | 0.0001 | Del - Urothelial Ca.; FRA9D |
| hsa-miR-030c-prec | miR-30c | 06q13 | 0.0001 | |
| hsa-miR-139-prec | miR-139 | 11q13 | 0.0001 | |
| hsa-miR-144-precNo2 | miR-144-prec | 17q11.2 | 0.0001 | Amp - Primary Breast ca. |
| hsa-miR-29b-2 = 102prec7.1 = 7.2 | miR-29b-2 | 07q32 | 0.0002 | Del - Prostate ca agressiveness; FRA7H |
| hsa-miR-125a-precNo2 | miR-125a-prec | 19q13.4 | 0.0002 | |
| hsa-miR-224-prec | miR-224 | Xq28 | 0.0002 | |
| hsa-miR-211-precNo1 | miR-211 | Xp11.3 | 0.0002 | Del - Malignant Mesothelioma. |
| hsa-miR-221-prec | miR-221 | Xp11.3 | 0.0002 | |
| hsa-miR-191-prec | miR-191 | 03p21 | 0.0002 | |
| hsa-miR-018-prec | miR-18 | 13q31 | 0.0003 | Amp - Follicular Lymphoma |
| hsa-miR-203-precNo2 | miR-203-prec | 14q32.33 | 0.0004 | Del - Nasopharyngeal ca. |
| hsa-miR-217-precNo2 | miR-217-prec | 02p16 | 0.0004 | |
| hsa-miR-204-precNo2 | miR-204-prec | 09q21.1 | 0.0004 | |
| hsa-miR-199a-1-prec | miR-199a-1 | 19p13.2 | 0.0005 | |
| hsa-miR-128b-precNo1 | miR-128b | 03p22 | 0.0005 | |
| hsa-miR-102-prec-1 | miR-102 | 01q32.2-32.3 | 0.0005 | Del - Prostate ca agressiveness |
| hsa-miR-140No2 | miR-140-prec | 16q22.1 | 0.0006 | |
| hsa-miR-199a-2-prec | miR-199a-2 | 01q23.3 | 0.0007 | |
| hsa-miR-010b-precNo2 | miR-10b-prec | 02q31 | 0.0008 | |
| hsa-miR-029a-2No1 | miR-29a-2 | 07q32 | 0.0008 | Del - Prostate ca agressiveness; FRA7H |
| hsa-miR-125a-precNo1 | miR-125a | 19q13.4 | 0.0010 | |
| hsa-miR-204-precNo1 | miR-204 | 09q21.1 | 0.0011 | |
| hsa-miR-181a-precNo1 | miR-181a | 09q33.1-34.13 | 0.0014 | Del - Bladder ca |
| hsa-miR-188-prec | miR-188 | Xp11.23-p11.2 | 0.0014 | |
| hsa-miR-200a-prec | miR-200a | 01p36.3 | 0.0014 | |
| hsa-miR-024-2-prec | miR-24-2 | 19p13.2 | 0.0014 | |
| hsa-miR-134-precNo2 | miR-134-prec | 14q32 | 0.0016 | Del - Nasopharyngeal ca. |
| hsa-miR-010a-precNo2 | miR-10a-prec | 17q21.3 | 0.0018 | |
| hsa-miR-029c-prec | miR-29c | 01q32.2-32.3 | 0.0021 | |
| hsa-miR-010a-precNo1 | miR-10a | 17q21.3 | 0.0022 | |
| hsa-let-7d-v2-precNo1 | let-7d-v2 | 12q14.1 | 0.0022 | Del - Urothelial carc; FRA9D |
| hsa-miR-205-prec | miR-205 | 01q32.2 | 0.0023 | |
| hsa-miR-129-precNo1 | miR-129 | 07q32 | 0.0023 | Del - Prostate ca agressiveness |
| hsa-miR-032-precNo2 | miR-32-prec | 09q31.2 | 0.0026 | Del - Lung ca.; FRA9E |
| hsa-miR-187-precNo2 | miR-187-prec | 18q12.1 | 0.0035 | |
| hsa-miR-125b-2-precNo1 | miR-125b-2 | 21q11.2 | 0.0036 | Del - Lung ca.(MA17) |
| hsa-miR-181c-precNo1 | miR-181c | 19p13.3 | 0.0036 | |
| hsa-miR-132-precNo2 | miR-132-prec | 17p13.3 | 0.0036 | Del - HCC |
| hsa-miR-215-precNo1 | miR-215 | 01q41 | 0.0036 | FRA1H |
| hsa-miR-136-precNo1 | miR-136 | 14q32 | 0.0036 | Del - Nasopharyngeal ca. |
| hsa-miR-030a-precNo2 | miR-30a-prec | 06q12-13 | 0.0040 | |
| hsa-miR-100-1/2-prec | miR-100 | 11q24.1 | 0.0040 | Del - Ovarian Ca.; FRA11B |
| hsa-miR-218-2-precNo1 | miR-218-2 | 05q35.1 | 0.0040 | |
| hsa-miR-193-precNo1 | miR-193 | 17q11.2 | 0.0052 | Del - Ovarian ca. |
| hsa-miR-027b-prec | miR-27b | 09q22.1 | 0.0058 | Del - Bladder ca; FRA9D |
| hsa-miR-220-prec | miR-220 | Xq25 | 0.0065 | |
| hsa-miR-024-1-precNo1 | miR-24-1 | 09q22.1 | 0.0065 | Del - Urothelial ca. |
| hsa-miR-019a-prec | miR-19a | 13q31 | 0.0071 | Amp - Follicular Ly |
| hsa-miR-196-2-precNo1 | miR-196-2 | 12q13 | 0.0082 | FRA12A |
| hsa-miR-022-prec | miR-22 | 17p13.3 | 0.0086 | Del - HCC |
| hsa-miR-183-precNo2 | miR-183-prec | 07q32 | 0.0086 | Del - Prostate ca agressiveness; FRA7H |
| hsa-miR-128a-precNo2 | miR-128a-prec | 02q21 | 0.0105 | Del - Gastric Ca |
| hsa-miR-203-precNo1 | miR-203 | 14q32.33 | 0.0109 | Del - Nasopharyngeal ca. |
| hsa-miR-033b-prec | miR-33b | 17p11.2 | 0.0109 | Amp - Breast ca. |
| hsa-miR-030d-precNo1 | miR-30d | 08q24.2 | 0.0111 | |

TABLE 11-continued microRNAs differentially expressed between the two main CLL clusters*.

| Oligonucleotide | miRNA | Chr location | P-value | Cancer-associated genomic regions |
|---|---|---|---|---|
| hsa-miR-133a-1 | miR-133a-1 | 18q11.1 | 0.0119 | |
| hsa-miR-007-3-precNo2 | miR-7-3-prec | 22q13.3 | 0.0128 | |
| hsa-miR-021-prec-17No2 | miR-21-prec | 17q23.2 | 0.0131 | Amp - Neuroblastoma |
| hsa-miR-208-prec | miR-208 | 14q11.2 | 0.0134 | Del - Malignant Mesothelioma |
| hsa-miR-154-prec1No2 | miR-154-prec | 14q32 | 0.0146 | Del - Nasopharyngeal ca. |
| hsa-miR-141-precNo2 | miR-141-prec | 12p13 | 0.0154 | |
| hsa-miR-024-1-precNo2 | miR-024-1-prec | 09q22.1 | 0.0169 | Del - Urothelial carc; FRA9D |
| hsa-miR-128a-precNo1 | miR-128a | 02q21 | 0.0170 | Del - Gastric Ca |
| hsa-miR-184-precNo2 | miR-184-prec | 15q24 | 0.0219 | |
| hsa-miR-019b-2-prec | miR-19b-2 | 13q31 | 0.0302 | |
| hsa-miR-132-precNo1 | miR-132 | 17p13.3 | 0.0303 | Del - Hepatocellular ca. (HCC) |
| hsa-miR-127-prec | miR-127 | 14q32 | 0.0326 | Del - Nasopharyngeal ca. |
| hsa-miR-202-prec | miR-202 | 10q26.3 | 0.0333 | |
| hsa-let-7g-precNo2 | let-7g-prec | 03p21.3 | 0.0350 | Del - Lung Ca., Breast Ca. |
| hsa-miR-222-precNo1 | miR-222 | Xp11.3 | 0.0351 | |
| hsa-miR-009-1No2 | miR-009-1-prec | 05q14 | 0.0382 | |
| hsa-miR-136-precNo2 | miR-136-prec | 14q32 | 0.0391 | Del - Nasopharyngeal ca. |
| hsa-miR-010b-precNo1 | miR-10b | 02q31 | 0.0403 | |
| hsa-miR-223-prec | miR-223 | Xq12-13.3 | 0.0407 | |

*The location in minimally deleted or minimally amplified or breakpoint regions or in fragile sites is presented.
HCC—Hepatocellular ca.;
AML—acute myeloid leukemia.

The two clusters may be distinguished by at least one clinico-biological factor. A high difference in the levels of ZAP-70 characterized the two groups: 66% (%) patients from the first cluster vs. 25% (4/16) patients from the second one have low levels of ZAP-70 (<20%) (P=0.04 at chi test) (Table 9). The mean value of ZAP-70 was 19% (±31% S.D.) vs. 35% (±30% S.D.), respectively or otherwise the two clusters can discriminate between patients who express and who do not express this protein (at levels <20% ZAP-70 is considered as non-expressed) (Table 9). ZAP-70 is a tyrosine kinase, which is a strong predictor of early disease progression, and low levels of expression are proved to be a finding associated with good prognosis (J. A. Orchard et al., Lancet 363, 105-11 (2004)).

The microarray data revealed specific molecular signatures predictive for subsets of CLL that differ in clinical behavior. CLL cases harbor deletions at chromosome 13q14.3 in approximately 50% of cases (F. Bullrich, C. M. Croce, Chronic Lymphoid leukemia. B. D. Chenson, Ed. (Dekker, New York, 2001)). As a single cytogenetic defect, these CLL patients have a relatively good prognosis, compared with patients with leukemia cells harboring complex cytogenetic changes (H. Dohner et al., N Engl J Med. 343, 1910-6. (2000)). It was also shown that deletion at 13q14.3 was associated with the presence of mutated immunoglobulin $V_H$ ($IgV_H$) genes (D. G. Oscier et al., Blood. 100, 1177-84 (2002)), another good prognostic factor. By comparing expression data of CLL samples with or without deletions at 13q14, we found that miR-16-1 was expressed at low levels in leukemias harboring deletions at 13q14 (p=0.03, ANOVA test). We also found that miR-24-2, miR-195, miR-203, miR-220 and miR-221 are expressed at significantly reduced levels, while miR-7-1, miR-19a, miR-136, miR-154, miR-217 and the precursor of miR-218-2 are expressed at significantly higher levels in the samples with 13q14.3 deletions, respectively (Table 12). All these genes are located in different regions of the genome and differ in their nucleotide sequences, excluding the possibility of cross-hybridization. Without wishing to be bound by any theory, these results suggest the existence of functional miRNA networks in which hierarchical regulation may be present, with some miRNA (such as miR-16-1) controlling or influencing the expression of other miRNA

TABLE 12 microRNAs signatures associated with prognosis in B-CLL[1].

| miRNA | Chr. location | P-value | Association | Observation |
|---|---|---|---|---|
| miR-7-1 | 9q21.33 | 0.030 | 13q14 normal | |
| miR-16-1 | 13q14.3 | 0.030 | IGVH mutations negative | |
| | | 0.023 | 13q14 deleted | |
| miR-19a | 13q31 | 0.024 | 13q14 normal | |
| miR-24-2 | 19p13.2 | 0.033 | 13q14 deleted | |
| miR-29c | 1q32.2-32.3 | 0.018 | IGVH mutations positive | cluster miR-29c-miR 102 |
| miR-102 | 1q32.2-32.3 | 0.023 | IGVH mutations positive | cluster miR-29c-miR 102 |
| miR-132 | 17p13.3 | 0.033 | IGVH mutations negative | |
| miR-136 | 14q32 | 0.045 | 13q14 normal | |
| miR-154 | 14q32 | 0.020 | 13q14 normal | |
| miR-186 | 1p31 | 0.038 | IGVH mutations negative | |
| mir-195 | 17p13 | 0.036 | 13q14 deleted | |
| miR-203 | 14q32.33 | 0.026 | 13q14 deleted | |
| miR-217-prec | 2p16 | 0.005 | 13q14 normal | |
| miR-218-2 | 5q35.1 | 0.019 | 13q14 normal | |
| miR-220 | Xq25 | 0.026 | 13q14 deleted | |
| miR-221 | Xp11.3 | 0.021 | 13q14 deleted | |

[1]The name of each miRNA is as in miRNA Registry and the disregulation of either active molecule or precursor is specified in the name.

The expression of mutated $IgV_H$ is a favorable prognostic marker (D. G. Oscier et al., Blood. 100, 1177-84 (2002)). We found a distinct miRNA signature composed of 5 differentially expressed genes (miR-186, miR-132, miR-16-1, miR-102 and miR-29c) that distinguished CLL samples that expressed mutated $IgV_H$ gene from those that expressed unmutated $IgV_H$ genes, indicating that miRNA expression profiles have prognostic significance in CLL. As a confirmation of our results is the observation that the common element between the del 13q14.3-related and the $IgV_H$-related signatures is miR-16-1. This gene is located in the common deleted region 13q14.3 and the presence of this particular deletion is associated with good prognosis. Therefore, miRNAs expand the spectrum of adverse prognostic markers in CLL, such as expression of ZAP-70, unmutated IgV$_H$, CD38, deletion at chromosome 11q23, or loss or mutation of TP53.

Example 12

Identification of miRNA Signature Profiles Associated with Prognostic Factors and Disease Survival in B-Cell Chronic Leukemia Samples Introduction Knowing that the expression profile of miRNome, the full complement of microRNAs in a cell, is different between malignant CLL cells and normal corresponding cells, we asked whether microarray analysis using the miRNACHIP could reveal specific molecular signatures predictive for subsets of CLL that differ in clinical behavior. The miRNome expression in 94 CLL samples was determined utilizing the microchip of Example 10. miRNA expression profiles were analyzed to determine if distinct molecular signatures are associated with the presence or absence of two prognostic markers, ZAP-70 expression and mutation of the IgV$_H$ gene. The microarray data revealed that two specific molecular signatures were associated with the presence or absence of each of these markers. An analysis of expression profiles from Zap-70 positive/IgV$_H$ unmutated (Umut) vs. Zap-70 negative/IgV$_H$ mutated (Mut) CLL samples revealed a unique signature of 17 genes that can distinguish these two subsets. Our results indicate that miRNA expression profiles have prognostic significance in CLL.

Materials and Methods

Patient Samples and Clinical Database. 94 CLL samples were used for this study, which were obtained after informed consent from patients diagnosed with CLL at the CLL Research Consortium institutions (L. Z. Rassenti et al. *N Engl. J. Med.* 351(9):893-901 (2004)). Briefly, blood was obtained from CLL patients and mononuclear cells were isolated through Ficoll/Hypaque gradient centrifugation (Amersham Pharmacia Biotech) and processed for RNA extraction according to described protocols (G. A. Calin et al., *Proc. Natl. Acad. Sc. U.S.A.* 99, 15524-15529 (2002)). For each sample, clinical and biological information, such as sex, age at diagnosis, Rai stage, presence/absence of treatment, time between diagnosis and therapy, ZAP-70 expression, and IgV$_H$ gene mutation status, were available and are described in Table 13.

TABLE 13

Characteristics of patients analyzed with the miRNACHIP.

| Characteristic | Value |
| --- | --- |
| Male sex - no. of patients (%) | 58 (61.7) |
| Age at diagnosis - years | |
| median | 57.3 |
| range | 38.2 |
| Therapy begun | |
| No | |
| No. of patients | 53 |
| Time since diagnosis - months | 87.07 |
| Yes | |
| No. of patients | 41 |
| Time between diagnosis & therapy - months | 40.27 |
| ZAP-70 level | |
| ≤20% | 48 |
| >20% | 46 |

TABLE 13-continued

Characteristics of patients analyzed with the miRNACHIP.

| Characteristic | Value |
| --- | --- |
| IgV$_H$ | |
| Unmutated (≥98% homology) | 57 |
| Mutated (<98% homology) | 37 |

RNA Extraction and Northern Blots. Total RNA isolation and RNA blotting were performed as described (G. A. Calin et al., *Proc Proc. Natl. Acad. Sc. U.S.A.* 99, 15524-15529 (2002)).

Microarray Experiments. Microarray experiments were performed as described in Example 11. Of note, for 76 microRNAs on the miRNACHIP, two specific oligonucleotides were synthesized—one identifying the active 22 nucleotide part of the molecule and the other identifying the 60-110 nucleotide precursor. All probes on these microarrays are 40-mer oligonucleotides spotted by contacting technologies and covalently attached to a polymeric matrix.

Data Analysis. After construction of the expression table with Genespring, data normalization was performed by using Bioconductor package. Analyses were carried out using the PAM package (Prediction Analysis of Microarrays) and SAM (Significance Analysis of Microarrays) software. The data were confirmed by Northern blotting for 4 microRNAs in 20 CLL samples, each. All data were submitted using MIAMExpress to the Array Express database.

Analysis of ZAP-70 and Sequence analysis of expressed IgV$_H$. Analyses were performed as described previously (L. Z. Rassenti et al. *N. Engl. J. Med.* 351(9):893-901 (2004)). Briefly, ZAP-70 expression was assessed by immunoblot analysis and flow cytometry, while the analysis of expressed IgV$_H$ was performed by direct sequencing.

Results

Comparison of miRNA expression in ZAP-70 positive vs. ZAP-70 negative CLL cells. Using 20% as a cutoff for defining ZAP-70 positivity, we constructed two classes that were constituted of 48 ZAP-70-negative and 46 ZAP-70-positive CLL samples, respectively. The analyses carried out using the PAM package identified an expression signature composed of 14 microRNAs (14/190 miRNAs on chip, 7.35%) with a PAM score >±0.02 (Table 14). Using the expression of these microRNAs, it is possible to predict with a low misclassification error (about 0.2 at cross-validation) the type of ZAP-70 expression in a patient's malignant B cells.

Comparison of miRNA expression in IgV$_H$ positive vs. IgV$_H$ negative CLL cells. The expression of a mutated IgV$_H$ gene is a favorable prognostic marker (D. G. Oscier et al., *Blood.* 100, 1177-84 (2002)). ZAP-70 expression is well correlated with the status of the IgV$_H$ gene. Therefore, we asked whether a specific microRNA signature can predict the mutated (Mut) vs. unmutated (Umut) status of this gene. Using the 98% cutoff for homology with germ-line IgV$_H$, we identified two groups of patients composed of 37 Umut 98% homology) and 57 Mut (<98% homology). Based on this analysis, 12 microRNAs can be used to correctly predict the Umut vs. Mut status of the gene with a low error (0.02) (Table 14). All of these genes are included in the previous signature.

Comparison of miRNA expression in Zap-70 positive/IgV$_H$ Umut vs. Zap-70 negative/IgV$_H$ Mut CLL cells. We divided the 94 CLL cases into 4 groups (Zap-70 positive/IgV$_H$ Umut, Zap-70 positive/IgV$_H$ Mut, Zap-70 negative/IgV$_H$ Umut and Zap-70 negative/IgV$_H$ Mut), and have found, using the PAM package, that the same unique signature composed of 17 genes can discriminate between the two main groups of patients, Zap70 positive/IgV$_H$ Umut and Zap-70 negative/IgV$_H$ Mut. In this case, we observed the lowest classification error (0.015 at cross validation). Only one patient was Zap-70 negative and IgV$_H$ Umut, and therefore was not used in the classification. When the remaining three classes were analyzed, the 10 patients belonging to the Zap-70 positive/IgV$_H$ Mut class were always misclassified, which indicates that there are no microRNAs on the miRNACHIP that can compose a different signature. The same unique signature was identified using another algorithm of microarray analysis, SAM, thereby confirming the reproducibility of our results. These results indicate that miRNA expression profiles have prognostic significance in CLL and can be used for diagnosing the disease state of a particular cancer by determining whether or not a given profile is characteristic of a cancer associated with one or more adverse prognostic markers.

TABLE 14

A miRNA signature associated with prediction factors and disease survival in CLL patients.

| Signature component | ZAP-70+ vs. Zap-70− | IgV$_H$ Mut vs. IgV$_H$ Umut | Zap70+/IgV$_H$ Umut vs. Zap70−/IgV$_H$ Mut | Short vs. Long time to initial therapy | Observation |
|---|---|---|---|---|---|
| mir-015a | −0.0728 vs. 0.076 | NA | −0.0372 vs. 0.0485 | NA | cluster 15a/16-1 del CLL, prostate ca. 13q13.4 (G. A. Calin et al., *Proc. Natl. Acad. Sic. USA.* 99, 15524-15529 (2002)) |
| mir-016-1 | −0.1396 vs. 0.1457 | −0.0852 vs. 0.1312 | −0.1444 vs. 0.1886 | NA | del CLL, prostate ca. 13q13.4 (G. A. Calin et al., *Proc. Natl. Acad. Sci. USA.* 99, 15524-15529 (2002)) |
| mir-016-2 | −0.1615 vs. 0.1685 | −0.0969 vs. 0.1493 | −0.1619 vs. 0.2113 | NA | identical 16-1/16-2 |
| mir-023a | −0.0235 vs. 0.0245 | 0.0647 vs. 0.0997 | −0.0748 vs. 0.0977 | 0.0587 vs. −0.019 | cluster 23a/24-2 |
| mir-023b | −0.0658 vs. 0.0686 | −0.0663 vs. 0.1021 | −0.0909 vs. 0.1187 | 0.0643 vs. −0.0208 | cluster 24-1/23b FRA 9D; del Urothelial ca. 9q22. (G. A Calin et al. *Proc. Natl. Acad. Sci. U.S.A.* 101(32): 11755-60 (2004)) |
| mir-024-1 | NA | −0.042 vs. 0.0648 | −0.0427 vs. 0.0558 | NA | FRA 9D; del Urothelial ca. 9q22 (ref (G. A. Calin et al. *Proc. Natl. Acad. Sci. U.S.A.* 101(32): 11755-60 (2004)) |
| mir-024-2 | NA | NA | −0.0272 vs. 0.0355 | 0.0696 vs. −0.0225 | |
| mir-029a | 0.0806 vs. −00842 | 0.0887 vs. −0.1367 | 0.1139 vs. −0.1487 | NA | cluster 29a/29b-1 FRA7H; del Prostate ca.7q32 (G. A. Calin et al. *Proc. Natl. Acad. Sci. U.S.A.* 101(32): 11755-60 (2004)) |
| mir-29b-2 | 0.1284 vs. −0.134 | 0.1869 vs. −0.2879 | 0.2065 vs. −0.2696 | NA | 1q32.2-32.3 |
| mir-029c | 0.1579 vs. −0.1648 | 0.1846 vs. −0.2844 | 0.2174 vs. −0.2839 | −0.0221 vs. 0.0072 | |
| mir-146 | −0.1518 vs. 0.1584 | −0.1167 vs. 0.1798 | −0.1803 vs. 0.2354 | 0.07 vs. −0.0227 | |
| mir-155 | −.0.1015 vs. 0.1059 | −0.0743 vs. 0.1145 | −0.1155 vs. 0.1508 | 0.1409 vs. −0.0456 | amp child Burkitt's lymphoma, colon ca. (M. Metzler et al. *Genes Chromosomes Cancer.* |

TABLE 14-continued

A miRNA signature associated with prediction factors and disease survival in CLL patients.

| Signature component | ZAP-70+ vs. Zap-70- | IgV$_H$ Mut vs. IgV$_H$ Umut | Zap70+/IgV$_H$ Umut vs. Zap70-/IgV$_H$ Mut | Short vs. Long time to initial therapy | Observation |
|---|---|---|---|---|---|
| | | | | | Feb; 39(2): 167-9 (2004)) and (M. Z. Michael et al. *Mol Cancer Res.* 1(12): 882-91 (2003)). |
| mir-181a | −0.0473 vs. 0.0494 | NA | −0.0279 vs. 0.0364 | 0.1862 vs. −0.0603 | Up-regulated in differentiated B ly (C. Z. Chen et al. *Science.* 303(5654): 83-6 (2004)). |
| mir-195 | −0.0679 vs. 0.0708 | NA | −0.053 vs. 0.0692 | NA | |
| mir-221 | −0.0812 vs. 0.0848 | −0.0839 vs. 0.1292 | −0.1157 vs. 0.1511 | 0.0343 vs. −0.0111 | cluster 221/222 |
| mir-222 | NA | NA | −0.022 vs. 0.0288 | 0.0458 vs. −0.0148 | |
| mir-223 | 0.0522 vs. −0.0544 | 0.1036 vs. −0.1596 | 0.1056 vs. −0.1379 | NA | Normally expression restricted to myeloid lineage (C. Z. Chen et al. *Science.* 303(5654): 83-6 (2004)). |

Note:
ZAP-70 negative = ZAP-70 expression ≤20%;
ZAP-70 positive = ZAP-70 expression >20%;
IgV$_H$ unmutated = homology ≥98%;
IgV$_H$ mutated = homology <98%.
The numbers indicate the PAM scores in the two classes (n score and y score).
mir-29b-2 was previously named mir-102.

Figure 5:
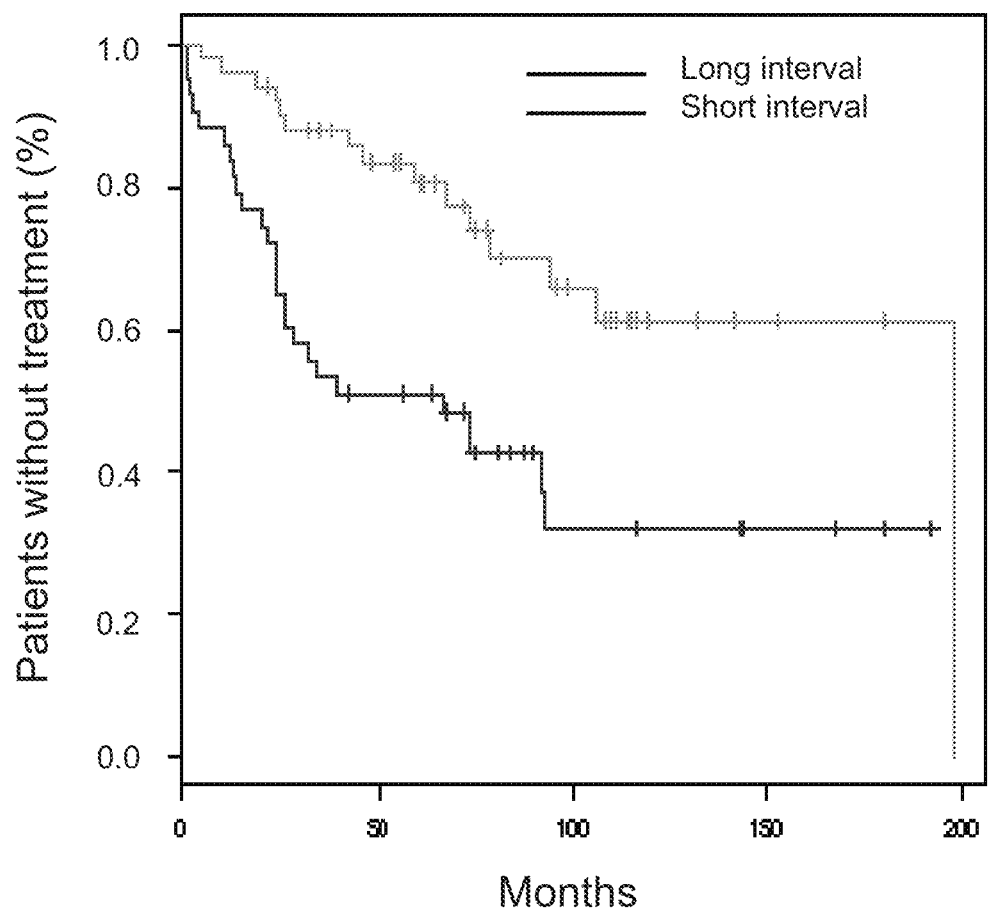
FIG. 5 shows Kaplan-Meier curves depicting the relationship between miRNA expression levels and the time from diagnosis to either the time of initial therapy or the present, if therapy had not commenced. The proportion of untreated patients with CLL is plotted against time since diagnosis. The patients are grouped according to the expression profile generated by 11 microRNA genes.

Association between miRNA expression and time to initial therapy. Treatment of patients according to the National Cancer Institute Working Group criteria (B. D. Cheson et al. *Blood.* 87(12):4990-7 (1996)) was performed when symptomatic or progressive disease developed. Of the 94 patients studied, 41 had initiated therapy (Table 13). We examined the relationship between the expression of 190 microRNA genes and either the time from diagnosis to initial therapy (for patients that have begun treatment) or from the time of diagnosis to the present (for those patients who haven't begun treatment), collectively representing the total group of 94 patients in the study. We found that the expression profile generated by a spectrum of 9 microRNAs, all components of the unique signature, can differentiate between two subsets of patients in the group of 94 tested—one subset with a short interval from diagnosis to initial therapy and the second subset with a significantly longer interval (see Table 14 and FIG. 5). The significance of Kaplan-Meier curves improves if we restrict the analyses to the two main groups of 83 patients (the Zap-70 positive/IgV$_H$ Umut and Zap-70 negative/IgV$_H$ Mut groups) or if we use only the 17 microRNAs from the signature (P decreases from <0.01 to P<0.005 and P<0.001, respectively). All of the microRNAs which can predict the time to initial therapy, with the exception of mir-29c, are overexpressed in the group characterized by a short interval from diagnosis to initial therapy.

Example 13

Identification of Sequence Alterations in miR Genes Associated with CLL

Introduction

Using tumor DNA from CLL samples, we screened more than 700 kb of tumor DNAs (mean 39 patients/miRNA for mean 500 bp/miRNA) for sequence alterations in each of 35 different miR genes. Very rare polymorphisms or tumor specific mutations were identified in 4 of the 39 CLL cases, affecting one of three different miR genes: miR-16-1, miR-27b and miR-206. In two other miR genes, miR-34b and miR-100, polymorphisms were identified in both CLL and normal samples with similar frequencies.

Materials and Methods

Detection of microRNA mutations. Thirty-five miR genes were analyzed for the presence of a mutation, including 16 members of the miR expression signature identified in Example 12 (mir-15a, mir-16-1, mir-23a, mir-23b, mir-24-1, mir-24-2, mir-27a, mir-27b, mir-29b-2, mir-29c, mir-146, mir-155, mir-181a, mir-221, mir-222, mir-223) and 19 other miR genes selected randomly (let-7a2, let-7b, mir-21, mir-30a, mir-30b, mir-30c, mir-30d, mir-30e, mir-32, mir-100, mir-108, mir-125b1, mir-142-5p, mir-142-3p, mir-193, mir-181a, mir-206, mir-213 and mir-224).

The algorithm for screening for miR gene mutations in CLL samples was performed as follows: the genomic region corresponding to each precursor miRNA from either 39 CLL samples or 3 normal mononuclear cell samples from healthy individuals was amplified, including at least 50 base pairs in the 5' and 3' extremities. For the miRNAs located in clusters covering less than one kilobase, the entire corresponding genomic region was amplified and sequenced using the Applied Biosystems Model 377 DNA sequencing system (PE, Applied Biosystems, Foster City, Calif.). When a deviation from the normal sequence was found, a panel of blood DNAs from 95 normal individuals was screened to confirm that the deviation represented a polymorphism. If the sequencing data were normal, an additional panel of 37 CLL cases was screened to determine the frequency of mutations in a total of 76 cancer patients. If additional mutations were found, another set of 65 normal DNAs was screened, to assess the frequency of the specific alteration in a total of 160 normal samples.

In vivo studies of mir-16-1 mutant effects. We constructed two mir-16-1/mir-15a expression vectors—one containing an 832 base pair genomic sequence that included both mir-16-1 and mir-15a, and another nearly identical construct containing the C to T mir-16-1 substitution, as shown in SEQ ID NO. 642—by ligating the relevant open reading frame in a sense orientation into the mammalian expression vector, pSR-GFP-Neo (OligoEngine, Seattle, Wash.). These vectors are referred to as mir-16-1-WT and mir-16-1-MUT, respectively. All sequenced constructs were transfected into 293 cells using Lipofectamine 2000 according to the manufacturer's protocol (Invitrogen, Carlsbad, Calif.). The expression of both mir-16-1-WT and mir-16-1-MUT constructs was assessed by Northern blotting as previously described (G. A. Calin et al., Proc. Natl. Acad. Sc. U.S.A. 99, 15524-15529 (2002)).

Results

Very rare polymorphisms or tumor specific mutations were identified in 4 of the 39 CLL cases, affecting one of three different miR genes: miR-16-1, miR-27b and miR-206 (Tables 15 and 16). In two other miR genes, miR-34b and miR-100, polymorphisms were identified in both CLL and normal samples with similar frequencies (see Tables 15, 16 and Results section below).

TABLE 15

Genetic variations in the genomic sequences of miR genes in CLL patients.

| miRNA | Mutation | CLL (%) | Other allele | Normals | miRNA CHIP | Observation |
|---|---|---|---|---|---|---|
| mir-16-1 | C to T (see SEQ ID NO. 642) | 2/76 (2.6) | Deleted (FISH, LOH) | 0/160 (0) | Reduced expression | Heterozygous in normal cells from both patients; Previous breast cancer; Mother died with CLL; sister died with breast cancer. |
| mir-27b | G to A (see SEQ ID NO. 646) | 1/39 (2.6) | Normal | 0/98 (0) | Normal expression | |
| mir-206 | G to A (see SEQ ID NO. 647) | 1/39 (2.6) | Normal | NA | NA | |
| mir-100 | G to A (see SEQ ID NO. 644) | 17/39 (43.5) | Normal | 2/3 | NA | |

TABLE 16

Sequences showing genetic variations in the miR genes of CLL patients.

| Name | Precursor Sequence (5' to 3') | SEQ ID NO. |
|---|---|---|
| hsa-mir-16-1-normal | GTCAGCAGTGCCTTAGCAGCACGTAAATATTGGCGTT AAGATTCTAAAATTATCTCCAGTATTAACTGTGCTGC TGAAGTAAGGTTGACCATACTCTAC | 641 |
| hsa-mir-16-1-MUT | GTCAGCAGTGCCTTAGCAGCACGTAAATATTGGCGTT AAGATTCTAAAATTATCTCCAGTATTAACTGTGCTGC TGAAGTAAGGTTGACCATACTTTAC | 642 |
| hsa-mir-100 | CCTGTTGCCACAAACCCGTAGATCCGAACTTGTGGTA TTAGTCCGCACAAGCTTGTATCTATAGGTATGTGTCT GTTAGGCAATCTCACGGACC | 643 |
| hsa-mir-100-MUT | CCTGTTGCCACAAACCCGTAGATCCGAACTTGTGGTA TTAGTCCGCACAAGCTTGTATCTATAGGTATGTGTCT GTTAGGCAATCTCACAGACC | 644 |
| hsa-mir-27b-normal | ACCTCTCTAACAAGGTGCAGAGCTTAGCTGATTGGTG AACAGTGATTGGTTTCCGCTTTGTTCACAGTGGCTAA | 645 |

TABLE 16-continued

Sequences showing genetic variations in the miR genes of CLL patients.

| Name | Precursor Sequence (5' to 3') | SEQ ID NO. |
|---|---|---|
| | GTTCTGCACCTGAAGAGAAGGTGAGATGGGGACAGT TAAGTTGGAGCCGCTGGGGCAGAGGCCGTTGCTGAC GGGC | |
| hsa-mir-27b-MUT | ACCTCTCTAACAAGGTGCAGAGCTTAGCTGATTGGTG AACAGTGATTGGTTTCCGCTTTGTTCACAGTGGCTAA GTTCTGCACCTGAAGAGAAGGTGAGATGGGGACAGT TAAGTTGGAGCCGCTGGGGCAGAGGCCGTTGCTGAC AGGC | 646 |
| has-mir-206 | TGCTTCCCGAGGCCACATGCTTCTTTATATCCCCATAT GGATTACTTTGCTATGGAATGTAAGGAAGTGTGTGGT TTCGGCAAGTG | 230 |
| has-mir-206-MUT | TGCTTCCCGAGGCCACATGCTTCTTTATATCCCCATAT GGATTACTTTACTATGGAATGTAAGGAAGTGTGTGGT TTCGGCAAGTG | 647 |
| hsa-mir-34b-normal | GTGCTCGGTTTGTAGGCAGTGTCATTAGCTGATTGTA CTGTGGTGGTTACAATCACTAACTCCACTGCCATCAA AACAAGGCACAGCATCACCGCCG | 648 |
| hsa-mir-34b-MUT | GTGCTCGGTTTGTAGGCAGTGTCATTAGCTGATTGTA CTGTGGTGGTTACAATCACTAACTCCACTGCCATCAA AACAAGGCACAGCATCACCACCG | 650 |

Note:
Each mutation/polymorphism is underlined and indicated in bold in the sequences marked "MUT".

Figure 6:
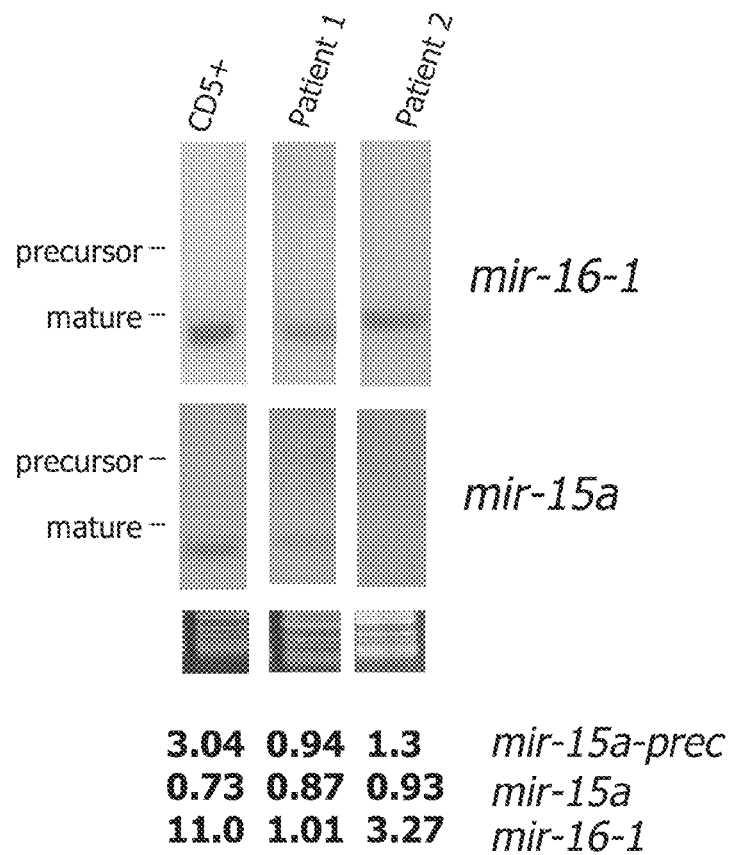
FIG. 6 shows the expression levels of miR-16-1 and miR-15a miRNAs in samples from two patients with a miR-16-1 mutation (see SEQ ID NO. 642) and in CD5+ cell samples from normal patients, both by Northern blot analysis (upper panels) and by miRNACHIP (expression level indicated by numbers below panels).
Figure 7C:
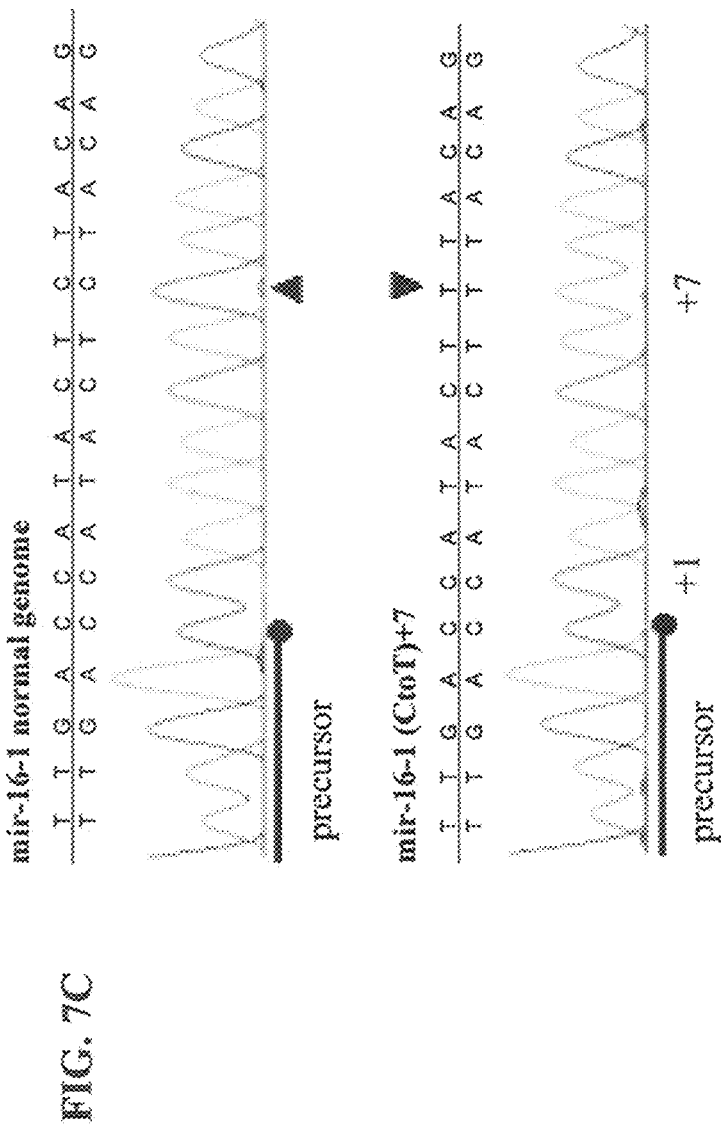
FIG. 7C presents the chromatograms for the genomic regions of samples having either normal miR-16-1/15a (top) or mutated miR-16-1/15a (CtoT)+7 (bottom). The precise position of the precursor (line with period at end) and the location of the mutation (arrowheads) are indicated.
Figure 7D:
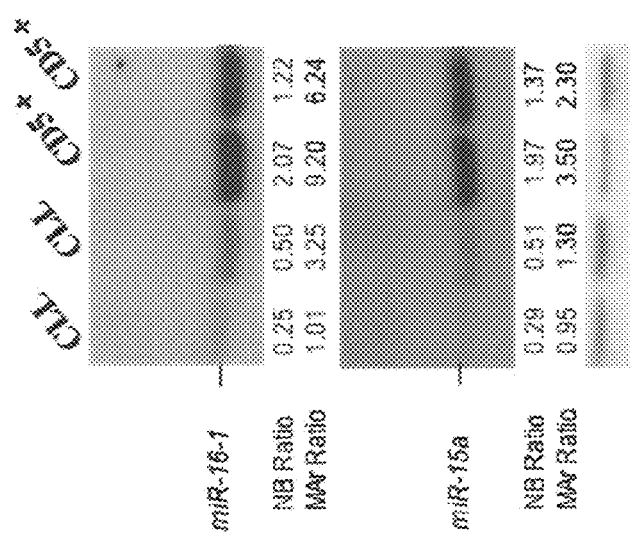
FIG. 7D shows the expression levels by miRNACHIP (MAr) and Northern blot (NB) analysis for miR-16-1 and miR-15a in samples from two normal CD5 pools (CD5+) and from both of the patients carrying the germline (CtoT)+7 mutation (CLL). The Northern blot band intensities were quantified using ImageQuantTL (Nonlinear Dynamics Ltd.). Data are presented as arbitrary units.

The miR-16-1 gene is located at 13q13.4. In 2 CLL patients out of 76 screened (2.6%), we found a homozygous C to T polymorphism (compare SEQ ID NO: 641 to SEQ ID NO: 642; Table 16), which is located in a 3' region of the miR-16-1 precursor (FIG. 7C) with strong conservation in all of the primates analyzed (E. Berezikov et al., Cell 120(1):21-4 (2005)), suggesting that this polymorphism has functional implications. By RT-PCR and Northern blotting we have shown that the precursor miRNA includes the 3' region harboring the base substitution. Both patients have a significant reduction in mir-16-1 expression in comparison with normal CD5+ cells by miRNACHIP and Northern blotting (FIG. 6, FIG. 7D). Further suggesting a pathogenic role, by FISH and LOH, we found a monoallelic deletion at 13q14.3 in the majority of examined cells. This substitution was not found in any of 160 normal control samples (p<0.05 using chi square analysis). In both patients, the normal cells from mucal mucosa were heterozygous for this abnormality. Therefore, this change is a very rare polymorphism or a germ-line mutation. In support of the latter is the fact that one of the patients has two relatives (mother and sister) who have been diagnosed with CLL and breast cancer, respectively. Therefore, this family fulfills the minimal criteria for "familial" CLL, i.e., two or more cases of B-CLL in first-degree living relatives (N. Ishibe et al., Leuk Lymphoma 42(1-2):99-108 (2001)).

Figure 7E:
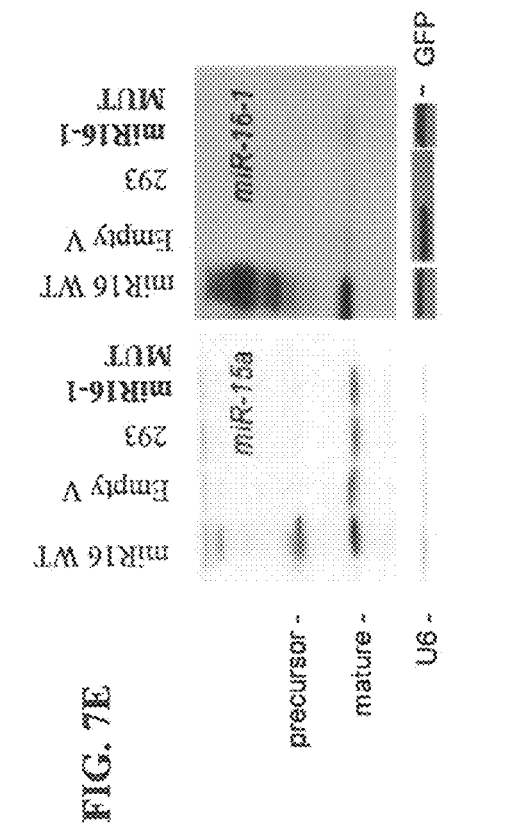
FIG. 7E is a Northern blot showing that the germline mutation in the pri-miR-16-1 is associated with abnormal expression of the active, mature miR-16-1 molecule. Levels of expression were assessed in 293 cells transfected with miR-16-1-WT, miR-16-1-MUT or Empty vector (Empty V), as indicated. Untransfected 293 cells were tested as a control. Normalization for loading was performed with a U6 probe (miR-15a; left panel) and the transfection levels were normalized with anti-GFP signal on cell lysates from the same pellet as that used for Northern blotting (miR-16-1; right panel).

To identify a possible pathogenic effect for this substitution, we inserted both the wild-type sequence of the mir-15a/mir-16-1 cluster, as well as the mutated sequence, into separate expression vectors. We transfected 293 cells, which have a low endogenous expression of this cluster. As a control, 293 cells transfected with an empty vector were tested. The expression levels of both mir-15a and mir-16-1 were significantly reduced in transfectants expressing the mutant construct in comparison to transfectants expressing the wild-type construct (FIG. 7E). The level of expression in transfectants expressing the mutant construct was comparable with the level of endogenous expression in 293 cells (FIG. 7E). Therefore, we conclude that the C to T change in miR-16-1 affects the processing of the pre-miRNA in mature miRNA.

The miR-27b gene is located on chromosome 9. A heterozygous mutation caused by a G to A change in the 3' region of the miR-27b precursor (compare SEQ ID NO: 645 to SEQ ID NO: 646; Table 16), but within the transcript of the 23b-27b-24-1 cluster, was identified in one out of 39 CLL samples. miRCHIP analysis indicated that miR-27b expression was reduced in this sample. This change has not been found in any of the 98 normal individuals screened to date.

The miR-34b gene is located at 11q23. Four CLL patients out of 39 carried two associated polymorphisms, a G to A polymorphism, as shown in SEQ. ID NO. 650, and a T to G polymorphism located in the 3' region of the miR-34b precursor. Both polymorphisms were within the transcript of the mir-34b-mir-34c cluster. One patient was found to be homozygous (presenting by FISH heterozygous abnormal chromosome 11q23), while the other three were heterozygous for the polymorphisms. The same frequency of mutation was found in 35 normal individuals tested.

Example 14

Identification of Abnormalities in the Genomic Sequences of miR Genes Associated with CLL Introduction Abnormally expressed cancer genes are frequently targets for genetic abnormalities, e.g., mutations that can either activate or inactivate their function. Therefore, we screened 42 microRNAs for germline or somatic mutations.

Materials and Methods

Detection of microRNA Gene Mutations.

The genomic region corresponding to each precursor miRNA, including at least 50 additional base pairs (bp) in the 5' and 3' extremities (i.e., flanking sequences), was amplified from 40 CLL samples and normal mononuclear cell samples from 3 healthy individuals. For the miRNAs located in clusters that were less than one kilobase (kb) in length, the entire corresponding genomic region was amplified and sequenced using the Applied Biosystems Model 377 DNA sequencing system (PE, Applied Biosystems, Foster City, Calif.). When a deviation from the normal sequence was found, a panel of blood DNAs from 160 normal individuals, as well as an additional panel of 35 CLL cases (total of 75 leukemia patients), were screened to confirm polymorphisms. All subjects were Caucasian, as indicated by medical records of CLL patients and information obtained during an interview for control patients. For 46 CLL patients, personal and/or familial cancer history was known. Forty-two miR genes were screened for germline or somatic mutations, including 15 members of the specific signature identified in Example 12, or members of the same cluster: miR-15a, miR-16-1, miR-23a, miR-23b, miR-24-1, miR-24-2, miR-27a, miR-27b, miR-29b-2, miR-29c, miR-146, miR-155, miR-221, miR-222, miR-223, as well as 27 other microRNAs that were selected randomly: let-7a2, let-7b, miR-17-3p, miR-17-5p, miR-18, miR-19a, miR-19b-1, miR-20, miR-21, miR-30b, miR-30c-1, miR-30d, miR-30e, miR-32, miR-100, miR-105-1, miR-108, miR-122, miR-125b-1, miR-142-5p, miR-142-3p, miR-193, miR-181a, miR-187, miR-206, miR-224, miR-346.

Results

Germline or somatic mutations were identified in miRNA genomic regions in 11 out of 75 (15%) CLL samples. Five different miRNAs were affected by mutations (5/42 miR genes analyzed, 12%): miR-16-1, miR-27b, miR-206, miR-29b-2 and miR-187. None of these mutations were found in a set of 160 individuals without cancer (p<0.0001) (see Table 17). The positions of the various mutations are shown relative to the position of the miR gene in FIG. 7A. All the abnormalities are localized in regions that are transcribed, as shown by RT-PCR (FIG. 7B). Eight of the 11 (73%) patients with abnormal miRNA sequences have a known personal or familial history of CLL or other hematopoietic or solid tumors (Table 17). Sequences containing the identified miR gene mutations, as well as their corresponding wild-type sequences, are shown in Table 16 for miR-16-1 and miR-27b and in Table 18 for miR-29b-2, miR-187 and miR-206. Two mutations were identified in miR-29b-2 and miR-206 (labeled MUT1 and MUT2, respectively, in Table 18). In addition, a polymorphism was detected in both CLL and normal samples with similar frequencies for three other miR genes: miR-29c, miR-122a and miR-187 (labeled MUT2) (see Tables 17 and 18).

TABLE 17

Genetic variations in the genomic sequences of miR genes in CLL patients.

| miRNA | Location** | CLL | Normals | miRNACHIP expression | a) Observations |
|---|---|---|---|---|---|
| miR-16-1 | Germline; pri-miRNA: CtoT substitution at +7 bp in the 3' flanking | 2/75 | 0/160 | Reduced to 15% and 40% of normal, respectively | Normal allele deleted in CLL cells in both patients (FISH, LOH). For one patient: History of previous breast cancer; mother with CLL (deceased); sister with breast cancer (deceased). |
| miR-27b | Germline; pri-miRNA: G toA substitution at +50bp in 3' flanking sequence | 1/75 | 0/160 | Normal | Mother with throat and lung cancer at age 58. Father with lung cancer at age 57. |
| miR-29b-2 | pri-miRNA: G to A substitution at +212 in 3' flanking sequence | 1/75 | 0/160 | Reduced to 75% | Sister with breast cancer at age 88 (still living). Brother with "some type of blood cancer" at age 70. |
| miR-29b-2 | pri-miRNA: A insertion at +107 in 3' flanking sequence | 3/75 | 0/160 | Reduced to 80% | Both patients have a family history of unspecified cancer. |
| miR-187 | pri-miRNA: T to C substitution at +73 in 3' flanking sequence | 1/75 | 0/160 | NA | Unknown |
| miR-206 | pre-miRNA: G to T substitution at position 49 of precursor | 2/75 | 0/160 | Reduced to 25% | Prostate cancer; mother with esophogeal cancer. Brother with prostate cancer; sister with breast cancer |

TABLE 17-continued

Genetic variations in the genomic sequences of miR genes in CLL patients.

| miRNA | Location** | CLL | Normals | miRNACHIP expression | a) Observations |
|---|---|---|---|---|---|
| miR-206 | Somatic; pri-miRNA: A to T substitution at −116 in 5' flanking sequence | 1/75 | 0/160 | Reduced to 25% (data only for one pt) | Aunt with leukemia (deceased) |
| miR-29c | pri-miRNA: G to A substitution at −31 in 5' flanking sequence | 2/75 | 1/160 | NA | Paternal grandmother with CLL; sister with breast cancer. |
| miR-122a | pre-miRNA: C to T substitution at position 53 of precursor | 1/75 | 2/160 | Reduced to 33% | Paternal uncle with colon cancer. |
| miR-187 | pre-miRNA: G to A substitution at position 34 of precursor | 1/75 | 1/160 | NA | Grandfather with polycythemia vera. Father has a history of cancer but not lymphoma. |

For each CLL patient/normal control, more than 12 kb of genomic DNA was sequenced. In total, ~627 kb of tumor DNA and about 700 kb of normal DNA was screened by direct sequencing. The positions of the mutations are reported with respect to the precursor miRNA molecule.
**When normal corresponding DNA from bucal mucosa was available, the alteration was identified as germline when present or somatic when absent, respectively.
FISH = fluorescence in situ hybridization;
LOH = loss of heterozygosity;
NA = not available.

TABLE 18

Sequences showing genetic variations in the miR genes of CLL patients.

| Name | Precursor Sequence (5' to 3') +/− 5' or 3' flanking genomic sequence | SEQ ID NO. |
|---|---|---|
| hsa-mir-29b-2-normal | CTTCTGGAAGCTGGTTTCACATGGTGGCTTAGATTTTT CCATCTTTGTATCTAGCACCATTTGAAATCAGTGTTTT AGGAGTAAGAATTGCAGCACAGCCAAGGGTGGACTG CAGAGGAACTGCTGCTCATGGAACTGGCTCCTCTCCT CTTGCCACTTGAGTCTGTTCGAGAAGTCCAGGGAAGA ACTTGAAGAGCAAAATACACTCTTGAGTTTGTTGGGT TTTGGGAGAGGTGACAGTAGAGAAGGGGGTTGTGTT TAAAATAAACACAGTGGCTTGAGCAGGGGCAGAGG | 651 |
| hsa-mir-29b-2-MUT1 (G to A substitution at +212 in 3' flanking sequence) | CTTCTGGAAGCTGGTTTCACATGGTGGCTTAGATTTTT CCATCTTTGTATCTAGCACCATTTGAAATCAGTGTTTT AGGAGTAAGAATTGCAGCACAGCCAAGGGTGGACTG CAGAGGAACTGCTGCTCATGGAACTGGCTCCTCTCCT CTTGCCACTTGAGTCTGTTCGAGAAGTCCAGGGAAGA ACTTGAAGAGCAAAATACACTCTTGAGTTTGTTGGGT TTTGGGAGAGGTGACAGTAGAGAAGGGGGTTGTGTT TAAAATAAACACAGTGGCTTGAGCAGGGGCAGAAG | 652 |
| hsa-mir-29b-2-MUT2 (A insertion at +107 in 3' flanking sequence) | CTTCTGGAAGCTGGTTTCACATGGTGGCTTAGATTTTT CCATCTTTGTATCTAGCACCATTTGAAATCAGTGTTTT AGGAGTAAGAATTGCAGCACAGCCAAGGGTGGACTG CAGAGGAACTGCTGCTCATGGAACTGGCTCCTCTCCT CTTGCCACTTGAGTCTGTTCGAGAAGTCCAGGGAAGA AACTTGAAGAGCAAAATACACTCTTGAGTTTGTTGGG TTTTGGGAGAGGTGACAGTAGAGAAGGGGGTTGTGT TTAAAATAAACACAGTGGCTTGAGCAGGGGCAGAGG | 653 |

TABLE 18-continued

Sequences showing genetic variations in the miR genes of CLL patients.

| Name | Precursor Sequence (5' to 3') +/- 5' or 3' flanking genomic sequence | SEQ ID NO. |
|---|---|---|
| hsa-mir-187-normal | GGTCGGGCTCACCATGACACAGTGTGAGACCTCGGG CTACAACACAGGACCCGGGCGCTGCTCTGACCCCTCG TGTCTTGTGTTGCAGCCGGAGGGACGCAGGTCCGCAG CAGAGCCTGCTCCGCTTGTCCTGAGGGACTCGACACA GGGGACTGCACAGAGACCATGGGAAAGTCCAGGCTC | 654 |
| hsa-mir-187-MUT1 (T to C substitution at +73 in 3' flanking sequence) | GGTCGGGCTCACCATGACACAGTGTGAGACCTCGGG CTACAACACAGGACCCGGGCGCTGCTCTGACCCCTCG TGTCTTGTGTTGCAGCCGGAGGGACGCAGGTCCGCAG CAGAGCCTGCTCCGCTTGTCCTGAGGGACTCGACACA GGGGACTGCACAGAGACCATGGGAAAGTCCAGGCCC | 655 |
| hsa-mir-187-MUT2 (G to A substitution at position 34 of precursor) | GGTCGGGCTCACCATGACACAGTGTGAGACTCGAGC TACAACACAGGACCCGGGCGCTGCTCTGACCCCTCG TGTCTTGTGTTGCAGCCGGAGGGACGCAGGTCCGCAG CAGAGCCTGCTCCGCTTGTCCTGAGGGACTCGACACA GGGGACTGCACAGAGACCATGGGAAAGTCCAGGCTC | 656 |
| has-mir-206 | GATTTAGGATGAGTTGAGATCCCAGTGATCTTCTCGC TAAGAGTTTCCTGCCTGGGCAAGGAGGAAAGATGCT ACAAGTGGCCCACTTCTGAGATGCGGGCTGCTTCTGG ATGACACTGCTTCCCGAGGCCACATGCTTCTTTATAT CCCCATATGGATTACTTTGCTATGGAATGTAAGGAAG TGTGTGGTTTCGGCAAGTG | 657 |
| has-mir-206-MUT1 (G to T substitution at position 49 of precursor) | GATTTAGGATGAGTTGAGATCCCAGTGATCTTCTCGC TAAGAGTTTCCTGCCTGGGCAAGGAGGAAAGATGCT ACAAGTGGCCCACTTCTGAGATGCGGGCTGCTTCTGG ATGACACTGCTTCCCGAGGCCACATGCTTCTTTATAT CCCCATATGGATTACTTTTCTATGGAATGTAAGGAAG TGTGTGGTTTCGGCAAGTG | 658 |
| has-mir-206-MUT2 (A to T substitution at -116 in 5' flanking sequence) | GTTTTAGGATGAGTTGAGATCCCAGTGATCTTCTCGC TAAGAGTTTCCTGCCTGGGCAAGGAGGAAAGATGCT ACAAGTGGCCCACTTCTGAGATGCGGGCTGCTTCTGG ATGACACTGCTTCCCGAGGCCACATGCTTCTTTATAT CCCCATATGGATTACTTTTCTATGGAATGTAAGGAAG TGTGTGGTTTCGGCAAGTG | 659 |
| hsa-mir-29c-normal | CGAGGTGCAGACCCTGGGAGCACCACTGGCCCATCT CTTACACAGGCTGACCGATTTCTCCTGGTGTTCAGAG TCTGTTTTTGTCTAGCACCATTTGAAATCGGTTATGAT GTAGGGGGA | 660 |
| hsa-mir-29c-MUT (G to A substitution at -31 in 5' flanking sequence) | CAAGGTGCAGACCCTGGGAGCACCACTGGCCCATCT CTTACACAGGCTGACCGATTTCTCCTGGTGTTCAGAG TCTGTTTTTGTCTAGCACCATTTGAAATCGGTTATGAT GTAGGGGGA | 661 |
| hsa-mir-122a-normal | CCTTAGCAGAGCTGTGGAGTGTGACAATGGTGTTTGT GTCTAAACTATCAAACGCCATTATCACACTAAATAGC TACTGCTAGGC | 662 |
| hsa-mir-122a-MUT (C to T substitution at position 53 of precursor) | CCTTAGCAGAGCTGTGGAGTGTGACAATGGTGTTTGT GTCTAAACTATCAAATGCCATTATCACACTAAATAGC TACTGCTAGGC | 663 |

Note:
The position of each mutation/polymorphism is underlined and indicated in bold in the sequences marked "MUT".

Example 15

A Unique MicroRNA Signature Associated with Prognostic Factors and Disease Progression in Chronic Lymphocytic Leukemia Introduction: In spite of extensive effort, little is known regarding the pathogenic events leading to the initiation and progression of B cell CLL, the most frequent adult leukemia in the Western world. On the contrary, several factors predicting the clinical course have been defined. CLL cells with few or no mutations in the immunoglobulin heavy-chain variable-region gene (IgV$_H$) or with high expression of the 70-kD zeta-associated protein positive (ZAP-70+) have an aggressive course, whereas patients with mutated clones or few ZAP-70+ B cells have an indolent course (Chiorazzi, N., et al., *N Engl. J. Med.* 352:804-815 (2005)). It was also found that genomic aberrations in CLL are important independent predictors of disease progression and survival (Dohner, H., et al., *N Engl. J. Med.* 343(26):1910-1916 (2000)). However, the molecular basis of these associations is largely unknown. Here, we performed genome wide expression profiling with the miRNACHIP in a large series of CLL samples with extensive clinical data to examine whether expression of these noncoding genes is associated with factors predicting the clinical course.

Materials and Methods

Patient samples and clinical database. Samples used for this study are described in detail in Example 12.

RNA extraction, Northern blots and miRNACHIP experiments. Procedures were performed as described (Calin, G. A., et al., *Proc. Natl. Acad. Sci. USA* 101(32):1175-1160 (2004); Liu, C.-G., et al., *Proc. Natl, Acad. Sci. USA* 101(26): 9740-9744 (2004)). Briefly, labeled targets from 5 μg of total RNA was used for hybridization on each miRNACHIP microarray chip containing 368 probes in triplicate, corresponding to 245 human and mouse miRNA genes. Of note, for 76 microRNAs on the miRNACHIP two specific oligos were synthesized one identifying the active 22 nt part of the molecule and the other for the 60-110 nt precursor (Liu, C.-G., et al., *Proc. Natl. Acad. Sci. USA* 101(26): 9740-9744 (2004)).

Data analysis. Raw data were normalized and analyzed in GeneSpring® software version 7.2 (Silicon Genetics, Redwood City, Calif.). Expression data were median centered using both GeneSpring normalization option or Global Median normalization of the Bioconductor package, without any substantial difference. Statistical comparisons were done both using the GeneSpring ANOVA tool and the SAM software (Significance Analysis of Microarray). MiRNA predictors were calculated by using PAM software (Prediction Analysis of Microarrays); the Support Vector Machine tool of GeneSpring was used for the Cross-validation and Test-set prediction. The Kaplan-Meier plot ("survival analysis" of the PAM software) was used to identify an association between miRNA expression and the time elapsing from CLL diagnosis and the beginning of therapy. miRNAs able to best separate the two groups were identified at the same time. All data were submitted using MIAMExpress to the Array Express database (accession numbers to be received upon revision). We validated the microarray data for 4 miRNAs (miR-16-1, miR-26a, miR-206 and miR-223) in 11 CLL samples and normal CD5 cells by solution hybridization detection as presented elsewhere (Calin, G. A., et al., *Proc. Natl. Acad. Sci. USA* 101(32):11755-11760 (2004)). Furthermore, miR-15a and miR-16-1 expression in the patients with germline mutation was confirmed by Northern blot.

Analysis of ZAP-70 and Sequence analysis of expressed $IgV_H$. These experiments were performed as described in Example 12.

Results

Comparison of miRNA expression in Zap-70 positive/$IgV_H$ Umut vs. Zap-70 negative/$IgV_H$ Mut CLL cells. In Example 12, a unique signature that can discriminate between the two main groups of CLL patients (i.e., Zap70 positive/$IgV_H$ Umut and Zap-70 negative/$IgV_H$ Mut), composed of 17 genes, was identified using the PAM package. Using additional algorithms for statistical and prediction analysis (i.e., SAM and GeneSpring) to validate the PAM signature, we found that a signature composed of 13 mature microRNAs could discriminate (at $P<0.01$) between Zap70 positive/$IgV_H$ Umut and Zap-70 negative/$IgV_H$ Mut patients (Tables 19 and 20). Furthermore, the prediction made using Support Vector Machine correctly classified all patients (Table 20). The majority of miRNAs (9 out of 13) were significantly overexpressed in the group with poor prognosis. The 10 patients belonging to the Zap-70 positive and VhMut group were equally assigned to groups good or poor prognosis, suggesting either that there are no microRNAs on the miRNACHIP whose expression can distinguish these two groups, that these two groups are not different with regard to microRNA expression profiles or that the groups are too small to be correctly classified.

We used the Support Vector Machine algorithm also to predict an additional independent set of 50 CLL samples with known ZAP-70 status (Table 21). When the 13 miRNAs of the identified signature were used, the prediction was made correctly in all cases, confirming, thereby confirming our results. Also confirming the microarray specificity, as reported in Liu, C.-G., et al., Proc. Natl. Acad. Sci. USA 101(26): 9740-9744 (2004), the signature did not include very similar members of the same families, such as miR-23a (1 base difference from miR-23b) and miR-15b (four bases difference from miR-15a), while the identical mature miRNAs miR-16-1 and miR-16-2 were both identified, indicating that the chip is able to discriminate between highly similar isoforms.

TABLE 19 miRNA signature associated with prognostic factors (ZAP70 and IgVH mutations) and disease progression in CLL patients*.

| Nr. Crt. | Component | Map | [0002] value | Group 4 expression | Putative targets* | Observation**** |
|---|---|---|---|---|---|---|
| 1 | miR-15a | 13q14.3 | 0.018 | high | NA | cluster 15a/16-1 del CLL & Prostate ca. |
| 2 | miR-195 | 17p13 | 0.017 | high | NA | del HCC |
| 3 | miR-221 | Xp11.3 | 0.010 | high | HECTD2, CDKN1B, NOVA1, ZFPM2, PHF2 | cluster 221/222 |
| 4 | miR-23b | 9q22.1 | 0.009 | high | FNBP1L, WTAP, PDE4B, SATB1, SEMA6D | cluster 24-1/23b FRA 9D; del Urothelial ca. |
| 5 | miR-155 | 21q21 | 0.009 | high | ZNF537, PICALM, RREB1, BDNF, QKI | amp child Burkitt's lymphoma |
| 6 | miR-223 | Xq12-13.3 | 0.007 | low | PTBP2, SYNCRIP, WTAP, FBXW7, QKI | normally expression restricted to myeloid lineage |
| 7 | miR-29a-2 | 7q32 | 0.004 | low | NA | cluster 29a-2/29b-1 FRA7H; del Prostate ca. |
| 8 | miR-24-1 | 9q22.1 | 0.003 | high | TOP1, FLJ45187, RSBN1L, RAP2C, PRPF4B | cluster 24-1/23b FRA 9D; del Urothelial ca. |
| 9 | miR-29b-2 (miR-102) | 1q32.2-32.3 | 0.0007 | low | NA | |
| 10 | miR-146 | 5q34 | 0.0007 | high | NOVA1, NFE2L1, C1orf16, ABL2, ZFYVE1 | |

TABLE 19-continued miRNA signature associated with prognostic factors (ZAP70 and IgVH mutations) and disease progression in CLL patients*.

| Nr. Crt. | Component | Map | [0002] value | Group 4 expression | Putative targets* | Observation**** |
|---|---|---|---|---|---|---|
| 11 | miR-16-1 | 13q14.3 | 0.0004 | high | BCL2, CNOT6L, USP15, PAFAH1B1, ESRRG | cluster 15a/16-1 del CLL, prostate ca. |
| 12 | miR-16-2 | 3q26.1 | 0.0003 | high | see miR-16-1 | identical miR-16-1 |
| 13 | miR-29c | 1q32.2-32.3 | 0.0002 | low | NA | |

Note:
*All the members of the signature are mature miRNAs;
**Group 4 includes patients with IgVh mutated and Zap-70 negative, both predictors of poor prognosis.
***top five predictions using TargetScan (Lewis, B. P., et al., Cell 120: 15-20 (2005)) were included.
NA—not available; for specific gene names - see the NCBI site.
****FRA = fragile site; del = deletion; HCC = hepatocellular carcinoma; ca. = carcinoma.

TABLE 20

List of miRNAs associated with prognostic factors and disease progression in CLL patients selected by Prediction Analysis of Microarrays (PAM) and ANOVA analysis (GeneSpring)*.

| Nr. crt. | PAM signature | n− score | y+ score | map | GeneSpring signature | Anova p-value | map |
|---|---|---|---|---|---|---|---|
| 1 | mir-222 | −0.022 | 0.0288 | Xp11.2 | mir-34-prec | 0.048 | 1p36.22 |
| 2 | mir-24-2 | −0.0272 | 0.0355 | 19p13.12 | mir-192-2/3-prec | 0.0457 | 11q13 |
| 3 | mir-181a | −0.0279 | 0.0364 | 1q32.1 | mir-15a-prec | 0.0353 | 13q14.3 |
| 4 | mir-15a | −0.0372 | 0.0485 | 13q14.3 | mir-17 | 0.0257 | 13q31 |
| 5 | mir-24-1 | −0.0427 | 0.0558 | 9q22.1 | mir-15a | 0.018 | 13q14.3 |
| 6 | mir-195 | −0.053 | 0.0692 | 17p13 | mir-195 | 0.0175 | 17p13 |
| 7 | mir-23a | −0.0748 | 0.0977 | 19p13.12 | mir-213-prec | 0.0153 | 1q31.3-q32.1 |
| 8 | mir-23b | −0.0909 | 0.1187 | 9q22.1 | mir-221 | 0.0105 | Xp11.3 |
| 9 | mir-223 | 0.1056 | −0.1379 | Xq12-13.3 | mir-023b | 0.00964 | 9q22.1 |
| 10 | mir-29a-2 | 0.1139 | −0.1487 | 7q32 | mir-155 | 0.00959 | 21q21 |
| 11 | mir-155 | −0.1155 | 0.1508 | 21q21 | mir-223 | 0.00774 | Xq12-13.3 |
| 12 | mir-221 | −0.1157 | 0.1511 | Xp11.3 | mir-132 | 0.00461 | 17p13.3 |
| 13 | mir-16-1 | −0.1444 | 0.1886 | 13q14.3 | mir-029a-2 | 0.00446 | 7q32 |
| 14 | mir-16-2 | −0.1619 | 0.2113 | 3q26.1 | mir-024-1 | 0.00311 | 9q22.1 |
| 15 | mir-146 | −0.1803 | 0.2354 | 5q34 | mir-29b-2 (102) | 0.000778 | 1q32.2-32.3 |
| 16 | mir-29b-2 (102) | 0.2065 | −0.2696 | 1q32.2-32.3 | mir-146 | 0.000753 | 5q34 |
| 17 | mir-029c | 0.2174 | −0.2839 | 1q32.2-32.3 | mir-016-1 | 0.00042 | 13q14.3 |
| 18 | | | | | mir-016-2 | 0.000327 | 3q26.1 |
| 19 | | | | | mir-029c | 0.000216 | 1q32.2-32.3 |

*the list of genes is in ascending order of significance, as represented by score or p value, respectively.

TABLE 21

Predictions of ZAP-70 status and Immunoglobulin heavy chain variable gene status according to miRNA expression in CLL patients*.

| | CLL | True Value | Prediction | n margin | y margin |
|---|---|---|---|---|---|
| PANEL 1 - 83 correct predictions, 0 incorrect predictions | CLL01 | Zap70 < 20 VhM | Zap70 < 20 VhM | 1.278 | −1.327 |
| | CLL02 | Zap70 < 20 VhM | Zap70 < 20 VhM | 1 | −1 |
| | CLL03 | Zap70 < 20 VhM | Zap70 < 20 VhM | 1.247 | −1.348 |
| | CLL04 | Zap70 < 20 VhM | Zap70 < 20 VhM | 1.16 | −1.388 |
| | CLL05 | Zap70 < 20 VhM | Zap70 < 20 VhM | 1 | −1 |
| | CLL06 | Zap70 < 20 VhM | Zap70 < 20 VhM | 1 | −1 |
| | CLL07 | Zap70 < 20 VhM | Zap70 < 20 VhM | 1 | −1.122 |
| | CLL08 | Zap70 < 20 VhM | Zap70 < 20 VhM | 1.391 | −1.595 |
| | CLL09 | Zap70 < 20 VhM | Zap70 < 20 VhM | 0.953 | −1.048 |
| | CLL10 | Zap70 < 20 VhM | Zap70 < 20 VhM | 1.059 | −1.333 |
| | CLL11 | Zap70 < 20 VhM | Zap70 < 20 VhM | 1 | −1 |
| | CLL12 | Zap70 < 20 VhM | Zap70 < 20 VhM | 0.997 | −1.261 |
| | CLL13 | Zap70 < 20 VhM | Zap70 < 20 VhM | 1.488 | −1.841 |
| | CLL14 | Zap70 < 20 VhM | Zap70 < 20 VhM | 2.171 | −2.582 |
| | CLL15 | Zap70 < 20 VhM | Zap70 < 20 VhM | 1.252 | −1.352 |
| | CLL16 | Zap70 < 20 VhM | Zap70 < 20 VhM | 1 | −1.188 |
| | CLL17 | Zap70 < 20 VhM | Zap70 < 20 VhM | 1.19 | −1.284 |
| | CLL18 | Zap70 < 20 VhM | Zap70 < 20 VhM | 1.747 | −2.062 |
| | CLL19 | Zap70 < 20 VhM | Zap70 < 20 VhM | 1.503 | −1.833 |

TABLE 21-continued

Predictions of ZAP-70 status and Immunoglobulin heavy
chain variable gene status according to miRNA expression in CLL patients*.

| | CLL | True Value | Prediction | n margin | y margin |
|---|---|---|---|---|---|
| | CLL20 | Zap70 < 20 VhM | Zap70 < 20 VhM | 1 | −1 |
| | CLL21 | Zap70 < 20 VhM | Zap70 < 20 VhM | 1 | −1 |
| | CLL22 | Zap70 < 20 VhM | Zap70 < 20 VhM | 1 | −1 |
| | CLL23 | Zap70 < 20 VhM | Zap70 < 20 VhM | 2.047 | −2.27 |
| | CLL24 | Zap70 < 20 VhM | Zap70 < 20 VhM | 1.464 | −1.527 |
| | CLL25 | Zap70 < 20 VhM | Zap70 < 20 VhM | 1 | −1 |
| | CLL26 | Zap70 < 20 VhM | Zap70 < 20 VhM | 1.034 | −1.034 |
| | CLL27 | Zap70 < 20 VhM | Zap70 < 20 VhM | 1.479 | −1.617 |
| | CLL28 | Zap70 < 20 VhM | Zap70 < 20 VhM | 2.355 | −2.57 |
| | CLL29 | Zap70 < 20 VhM | Zap70 < 20 VhM | 1 | −1 |
| | CLL30 | Zap70 < 20 VhM | Zap70 < 20 VhM | 1 | −1 |
| | CLL31 | Zap70 < 20 VhM | Zap70 < 20 VhM | 1 | −1 |
| | CLL32 | Zap70 < 20 VhM | Zap70 < 20 VhM | 1 | −1 |
| | CLL33 | Zap70 < 20 VhM | Zap70 < 20 VhM | 2.229 | −2.496 |
| | CLL34 | Zap70 < 20 VhM | Zap70 < 20 VhM | 2.683 | −2.931 |
| | CLL35 | Zap70 < 20 VhM | Zap70 < 20 VhM | 1 | −1 |
| | CLL36 | Zap70 < 20 VhM | Zap70 < 20 VhM | 2.578 | −2.768 |
| | CLL37 | Zap70 < 20 VhM | Zap70 < 20 VhM | 2.079 | −2.34 |
| | CLL38 | Zap70 < 20 VhM | Zap70 < 20 VhM | 1.745 | −1.814 |
| | CLL39 | Zap70 < 20 VhM | Zap70 < 20 VhM | 1.559 | −1.699 |
| | CLL40 | Zap70 < 20 VhM | Zap70 < 20 VhM | 2.608 | −3.005 |
| | CLL41 | Zap70 < 20 VhM | Zap70 < 20 VhM | 2.357 | −2.676 |
| | CLL42 | Zap70 < 20 VhM | Zap70 < 20 VhM | 1.102 | −1.303 |
| | CLL43 | Zap70 < 20 VhM | Zap70 < 20 VhM | 1 | −1 |
| | CLL44 | Zap70 < 20 VhM | Zap70 < 20 VhM | 2.464 | −2.629 |
| | CLL45 | Zap70 < 20 VhM | Zap70 < 20 VhM | 1 | −1 |
| | CLL46 | Zap70 < 20 VhM | Zap70 < 20 VhM | 1 | −1 |
| | CLL47 | Zap70 < 20 VhM | Zap70 < 20 VhM | 2.074 | −2.271 |
| | CLL48 | Zap70 > 20 VhUM | Zap70 > 20 VhUM | −1 | 1 |
| | CLL49 | Zap70 > 20 VhUM | Zap70 > 20 VhUM | −1.179 | 1.487 |
| | CLL50 | Zap70 > 20 VhUM | Zap70 > 20 VhUM | −1 | 0.88 |
| | CLL51 | Zap70 > 20 VhUM | Zap70 > 20 VhUM | −1 | 1 |
| | CLL52 | Zap70 > 20 VhUM | Zap70 > 20 VhUM | −1.836 | 2.405 |
| | CLL53 | Zap70 > 20 VhUM | Zap70 > 20 VhUM | −1 | 1 |
| | CLL54 | Zap70 > 20 VhUM | Zap70 > 20 VhUM | −1.334 | 1.649 |
| | CLL55 | Zap70 > 20 VhUM | Zap70 > 20 VhUM | −1 | 1.229 |
| | CLL56 | Zap70 > 20 VhUM | Zap70 > 20 VhUM | −1 | 1 |
| | CLL57 | Zap70 > 20 VhUM | Zap70 > 20 VhUM | −1 | 1 |
| | CLL58 | Zap70 > 20 VhUM | Zap70 > 20 VhUM | −1.171 | 1.566 |
| | CLL59 | Zap70 > 20 VhUM | Zap70 > 20 VhUM | −1 | 1 |
| | CLL60 | Zap70 > 20 VhUM | Zap70 > 20 VhUM | −1 | 1 |
| | CLL61 | Zap70 > 20 VhUM | Zap70 > 20 VhUM | −1.505 | 1.976 |
| | CLL62 | Zap70 > 20 VhUM | Zap70 > 20 VhUM | −1.095 | 1.46 |
| | CLL63 | Zap70 > 20 VhUM | Zap70 > 20 VhUM | −2.297 | 2.717 |
| | CLL64 | Zap70 > 20 VhUM | Zap70 > 20 VhUM | −1.187 | 1.381 |
| | CLL65 | Zap70 > 20 VhUM | Zap70 > 20 VhUM | −1 | 1 |
| | CLL66 | Zap70 > 20 VhUM | Zap70 > 20 VhUM | −1.344 | 1.479 |
| | CLL67 | Zap70 > 20 VhUM | Zap70 > 20 VhUM | −1.876 | 2.049 |
| | CLL68 | Zap70 > 20 VhUM | Zap70 > 20 VhUM | −1 | 1 |
| | CLL69 | Zap70 > 20 VhUM | Zap70 > 20 VhUM | −1.89 | 1.987 |
| | CLL70 | Zap70 > 20 VhUM | Zap70 > 20 VhUM | −2.658 | 2.938 |
| | CLL71 | Zap70 > 20 VhUM | Zap70 > 20 VhUM | −1.556 | 1.967 |
| | CLL72 | Zap70 > 20 VhUM | Zap70 > 20 VhUM | −2.574 | 2.81 |
| | CLL73 | Zap70 > 20 VhUM | Zap70 > 20 VhUM | −1 | 1 |
| | CLL74 | Zap70 > 20 VhUM | Zap70 > 20 VhUM | −1 | 1 |
| | CLL75 | Zap70 > 20 VhUM | Zap70 > 20 VhUM | −1 | 1 |
| | CLL76 | Zap70 > 20 VhUM | Zap70 > 20 VhUM | −2.671 | 3.041 |
| | CLL77 | Zap70 > 20 VhUM | Zap70 > 20 VhUM | −1 | 1.376 |
| | CLL78 | Zap70 > 20 VhUM | Zap70 > 20 VhUM | −1 | 1 |
| | CLL79 | Zap70 > 20 VhUM | Zap70 > 20 VhUM | −1.678 | 1.914 |
| | CLL80 | Zap70 > 20 VhUM | Zap70 > 20 VhUM | −2.416 | 2.953 |
| | CLL81 | Zap70 > 20 VhUM | Zap70 > 20 VhUM | −1 | 1 |
| | CLL82 | Zap70 > 20 VhUM | Zap70 > 20 VhUM | −1.782 | 1.846 |
| | CLL83 | Zap70 > 20 VhUM | Zap70 > 20 VhUM | −2.307 | 2.716 |
| PANEL 2 - 50 | CLL95 | Zap70 < 20 | Zap70 < 20 | 8.494 | −8.494 |
| correct predictions, | CLL96 | Zap70 < 20 | Zap70 < 20 | 1 | −1 |
| 0 incorrect predictions | CLL97 | Zap70 < 20 | Zap70 < 20 | 0.763 | −0.763 |
| | CLL98 | Zap70 < 20 | Zap70 < 20 | 11.19 | −11.19 |
| | CLL99 | Zap70 < 20 | Zap70 < 20 | 7.561 | −7.561 |
| | CLL100 | Zap70 < 20 | Zap70 < 20 | 14.51 | −14.51 |
| | CLL101 | Zap70 < 20 | Zap70 < 20 | 5.585 | −5.585 |
| | CLL102 | Zap70 < 20 | Zap70 < 20 | 1 | −1 |
| | CLL103 | Zap70 < 20 | Zap70 < 20 | 10.09 | −10.09 |
| | CLL104 | Zap70 < 20 | Zap70 < 20 | 5.521 | −5.521 |
| | CLL105 | Zap70 < 20 | Zap70 < 20 | 7.33 | −7.33 |

TABLE 21-continued

Predictions of ZAP-70 status and Immunoglobulin heavy chain variable gene status according to miRNA expression in CLL patients*.

| CLL | True Value | Prediction | n margin | y margin |
|---|---|---|---|---|
| CLL106 | Zap70 < 20 | Zap70 < 20 | 3.264 | −3.264 |
| CLL107 | Zap70 < 20 | Zap70 < 20 | 7.774 | −7.774 |
| CLL108 | Zap70 < 20 | Zap70 < 20 | 5.3 | −5.3 |
| CLL109 | Zap70 < 20 | Zap70 < 20 | 4.34 | −4.34 |
| CLL110 | Zap70 < 20 | Zap70 < 20 | 1.822 | −1.822 |
| CLL111 | Zap70 < 20 | Zap70 < 20 | 3.879 | −3.879 |
| CLL112 | Zap70 < 20 | Zap70 < 20 | 8.514 | −8.514 |
| CLL113 | Zap70 < 20 | Zap70 < 20 | 5.866 | −5.866 |
| CLL114 | Zap70 < 20 | Zap70 < 20 | 10.69 | −10.69 |
| CLL115 | Zap70 < 20 | Zap70 < 20 | 4.141 | −4.141 |
| CLL116 | Zap70 < 20 | Zap70 < 20 | 1 | −1 |
| CLL117 | Zap70 < 20 | Zap70 < 20 | 1 | −1 |
| CLL118 | Zap70 < 20 | Zap70 < 20 | 1 | −1 |
| CLL119 | Zap70 < 20 | Zap70 < 20 | 10.11 | −10.11 |
| CLL120 | Zap70 > 20 | Zap70 > 20 | −3.109 | 3.109 |
| CLL121 | Zap70 > 20 | Zap70 > 20 | −4.722 | 4.722 |
| CLL122 | Zap70 > 20 | Zap70 > 20 | −5.166 | 5.166 |
| CLL123 | Zap70 > 20 | Zap70 > 20 | −7.828 | 7.828 |
| CLL124 | Zap70 > 20 | Zap70 > 20 | −7.468 | 7.468 |
| CLL125 | Zap70 > 20 | Zap70 > 20 | −11.44 | 11.44 |
| CLL126 | Zap70 > 20 | Zap70 > 20 | −1 | 1 |
| CLL127 | Zap70 > 20 | Zap70 > 20 | −6.617 | 6.617 |
| CLL128 | Zap70 > 20 | Zap70 > 20 | −7.011 | 7.011 |
| CLL129 | Zap70 > 20 | Zap70 > 20 | −7.479 | 7.479 |
| CLL130 | Zap70 > 20 | Zap70 > 20 | −9.568 | 9.568 |
| CLL131 | Zap70 > 20 | Zap70 > 20 | −5.286 | 5.286 |
| CLL132 | Zap70 > 20 | Zap70 > 20 | −5.045 | 5.045 |
| CLL133 | Zap70 > 20 | Zap70 > 20 | −1 | 1 |
| CLL134 | Zap70 > 20 | Zap70 > 20 | −1 | 1 |
| CLL135 | Zap70 > 20 | Zap70 > 20 | −1.324 | 1.324 |
| CLL136 | Zap70 > 20 | Zap70 > 20 | −1 | 1 |
| CLL137 | Zap70 > 20 | Zap70 > 20 | −1 | 1 |
| CLL138 | Zap70 > 20 | Zap70 > 20 | −9.649 | 9.649 |
| CLL139 | Zap70 > 20 | Zap70 > 20 | −9.264 | 9.264 |
| CLL140 | Zap70 > 20 | Zap70 > 20 | −7.13 | 7.13 |
| CLL141 | Zap70 > 20 | Zap70 > 20 | −11.77 | 11.77 |
| CLL142 | Zap70 > 20 | Zap70 > 20 | −2.986 | 2.986 |
| CLL143 | Zap70 > 20 | Zap70 > 20 | −1 | 1 |
| CLL144 | Zap70 > 20 | Zap70 > 20 | −1 | 1 |

*Prediction for 83 CLLs, from groups 1 and 4 (see text). Classification was generated by the 'Support Vector Machines' algorithm (Kernel Function used: Polynomial Dot Product (Order 2). Diagonal Scaling Factor: 0).
The miRNA signature associated with prognostic factors was generated using panel 1 samples and then tested to cross validate the panel 1 and to predict the status of samples from panel 2.

Association Between miRNA Expression and Time to Initial Therapy.

This analysis was performed as described in Example 12. All of the microRNAs which can predict the time to initial therapy, with the exception of mir-29c, are overexpressed in the group characterized by a short interval from diagnosis to initial therapy (Table 22). The PAM score for each of the components of microRNA signature associated with the time from diagnosis to initial therapy is presented in Table 23.

TABLE 22

Relative expression levels of microRNAs predictive of the time interval from diagnosis to initial therapy.

| | Short interval | Long interval |
|---|---|---|
| | microarray expression | |
| hsa-mir-181a | High | Low |
| hsa-mir-155 | High | Low |
| hsa-mir-146 | High | Low |
| hsa-mir-024-2 | High | Low |
| hsa-mir-023b | High | Low |
| hsa-mir-023a | High | Low |
| hsa-mir-222 | High | Low |
| hsa-mir-221 | High | Low |
| hsa-mir-029c | Low | High |

TABLE 23

PAM score for each of the components of microRNA signature associated with the time from diagnosis to initial therapy.

| | 1 score | 2 score |
|---|---|---|
| hsa-mir-181a | 0.1862 | −0.0603 |
| hsa-mir-155 | 0.1409 | −0.0456 |
| hsa-mir-146 | 0.07 | −0.0227 |
| hsa-mir-024-2 | 0.0696 | −0.0225 |
| hsa-mir-023b | 0.0643 | −0.0208 |
| hsa-mir-023a | 0.0587 | −0.019 |
| hsa-mir-222 | 0.0458 | −0.0148 |

TABLE 23-continued

PAM score for each of the components of microRNA
signature associated with the time from diagnosis to initial therapy.

|  | 1 score | 2 score |
|---|---|---|
| hsa-mir-221 | 0.0343 | −0.0111 |
| hsa-mir-029c | −0.0221 | 0.0072 |

Note:
Score 1 characterize the short time;
score 2 the long time from diagnosis to initial therapy in a panel of 94 CLL patients.

The relevant teachings of all publications cited herein that have not explicitly been incorporated by reference, are incorporated herein by reference in their entirety. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A method for inhibiting a miR-21 gene product in lung cancer cells, comprising delivering to the lung cancer cells an antisense nucleic acid that binds to the miR-21 gene product, thereby inhibiting the miR-21 gene product in the lung cancer cells.

2. The method of claim 1, wherein the antisense nucleic acid is selected from the group consisting of a single-stranded RNA, a single-stranded DNA, a single-stranded RNA-DNA chimera and a single-stranded PNA.

3. The method of claim 1, wherein the antisense nucleic acid contains one or more modifications to the nucleic acid backbone, a sugar moiety, a base moiety or a combination thereof.

4. The method of claim 1, wherein the antisense nucleic acid is at least 95% complementary to a miR-21 gene product nucleotide sequence selected from the group consisting of SEQ ID NO:49, SEQ ID NO:50 and nucleotides 8-29 of SEQ ID NO:49.

5. The method of claim 1, wherein the antisense nucleic acid is 100% complementary to a miR-21 gene product nucleotide sequence selected from the group consisting of SEQ ID NO:49, SEQ ID NO:50 and nucleotides 8-29 of SEQ ID NO:49.

* * * * *